US011898154B2

(12) United States Patent
Le Fourn et al.

(10) Patent No.: US 11,898,154 B2
(45) Date of Patent: Feb. 13, 2024

(54) ENHANCED TRANSGENE EXPRESSION AND PROCESSING

(71) Applicant: Selexis S.A., Plan-les-Ouates (CH)

(72) Inventors: Valerie Le Fourn, Plan-les-Ouates (CH); Nicolas Mermod, Plan-les-Ouates (CH); Alexandre Regamey, Plan-les-Ouates (CH); Montse Buceta, Plan-les-Ouates (CH); Deborah Ley, Plan-les-Ouates (CH); Niamh Harraghy, Plan-les-Ouates (CH); Kaja Kostyrko, Plan-les-Ouates (CH); Pierre-Alain Giro, Plan-les-Ouates (CH); David Calabrese, Plan-les-Ouates (CH)

(73) Assignee: SELEXIS S.A., Plan-les-Ouates (CH)

( * ) Notice: Subject to any disclaimer, the term of this patent is extended or adjusted under 35 U.S.C. 154(b) by 0 days.

(21) Appl. No.: 14/761,460

(22) PCT Filed: Feb. 1, 2014

(86) PCT No.: PCT/IB2014/000100

§ 371 (c)(1),
(2) Date: Jul. 16, 2015

(87) PCT Pub. No.: WO2014/118619

PCT Pub. Date: Aug. 7, 2014

(65) Prior Publication Data

US 2015/0361451 A1 Dec. 17, 2015

Related U.S. Application Data

(60) Provisional application No. 61/759,802, filed on Feb. 1, 2013, provisional application No. 61/800,244, filed on Mar. 15, 2013, provisional application No. 61/806,634, filed on Mar. 29, 2013.

(51) Int. Cl.

| | |
|---|---|
| ***C12N 15/85*** | (2006.01) |
| ***C07K 16/00*** | (2006.01) |
| ***C07K 16/24*** | (2006.01) |
| ***C07K 16/32*** | (2006.01) |
| ***C12N 15/90*** | (2006.01) |

(52) U.S. Cl.

CPC .............. *C12N 15/85* (2013.01); *C07K 16/00* (2013.01); *C07K 16/241* (2013.01); *C07K 16/32* (2013.01); *C12N 15/90* (2013.01); *C07K 2317/10* (2013.01); *C07K 2317/24* (2013.01); *C12N 2800/107* (2013.01); *C12N 2800/90* (2013.01); *C12N 2830/46* (2013.01)

(58) Field of Classification Search

None

See application file for complete search history.

(56) References Cited

U.S. PATENT DOCUMENTS

| | | | | |
|---|---|---|---|---|
| 2003/0087342 A1* | 5/2003 | Mermod | ................ | C12N 15/85 435/69.1 |
| 2004/0203158 A1* | 10/2004 | Hackett | .................. | C12N 15/85 435/473 |
| 2004/0235011 A1 | 11/2004 | Cooper et al. | | |
| 2010/0105140 A1* | 4/2010 | Fahrenkrug | .............. | C12N 9/22 435/455 |

FOREIGN PATENT DOCUMENTS

| | | |
|---|---|---|
| EP | 0743365 A2 | 11/1996 |
| WO | 2005010046 A1 | 2/2005 |
| WO | 2007021353 A2 | 2/2007 |
| WO | 2009042971 A2 | 4/2009 |
| WO | 2010118360 A1 | 10/2010 |
| WO | 2011033375 A2 | 3/2011 |

OTHER PUBLICATIONS

Nakanishi et al. piggyBac Transposon-mediated Long-term Gene Expression in Mice. The American Society of Cell & Gene Therapy, 2010. 18(4):707-714.*

Harraghy et al, Using Matrix Attachment Regions to Improve Recombinant Protein Production, In: Hartley J. (eds) Protein Expression in Mammalian Cells. Methods in Molecular Biology (Methods and Protocols), vol. 801. pp. 93-110. Humana Press. https://doi.org/10.1007/978-1-61779-352-3_7 (Online Sep. 4, 2011).*

Anyong et al., "Distinct roles of chromatin-associated proteins MDC1 and 53BP1 in mammalian double-strand break repair," in Molecular Cell, vol. 28, No. 6, Dec. 28, 2007, pp. 1045-1057.

Mattia et al., "CHO cell lines generated by PiggyBac transposition," in BMC Proceedings, Biomed Central Ltd, vol. 5, No. suppl 8, Nov. 22, 2011, p. P31.

Ley et al., "MAR Elements and Transposons, for Improved Transgene Integration and Expression," in PLoS One, vol. 8, No. 4, Apr. 30, 2013, pp. e62784.

Extended European Search Report and Written Opinion for EP 19 15 3376.9 dated Jul. 26, 2019.

Kazuo Niwano et al: "Lentiviral Vector-mediated SERCA2 Gene Transfer Protects Against Heart Failure and Left Ventricular Remodel ing After Myocardial Infarction in Rats", Molecular Therapy, vol. 16, No. 6, Jun. 1, 2008, pp. 1026-1032.

(Continued)

*Primary Examiner* — Christopher M Babic
*Assistant Examiner* — Kimberly A Aron
(74) *Attorney, Agent, or Firm* — Agris & von Natzmer LLP; Joyce von Natzmer

(57) ABSTRACT

Disclosed are constructs and methods for expressing DNAs of interest in particular in non-primate eukaryotic host cells that display advantages with regard quantity and quality of expression including high stability of expression and, if appropriate, transport of the expression product out of the cell.

38 Claims, 25 Drawing Sheets

Specification includes a Sequence Listing.

(56) References Cited

OTHER PUBLICATIONS

Y. Kawai et al: “Acetylation-Deacetylation of the Transcription Factor Nrf2 (Nuclear Factor Erythroid 2-related Factor 2) Regulates Its Transcriptional Activity and Nucleocytoplasmic Localization”, Journal of Biological Chemistry, vol. 286, No. 9, Mar. 4, 2011, pp. 7629-7640.

* cited by examiner

A
+PB
-PB
no selection
Mean GFP fluorescence (RLU)
0
100
200
300
Puro-GFP
Puro-Spacer-GFP
Puro-MAR-GFP
Puro-GFP-Spacer
Puro-GFP-MAR
Puro-GFP-itr-Spacer
Puro-GFP-itr-MAR
B
with puromycin selection
1000
2000
3000
Puro
GFP A
Parental CHO-M
Rad51-shRNA pool
Rad51-shRNA clone 16
Rad51-shRNA clone 26
Green Fluorescence (GRN-HLog)
B
Percent of total population
120
100
80
60
40
20
0
clone 8
clone 16
clone 17
clone 22
clone 26
CHO-M
M1
M2
M3
C
M3 cells (% total)
100
80
60
40
20
0
Time (days)
4
8
9
11
16
17
19
22
26
CHO-M
D
Specific productivity (pcd)
1
0.8
0.6
0.4
0.2
0
Week 1
Week 2
Week 3
8
16
17
22
26
Clone number GFP expression and stability (2 months)
t=0
t=7 weeks
SGE3' (1_68)
pSVpuro>CGAPD<168
SGE3'(X_29)
pSVpuro>CGAPD>X29
LmnB2 (Ctr)
pSVpuro>CGAPD<LmnB2
Green Fluorescence (GRN-HLog)
10e0
10e1
10e2
10e3
10e4
0
10
20
30
40

ENHANCED TRANSGENE EXPRESSION AND PROCESSING

CROSS-REFERENCE TO RELATED APPLICATIONS

This is the U.S. national stage of International application PCT/IB2014/000100, filed Feb. 1, 2014 designating the United States and claiming priority to U.S. provisional application No. 61/759,802, filed Feb. 1, 2013, U.S. provisional application No. 61/806,634, filed Mar. 29, 2013 and U.S. provisional application No. 61/800,244, filed Mar. 15, 2013.

INCORPORATION OF SEQUENCE LISTING

The sequence listing is hereby incorporated by reference. A copy of a text file of this sequence listing named "3024-192NS-SEQ_4-3-17_ST25.txt", which is 352 kilobytes (measured in MS-WINDOWS), dated Apr. 3, 2017 was submitted on Apr. 3, 2017 via the USPTO EFS system.

FIELD OF THE INVENTION

The invention is directed at providing nucleic acid constructs and proteins that are involved in or act on metabolic pathways that mediate or influence cellular metabolism, e.g., translocation across the ER membrane and/or secretion across the cytoplasmic membrane as well as methods to influence cellular metabolism. The invention is also directed at the production and use of recombinant mammalian cells in which, e.g., translocation/secretion of a wide variety of heterologous proteins (transgene expression products) is altered. The methods, nucleic acid constructs are generally designed to improve transgene expression.

BACKGROUND OF THE INVENTION

The biotechnological production of therapeutical proteins as well as gene and cell therapy depends on the successful expression of transgenes introduced into a eukaryotic cell. Successful transgene expression generally requires integration of the transgene into the host chromosome and is limited, among others, by the number of transgene copies integrated and by epigenetic effects that can cause low or unstable transcription and/or high clonal variability. Failing or reduced transport of the transgene expression product out of the cell also often limits production of therapeutical proteins as well as gene and cell therapy.

The publications and other materials, including patents, patent applications and accession numbers, used herein to illustrate the invention and, in particular, to provide additional details respecting the practice are incorporated herein by reference in their entirety.

To increase and stabilize transgene expression in mammalian cells, epigenetic regulators are being increasingly used to protect transgenes from negative position effects (Bell and Felsenfeld, 1999). These epigenetic regulators include boundary or insulator elements, locus control regions (LCRs), stabilizing and antirepressor (STAR) elements, ubiquitously acting chromatin opening (UCOE) elements and the aforementioned matrix attachment regions (MARs). All of these epigenetic regulators have been used for recombinant protein production in mammalian cell lines (Zahn-Zabal et al., 2001; Kim et al., 2004) and for gene therapies (Agarwal et al., 1998; Allen et al., 1996; Castilla et al., 1998).

The transgene expression product often encounters different bottlenecks during processing and transport out of the cell: The cell that is only equipped with the machinery to process and transport its innate proteins can get readily overburdened by the transport of certain types of transgene expression products, especially when they are produced at abnormally high levels as often desired, letting the product aggregate within the cell and/or, e.g., preventing proper folding of a functional protein product.

Different approaches have been pursued to overcome transportation and processing bottlenecks. For example, CHO cells with improved secretion properties were engineered by the expression of the SM proteins Munc18c or Sly1, which act as regulators of membranous vesicles trafficking and hence secreted protein exocytosis (U.S. Patent Publication 20090247609). The X-box-binding protein 1 (Xbp1), a transcription factor that regulates secretory cell differentiation and ER maintenance and expansion, or various protein disulfide isomerases (PDI), have been used to decrease ER stress and increase protein secretion (Mohan et at 2007). Other attempts to increase protein secretion included the expression of the chaperones ERp57, calnexin, calreticulin and BiP1 in CHO cells (Chung et al., 2004). Expression of a cold shock-induced protein, in particular the cold-inducible RNA-binding protein (CIRP), was shown to increase the yield of recombinant γ-interferon. Attempts were also made to overexpress proteins of the secretory complexes. However, for instance, Lakkaraju et al. (2008) reported that exogenous SRP14 expression in WT human cells (e.g. in cells that were not engineered to express low SRP14 levels) did not improve secretion efficiency of the secreted alkaline phosphatase protein.

Thus, there is a need for efficient, reliable transgene expression, e.g., recombinant protein production and for gene therapy. There is also a need to successfully transport the transgene expression product outside the cell.

This and other needs in the art are addressed by embodiments of the present invention.

SUMMARY OF THE INVENTION

The invention is, in one embodiment directed at a recombinant nucleic acid molecule comprising:

(a) a 5' and a 3' transposon-specific inverted terminal repeat (ITR), (b) at least one nucleic acid sequence encoding a transgene expression processing (TEP) protein or a TEP functional RNA, located between the 5' and 3' ITRs and which is under the control of a promoter, and (c) optionally at least one transgene also located between the 5' and 3' ITRs and which is under the control of a transgene promoter, wherein said nucleic acid molecule is optionally part of a vector.

The recombinant nucleic acid molecule may comprise at least one epigenetic regulatory element, in particular at least one MAR (matrix attachment region) element.

The MAR element may be located between the 5' and a 3' ITRs. A transgene such as an antibiotic resistance gene or a gene encoding an immunoglobulin, optionally under the control of a further promoter, may be located between the 5' and a 3' ITR such as between the 5' ITR and the MAR.

The TEP protein or TEP functional RNA may be a protein or a functional RNA that is, directly or indirectly, involved in integration of nucleic acid sequences into a genome, processing or translation of the transgene RNA product or is involved in ER translocation, secretion, processing, folding, ER-Golgy-plasma membrane transport, glycosylation and/ or another post-translational modification of proteins such as transgene expression products.

The TEP protein may be a protein of the protein secretion pathway, a protein of the DNA recombination or repair pathways, a protein processing or metabolic protein including chaperones such as BiP, or a combination thereof.

The TEP protein may be one or more of the following proteins of the protein secretion pathway: hSRP14, hSec61α1, hSec61β, hSec61γ, hSRP54, hSRP9, hSRPRα, hSRPβ, and hCANX.

The TEP protein may also correspond to one or more of the following amino acid sequences of proteins of the protein secretion pathway: hSRP14 having SEQ ID NO: 13, hSec61α1 having SEQ ID NO: 15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29 and/or may correspond to amino acid sequences having more than 80%, 90%, 95% or 98% sequence identity with the specified sequences.

The TEP protein may be one or more of the following protein processing or metabolic proteins: hUCP4, hCMP-SAT, rST6Gal1, hCOMSC, hT-Synthase, hP4HA1, hP4HB, hGILZ, hCyPB, hNRF2, hHK1, hPDI, hPIN1, hSEPW1, hCALR, hDDOST, hHSP40, hATP5A1, hSERCA2, hPDIA4, hHSC70/HSPA8, hHYOU1, hCMP-SAS, hBeclin-1, hERdj3, CHO-AGE, hWip1, hRTP4, hREEP2, hDPM1 and hDRiP78.

The TEP protein may also correspond to one or more of the following amino acid sequences of protein processing or metabolic proteins: hUCP4 having SEQ ID NO: 31, hCMP-SAT having SEQ ID NO: 33, rST6Gal1 having SEQ ID NO: 35, hCOMSC having SEQ ID NO: 37, hT-Synthase having SEQ ID NO: 39, hP4HA1 having SEQ ID NO: 41, hP4HB having SEQ ID NO: 43, hGILZ having SEQ ID NO: 45, hCyPB having SEQ ID NO: 47, hNRF2 having SEQ ID NO: 49, hHK1 having SEQ ID NO: 51, hPDI having SEQ ID NO: 53, hPIN1 having SEQ ID NO: 55, hSEPW1 having SEQ ID NO: 57, hCALR having SEQ ID NO: 59, hDDOST having SEQ ID NO: 62, hHSP40 having SEQ ID NO: 64, hATP5A1 having SEQ ID NO: 66, hSERCA2 having SEQ ID NO: 68, hPDIA4 having SEQ ID NO: 70, hHSC70/HSPA8 having SEQ ID NO: 72, hHYOU1 having SEQ ID NO: 74, hCMP-SAS having SEQ ID NO: 76, hBeclin-1 having SEQ ID NO: 78, hERdj3 having SEQ ID NO: 80, CHO-AGE having SEQ ID NO: 82, hWip1 having SEQ ID NO: 84, hRTP4 having SEQ ID NO: 86, hREEP2 having SEQ ID NO: 88, hDPM1 having SEQ ID NO: 90 and hDRiP78 having SEQ ID NO: 92 and/or may correspond to amino acid sequences having more than 80%, 90%, 95% or 98% sequence identity with the specified sequences.

The TEP protein may be a chaperone, in particular, a BiP protein, more in particular, a modified *drosophila* BIP protein derivative (DroBiP) having 80%, 90%, 95% or 100% sequence identity with the SEQ ID NO.: 60.

The MAR element may be selected from SEQ ID NOs: 1 (MAR 1-68), 2 (MAR 1_6), 3 (MAR X_S29), 4 (MAR S4), 5 (chicken lysozyme MAR), or preferably is an engineered, in particular rearranged counterpart and/or has at least 80%, 90%, 95%, 98%, 99% or 100% sequence identity with any one of SEQ ID NOs: 1 to 5 or with any one of SEQ ID NOs: 6 to 10.

The TEP functional RNA within said cell may comprise/consist of nucleic acid sequences encoding a functional RNA, preferably a miRNA or a shRNA, that interferes with the expression of at least one protein of a DNA recombination or repair pathway, such as, but not limited to, Rad51, Rad51B, Rad51C, Rad51D, Xrcc2, Xrcc3, Rad52, Rad54, Brca1, Brca2, Cyclin D1, Ercc, MDC1, Bard1, Ligase 1, Mre11 and/or 53BP1.

The TEP functional RNA may also interfere with expression of ngenes having at least 80%, 90%, 95%, 98% or 100% sequence identity with Rad51 having SEQ ID NO: 93, Rad51B having SEQ ID NO: 94, Rad51C having SEQ ID NO: 95, Rad51D having SEQ ID NO: 96, Xrcc2 having SEQ ID NO: 99, Xrcc3 having SEQ ID NO: 100, Rad52 having SEQ ID NO: 97, Rad54 having SEQ ID NO: 98, Brca1 having SEQ ID NO: 101, Brca2 having SEQ ID NO: 102, Cyclin D1 having SEQ ID NO: 103, Ercc1 having SEQ ID NO: 104, MDC1 having SEQ ID NO: 105, Bard1 having SEQ ID NO: 106, Ligase 1 having SEQ ID NO: 107, Mre11 having SEQ ID NO: 108 and/or 53BP1 having SEQ ID NO: 109.

The recombinant nucleic acid molecule may be at least 5000, 6000, 7000, 8000, 90000 or 10000 bps long.

The 5' and a 3' ITRs may be 5' and 3' ITRs of the Sleeping Beauty or preferably PiggyBac Transposon.

Upon a first transfection of one of the recombinant nucleic acid molecules and a second, subsequent, transfection of a further recombinant nucleic acid molecule containing a transgene into a mammalian cell, transgene integration and/or expression may be increased in said cell relative to a cell not subject to said first transfection.

The TEP coding sequence or TEP functional RNA mentioned herein may be part of a vector including an expression vector. The vector may comprise a singular MAR element, two or more MAR elements, wherein said element(s) may be located between the 5' and 3' ITRs.

E.g., the vector may comprise two MAR elements. A first MAR element may be positioned upstream of the TEP or TEP functional RNA and a second MAR element may be positioned downstream of the TEP or TEP functional RNA, wherein the first MAR element may comprise a MAR 16 element and/or an element that has at least 80%, 90%, 95%, 98%, 99% or 100% sequence identity with SEQ ID NO. 2, in particular a rearranged MARs based on MAR 1-6, more in particular elements that have at least 80%, 90%, 95%, 98%, 99% or 100% sequence identity with SEQ ID NO: 8 (MARs 1_6R2) and the second MAR element may comprise a MAR 1-68 element and/or an element that has at least 80%, 90%, 95%, 98%, 99% or 100% sequence identity with SEQ ID NO. 1.

The vector may also comprise a singular MAR element. The singular MAR element may be positioned downstream of the TEP or TEP functional RNA, wherein the singular MAR element may be a MAR 1-68 or a MAR X-29 element and/or an element that has at least 80%, 90%, 95%, 98%, 99% or 100% sequence identity with SEQ ID NOs. 1 or 3, in particular a rearranged MAR based on MAR 1-68 or a MAR X-29, in particular an element that has at least 80%, 90%, 95%, 98%, 99% or 100% sequence identity with SEQ ID NOs: 6, 7 or 10 (MARs 1_68R, 1_68R2 or X_29R3) or 9, and may preferably a MAR X-29 element and/or an element that has at least 80%, 90%, 95%, 98%, 99% or 100% sequence identity with SEQ ID NO. 3.

The TEP or TEP functional RNA may be under the control of an EF1 alpha promoter and is optionally followed by a BGH polyA signal.

The vector may comprise promoter(s) and/or enhancer(s) or fusions thereof such as GAPDH, SV40p, CMV, CHO EF1 alpha, CHO Actb and/or CHO Hspa5, or engineered fusions thereof, such as CGAPDH.

The promoters which are part of the vector may be GAPDH having SEQ ID NO: 111, SV40p having SEQ ID NO: 114, CMVp having SEQ ID NO: 113, CHO Ef1 alpha having SEQ ID NO:112, CHO Actb having SEQ ID NO: 115, CHO Hspa5 having SEQ ID NO: 116, and/or fusions thereof such as CGAPDH having SEQ ID NO: 11, or may have nucleic acid sequences having more than 80%, 90%, 95% or 98% sequence identity with the specified sequences.

The invention is also directed at a method for expressing a TEP or TEP functional RNA comprising:

providing a recombinant mammalian cell comprising a transgene, and the vector is an expression vector which expresses the TEP or TEP functional RNA, wherein the TEP or TEP functional RNA expressed via said vector optionally increases an expression of a transgene in said mammalian cell by at least 10%, at least 20%, at least 30%, at least 40%, at least 50%, at least 60% or at least 70%.

The vector may comprise a singular MAR X-29 element and/or a nucleic acid sequence having at least 80%, 90%, 95%, 98%, 99% or 100% sequence identity with SEQ ID NO. 3 and wherein, after more than 4, 5, 6, 7, 8, 9, 10, 11, 12, 13 or 14 weeks of cultivation, the TEP or TEP functional RNA expressed via said vector may increase an expression of a gene of interest by at least 10%, at least 20%, at least 30%, at least 40%, at least 50%, at least 60% or at least 70%.

The invention is also directed at a recombinant mammalian cell comprising not more than 20, 15, 10 or 5 of the recombinant nucleic acid molecule, preferably integrated into the genome of the cell as single copies.

As noted above, the TEP protein may be one or more of the following proteins of the protein secretion pathway: hSRP14, hSec61α1, hSec61β, hSec61γ, hSRP54, hSRP9, hSRPRα, hSRPβ, and hCANX.

The TEP protein may also correspond to one or more of the following amino acid sequences of proteins of the protein secretion pathway: hSRP14 having SEQ ID NO: 13, hSec61α1 having SEQ ID NO: 15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29 and/or may correspond to amino acid sequences having more than 80%, 90%, 95% or 98% sequence identity with the specified sequences The TEP protein may be one or more of the following protein processing or metabolic proteins: hUCP4, hCMP-SAT, rST6Gal1, hCOMSC, hT-Synthase, hP4HA1, hP4HB, hGILZ, hCyPB, hNRF2, hHK1, hPDI, hPIN1, hSEPW1, hCALR, hDDOST, hHSP40, hATP5A1, hSERCA2, hPDIA4, hHSC70/HSPA8, hHYOU1, hCMP-SAS, hBeclin-1, hERdj3, CHO-AGE, hWip1, hRTP4, hREEP2, hDPM1 and hDRiP78.

The TEP protein may also correspond to one or more of the following amino acid sequences of protein processing or metabolic proteins: hUCP4 having SEQ ID NO: 31, hCMP-SAT having SEQ ID NO: 33, rST6Gal1 having SEQ ID NO: 35, hCOMSC having SEQ ID NO: 37, hT-Synthase having SEQ ID NO: 39, hP4HA1 having SEQ ID NO: 41, hP4HB having SEQ ID NO: 43, hGILZ having SEQ ID NO: 45, hCyPB having SEQ ID NO: 47, hNRF2 having SEQ ID NO: 49, hHK1 having SEQ ID NO: 51, hPDI having SEQ ID NO: 53, hPIN1 having SEQ ID NO: 55, hSEPW1 having SEQ ID NO: 57, hCALR having SEQ ID NO: 59, hDDOST having SEQ ID NO: 62, hHSP40 having SEQ ID NO: 64, hATP5A1 having SEQ ID NO: 66, hSERCA2 having SEQ ID NO: 68, hPDIA4 having SEQ ID NO: 70, hHSC70/HSPA8 having SEQ ID NO: 72, hHYOU1 having SEQ ID NO: 74, hCMP-SAS having SEQ ID NO: 76, hBeclin-1 having SEQ ID NO: 78, hERdj3 having SEQ ID NO: 80, CHO-AGE having SEQ ID NO: 82, hWip1 having SEQ ID NO: 84, hRTP4 having SEQ ID NO: 86, hREEP2 having SEQ ID NO: 88, hDPM1 having SEQ ID NO: 90 and hDRiP78 having SEQ ID NO: 92 and/or may correspond to amino acid sequences having more than 80%, 90%, 95% or 98% sequence identity with the specified sequences.

The TEP protein may be a chaperone, in particular, a BiP protein, more in particular, a engineered *drosophila* BIP protein derivative (DroBiP) having 80%, 90%, 95% or100% sequence identity with the SEQ ID NO.: 60.

The TEP functional RNA within the recombinant mammalian cell may comprise/consist of nucleic acid sequence(s) encoding a functional RNA, preferably a miRNA or a shRNA, that interferes with the expression of at least one recombination protein, preferably an HR gene, such as, but not limited to, Rad51, Rad51B, Rad51C, Rad51D, Xrcc2, Xrcc3, Rad52, Rad54, Brca1, Brca2, Cyclin D1, Ercc1, MDC1, Bard1, Ligase 1, Mre11 and/or 53BP1. The nucleic acids may have at least 80%, 90%, 95%, 98% or 100% sequence identity with Rad51 having SEQ ID NO: 93, Rad51B having SEQ ID NO: 94, Rad51C having SEQ ID NO: 95, Rad51D having SEQ ID NO: 96, Xrcc2 having SEQ ID NO: 99, Xrcc3 having SEQ ID NO: 100, Rad52 having SEQ ID NO: 97, Rad54 having SEQ ID NO: 98, Brca1 having SEQ ID NO: 101, Brca2 having SEQ ID NO: 102, Cyclin D1 having SEQ ID NO: 103, Ercc1 having SEQ ID NO: 104, MDC1 having SEQ ID NO: 105, Bard1 having SEQ ID NO: 106, Ligase 1 having SEQ ID NO: 107, Mre11 having SEQ ID NO: 108 and/or 53BP1 having SEQ ID NO: 109.

The recombinant mammalian cell may a primary stem cell, a hamster, e.g., CHO (Chinese hamster ovary), cell or a human, e.g., HEK293 cell.

The invention is also directed at a recombinant mammalian cell comprising:

a.) at least one TEP functional RNA and/or at least one recombinant nucleic acid sequence encoding a TEP protein or encoding TEP functional RNA, and b) a recombinant nucleic acid molecule comprising:

(i) at least one transgene of interest, and (ii) optionally, a MAR element.

As noted above, the TEP protein may be one or more of the following proteins of the protein secretion pathway: hSRP14, hSec61α1, hSec61β, hSec61γ, hSRP54, hSRP9, hSRPRα, hSRPβ, and hCANX.

The TEP protein may also correspond to one or more of the following amino acid sequences of proteins of the protein secretion pathway: hSRP14 having SEQ ID NO: 13, hSec61α1 having SEQ ID NO: 15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29 and/or may correspond to amino acid sequences having more than 80%, 90%, 95% or 98% sequence identity with the specified sequences.

The TEP protein may be one or more of the following protein processing or metabolic proteins: hUCP4, hCMP-SAT, rST6Gal1, hCOMSC, hT-Synthase, hP4HA1, hP4HB, hGILZ, hCyPB, hNRF2, hHK1, hPDI, hPIN1, hSEPW1, hCALR, hDDOST, hHSP40, hATP5A1, hSERCA2, hPDIA4, hHSC70/HSPA8, hHYOU1, hCMP-SAS, hBeclin-1, hERdj3, CHO-AGE, hWip1, hRTP4, hREEP2, hDPM1 and hDRiP78.

The TEP protein may also correspond to one or more of the following amino acid sequences of protein processing or metabolic proteins: hUCP4 having SEQ ID NO: 31, hCMP- SAT having SEQ ID NO: 33, rST6Gal1 having SEQ ID NO: 35, hCOMSC having SEQ ID NO: 37, hT-Synthase having SEQ ID NO: 39, hP4HA1 having SEQ ID NO: 41, hP4HB having SEQ ID NO: 43, hGILZ having SEQ ID NO: 45, hCyPB having SEQ ID NO: 47, hNRF2 having SEQ ID NO: 49, hHK1 having SEQ ID NO: 51, hPDI having SEQ ID NO: 53, hPIN1 having SEQ ID NO: 55, hSEPW1 having SEQ ID NO: 57, hCALR having SEQ ID NO: 59, hDDOST having SEQ ID NO: 62, hHSP40 having SEQ ID NO: 64, hATP5A1 having SEQ ID NO: 66, hSERCA2 having SEQ ID NO: 68, hPDIA4 having SEQ ID NO: 70, hHSC70/HSPA8 having SEQ ID NO: 72, hHYOU1 having SEQ ID NO: 74, hCMP-SAS having SEQ ID NO: 76, hBeclin-1 having SEQ ID NO: 78, hERdj3 having SEQ ID NO: 80, CHO-AGE having SEQ ID NO: 82, hWip1 having SEQ ID NO: 84, hRTP4 having SEQ ID NO: 86, hREEP2 having SEQ ID NO: 88, hDPM1 having SEQ ID NO: 90 and hDRiP78 having SEQ ID NO: 92 and/or may correspond to amino acid sequences having more than 80%, 90%, 95% or 98% sequence identity with the specified sequences.

The TEP protein may be a chaperone, in particular, a BiP protein, more in particular, a synthetic *drosophila* BIP protein derivative (DroBiP) having 80%, 90%, 95% or 100% sequence identity with the SEQ ID NO.: 60.

The functional RNA may be a transiently transfected siRNA or an shRNA which is transcribed from said at least one isolated nucleic acid sequence, wherein the siRNA or the processed shRNA is a 20, 21, 22, 23, 24 or 25 base pairs long antisense RNA which is fully complimentary to 20, 21, 22, 23, 24 or 25 consecutive nucleotides of a mRNA of at least one target gene that is part of the NHEJ (non-homologous end-joining), HR (homologous recombination), MMEJ (Microhomolgoy mediated end joining) recombinant pathway or is a DNA repair protein such as MDC1 (mediator of DNA-damage checkpoint 1).

The at least one target gene that may be part of:

the DNA repair and NHEJ is

53BP1 (Tumor suppressor p53-binding protein 1), the HR is

Rad51 (DNA repair protein RAD51), Rad51B (DNA repair protein RAD51 homolog 2), Rad51C (DNA repair protein RAD51 homolog 3), Rad51D (DNA repair protein RAD51 homolog 4), Rad52 (DNA repair protein RAD52), Rad54 (DNA repair and recombination protein RAD54), Xrcc2 (X-ray repair complementing defective repair in Chinese hamster cells 2), Xrcc3 (X-ray repair complementing defective repair in Chinese hamster cells 3), Brca1 (breast cancer 1, early onset), Brca2 (breast cancer 2, early onset), Bard1 (BRCA1 associated RING domain 1), the MMEJ is Ercc1 (excision repair cross-complementing rodent repair deficiency, complementation group 1), Mre11 (meiotic recombination 11)

Ligase1 (DNA ligase 1), and/or

Is the DNA repair protein MDC1.

The target genes may be nucleic acids having at least 80%, 90%, 95%, 98% or 100% sequence identity with Rad51 having SEQ ID NO: 93, Rad51B having SEQ ID NO: 94, Rad51C having SEQ ID NO: 95, Rad51D having SEQ ID NO: 96, Xrcc2 having SEQ ID NO: 99, Xrcc3 having SEQ ID NO: 100, Rad52 having SEQ ID NO: 97, Rad54 having SEQ ID NO: 98, Brca1 having SEQ ID NO: 101, Brca2 having SEQ ID NO: 102, Cyclin D1 having SEQ ID NO: 103, Ercc1 having SEQ ID NO: 104, MDC1 having SEQ ID NO: 105, Bard1 having SEQ ID NO: 106, Ligase 1 having SEQ ID NO: 107, Mre11 having SEQ ID NO: 108 and/or 53BP1 having SEQ ID NO: 109.

The at least one transgene may express a therapeutic protein such as an immunoglobulin, a hormone such as erythropoietin, or a growth factor and wherein, optionally, in the recombinant mammalian cell transgene integration and/or expression is increased relative to a cell not comprising said recombinant nucleic acid molecule(s).

The recombinant mammalian cell may comprise at least two TEP functional RNAs, wherein one or both of the TEP RNAs are transiently transfected siRNA, or are expressed by said isolated nucleic acid sequence(s) encoding a TEP functional RNA.

The recombinant mammalian cell may comprise a MAR element.

The invention is also directed at a method for transfecting mammalian cells, in particular hamster cells, comprising:

transfecting, optionally in a first transfection, said mammalian cells with (i) at least one of said recombinant nucleic acids molecules of any one of claims 1 to 13 and/or (ii) at least one isolated TEP functional RNA and at least one transgene which is, optionally, part of a recombinant nucleic acid molecule which is optionally transfected in a second, subsequent transfection, optionally together with an isolated nucleic acid or mRNA expressing a transposase which recognizes the 5' and the 3' ITR.

The recombinant mammalian cell may be transfected with more than one, including at least two, at least three or at least four of said recombinant nucleic acid molecules encoding one, two or three of the following: hSRP14, hSec61α1, hSec61β, hSec61γ, hSRP54, hSRP9, hSRPRα, hSRPβ, and hCANX.

I may also be transfected with hSRP14 having SEQ ID NO: 13, hSec61α1 having SEQ ID NO: 15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29 and/or with amino acid sequences having more than 80%, 90%, 95% or 98% sequence identity with the specified sequences.

Any of the recombinant nucleic acid molecules may part of a vector, wherein the vectors may be co-transfected.

The co-transfection of vectors encoding several TEP proteins, preferably a co-transfection of recombinant, nucleic acid molecules encoding proteins SRP14, SRP9 and SRP54 may increase transgene integration and/or expression in said cell relative to a cell not subject to such co-transfection. Co-transfection of vectors comprising nucleic acid sequences have at least 80%, 90%, 95%, 98% or 100% SEQ ID NO: 12, SEQ ID NO: 22, SEQ ID NO: 20 is also within the scope of the present invention.

A number of said mammalian cells that stably express said TEP protein or TEP functional RNA may be obtained to obtain recombinant mammalian cells and wherein said number of recombinant mammalian cells may be independent from the presence of said MAR element. The mammalian cells may be transfected a second and optionally third time.

Preferably, at least 30%, 40% or 45% of said mammalian cells may become recombinant mammalian cells and express said transgene.

The mammalian cell may be transfected with said at least one isolated TEP functional RNA and a vector comprising said at least one transgene and optionally a 3' ITR and 5' ITR flanking said at least one transgene, optionally together with an isolated nucleic acid or mRNA expressing a transposase with recognizes the 5' and the 3' ITR.

The transgene may be a therapeutic protein such as an immunoglobulin, hormone, cytokine or growth factor.

The recombinant nucleic acid molecule may comprise optionally a selection marker and wherein the at least one transgene is expressed (a) without selection for said marker, or (b) with selection for said marker, e.g. via a selection agent contained in a culture medium, and (c) in absence of transposase, or (d) in presence of transposase.

The TEP functional RNA may be encoded by a recombinant nucleic acid sequences encoding a shRNA or miRNA, or may comprise/consist of a siRNA that interferes with the expression of at least one HR gene, such as, but not limited to, Rad51, Rad51B, Rad51C, Rad51D, Xrcc2, Xrcc3, Rad52, Rad54, Brca1, Brca2, Cyclin D1, Ercc1, MDC1, Bard1, Ligase 1, Mre11 and/or 53BP1.

The TEP functional RNA may also interfere with expression of genes having at least 80%, 90%, 95%, 98% or 100% sequence identity with Rad51 having SEQ ID NO: 93, Rad51B having SEQ ID NO: 94, Rad51C having SEQ ID NO: 95, Rad51D having SEQ ID NO: 96, Xrcc2 having SEQ ID NO: 99, Xrcc3 having SEQ ID NO: 100, Rad52 having SEQ ID NO: 97, Rad54 having SEQ ID NO: 98, Brca1 having SEQ ID NO: 101, Brca2 having SEQ ID NO: 102, Cyclin D1 having SEQ ID NO: 103, Ercc1 having SEQ ID NO: 104, MDC1 having SEQ ID NO: 105, Bard1 having SEQ ID NO: 106, Ligase 1 having SEQ ID NO: 107, Mre11 having SEQ ID NO: 108 and/or 53BP1 having SEQ ID NO: 109.

The transgene integration and/or expression may be increased in such a cell relative to a cell not transfected with said isolated nucleic acid molecules and/or said at least one of said isolated TEP functional RNAs.

The invention is also directed at a kit comprising in one container at least one vector comprising the any one of the recombinant nucleic acid molecules according to claims 1 to 13 and, in a second optional container a vector encoding a compatible transposase and in a further container instruction of how to use the vector or vectors.

The kit mentioned above, wherein more than one vector is provided in one or more containers and wherein the TEP proteins are at least two of the following: a chaperone, SRP14, SRP9, SRP54, SR or a translocon.

The kit mentioned above, wherein the TEP functional RNA(s) within said vector(s) comprise(s)/consist(s) of nucleic acid sequences encoding a miRNA, siRNA or a shRNA that interferes with the expression of at least one HR gene, such as, but not limited to, Rad51, Rad51B, Rad51C, Rad51D, Xrcc2, Xrcc3, Rad52, Rad54, Brca1, Brca2-Cyclin D1, Ercc1, MDC1, Bard1, Ligase 1, Mre11 and/or 53BP1, and preferably in a further container siRNA(s) that interferes with the expression of at least one other HR gene, such as, but not limited to, Rad51, Rad51B, Rad51C, Rad51D, Xrcc2, Xrcc3, Rad52, Rad54, Brca1, Brca2, Cyclin D1, Ercc1, MDC1, Bard1, Ligase 1, Mre11 and/or 53BP1.

The HR gene may correspond to nucleic acids having at least 80%, 90%, 95%, 98% or 100% sequence identity with Rad51 having SEQ ID NO: 93, Rad51B having SEQ ID NO: 94, Rad51C having SEQ ID NO: 95, Rad51D having SEQ ID NO: 96, Xrcc2 having SEQ ID NO: 99, Xrcc3 having SEQ ID NO: 100, Rad52 having SEQ ID NO: 97, Rad54 having SEQ ID NO: 98, Brca1 having SEQ ID NO: 101, Brca2 having SEQ ID NO: 102, Cyclin D1 having SEQ ID NO: 103, Ercc1 having SEQ ID NO: 104, MDC1 having SEQ ID NO: 105, Bard1 having SEQ ID NO: 106, Ligase 1 having SEQ ID NO: 107, Mre 11 having SEQ ID NO: 108 and/or 53BP1 having SEQ ID NO: 109.

The invention is also directed towards the use of the recombinant nucleic acids disclosed herein and/or the recombinant mammalian cells disclosed herein, preferably for increasing transgene integration and/or expression.

The invention is also directed at an expression vector comprising:

(a) a transgene which is flanked, upstream by a promoter and downstream by a polyadenylation signal, (b) a singular MAR element downstream of the polyadenylation signal, or (c) a first MAR element upstream of the transgene of interest and a second MAR element downstream of said transgene integration site.

The singular or first and second MAR elements may be selected from MAR elements 1_68, 1_6, 1_6R2, 1_68R, 1_68R2, X_29R3 or X_29 or elements that have at least 80%, 90%, 95%, 98%, 99% or 100% sequence identity with SEQ ID NOs: 1, 2, 3, 6, 7, 8, 9 or 10.

The singular or first and second MAR(s) may be selected from rearranged MAR elements 1_6R2, 1_68R, 1_68R2 or X_29R3 or elements that have at least 80%, 90%, 95%, 98%, 99% or 100% sequence identity with SEQ ID NOs: 6, 7, 8, or 10, wherein, optionally, the MAR element(s) increase an expression of the transgene of interest by at least 10%, at least 20%, at least 30%, at least 40%, at least 50%, at least 60% or at least 70% relative to their non-rearranged counterparts.

The promoter may be an EF1 alpha promoter and the polyadenylation signal is a BGH polyA signal.

The vector may comprise promoter(s) and/or enhancer(s) or fusions thereof such as GAPDH, CGAPD, CSV40p, CMVp, CHO Ef1alpha, CHO Actb or CHO Hspa5.

The promoters may be GAPDH having SEQ ID NO: 111, CGAPDH having SEQ ID NO: 11, SV40p having SEQ ID NO: 114, CMVp having SEQ ID NO: 113, CHO EF1 alpha having SEQ ID NO:112, CHO Actb having SEQ ID NO: 115 and/or CHO Hspa5 having SEQ ID NO: 116 and nucleic acid sequences having more than 80%, 90%, 95% or 98% sequence identity with the specified sequences.

The promoter may be GAPDH promoter and comprises a CMV enhancer.

The first and/or second MAR, enhancer, promoter, transgene of interest and polyadenylation signal may be located between a 5' and 3' ITR.

In certain embodiment, the expression vector may comprise:

(a) a singular MAR element downstream of the polyadenylation signal, wherein said singular MAR element is preferably a MAR 1-68 or a MARX-29 element and/or an element that has at least 80%, 90%, 95%, 98%, 99% or 100% sequence identity with SEQ ID NOs. 1 or 3, in particular a rearranged MAR based on MAR 1-68 or a MAR X-29, in particular an element that has at least 80%, 90%, 98%, 95%, 98%, 99% or 100% sequence identity with SEQ ID Nos: 6, 7 OR 10 (MARs 1_68R, 1_68R2 or X_29R3) or SEQ ID NO: 9, and is preferably a MAR X-29 element and/or has at least 80%, 90%, 95%, 98%, 99% or 100% sequence identity with SEQ ID NO. 3, or (b) a first MAR element upstream of the transgene of interest and a second MAR element downstream of said transgene of interest wherein the first MAR element, preferably comprises a 16 element and/or has at least 80%, 90%, 95%, 98%, 99% or 100% sequence identity with SEQ ID NO. 2, in particular with rearranged MARs based on MAR 1-6, in particular elements that have at least 80%, 90%, 95%, 98%, 99% or 100% sequence identity with SEQ ID NO: 8 (MAR 1_6R2) and the second MAR element that preferably comprises a MAR 1-68 element and/or has at least 80%, 90%, 95%, 98%, 99% 01100% sequence identity with SEQ ID NO.1.

The expression vector may comprise a singular MAR element and the singular MAR element may be positioned downstream of the polyadenylation site and is a MAR 1-68 or a MAR X-29 and/or has at least 80%, 90%, 95%, 98%, 99% or 100% sequence identity with SEQ ID NOs. 1 or 3, in particular rearranged MARs based on MAR 1-68 or a MAR X-29, in particular elements at least 80%, 90%, 95%, 98%, 99% or 100% sequence identity with SEQ ID Nos: 6, 7 OR 10 (MARs 168R, 1_68R2 or X_29R3) or 9, and may be preferably a MAR X-29-derived element and/or has at least 80%, 90%, 95%, 98%, 99% or 100% sequence identity with SEQ ID NO. 3.

The first MAR element may be upstream of the transgene of interest and a second MAR element downstream of said transgene of interest, wherein the first MAR element may comprise a MAR 1_6 element and/or may have at least 80%, 90%, 95%, 98%, 99% or 100% sequence identity with SEQ ID NO 2 and the second MAR element may comprise a MAR 1_68 element and/or may have at least 80%, 90%, 95%, 98%, 99% or 100% sequence identity with SEQ ID NO. 1.

The invention is also directed at a method for expressing a transgene comprising:

providing a recombinant mammalian cell comprising one of the vectors mentioned above comprising said transgene and expressing the transgene, wherein said MAR elements(s) may increase an expression of the transgene preferably by at least 10%, at least 20%, at least 30%, at least 40%, at least 50%, at least 60% or at least 70%. The vector may comprise a singular MAR X_29 element and/or a nucleic acid that may have at least 80%, 90%, 95%, 98%, 99% or 100% sequence identity with SEQ ID NO. 3 and wherein, after more than 4, 5, 6, 7, 8, 9, 10, 11, 12, 13 or 14 weeks of culture, the MAR element may increase an expression of the transgene of interest by at least 10%, at least 20%, at least 30%, at least 40%, at least 50%, at least 60% or at least 70%.

To test whether adding a MAR element to the PB (PiggyBack) transposon may affect transposition efficiency and transgene expression, and to assess whether the location of the MAR in the construct had any influence on these effects, a series of transposon donor constructs containing the GFP and puromycin resistance (Puro) gene were designed, in which the MAR 1_68 or a control neutral spacer DNA sequence were inserted at different positions in the plasmid. The parental Puro-GFP transposon plasmid without an insert was used as a control of transposition, to distinguish the impact of increased transposon size relative to effect of the MAR or spacer sequence addition.

Figure 2:
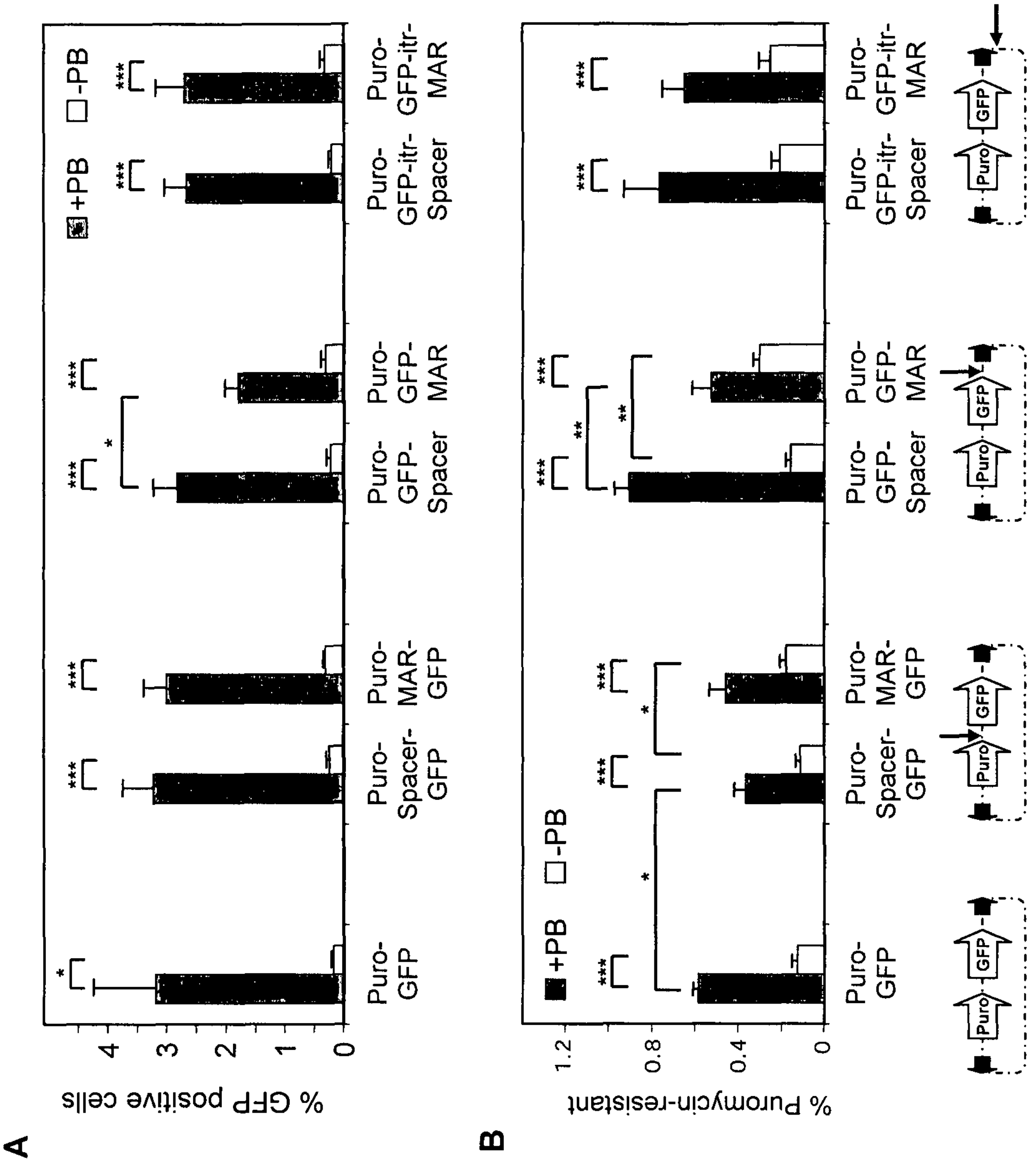

FIG. 2 Transposon Vectors: Transposition Efficiency

Transposition efficiency of the various transposon constructs was measured by assessing the (A) percentage of GFP-expressing cells after transfection and three weeks of cultivation without antibiotic selection and (B) by counting puromycin-resistant colonies.

Figure 3:
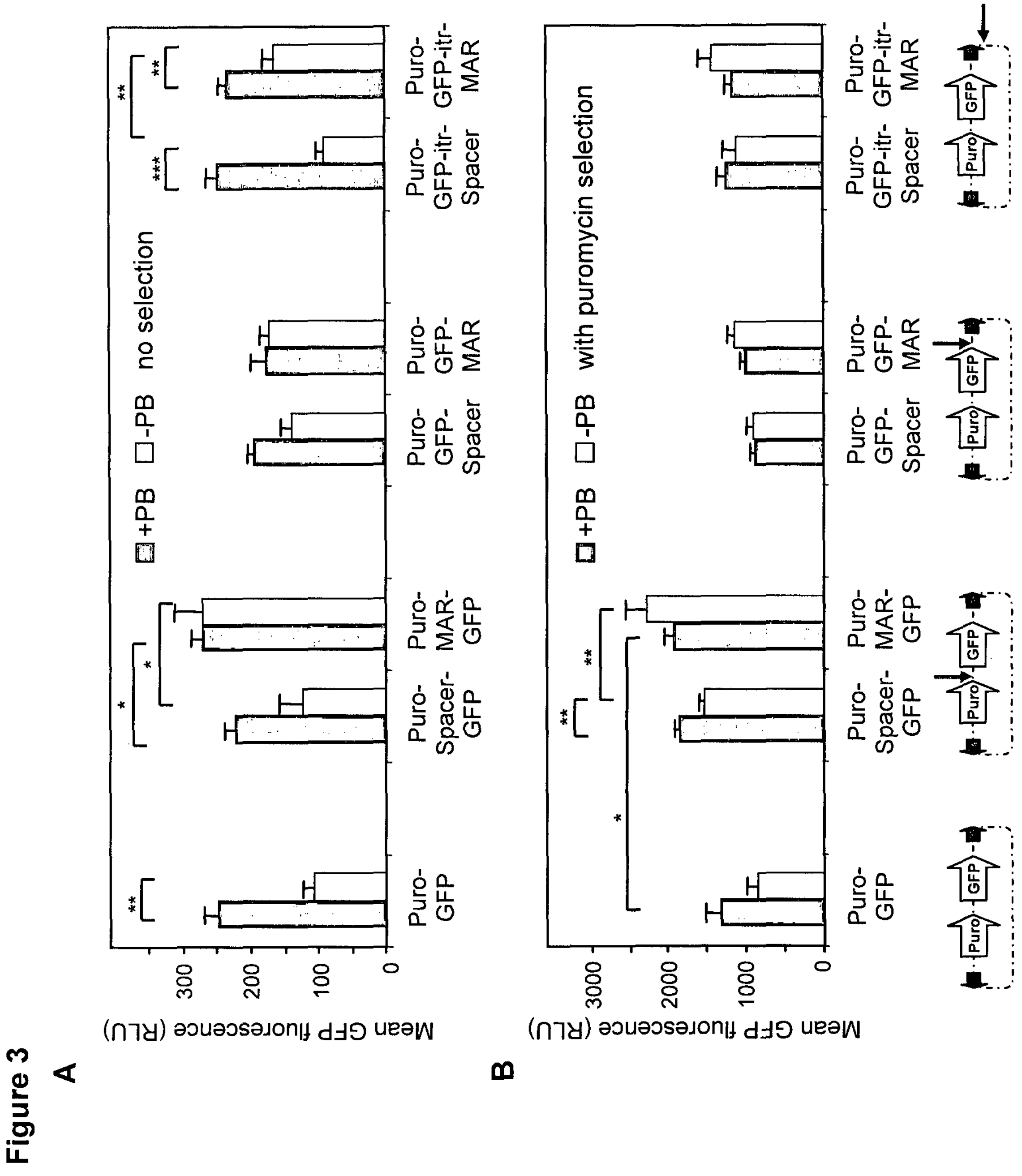

FIG. 3 Transposon Vectors: Expression Level

Analysis of the expression level allowed by different Transposon vectors transfected with (+PB) or without (−PB) transposase expression plasmid, by probing the GFP fluorescence levels of the CHO cells after 3 weeks of culture without (A) or with (B) secretion for puromycin resistance following the transfection, taking into account the fluorescence of GFP-positive cells only.

Figure 4:
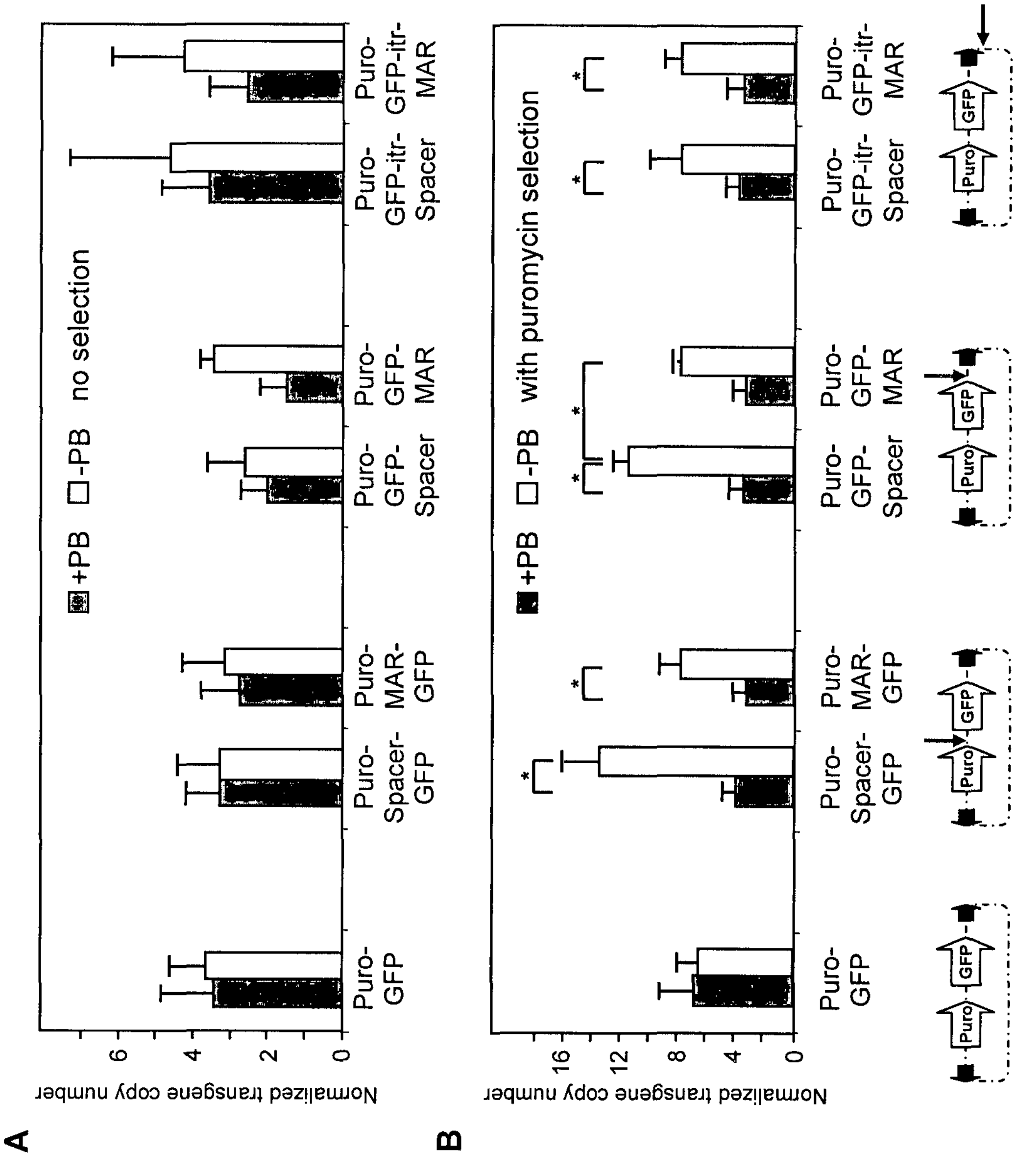

FIG. 4 Effect of the MAR and Transposase on Transgene Genomic Integration

Figure 1:
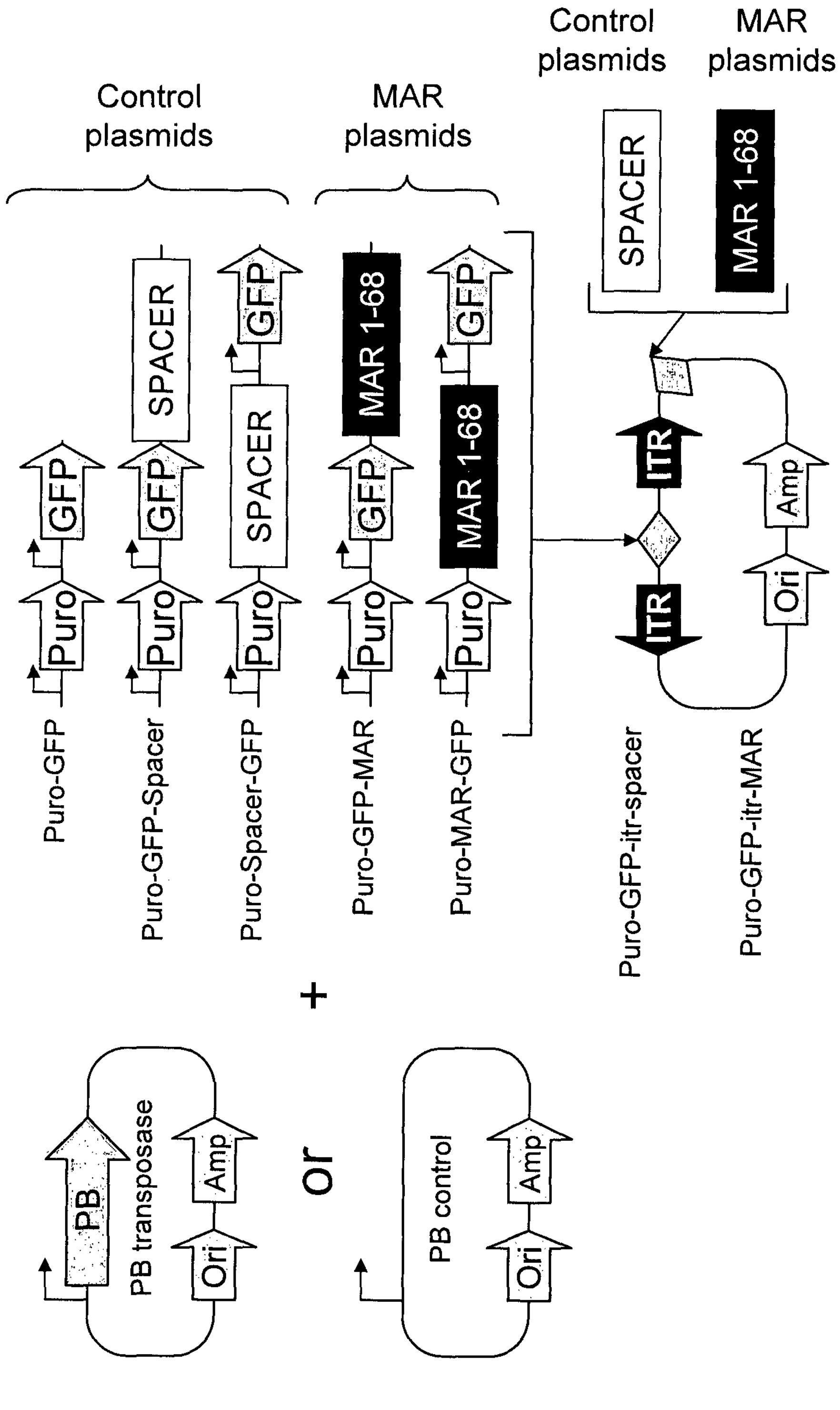
FIG. 1. Transposon Vector Construction

The number of integrated GFP transgene copies was determined using qPCR, and values were normalized relative to the cellular B2M gene, using genomic DNA isolated from unselected CHO cells (A), or puromycin-resistant cells (B) generated as described in the legends to FIGS. 1-3. Values represent the means±SEM (n=3). *P<0.05.

Figure 5:
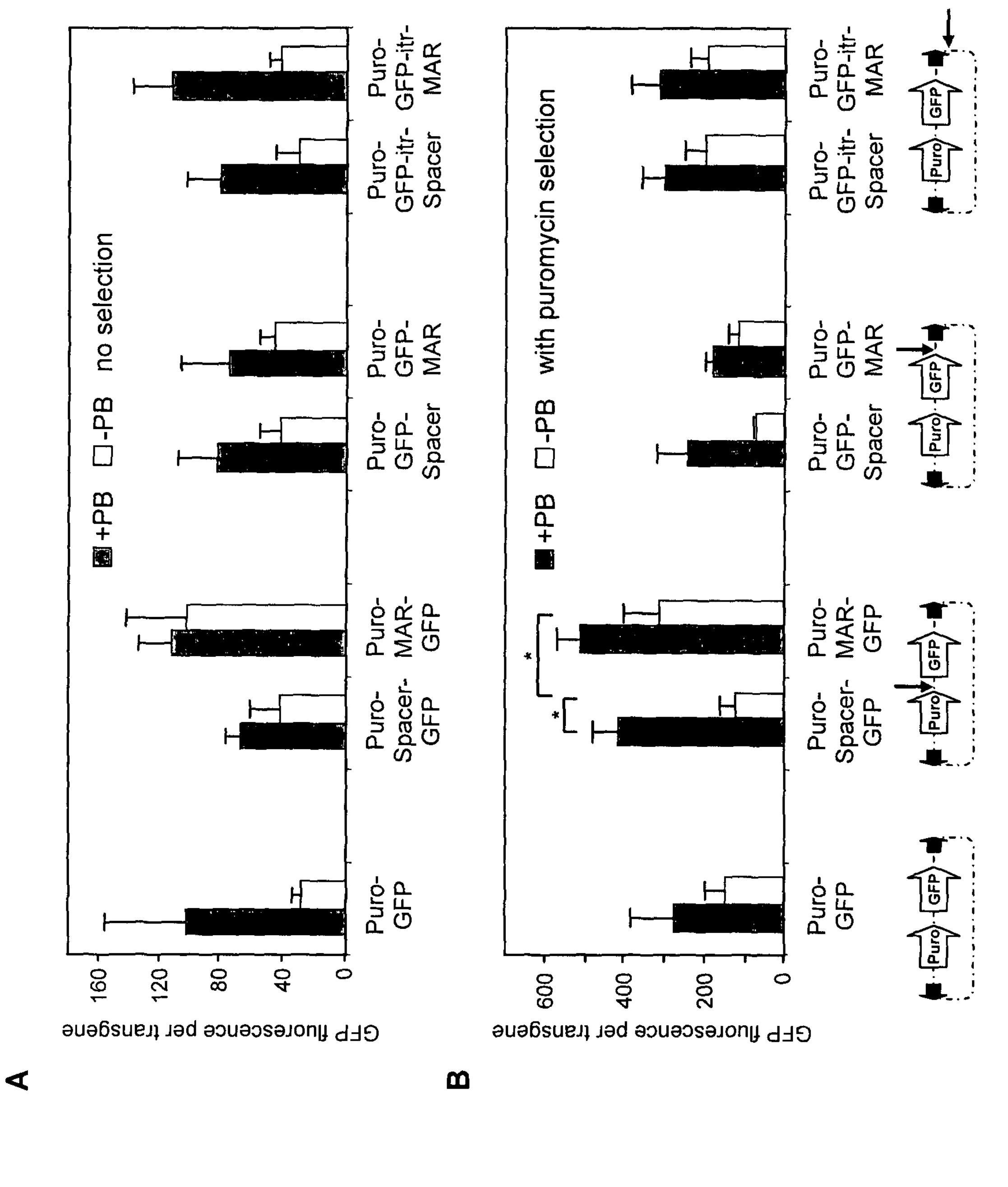

FIG. 5 Transgene Expression Per Transgene

Assessment of the intrinsic expression potential of the vectors, independently from their propensity to integrate in the genome, without (A) and with (B) puromycin selection.

Figure 6:
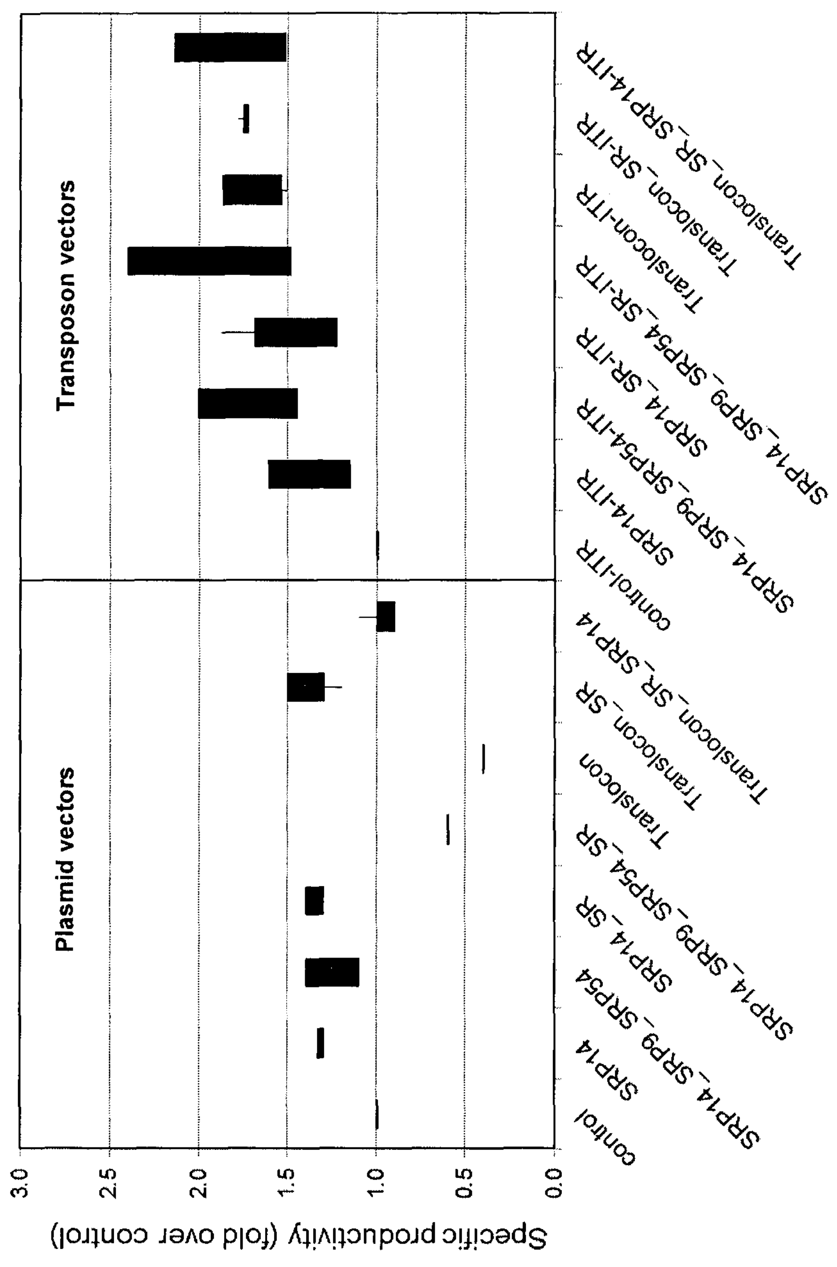

FIG. 6 Effect of the expression of secretion proteins from transposable and plasmid vectors on recombinant protein (transgene) expression. Transposable or regular plasmid vectors were constructed to express secretion proteins SRP9, SRP14, SRP54, the SRP receptor alpha and beta subunits (SR), or the Translocon. Transposable vectors were co-transfected with the PiggyBack transposase vector (right panel), whereas the non-transposable plasmid vectors were transfected alone (left panel), in a cell clone expressing the Infliximab antibody as described herein. After three weeks of culture with selection (left panel) or without selection (right panel), the levels of secreted infliximab antibody were assayed from cell culture supernatants. As can bee seen, the specific productivity, that is the relative expression of a cell containing a sequence encoding a transgene expression processing (TEP) protein or TEP functional RNA was increased when using the transposon vector, from between 0.25-1.5 to between 1-2.5, respectively, relative to the parental cell without a TEP.

Figure 7:
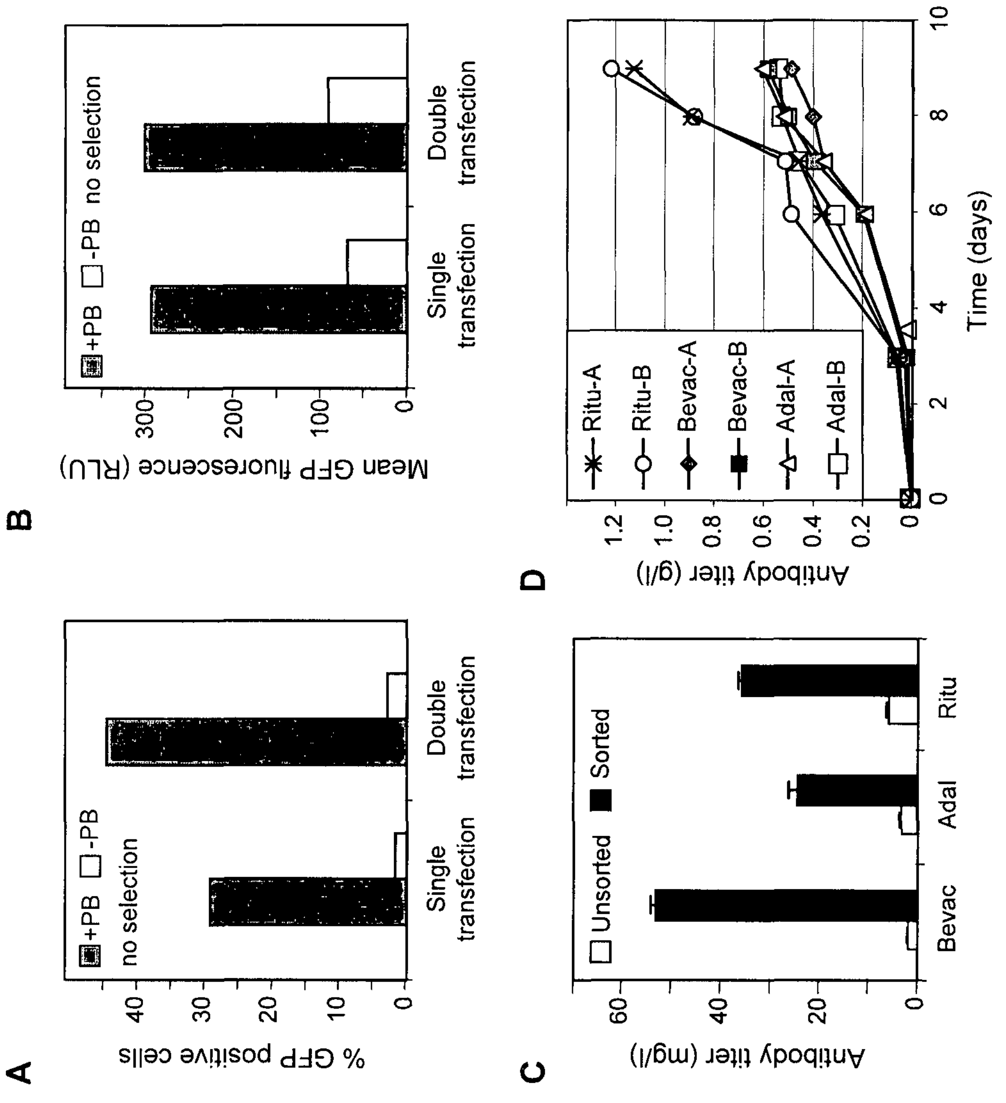

FIG. 7: Recombinant Protein Expression from Electroporated CHO-M Cell Suspensions (A) CHO-M cells that were electroporated once or twice with the MAR X-29-bearing GFP-expression transposon vector in the presence (+PB) or absence (−PB) of the piggyBac transposase. The percentage of stable GFP-expressing cells after 3 weeks of culture performed in the absence of selection is shown.

(B) Mean of the GFP fluorescence of the GFP-positive cells.

(C) cDNAs encoding immunoglobulin light and heavy chains of the Bevacizumab (Beva), Adalimumab (Adal) and Rituximab (Ritu) antibody were introduced in MAR X29-containing transposon plasmids instead of GFP. The light and heavy chain transposon constructs were electroporated three times at 12 days intervals with the piggyBac transposase expression vector in CHO-M cells. The levels of immunoglobulin secreted in the culture supernatants of polyclonal cell pools grown without selection is shown (open bars). Alternatively, the unselected polyclonal cell populations were sorted by panning cells displaying immunoglobulins at their surface using magnetic micro-beads: The levels of secreted immunoglobulins for the unsorted populations are shown (closed bars).

(D) Immunoglobulin-expressing colonies were sorted from transfected cell populations using a colony-picking device, and two clones expressing each of the three immunoglobulins were grown in fed-batch cultures in spin-tube bioreactors. The levels of secreted immunoglobulins are shown and were determined as for panel (C).

Figure 8:
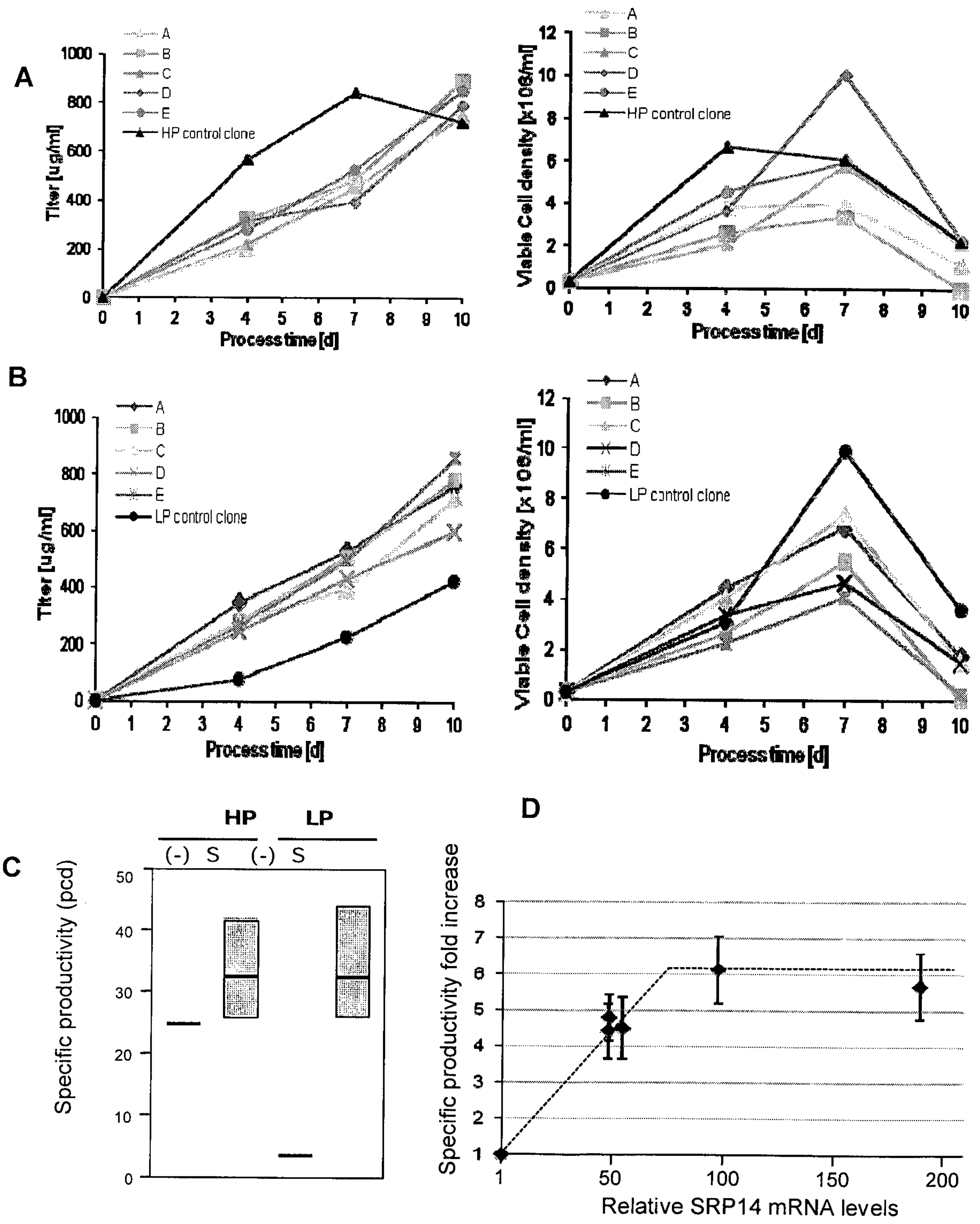

FIG. 8 Heterologous Expression of SRP14 Improves Trastuzumab Secretion and Restores Infliximab Secretion CHO-K1 HP and LP clones expressing the Trastuzumab (A) or Infliximab (B) immunoglobulins at the highest obtained levels, stably re-transfected with the SRP14 expression vector and monoclonal populations were isolated. The derived subclones, labeled A to E, were evaluated for cell growth and production in batch culture conditions. Cell density (cells/ml) and IgG titer (μg/ml) were plotted for each sampling day through the 7 days of culture. (C) Specific productivity distribution of the TrastuzuMab (HP) and InflixiMab (LP) subclones after transfection with the SRP14 expression vector (lanes S) as compared to that of the parental HP and LP clones (−). (D) The relative levels of SRP14 mRNA was determined for the 5 individual SRP14-LP A-E subclones and the parental control LP clone, and they were plotted relative to the specific IgG productivity from 4 culture runs. mRNA and specific productivity mean and standard deviation values are expressed as the fold increase over those of the LP control clone.

Figure 9:
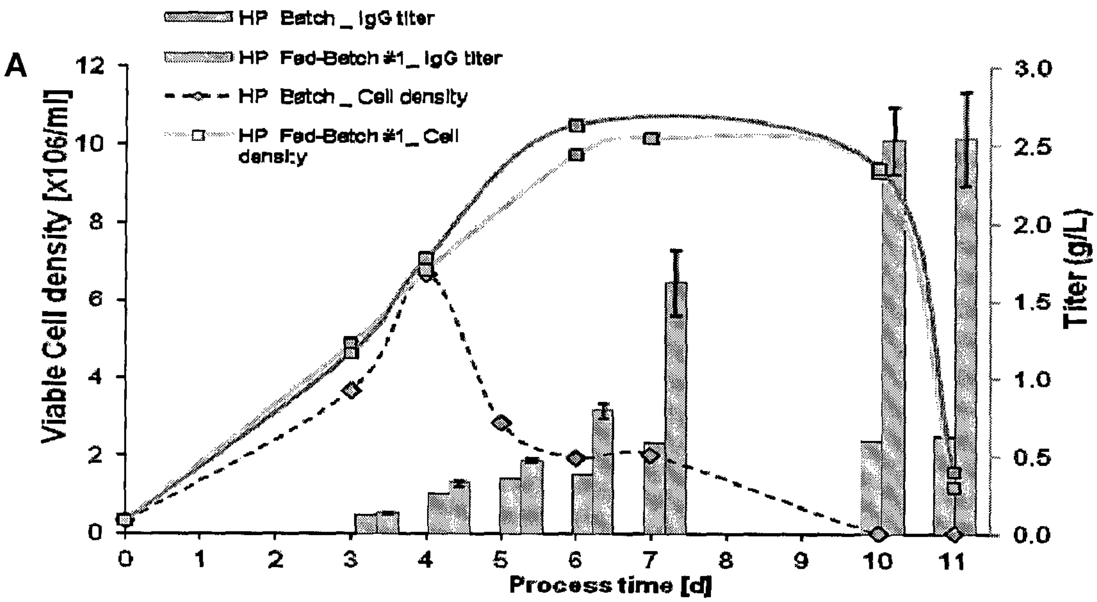
Figure 9:
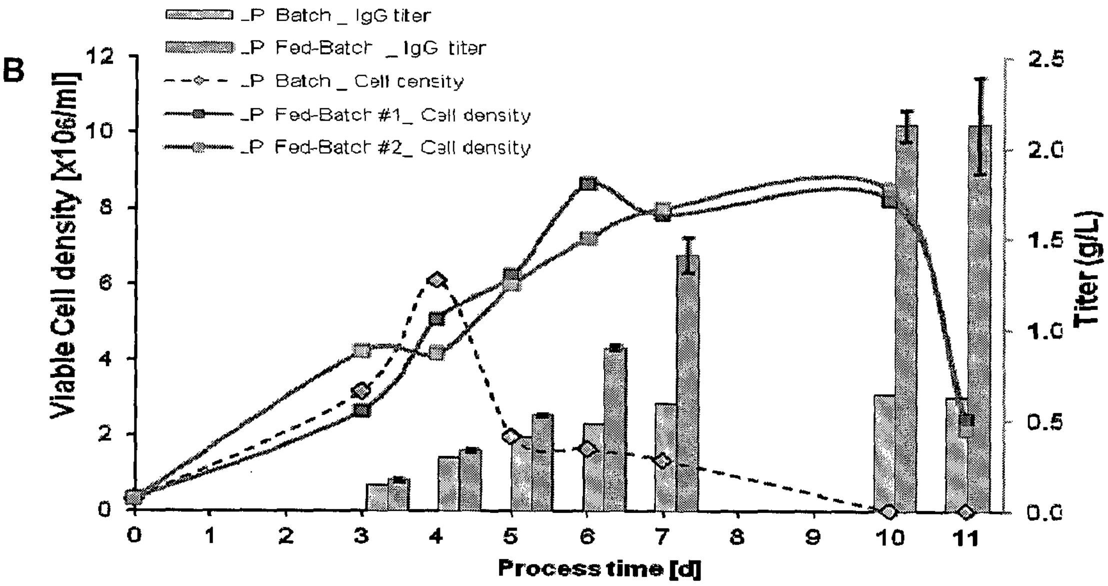

FIG. 9 Heterologous Expression of SRP14 Mediates High Yield of the Hard-to-Express Immunoglobulin in a Production Process The SRP14 vector-transfected TrastuzuMab HP subclone B (A) and InflixiMab LP subclone E (B), as analysed in FIG. 8, were cultivated in 125 ml ventilated shake flask vessel with a working volume of 25 ml in fed-batch cultures, and the viable cell density and IgG titer were determined during an 11-days time course.

Figure 10:
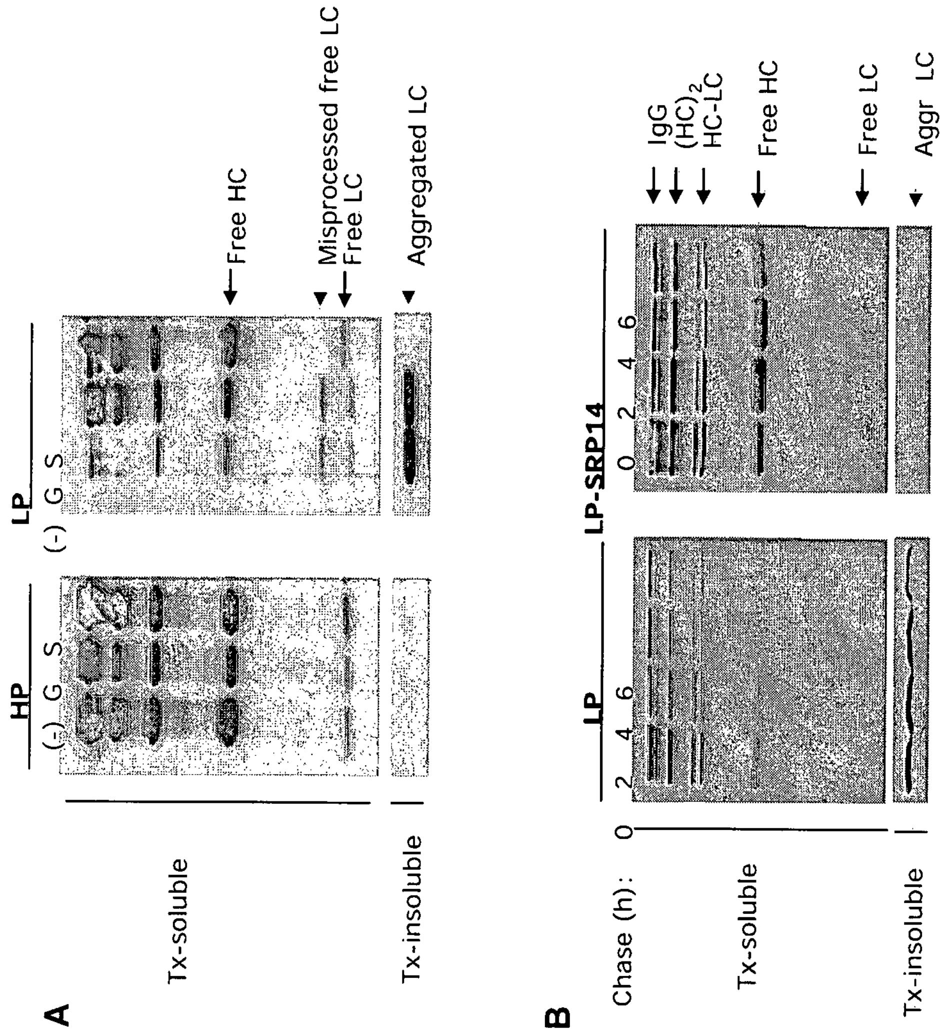

FIG. 10 SRP14 Expression Abolishes Light Chain Aggregation by CHO Cell Clones (A) The supernatants and pellets of Tx100-permeabilized cells collected by centrifugation were analyzed by SDS-PAGE, as depicted by the Tx-100 soluble and Tx-100 insoluble labeled panels, respectively, for the LP-derived SRP14-LP subclone E and the HP-derived SRP14-HP subclone B (lanes S), or for CHO subclones expressing a control GFP protein (lanes G). Arrowheads show the misprocessed free LC and aggregated (Aggr.) LC. (B) Chase analysis of the various LC, HC and IgG assembly intermediates species produced by SRP14-LP clone E and LP-control clone E was performed and results are shown.

Figure 11:
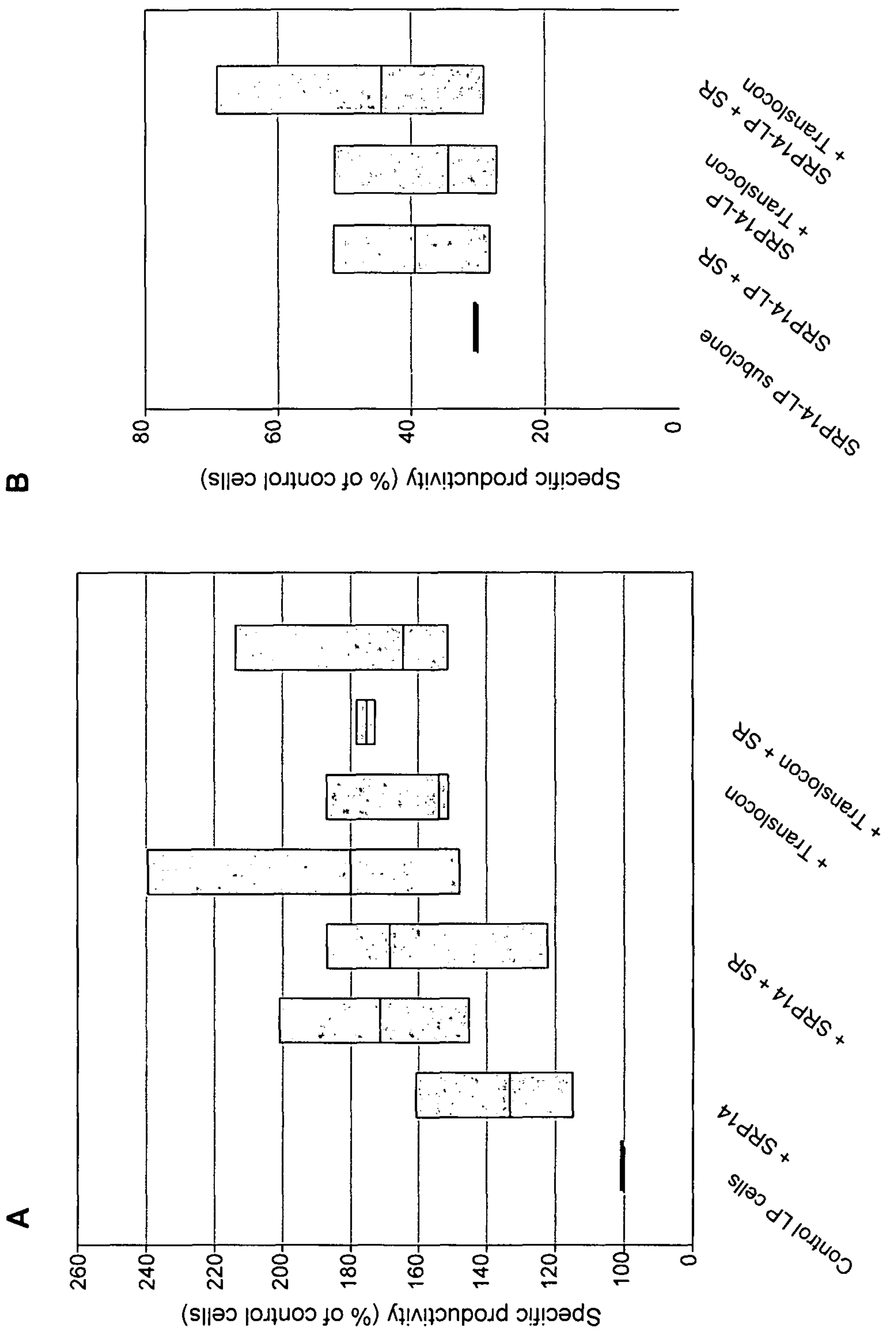

FIG. 11 Effect of Combined Expression of SRP, SR and Translocon Subunits on Immunoglobulin Secretion (A) An Infliximab LP clone E was re-transfected with various combinations of SRP, SR and translocon transposable expression vectors. The specific productivity of the resulting cell pools was then evaluated in batch cultivation and represented as a % of the LP-control cells pcd values. Box-plots represent the median, upper and lower quartiles of the normalized specific productivities determined at day 3 of independent culture runs. (B) The SRP14-expressing infliximab producing cell subclone E was re-transfected with various SR and translocon transposable expression vector combinations. The specific productivity of cell pools is represented as for panel A.

Figure 12:
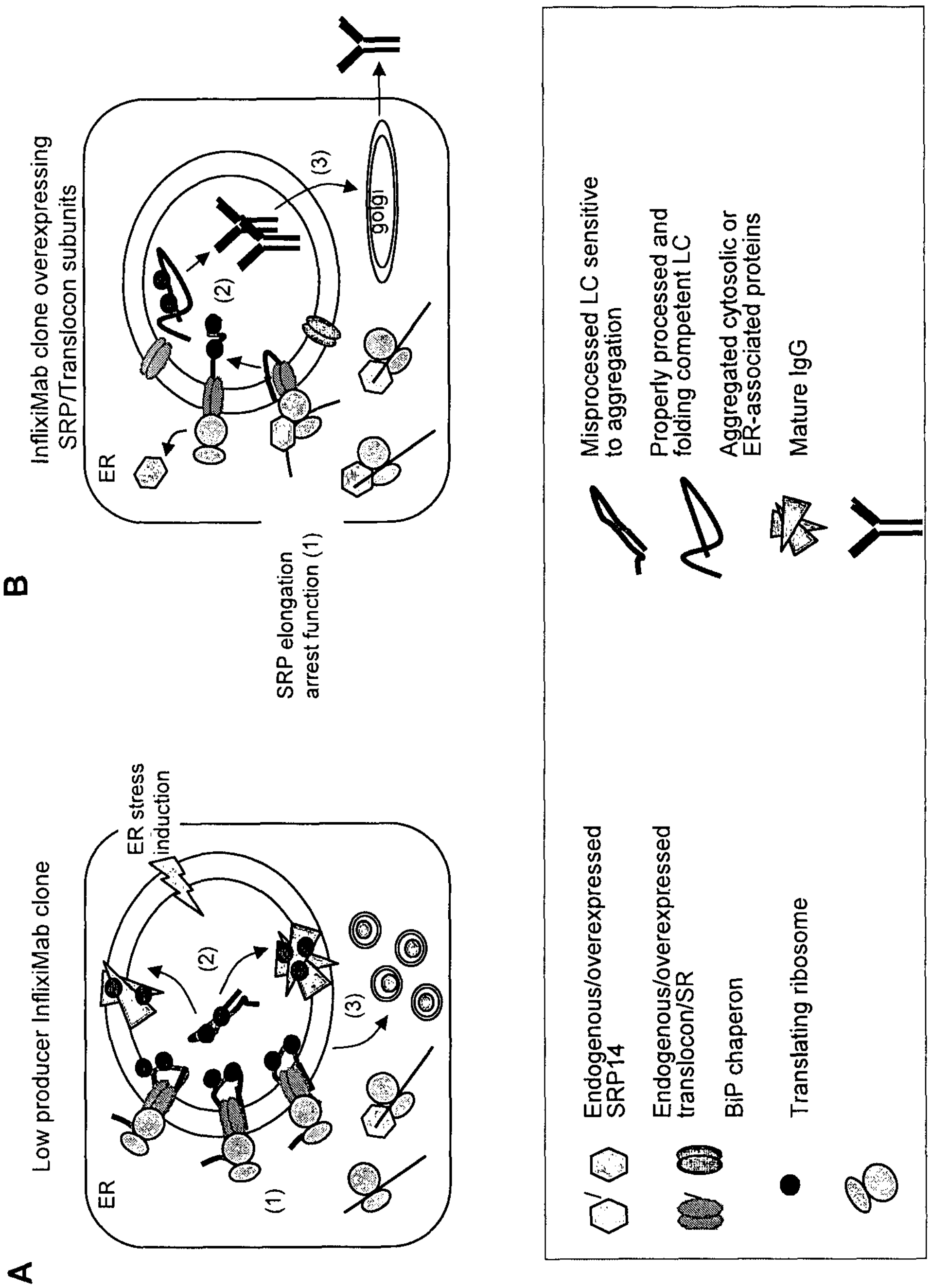

FIG. 12 Model for the Rescue of Infliximab Secretion from SRP14-Expressing Clones Model of the IgG folding and secretion by low producer clones before (A) and after SRP/Translocon subunits overexpression (B). The data indicate that neosynthetized LC produced by low producer clones exhibit improper processing and folding state. Signal peptide misprocessing of the Infliximab LC may lead to the saturation of the ER co-translational translocation machinery (panel A, number 1). Its aggregation in the ER within IgG assembly-incompetent aggregated LC forms (panel A, number 2) induce ER stress and trigger the formation of autophagosome-like structure (panel A, number 3). Overexpression of the SRP14 and others SRP/translocon components proteins fully rescued the processing and secretion of the InflixiMab IgG (panel B). SRP14 elongation arrest activity possibly delays LC ER translocation during translation of its mRNA (panel B, number 1). This would favor in turn the correct processing of the LC and its proper interaction with ER folding chaperones (panel B, number 2). The maintenance of the neosynthetized LC in an IgG assembly-competent state thus restores high yield secretion of fully-assembled antibodies (panel B, number 3).

Figure 13:
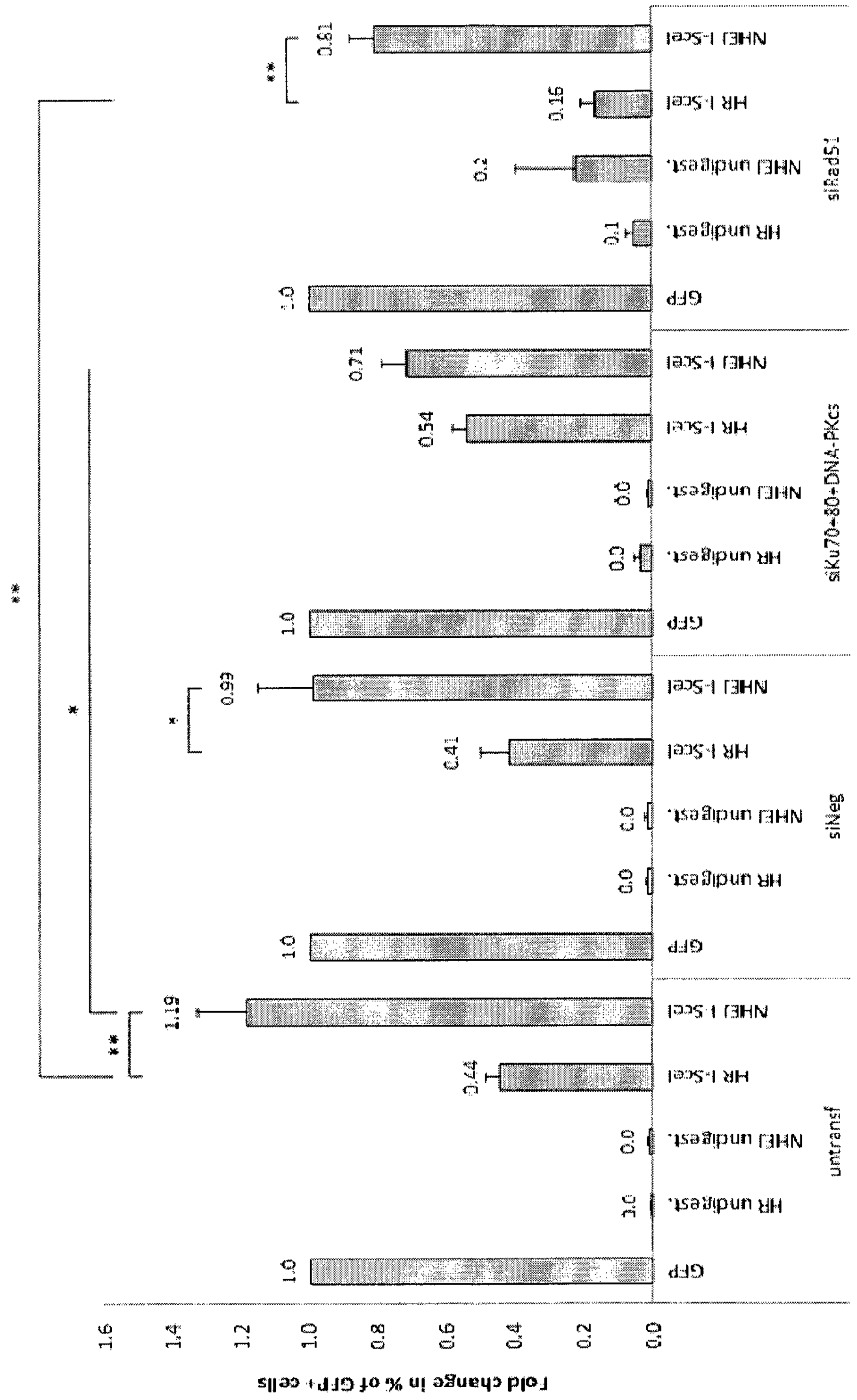

FIG. 13 Effect of si-RNA Knock-Down of HR and NHEJ on Expression

Fold differences in the percentage of GFP-positive cells (with respect to cells transfected with a GFP control plasmid shown here as 1.0) representing the frequencies of recombination events in untreated cells (mock), cells treated with negative siRNA (siNeg), siRNAs against NHEJ factors (siKu70+80+DNA-PKcs) and anti-HR siRNA (siRad51). The GFP lanes show a positive control of GFP expressing cells. The HR undigest. and NHEJ undigest.-labeled lanes show negative control cells, i.e. cells transfected with circular HR and NHEJ report plasmids. The HR I-SceI and NHEJ I-SceI-labelled lanes indicate cells transfected with SceI-cleaved reporter plasmids that restore GFP expression upon DNA cleavage repair by homologous recombination or non-homologous end joining, respectively. The figure shows the efficacy of the siRNA to inhibit HR or NHEJ, as indicated by the percent of GFP-positive cells, which was normalized to the percent of dsRed-positive cells and expressed as the fold change over the percentage of the GFP control cells, which was set to 1. Mean of 3 experiments, error bars show standard error of the mean. Statistical significance determined by unpaired Student's t-test; significance level $p<0.05$ (*) and $p<0.01$ (**).

Figure 14:
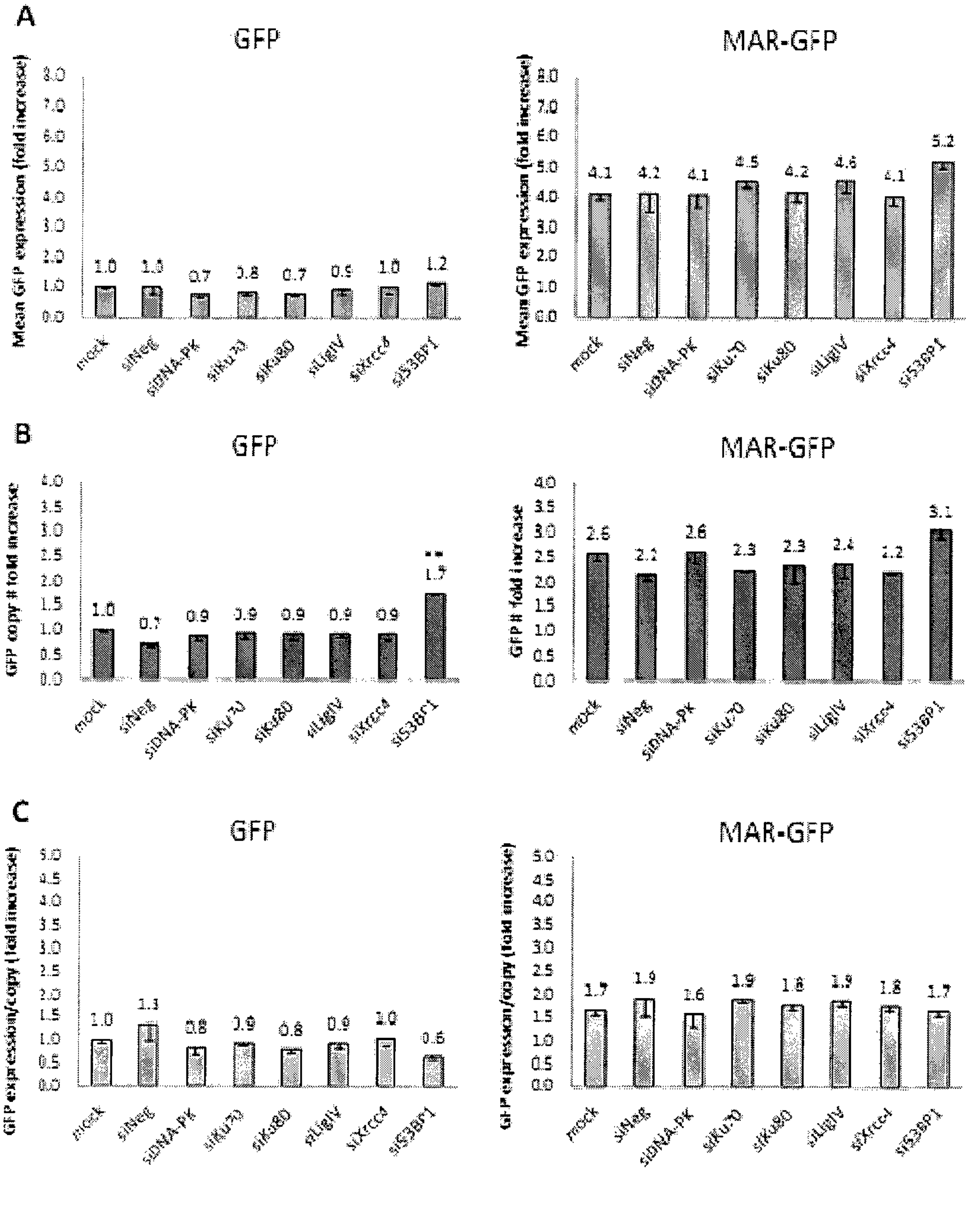

FIG. 14 Effect of MARs in siRNA Knock-Down of NHEJ

The fold increase in GFP expression and integration CHO cells treated with siRNAs against NHEJ factors and retransfected with a GFP or MAR-GFP plasmids is shown. The average GFP fluorescence, copy number and fluorescence per GFP copy is shown as a fold increase over the result obtained from untreated cells (marked as 'mock') transfected with the GFP plasmid. A) Flow cytometry results, B) analysis of GFP copy number in the genome by qPCR, C) average fluorescence of each integrated GFP gene (calculated for each experiment as a ratio between expression and copy number). Mean of 3 or more experiments; statistical significance determined by unpaired Student's t-test. Asterisks indicate significant differences between the siRNA-treated sample and corresponding untreated control; significance levels: $p<0.05$ (*), $p<0.01$ (**); error bars show standard error of the mean.

Figure 15:
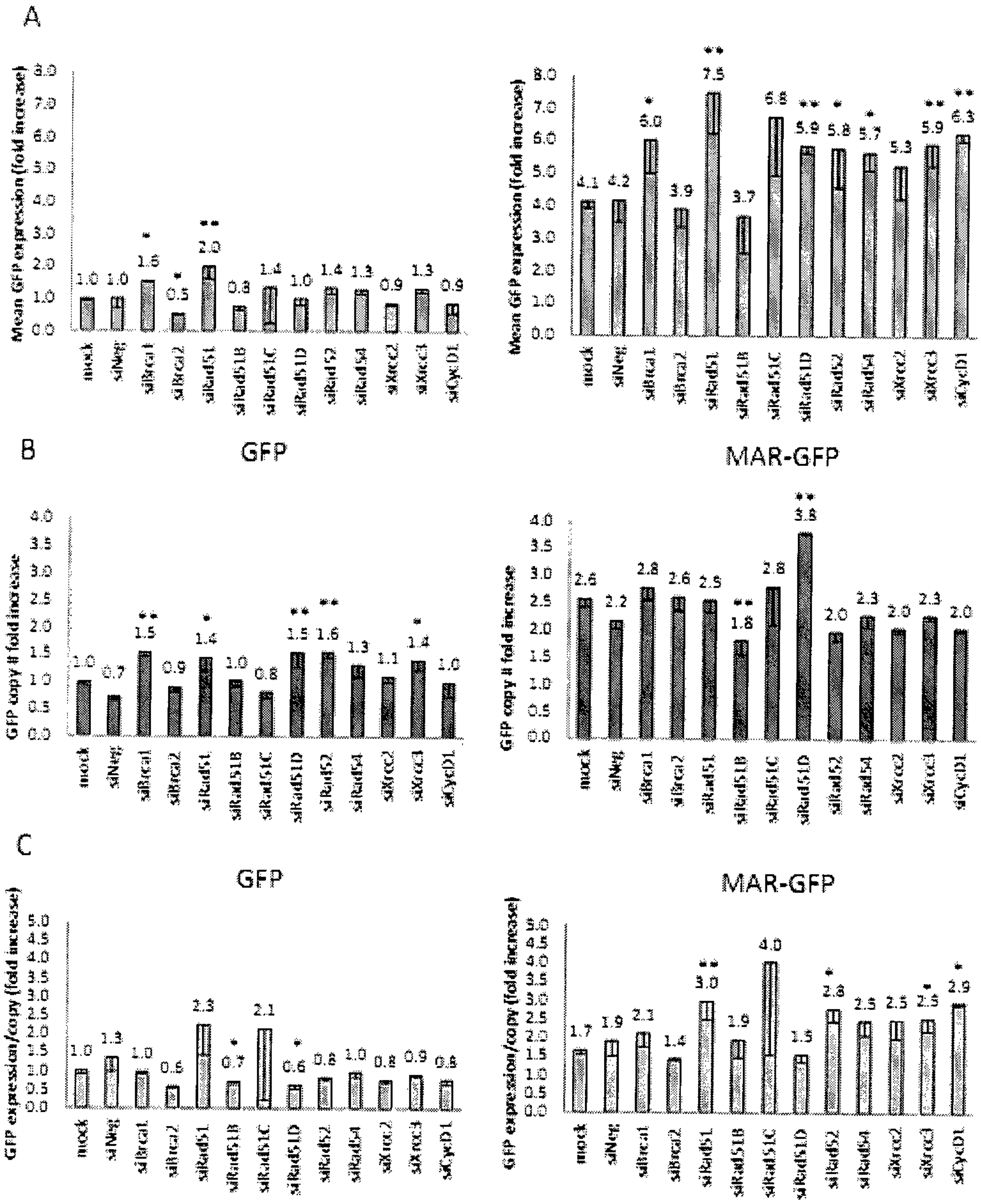

FIG. 15 Effect of MARs in siRNA Knock-Down of HR

The fold increase in GFP expression and integration CHO cells treated with siRNAs against HR factors and retransfected with a GFP or MAR-GFP plasmids. The average GFP fluorescence, copy number and fluorescence per GFP copy is shown as a fold increase over the result obtained from untreated cells (marked as 'mock') transfected with the GFP plasmid. A) Flow cytometry results, B) analysis of GFP copy number in the genome by qPCR, C) average fluorescence of each integrated GFP gene (calculated for each experiment as a ratio between expression and copy number). Mean of 3 or more experiments; statistical significance determined by unpaired Student's t-test. Asterisks indicate significant differences between the siRNA-treated sample and corresponding untreated control; significance levels: $p<0.05$ (*), $p<0.01$ (**); error bars show standard error of the mean.

Figure 16A:
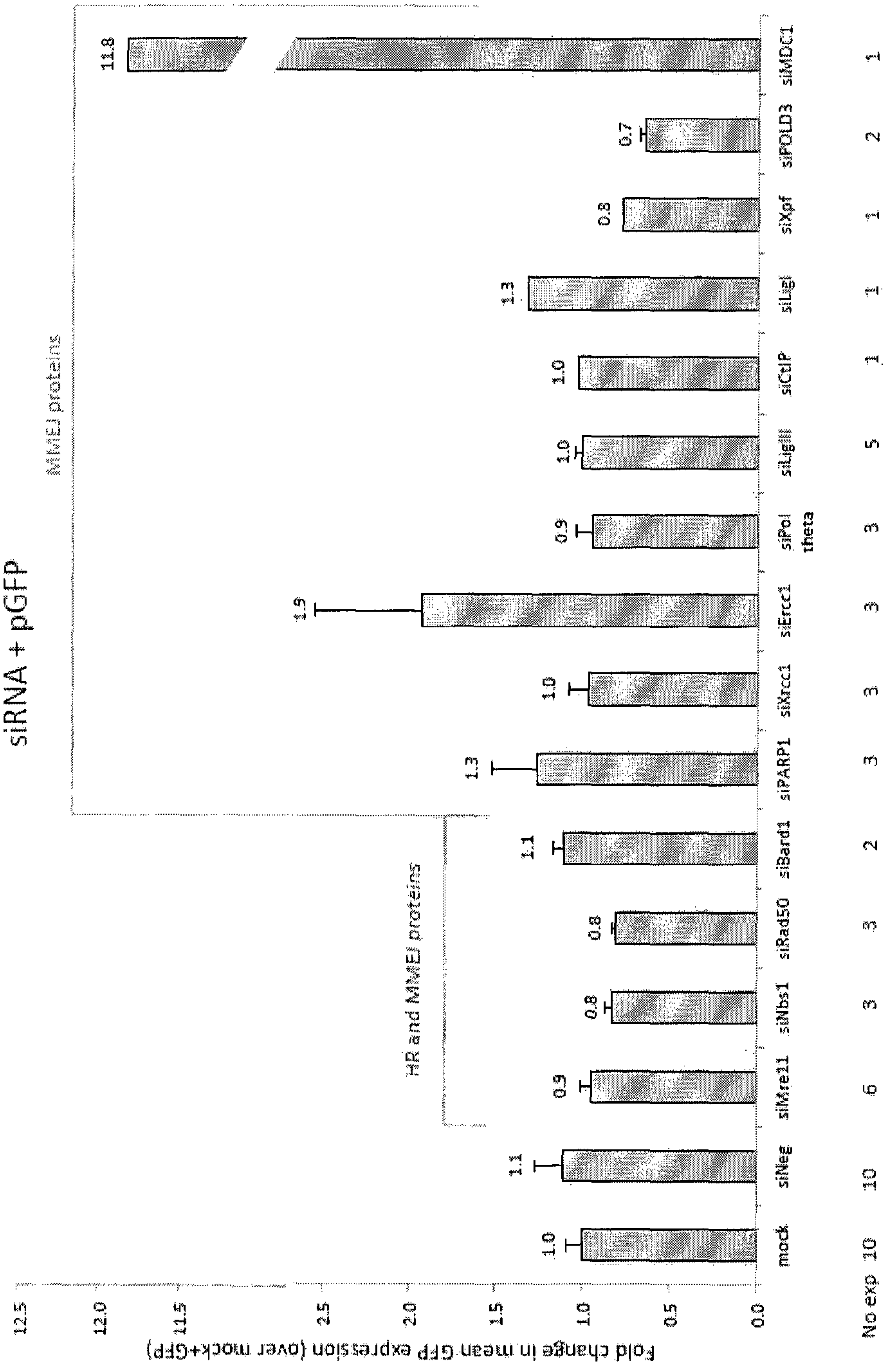
Figure 16B:
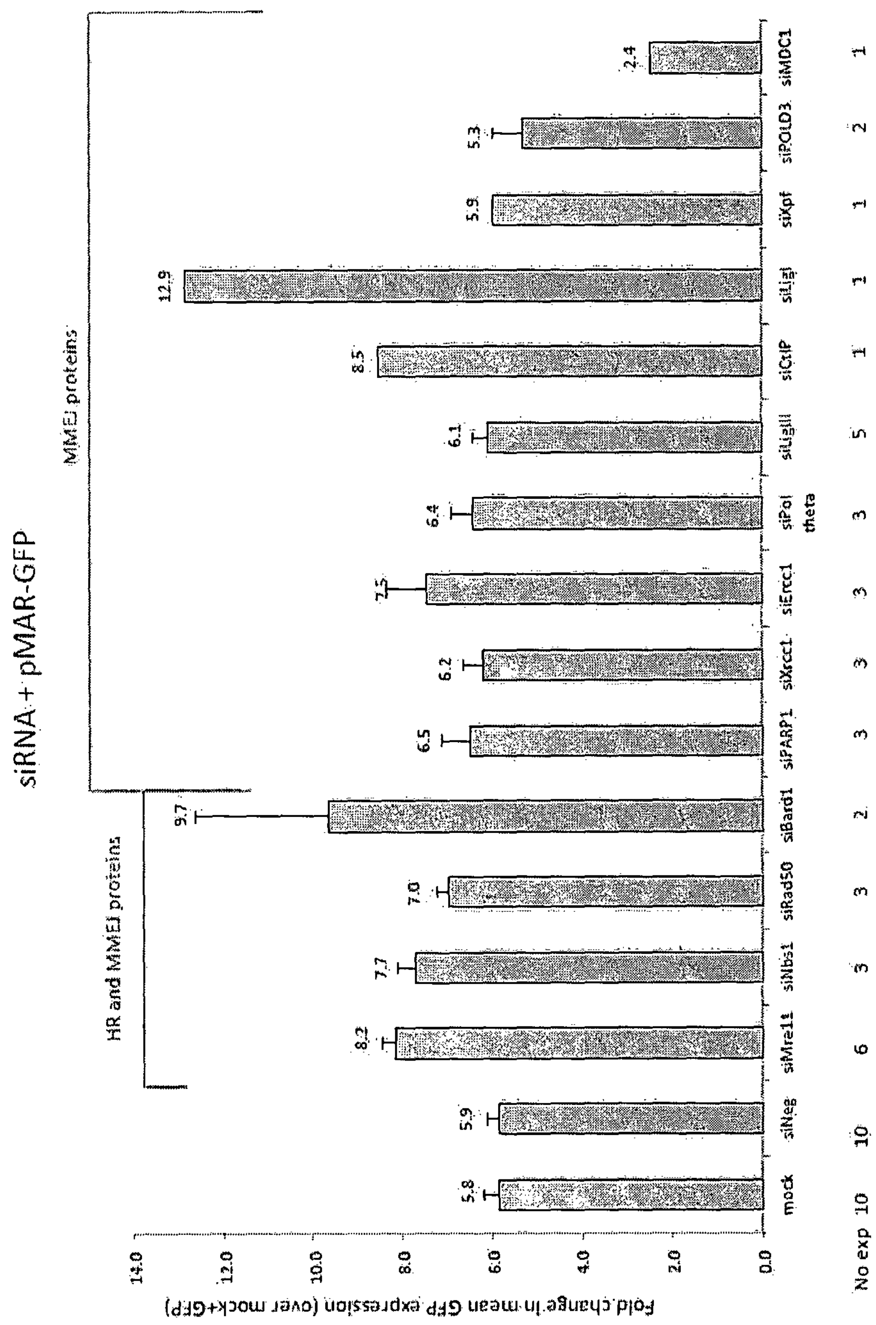

FIG. 16 Effect of MARs in siRNA Knock-Down of MMEJ

GFP expression and integration CHO cells treated with siRNAs against MMEJ factors (and some HR factors) and retransfected with a GFP (A) or MAR-GFP plasmids (B) is shown. The average GFP fluorescence, copy number and fluorescence per GFP copy is shown as a fold increase over the result obtained from untreated cells (marked as 'mock') transfected with the GFP plasmid. The figures show the flow cytometry results. Shown is the mean of the number of experiments indicated at the bottom. Cells transfected with siMDC1, expressed GFP even without MAR, at a 11.8 higher rate as cells not transfected with siMDC. Particularly good results could also be achieved with certain plasmids that did contain MAR, namely siBard1 and siLigl.

Figure 17:
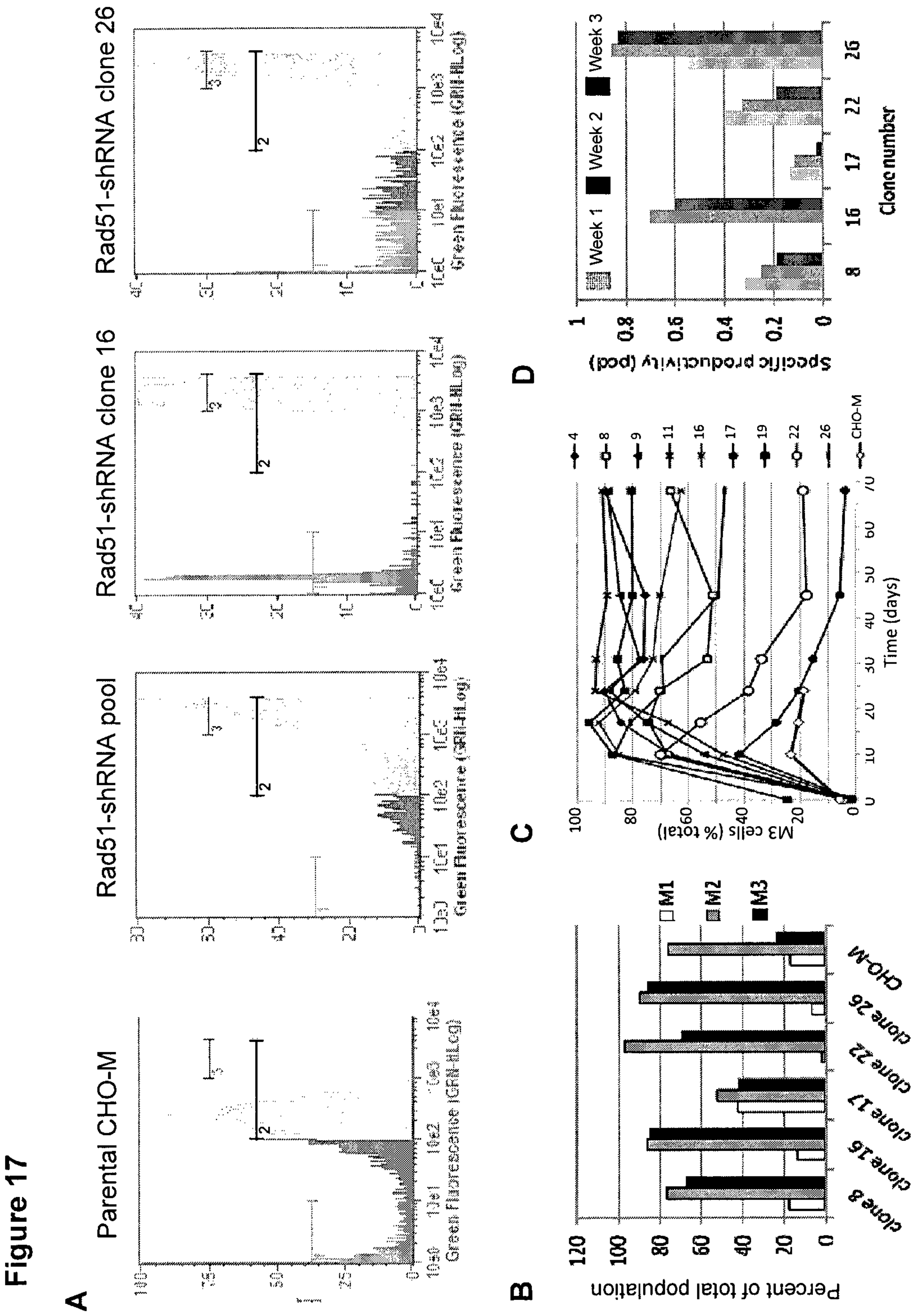

FIG. 17 Effect of si-RNA-Mediated Knock-Down of a HR Protein

The figure shows that higher GFP and immunoglobulin expression can be achieved from CHO-M cells stably expressing a Rad51-directed shRNA. CHO-M cells were transfected with a PiggyBac-derived transposable Rad51 shRNA expression vector, and the polyclonal cell pool as well as cell clones derived thereof were retransfected with a GFP expression plasmid along with the parental CHO-M cells. The GFP fluorescence of the parental CHO-M, of the Rad51-shRNA expressing cell pool and of the derived clones was assessed 10 days after selection for stable expression of the GFP and puromycin resistance genes. The fluorescence profiles of two of the most fluorescent clones are shown next to those of the cell pool and parental cells (A), as well as the percentage of cells in the M1, M2 and M3 sectors 10 days after selection for puromycin resistance (B), as depicted by the horizontal bars labeled 1, 2 and 3 in panel A. The proportion of highly expressing M3 cells was followed during 68 days of further culture without selection to show that higher and more stable expression can be obtained from the shRNA-expressing cell clones when compared to the parental CHO_M cells (C). Alternatively, an expression plasmids encoding the light and heavy chains of the Infliximab antibody were transfected into representative clones, and the specific productivity of secreted immunoglobulin was assessed after selection during three weeks of further culture without antibiotic.

FIG. 18 Effect of various human recombinant upstream MARs on the percentile of high and very high producer cells (% M3/M2), as assessed for GFP fluorescence by FACS analysis in a two MAR construct. (A) The MAR elements were rearranged derivatives of MAR X-29 (X_29R2 (SEQ ID NO: 9), X_29R3 (SEQ ID NO: 10), MAR 1-42 (1_42R2Bis, 1_42R3), MAR 1-6 (1_6R2 (SEQ ID NO: 8), 1_6R3) or MAR 1-68 (1_68R2 (SEQ ID NO: 7), as indicated in the names of the constructs. (B) Typical FACS profiles obtained for the best upstream MAR elements (MAR 1_68R (SEQ ID NO: 6)).

Figure 19:
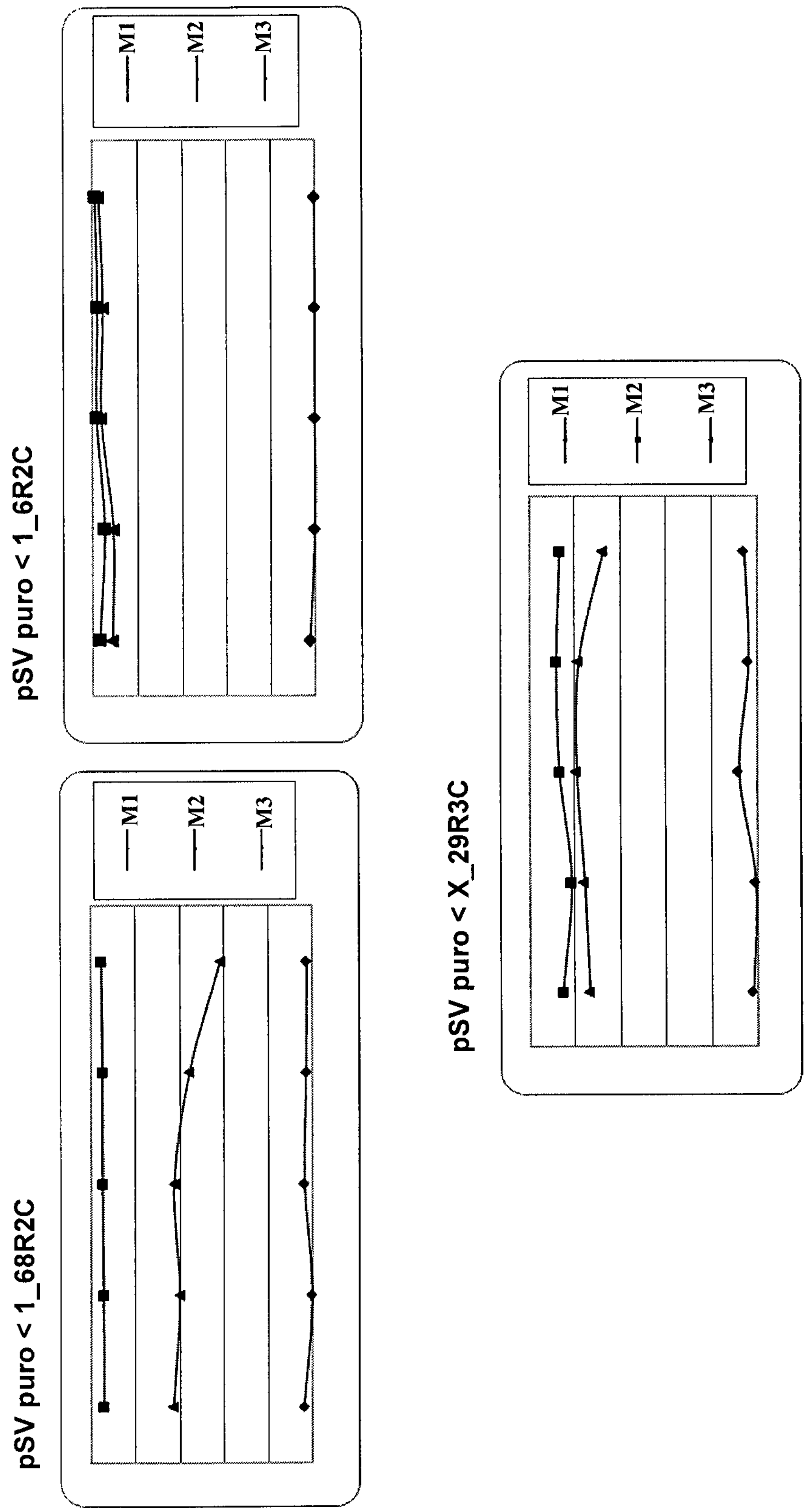

FIG. 19 Stability of Expression in a Two MAR Vector

Polyclonal populations constructed from vectors containing the 1_68R2, 1_6R2 and X_29R3 MAR derivatives was tested over a period of 5 weeks of culture without selection and GFP fluorescence was assessed weekly over this period. The percentile of the M3 subpopulation were assessed: 1_6R2 element as the upstream MAR and the unrearranged MAR 1-68 as downstream MAR were the best tested combination of vector with two MARs. M1 and M2 subpopulations are also shown.

Figure 20A:
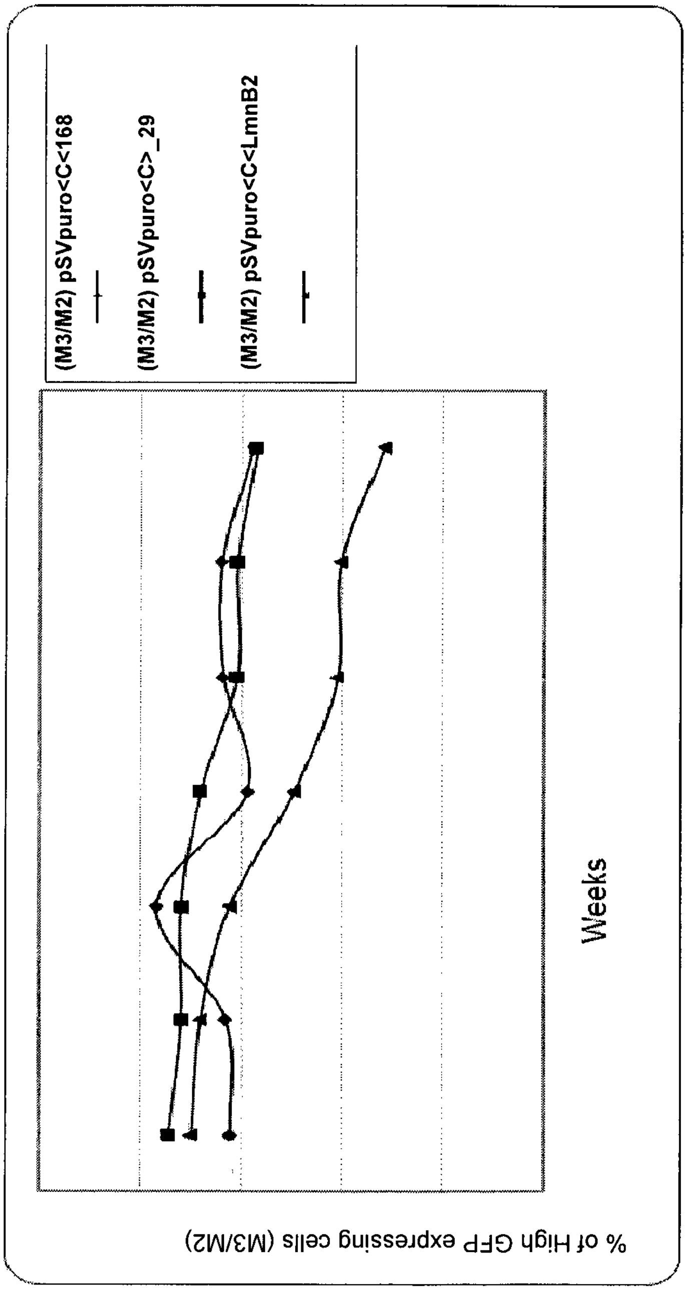
Figure 20B:
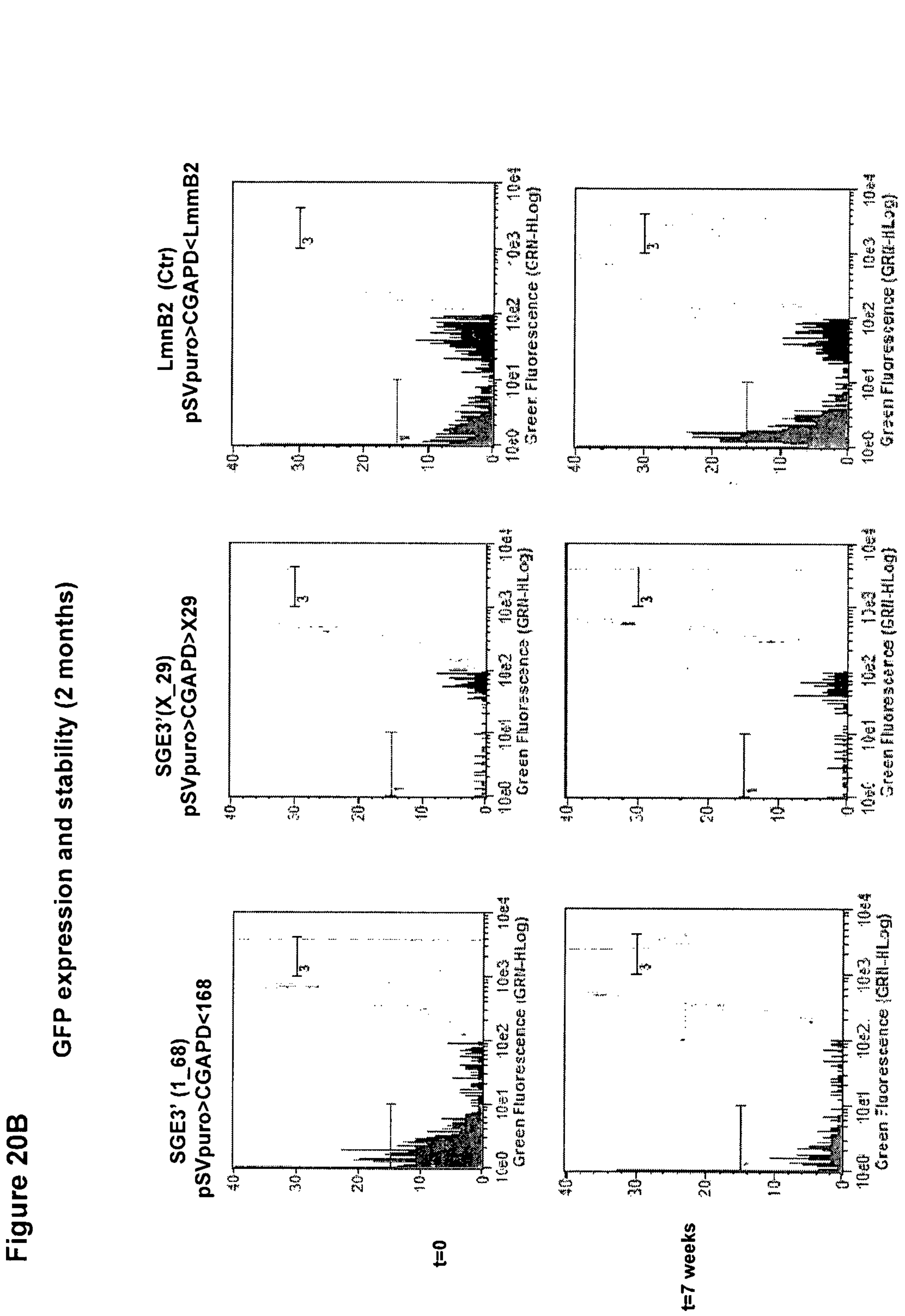

FIG. 20 Expression Vectors Containing a Single Genetic Element

MAR 1_68 and X_29 were tested and used in combination with the LmnB2 replicator. The MARs were positioned downstream the transgene expression cassette and were assessed in transgene transfection assay over a period of two months. The polyclonal population of stably transfected cells was selected for antibiotic resistance during two weeks and tested for GFP fluorescence by fluorescence-activated cell sorter (FACS) analysis during seven weeks. The proportion of high producer M3 cells is shown in (A), while typical FACS profiles are shown in (B).

Figure 21:
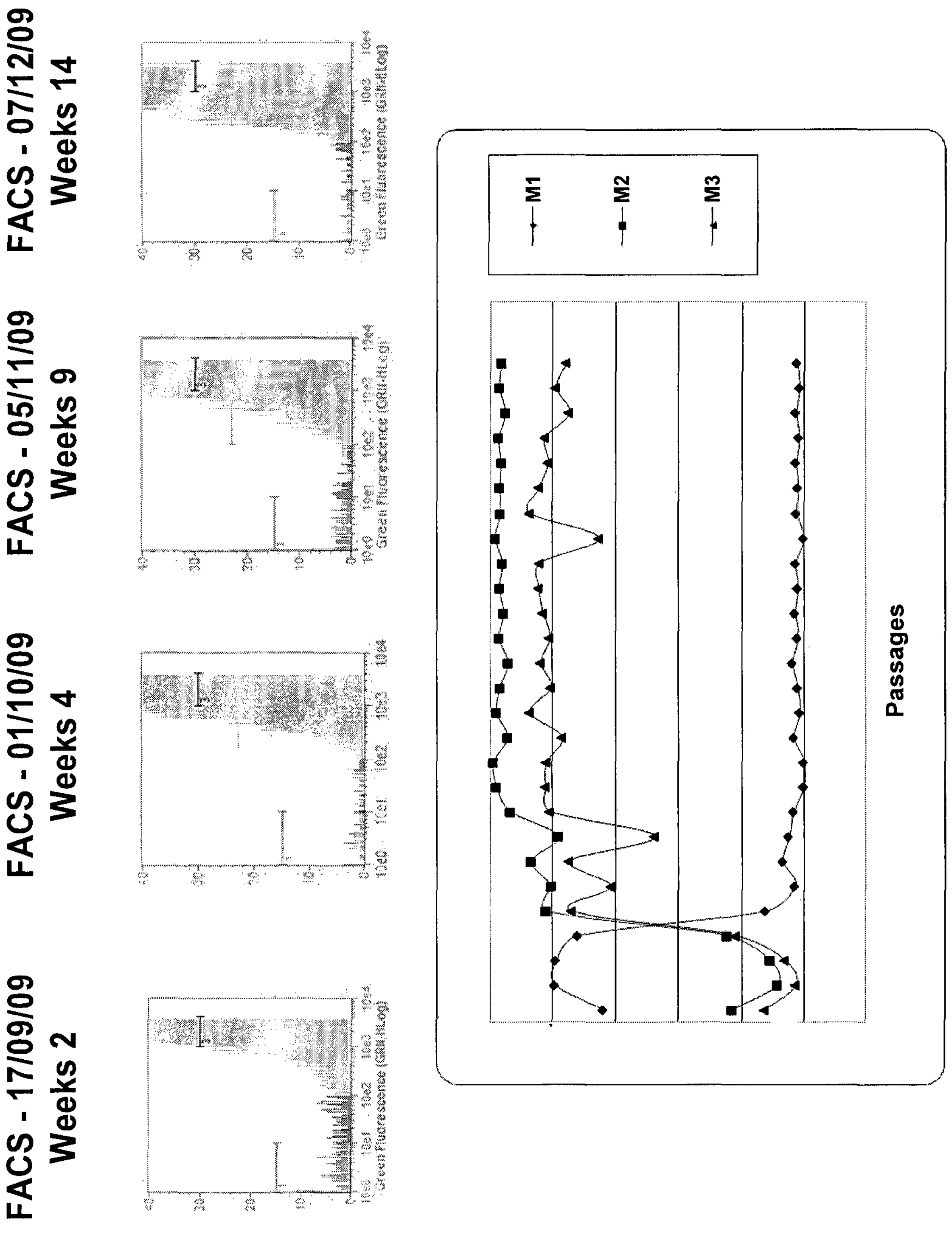

FIG. 21 Expression Vectors Containing a Single Genetic Element: X-29

Stability assay of the X_29 vector: The expression vector containing a single X_29 downstream the expression cassette is shown to be stable and to give a very high percentile of M2 and M3 subpopulations even after 14 weeks of culture (27 passages).

Figure 22:
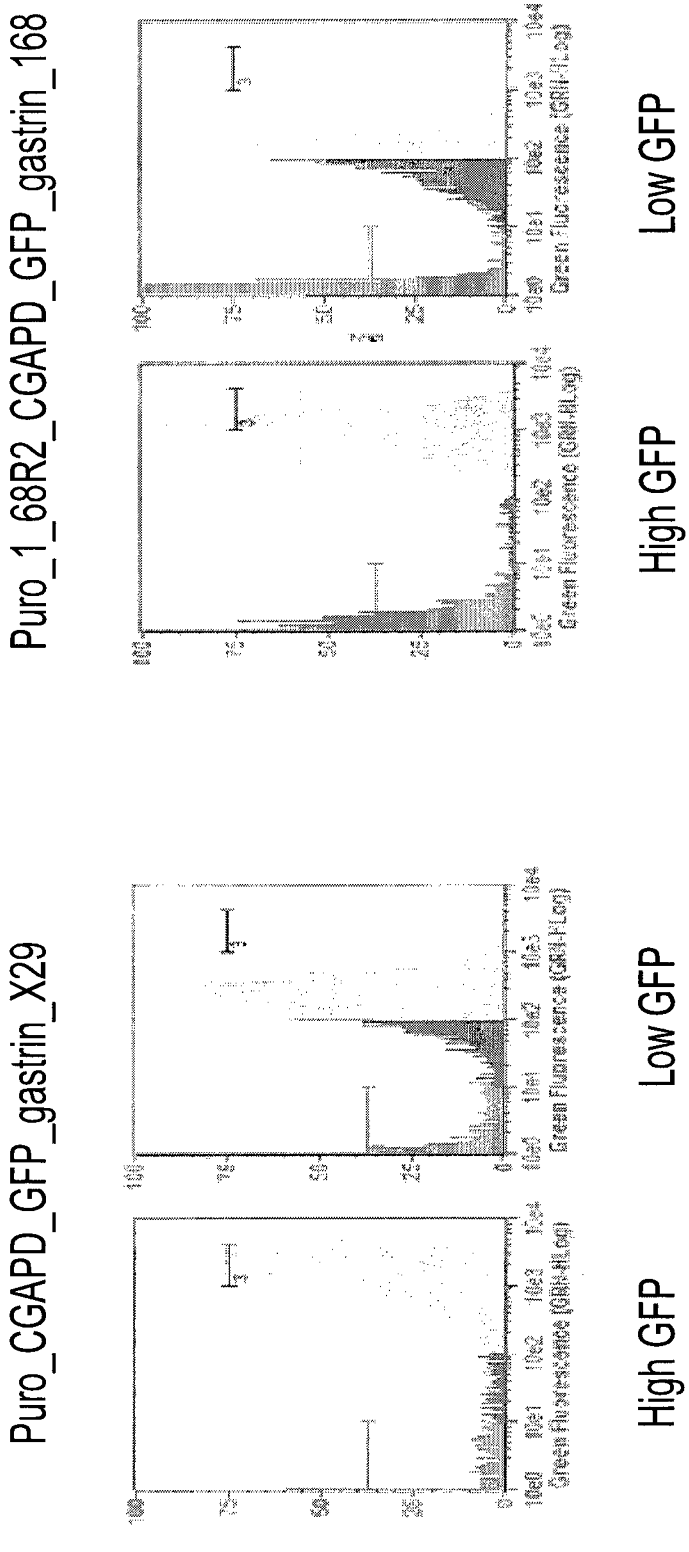

FIG. 22 Comparative Analysis of Stably Transfected CHO Populations After 24 Weeks of Antibiotic Selection A vector with a single X_29 MAR downstream the expression cassette (Puro_CGAPD_GFP_gastrin_X29) increases the occurrence of high GFP expressing cells and also the stability of the expression over time compare to the vector with two MARS with 1_6R2 as upstream MAR and 1_68 as downstream MAR (Puro_1_6R2_CGAPD_GFP_gastrin_1_68).

DETAILED DESCRIPTION OF VARIOUS AND PREFERRED EMBODIMENTS

A transgene as used in the context of the present invention is an isolated deoxyribonucleotide (DNA) sequence coding for a given mature protein (also referred to herein as a DNA encoding a protein), for a precursor protein or for a functional RNA that does not encode a protein (non-coding RNA). A transgene is isolated and introduced into a cell to produce the transgene product. Some preferred transgenes according to the present invention are transgenes encoding immunoglobulins (Igs) and Fc-fusion proteins and other proteins, in particular proteins with therapeutical activity ("biotherapeutics"). For instance, certain immunoglobulins such as Infliximab (Remicade) or other secreted proteins such as coagulation factor VIII, are notably difficult to express, because of mostly uncharacterized cellular bottlenecks. With the help of the recombinant nucleic acid molecules, vectors and methods of the present invention these bottlenecks may be identified and/or opened. This generally increases the amount of therapeutic proteins that can be produced and/or their quality, such as e.g. their processing and the homogeneity of post-translational modifications such as glycosylation.

As used herein, the term transgene shall, in the context of a DNA encoding a protein, not include untranscribed flanking regions such as RNA transcription initiation signals, polyadenylation addition sites, promoters or enhancers. Other preferred transgenes include DNA sequences encoding functional RNAs. Thus, the term transgene is used in the present context when referring to a DNA sequence that is introduced into a cell such as an eukaryotic host cell via transfection (which includes in the context of the present invention also transduction, i.e., the introduction via viral vectors) and which encodes the product of interest also referred to herein as the "transgene expression product", e.g., "heterologous proteins". The transgene might be functionally attached to a signal peptide coding sequence, which encodes a signal peptide which in turn mediates and/or facilitates translocation and/or secretion across the endoplasmic reticulum and/or cytoplasmic membrane and is removed prior or during secretion.

Small interfering RNAs (siRNA) are double stranded RNA molecules, generally 20-25 base pairs long which play a role in RNA interference (RNAi) by interfering with the expression of specific genes with complementary nucleotide sequence. A siRNA can be directly introduced into the cells or can be expressed in the cell via a vector. An isolated TEP siRNA as referred to herein is such a 20-25 base pair long siRNA that is usually introduced directly into the cell, i.e., without being expressed via a nucleic acid that has been introduced into the cell.

A small/short hairpin RNA (shRNA) is a sequence of RNA that makes a tight hairpin turn that can be used to silence target gene expression via RNAi. Expression of shRNA in cells is typically accomplished by delivery of plasmids or viral vectors such as retroviral vectors. To create shRNAs, a siRNA sequence is usually modified to introduce a short loop between the two strands of the siRNA. A nucleic acid encoding the shRNA is then delivered via a vector into the cell and are transcribed into short hairpin RNA (shRNA), which can be processed into a functional siRNA by Dicerin its usual fashion.

An si/shRNA is capable of sequence-specifically reducing expression of a target gene. The shRNA may hybridize to a region of an mRNA transcript encoding the product of the target gene, thereby inhibiting target gene expression via RNA interference. Bi-functional shRNAs have more than one target, e.g., the coding region as well as certain untranslated regions of an mRNA. Integration into the cell genome facilitates long-lasting or constitutive gene silencing that may be passed on to progeny cells.

A microRNA (miRNA) is a small RNA molecule, e.g., 20 to 24, in particular 22 nucleotides long, which functions in transcriptional and post-transcriptional regulation of gene expression via pairing with complementary sequences within mRNAs. Gene silencing may occur either via transgene transcription inhibition, mRNA degradation or preventing mRNA from being translated. miRNAs can be expressed by delivery of plasmids or viral vectors such as retroviral vectors. Alternatively, RNA molecules inhibiting or mimicking miRNA can by synthesized and transfected directly in cells.

A "Sequence encoding a transgene expression processing (TEP) protein or TEP functional RNA" allows the expression or the increased expression of the given TEP protein following its transfer into a cell, whereas the sequence encoding a non-coding functional RNAs inhibit the expression of cellular proteins, respectively. The TEP proteins can be identical or similar to cellular proteins, or they can be proteins from a distinct cell or species. The cellular proteins whose expression is, e.g., inhibited by functional RNAs are constituent proteins of the cell into which functional RNAs are introduced. The TEP protein may also supplement the expression of another cellular protein and as a result, preferably, enhance the expression of a transgene. The proteins may be involved in recombination; in mRNA translational processes; in ER translocation, secretion, processing or folding of polypeptides, in ER-Golgy-plasma membrane transport, glycosylation and/or another post-translational modification. Functional RNAs include, e.g., siRNAs, shRNAs, microRNAs, lariat-form spliced RNA, short-temporary sense RNA (stRNA), antisense RNA (aRNA), ribozyme RNA and other RNAs, in particular those that can knock-down target gene expression. In a particular preferred embodiment, these proteins are involved in the "The Protein secretion pathway" or in "The Recombination pathways", but also include certain protein processing or metabolic proteins as described below.

TEP functional RNAs may not only be expressed from a nucleic acid sequence as described above, but may be directly introduced into the cell. This, in particular is true for isolated TEP siRNAs.

The term an "isolated nucleic acid molecule" is in the context of the present invention is equivalent to a "recombinant nucleic acid molecule", i.e., a nucleic acid molecule that, does not exist, in this form in nature, but has been constructed starting from parts that do exist in nature.

A nucleic acid sequence, such as a DNA or RNA, is complimentary to another DNA or RNA, if the nucleotides of, e.g., two single stranded DNA stands or two single stranded RNA strands can form stable hydrogen bonds, such as a hydrogen bond between guanine (G) with cytosine (C). In the cell, complementary base pairing allows, e.g., cells to copy information from one generation to another. In RNA interference (RNAi) complementary base pairing allows, the silencing or complete knock-out of certain target genes. Essentially, siRNA, shRNA or miRNA sequence specifically reduce or knock-out expression of a target gene by having a single RNA strand (e.g. the anti-sense strand in siRNA) align with RNA, in particularly the mRNA of the host cell. The degree of complementarity between two nucleic acid strands may vary, from complete complementarity (each nucleotide is across from its opposite) to partial complementary (50%, 60%, 70%, 80%, 90% or 95%). The degree of complementarity determines the stability of the complex and thus how successfully a gene can be, e.g., knocked-out. Thus, complete or at least 95% complementarity are preferred.

The activity of siRNAs in RNAi is largely dependent on its binding ability to the RNA-induced silencing complex (RISC). Binding of the duplex siRNA to RISC is followed by unwinding and cleavage of the sense strand with endonucleases. The remaining anti-sense strand-RISC complex can then bind to target mRNAs for initiating transcriptional silencing.

Within the context of the present invention transgenes, as defined above, express generally proteins whose production in larger quantities is desired, e.g. for pharmaceutical use, while sequences encoding TEP proteins/functional RNAs, or the functional RNAs themselves, are designed to help the expression of such transgenes either directly or indirectly. An "exemplary list of TEP proteins expressed using transposon vectors" is listed as TABLE A. As the person skilled in the art will appreciate, the huge majority of these proteins have been disclosed in the art and Table A discloses both the NCBI reference sequence numbers for the respective proteins as well as the nucleic acid sequence encoding the same. The last column provides sequence identifiers for certain of those sequences. The person skilled in the art will appreciate that variants of the proteins as well a sequences with more then 80%, 90%, 95% or 98% sequence identity are part of the present invention.

An "exemplary list of shRNA expressed using, e.g., specific piggybac transposon vectors" is listed as TABLE B. As the person skilled in the art will appreciate, such shRNAs can be readily constructed when a target gene has been selected. For example any one of the known genes of the recombination pathway is a ready target gene. However, other genes, such as genes for the proteins set forth in Table A may be ready targets for siRNAs generated from those shRNAs. TABLE C is a list of examples of siRNAs (sense strand) and examples of shRNAs created from corresponding siRNAs. The antisense strand of the siRNA is ultimately used to block and/or provoke the degradation of a cellular mRNA. This generally leads to reduced levels of the protein encoded by the mRNA.

Identity means the degree of sequence relatedness between two nucleotide sequences as determined by the identity of the match between two strings of such sequences, such as the full and complete sequence. Identity can be readily calculated. While there exists a number of methods to measure identity between two nucleotide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in Guide to Huge Computers, Martin J. Bishop, ed., Academic Press, San Diego, 1994, and Carillo, H., and Lipman, D., SIAM J Applied Math. 48: 1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., Nucleic Acids Research 12(1). 387 (1984)), BLASTP, BLASTN, FASTA (Altschul et al. (1990); Altschul et al. (1997)). The well-known Smith Waterman algorithm may also be used to determine identity.

As an illustration, by a nucleic acid comprising a nucleotide sequence having at least, for example, 95% "identity" with a reference nucleotide sequence means that the nucleotide sequence of the nucleic acid is identical to the reference sequence except that the nucleotide sequence may include up to five point mutations per each 100 nucleotides of the reference nucleotide sequence. In other words, to obtain a nucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Sequence identities of more about 60%, about 70%, about 75%, about 85% or about 90% for any sequence disclosed herein (e.g., by SEQ IDs. And/or by accession numbers) are also within the scope of the present invention.

A nucleic acid sequence having substantial identity to another nucleic acid sequence refers to a sequence having point mutations, deletions or additions in its sequence that have no or marginal influence on the respective method described and is often reflected by one, two, three or four mutations in 100 bps.

The invention is directed to both polynucleotide and polypeptide variants. A "variant" refers to a polynucleotide or polypeptide differing from the polynucleotide or polypeptide disclosed, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids disclosed herein are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. Variants of any of nucleic acid molecules disclosed herein are part of the present invention.

A promoter sequence or just promoter is a nucleic acid sequence which is recognized by a host cell for expression of a specific nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell. Promoters according to the present invention include inducible and non-inducible promoters. A nucleic acid sequence is under control of a promoter is the promoter exercises its function on said nucleic acid.

CGAPDH (also referred to herein as C_GAPDH) is an enhancer-promoter fusion, which comprises the human GAPDH promoter and the human CMV immediate early gene enhancer. In one embodiment, to produce it, the human GAPDH promoter and its 5'UTR were PCR amplified from human HEK293 cell genomic DNA. The product was placed downstream of the human CMV immediate early gene enhancer. See. SEQ ID NO: 11 for a representative sequence. Sequences having at least 80%, 90%, 95%, 98%, 99% or 100% sequence identity with SEQ ID NO. 11 are also within the scope of the present invention. Other desirable promoter(s) and/or enhancer(s) or fusions thereof are, but not limited to, the CMV IE enhancer, the human GAPDH promoter, the human Ef1 alpha promoter, the CMV promoter, the SV40 promoter, the CHO Actb promoter or the CHO Hspa5 promoter. These elements are well known in the art and sample sequences are listed under SEQ ID NOs: 110 to 116. As the person skilled in the art will understand, variants thereof are also part of the present inventions and well as element that have at least 80%, 90%, 95%, 98%, 99% or 100% sequence identity with any one of SEQ ID NOs: 110 to 116.

A "transposon" is a mobile genetic element that efficiently transposes between vectors and chromosomes via a "cut and paste" or "copy and paste" mechanism. During transposition, the transposase (e.g., the PB transposase in the PiggyBac transposon system) recognizes transposon-specific inverted terminal repeat sequences (ITRs) located on both ends of the transposon (there is a 5'- and a 3' ITR to any transposon system) and moves the contents from the original sites and integrates them into chromosomal sites, such as TTAA chromosomal sites. The powerful activity of the PiggyBac transposon system enables genes of interest between the two ITRs to be easily mobilized into target genomes. The PiggyBac transposon system is described, e.g., in 2010/0154070, which is incorporated herein by reference in its entirety.

MAR elements (MAR constructs, MAR sequences, S/MARs or just MARs) belong to a wider group of epigenetic regulator elements which also include boundary or insulator elements such as cHS4, locus control regions (LCRs), stabilizing and antirepressor (STAR) elements, ubiquitously acting chromatin opening (UCOE) elements or histone modifiers such as histone deacetylase (HDAC).

MAR elements may be defined based on the identified MAR they are primarily based on: A MAR S4 construct is, accordingly, a MAR elements that whose majority of nucleotide (50% plus, preferably 60%, 70% or 80%) are based on MAR S4. Several simple sequence motifs such as high in A and T content have often been found within MARs Other motifs commonly found are the A-box, the T-box, DNA unwinding motifs, SATB1 binding sites (H-box, A/T/C25) and consensus topoisomerase II sites for vertebrates or *Drosophila.*

MARs are generally characterized as sequences in the DNA of eukaryotic chromosomes where the nuclear matrix attaches. The properties of MAR are only in part defined by their primary structure. For example, a typical primary structure found in MAR elements such as AT rich regions are known to result in tertiary structures, namely in certain curvatures that define the function of the MAR. Thus, MARs are often defined not only by their primary structure, but also by their secondary, tertiary structure, e.g. their degree of curvature and/or physical properties such as melting temperature.

An AT/TA-dinucleotide rich bent DNA region (hereinafter referred to as "AT-rich region") as commonly found in MAR elements is a bent DNA region comprising a high number of A and Ts, in particular in form of the dinucleotides AT and TA. In a preferred embodiment, it contains at least 10% of dinucleotide TA, and/or at least 12% of dinucleotide AT on a stretch of 100 contiguous base pairs, preferably at least 33% of dinucleotide TA, and/or at least 33% of dinucleotide AT on a stretch of 100 contiguous base pairs (or on a respective shorter stretch when the AT-rich region is of shorter length), while having a bent secondary structure. However, the "AT-rich regions" may be as short as about 30 nucleotides or less, but is preferably about 50 nucleotides, about 75 nucleotides, about 100 nucleotides, about 150, about 200, about 250, about 300, about 350 or about 400 nucleotides long or longer.

Some binding sites are also often have relatively high A and T content such as the SATB1 binding sites (H-box, A/T/C25) and consensus Topoisomerase II sites for vertebrates (RNYNNCNNGYNGKTNYNY, SEQ ID NO: 117) or *Drosophila* (GTNWAYATTNATNNR, SEQ ID NO: 118). However, a binding site region (module), in particular a TFBS region, which comprises a cluster of binding sites, can be readily distinguished from AT and TA dinucleotides rich regions ("AT-rich regions") from MAR elements high in A and T content by a comparison of the bending pattern of the regions. For example, for human MAR 1.sub.-68, the latter might have an average degree of curvature exceeding about 3.8 or about 4.0, while a TFBS region might have an average degree of curvature below about 3.5 or about 3.3. Regions of an identified MAR can also be ascertained by alternative means, such as, but not limited to, relative melting temperatures, as described elsewhere herein. However, such values are specie specific and thus may vary from specie to specie, and may, e.g., be lower. Thus, the respective AT and TA dinucleotides rich regions may have lower degrees of curvature such as from about 3.2 to about 3.4 or from about 3.4 to about 3.6 or from about 3.6 to about 3.8, and the TFBS regions may have proportionally lower degrees of curvatures, such a below about 2.7, below about 2.9, below about 3.1, below about 3.3. In SMAR Scan II, respectively lower window sizes will be selected by the skilled artisan.

A MAR element, a MAR construct, a MAR sequence, a S/MAR or just a MAR according to the present invention is a nucleotide sequence sharing one or more (such as two, three or four) characteristics such as the ones described above with a naturally occurring "SAR" or "MAR" Preferably such a MAR element, a MAR construct, a MAR sequence, a S/MAR or just a MAR has at least one property that facilitates protein expression of any gene influenced by said MAR. A MAR element has generally also the feature of being an isolated and/or purified nucleic acid preferably displaying MAR activity, in particular, displaying transcription modulation, preferably enhancement activity, but also displaying, e.g., expression stabilization activity and/or other activities.

The terms MAR element, MAR construct, a MAR sequence, a S/MAR or just a MAR also includes, in certain embodiments, enhanced MAR constructs that have properties that constitute an enhancement over an natural occurring and/or identified MAR on which a MAR construct according to the present invention may be based. Such properties include, but are not limited to, reduced length relative to the full length natural occurring and/or identified MAR, gene expression/transcription enhancement, enhancement of stability of expression, tissue specificity, inducibility or a combination thereof. Accordingly, a MAR element that is enhanced may, e.g., comprise less than about 90%, preferably less than about 80%, even more preferably less than about 70%, less than about 60%, or less than about 50% of the number of nucleotides of an identified MAR sequence. A MAR element may enhance gene expression and/or transcription of a transgene upon transformation of an appropriate cell with said construct.

A MAR element is preferably inserted upstream of a promoter region to which a gene of interest is or can be operably linked. However, in certain embodiments, it is advantageous that a MAR element is located upstream as well as downstream or just downstream of a gene/nucleotide acid sequence of interest. Other multiple MAR arrangements both in cis and/or in trans are also within the scope of the present invention.

Synthetic, when used in the context of a MAR element refers to a MAR whose design involved more than simple reshuffling, duplication and/or deletion of sequences/regions or partial regions, of identified MARs or MARs based thereon. In particular, synthetic MARs/MAR elements generally comprise one or more, preferably one, region of an identified MAR, which, however, might in certain embodiment be synthesized or modified, as well as specifically designed, well characterized elements, such as a single or a series of TFBSs, which are, in a preferred embodiment, produced synthetically. These designer elements are in many embodiments relatively short, in particular, they are generally not more than about 300 bps long, preferably not more than about 100, about 50, about 40, about 30, about 20 or about 10 bps long. These elements may, in certain embodiments, be multimerized. Such synthetic MAR elements are also part of the present invention and it is to be understood that generally the present description can be understood that anything that is said to apply to a "MAR element" equally applies to a synthetic MAR element.

Functional fragments of nucleotide sequences of identified MAR elements are also included as long as they maintain functions of a MAR element as described above.

Some preferred identified MAR elements include, but are not limited to, MAR 1_68, MAR X_29, MAR 1_6, MAR S4, MAR S46 including all their permutations as disclosed in WO2005040377 and US patent publication 20070178469, which are specifically incorporated by reference into the present application for the disclosure of the sequences of these and other MAR elements. The chicken lysozyme MAR is also a preferred embodiment (see, U.S. Pat. No. 7,129,062, which is also specifically incorporated herein for its disclosure of MAR elements).

If a vector is said to comprise a singular MAR this means that in this vector there is one MAR and there are no other MARs within the vector either of the same or a different type or structure.

In certain embodiments of the invention, there are multiple MARs, which may be of the the same or a different type or structure and which may all be located downstream of a gene of interest. This is called a singular MAR cluster.

If something, such as a number of cells stably expressing a polypeptide, is said to be "independent" from the presence of, e.g., a sequence, then the sequence does not influence (e.g., the number of cells stably expressing a polypeptide) to any statistically significant extent.

A transgene or sequence encoding a transgene expression processing protein or functional RNA of the present invention is often part of a vector.

A vector according to the present invention is a nucleic acid molecule capable of transporting another nucleic acid, such as a transgene that is to be expressed by this vector, to which it has been linked, generally into which it has been integrated. For example, a plasmid is a type of vector, a retrovirus or lentivirus is another type of vector. In a preferred embodiment of the invention, the vector is linearized prior to transfection. An expression vector comprises regulatory elements or is under the control of such regulatory elements that are designed to further the transcription and/or expression of a nucleic acid sequence carried by the expression vector. Regulatory elements comprise enhancers and/or promoters, but also a variety of other elements described herein (see also "Vector Design").

The vector sequence of a vector is the DNA or RNA sequence of the vector excluding any "other" nucleic acids such as transgenes as well as genetic elements such as MAR elements.

An eukaryotic, including a mammalian cell, such as a recombinant mammalian cell/eukaryotic host cell, according to the present invention is capable of being maintained under cell culture conditions. Non-limiting examples of this type of cell are non-primate eukaryotic host cells such as Chinese hamster ovary (CHOs) cells and baby hamster kidney cells (BHK, ATCC CCL 10). Primate eukaryotic host cells include, e.g., human cervical carcinoma cells (HELA, ATCC CCL 2) and monkey kidney CV1 line transformed with SV40 (COS-7, ATCC CRL-1587). A recombinant eukaryotic host cell or recombinant mammalian cell signifies a cell that has been modified, e.g., by transfection with, e.g., a transgenic sequence and/or by mutation. The eukaryotic host cells or recombinant mammalian cells are able to perform post-transcriptional modifications of proteins expressed by said cells. In certain embodiments of the present invention, the cellular counterpart of the eukaryotic (e.g., non-primate) host cell is fully functional, i.e., has not been, e.g., inactivated by mutation. Rather the transgenic sequence (e.g., primate) is expressed in addition to its cellular counterpart (e.g., non-primate).

Transfection according to the present invention is the introduction of a nucleic acid into a recipient eukaryotic cell, such as, but not limited to, by electroporation, lipofection, generally via a non-viral vector (vector mediated transfection) or via chemical means including those involving polycationic lipids. Non vector mediated transfection includes, for example, the direct introduction of an isolated TEP siRNAs into a cell. In a transiently transfected cell the, e.g., siRNA only remains transiently. In the context of the present invention there may by a first transfection with at least one nucleic acid molecule with a sequence encoding a transgene expression processing (TEP) protein or TEP functional RNA or, alternatively, directly with a TEP functional RNA (e.g., a siRNA) and a second, subsequent, transfection with a nucleic acid encoding the transgene. Both the first and the second transfection can be repeated. The, e.g., siRNA is introduced during the first transfection, acts, in particular inhibits, a recombination protein (a protein that is involved in the recombination events in the transfected cell). After this the transgene is introduced during the second subsequent transfection.

Transcription means the synthesis of RNA from a DNA template. "Transcriptionally active" refers to, e.g., a transgene that is being transcribed. Translation is the process by which RNA makes protein.

An enhancement of secretion is measured relative to a value obtained from a control cell that does not comprise the respective transgenic sequence. Any statistically significant enhancement relative to the value of a control qualifies as a promotion.

A selection marker, is a nucleic acid that contains a gene whose product confers resistance to an selection agent antibiotic (e.g., chloramphenicol, ampicillin, gentamycin, streptomycin, tetracyclin, kanamycin, neomycin, puromycin) or the ability to grow on selective media (e.g., DHFR (dihydrofolate reductase).

The class of proteins known as chaperones has been defined as a protein that binds to and stabilizes an otherwise unstable conformer of another protein and, by controlled binding and release, facilitates its correct fate in vivo, be it folding, oligomeric assembly, transport to a particular subcellular compartment, or disposal by degradation. BiP (also known as GRP78, Ig heavy chain binding protein and Kar2p in yeast) is an abundant about 70 kDa chaperone of the hsp 70 family, resident in the endoplasmic reticulum (ER), which amongst other functions, serves to assist in transport in the secretory system and fold proteins. Protein disulphide isomerase (PDI) is a chaperone protein, resident in the ER that is involved in the catalysis of disulphide bond formation during the post-translational processing of proteins.

Cellular Metabolic Engineering

In cellular metabolic engineering, e.g., the processes inherent in the expressing cell are altered. For example, certain proteins of the secretion pathway are, e.g., overexpressed. Alternatively, recombination events are altered by influencing recombination pathways.

The Protein Secretion Pathway

The secretion of proteins is a process common to organisms of all three kingdoms. This complex secretion pathway requires most notably the protein translocation from the cytosol across the cytoplasmic membrane of the cell. Multiple steps and a variety of factors are required to for the protein to reach its final destination. In mammalian cells, this secretion pathway involves two major macromolecular assemblies, the signal recognition particle (SRP) and the secretory complex (Sec-complex or translocon). The SRP is composed of six proteins with masses of 9, 14, 19, 54, 68 and 72 kDa and a 7S RNA and the translocon is a donut shaped particle composed of Sec61αβγ, Sec62 and Sec63. Accession numbers (in parenthesis) for the human version of some of these proteins are as follows: hSRP14 (Acc. No. X73459.1); hSRP9 (NM_001130440); hSRP54 (NM_003136); hSRPRα (NM_003139); hSRPRβ (NM_021203); hSEC61α1 (NM_013336); hSEC61β (L25085.1); hSEC61γ (AK311845.1).

The first step in protein secretion depends on the signal peptides, which comprises a specific peptide sequence at the amino-terminus of the polypeptide that mediates translocation of nascent protein across the membrane and into the lumen of the endoplasmic reticulum (ER). During this step, the signal peptide that emerges from the leading translating ribosome interacts with the subunit of the SRP particle that recognizes the signal peptide, namely, SRP54. The SRP binding to the signal peptide blocks further elongation of the nascent polypeptide resulting in translation arrest. The SRP9 and -14 proteins are required for the elongation arrest (Walter and Blobel 1981). In a second step, the ribosome-nascent polypeptide-SRP complex is docked to the ER membrane through interaction of SRP54 with the SRP receptor (SR) (Gilmore, Blobel et al. 1982; Pool, Stumm et al. 2002). The SR is a heterodimeric complex containing two proteins, SRα and SRβ that exhibit GTPase activity (Gilmore, Walter et al. 1982). The interaction of SR with SRP54 depends on the binding of GTP (Connolly, Rapiejko et al. 1991). The SR coordinates the release of SRP from the ribosome-nascent polypeptide complex and the association of the exit site of the ribosome with the Sec61 complex (translocon). The growing nascent polypeptide enters the ER through the translocon channel and translation resumes at its normal speed. The ribosome stays bound on the cytoplasmic face of the translocon until translation is completed. In addition to ribosomes, translocons are closely associated with ribophorin on the cytoplasmic face and with chaperones, such as calreticulin and calnexin, and protein disulfide isomerases (PDI) and oligosaccharyl transferase on the luminal face. After extrusion of the growing nascent polypeptide into the lumen of the ER, the signal peptide is cleaved from the pre-protein by an enzyme called a signal peptidase, thereby releasing the mature protein into the ER. Following post-translational modification, correct folding and multimerization, proteins leave the ER and migrate to the Golgi apparatus and then to secretory vesicles. Fusion of the secretory vesicles with the plasma membrane releases the content of the vesicles in the extracellular environment.

Remarkably, secreted proteins have evolved with particular signal sequences that are well suited for their own translocation across the cell membrane. The various sequences found as distinct signal peptides might interact in unique ways with the secretion apparatus. Signal sequences are predominantly hydrophobic in nature, a feature which may be involved in directing the nascent peptide to the secretory proteins. In addition to a hydrophobic stretch of amino acids, a number of common sequence features are shared by the majority of mammalian secretion signals. Different signal peptides vary in the efficiency with which they direct secretion of heterologous proteins, but several secretion signal peptides (i.e. those of interleukin-, immunoglobulin-, histocompatibility receptor-signal sequence, etc) have been identified which may be used to direct the secretion of heterologous recombinant proteins. Despite similarities, these sequences are not optimal for promoting efficient secretion of some proteins that are difficult to express, because the native signal peptide may not function correctly out of the native context, or because of differences linked to the host cell or to the secretion process. The choice of an appropriate signal sequence for the efficient secretion of a heterologous protein may be further complicated by the interaction of sequences within the cleaved signal peptide with other parts of the mature protein (Johansson, Nilsson et al. 1993).

The Recombination Pathways

The recombination pathways, also known as DNA recombination pathways, are cellular pathways that lead to DNA damage repair, such as the joining of DNA molecule extremities after chromosomal double-strand breaks, and to the exchange or fusion of DNA sequences between chromosomal and non-chromosomal DNA molecules, such as e.g. the crossing-over of chromosomes at meiosis or the rearrangement of immunoglobulin genes in lymphocytic cells. The three main recombination pathways are the homologous recombination pathway (HR), the non-homologous end-joining pathway (NHEJ) and the microhomology-mediated end-joining (MMEJ) and alternative end-joining (Alt-EJ) pathway.

The Mechanisms of Homologous Recombination (HR), Non-Homologous End-Joining (NHEJ) and Microhomology Mediated End Joining (MMEJ)

Transgenes Use the Recombination Machineries to Integrate at a Double Strand Break into the Host Genome.

Double-strand breaks (DSBs), are the biologically most deleterious type of genomic damage potentially leading to cell death or a wide variety of genetic rearrangements. Accurate repair is essential for the successful maintenance and propagation of the genetic information.

There are two major DSB repair mechanisms: non-homologous end-joining (NHEJ) and homologous recombination (HR). A third mechanism, called microhomology-mediated end joining (MMEJ) often takes effect when the two major DSB repair mechanisms fail. Homologous recombination is a process for genetic exchange between DNA sequences that share homology and is operative predominantly during the S/G2 phases of the cell cycle, while NHEJ simply pieces together two broken DNA ends, usually with no sequence homology, and it functions in all phases of the cell cycle but is of particular importance during G0-G1 and early S-phase of mitotic cells (Wong and Capecchi, 1985; Delacote and Lopez, 2008). In vertebrates, HR, NHEJ and MMEJ differentially contribute to DSB repair, depending on the nature of the DSB and the phase of the cell cycle (Takata et al., 1998).

NHEJ: Basic Mechanisms

Conceptually, the molecular mechanism of the NHEJ process seems to be simple: 1) a set of enzymes capture the broken DNA molecule, 2) a molecular bridge that brings the two DNA ends together is formed and 3) the broken molecules are re-ligated. To perform such reactions, the NHEJ machinery in mammalian cells involves two protein complexes, the heterodimer Ku80/Ku70 associated with DNA-PKcs (catalytic subunit of DNA-dependent protein kinase) and DNA ligase IV with its co-factor XRCC4 (X-ray-complementing Chinese hamster gene 4) and many protein factors, such as Artemis and XLF (XRCC4-like factor; or Cernunnos) (Delacote et al., 2002). NHEJ is frequently considered as the error-prone DSB repair because it simply pieces together two broken DNA ends, usually with no sequence homology and it generates small insertions and deletions (Moore and Haber, 1996; Wilson et al., 1999). NHEJ provides a mechanism for the repair of DSBs throughout the cell cycle, but is of particular importance during G0-G1 and early S-phase of mitotic cells (Takata et al., 1998; Delacote and Lopez, 2008). The repair of DSBs by NHEJ is observed in organisms ranging from bacteria to mammals, indicating that it has been conserved during evolution.

After DSB formation the key step in NHEJ repair pathway is the physical juxtaposition of the broken DNA ends. NHEJ is initiated by the association of the Ku70/80 heterodimer protein complex to both ends of the broken DNA molecule to capture, tether the ends together and create a scaffold for the assembly of the other NHEJ key factors. The DNA-bound Ku heterodimer complex recruits DNA-PKcs to the DSB, a 460 kDa protein belonging to the PIKK (phosphoinositide 3-kinase-like family of protein kinases) (Gottlieb and Jackson, 1993) and activates its serine/threonine kinase function (Yaneva et al., 1997). Two DNA-PKcs molecules interact together across the DSB, thus forming a molecular bridge between both broken DNA ends and inhibit their degradation (DeFazio et al., 2002). Then, DNA ends can be directly ligated, although the majority of termini generated from DSB have to be properly processed prior to ligation (Nikjoo et al., 1998). Depending of the nature of the break, the action of different combinations of processing enzymes may be required to generate compatible overhangs, by filling gaps, removing damaged DNA or secondary structures surrounding the break. This step in the NHEJ process is considered to be responsible for the occasional loss of nucleotides associated with NHEJ repair. One key end-processing enzyme in mammalian NHEJ is Artemis, a member of the metallo-β-lactamase superfamily of enzymes, which was discovered as the mutated gene in the majority of radiosensitive severe combined immunodeficiency (SCID) patients (Moshous et al., 2001). Artemis has both a 5'→3' exonuclease activity and a DNA-PKcs-dependent endonuclease activity towards DNA-containing ds-ss transitions and DNA hairpins (Ma et al., 2002). Its activity is also regulated by ATM. Thus, Artemis seems likely to be involved in multiple DNA-damage responses. However, only a subset of DNA lesions seem to be repaired by Artemis, as no major defect in DSB repair were observed in Artemis-lacking cells (Wang et al., 2005, Darroudi et al., 2007).

DNA gaps must be filled in to enable the repair. Addition of nucleotides to a DSB is restricted to polymerases μ and λ (Lee et al., 2004; Capp et al., 2007). By interaction with XRCC4, polynucleotide kinase (PNK) is also recruited to DNA ends to permit both DNA polymerization and ligation (Koch et al., 2004). Finally, NHEJ is completed by ligation of the DNA ends, a step carried out by a complex containing XRCC4, DNA ligase IV and XLF (Grawunder et al., 1997). Other ligases can partially substitute DNA ligase IV, because NHEJ can occur in the absence of XRCC4 and Ligase IV (Yan et al., 2008). Furthermore, studies showed that XRCC4 and Ligase IV do not have roles outside of NHEJ, whereas in contrast, KU acts in other processes such as transcription, apoptosis, and responses to microenvironment (Monferran et al., 2004; Müller et al., 2005; Downs and Jackson, 2004).

The NHEJ may be decreased or shut down in different ways, many of which directly affect the above referenced proteins (e.g., the heterodimer Ku80/Ku70, DNA-PKcs, but in particular DNA ligase IV, XRCC4, Artemis and XLF (XRCC4-like factor; or Cernunnos), PIKK (phosphoinositide 3-kinase-like family of protein kinases).

HR: Basic Mechanisms

Homologous recombination (HR) is a very accurate repair mechanism. A homologous chromatid serves as a template for the repair of the broken strand. HR takes place during the S and G2 phases of the cell cycle, when the sister chromatids are available. Classical HR is mainly characterized by three steps: 1) resection of the 5' of the broken ends, 2) strand invasion and exchange with a homologous DNA duplex, and 3) resolution of recombination intermediates. Different pathways can complete DSB repair, depending on the ability to perform strand invasion, and include the synthesis-dependent strand-annealing (SDSA) pathway, the classical double-strand break repair (DSBR) (Szostak et al, 1983), the break-induced replication (BIR), and, alternatively, the single-strand annealing (SSA) pathway. All HR mechanisms are interconnected and share many enzymatic steps.

The first step of all HR reactions corresponds to the resection of the 5'-ended broken DNA strand by nucleases with the help of the MRN complex (MRE11, RAD50, NBN (previously NBS1, for Nijmegen breakage syndrome 1)) and CtIP (CtBP-interacting protein) (Sun et al., 1991; White and Haber, 1990). The resulting generation of a 3' single-stranded DSB is able to search for a homologous sequence. The invasion of the homologous duplex is performed by a nucleofilament composed of the 3'ss-DNA coated with the RAD51 recombinase protein (Benson et al., 1994). The requirement of the replication protein A (RPA), an heterotrimeric ssDNA-binding protein, involved in DNA metabolic processes linked to ssDNA in eukaryotes (Wold, 1997), is necessary for the assembly of the RAD51-filament (Song and sung, 2000). Then RAD51 interacts with RAD52, which has a ring-like structure (Shen et al., 1996) to displace RPA molecules and facilitate RAD51 loading (Song and sung, 2000). Rad52 is important for recombination processes in yeast (Symington, 2002). However, in vertebrates, BRCA2 (breast cancer type 2 susceptibility protein) rather than RAD52 seems to play an important role in strand invasion and exchange (Davies and Pellegrini, 2007; Esashi et al., 2007). RAD51/RAD52 interaction is stabilized by the binding of RAD54. RAD54 plays also a role in the maturation of recombination intermediates after D-loop formation (Bugreev et al., 2007). In the other hand, BRCA1 (breast cancer 1) interacts with BARD1 (BRCA1 associated RING domain 1) and BACH1 (BTB and CNC homology 1) to perform ligase and helicase DSB repair activity, respectively (Greenberg et al., 2006). BRCA1 also interacts with CtIP in a CDK-dependent manner and undergoes ubiquitination in response to DNA damage (Limbo et al., 2007). As a consequence, BRCA1, CtIP and the MRN complex play a role in the activation of HR-mediated repair of DNA in the S and G2 phases of the cell cycle.

The invasion of the nucleofilament results in the formation of a heteroduplex called displacement-loop (D-loop) and involves the displacement of one strand of the duplex by the invasive strand and the pairing with the other. Then, several HR pathways can complete the repair, using the homologous sequence as template to replace the sequence surrounding the DSB. Depending of the mechanism used, reciprocal exchanges (crossovers) between the homologous template and the broken DNA molecule may be or may not be associated to HR repair. Crossovers may have important genetic consequences, such as genome rearrangements or loss of heterozygosity.

The five Rad51 paralogs are also involved in homologous recombination: Xrcc2, Xrcc3, Rad51B, Rad51C, Rad51D (Suwaki et al., 2011). Rad51 paralogs form two types of complexes: one termed BCDX2 comprises Rad51B, Rad51C, Rad51D and Xrcc2; the other contains Rad51C and Xrcc3 (CX3) (Masson et al., 2001). The first complex has been proposed to participate in the formation and/or stabilization of the Rad51-DNA complex (Masson et al., 2001). The role of the second complex seems to be branch migration and resolution of the Holliday junction (Liu et al., 2007).

As previously reported, increasing the HR relative to the NHEJ (see US patent pub. 20120231449, which is incorporated herein by reference in its entirety) can be used to enhance and/or facilitate transgene expression.

The present invention focuses on decreasing or shutting down HR. The HR may be decreased or shut down in different ways, many of which directly affect the above referenced proteins (e.g., proteins of the MRN complex (MRE11, RAD50, NBN (previously NBS1, for Nijmegen breakage syndrome 1)) and CtIP (CtBP-interacting protein), RAD51, the replication protein A (RPA), Rad52, BRCA2 (breast cancer type 2 susceptibility protein), RAD54, BRCA1 (breast cancer 1) interacts with BARD1 (BRCA1 associated RING domain 1), BACH1 (BTB and CNC homology 1)). The present invention focuses on the production of RNAs, such as siRNAs to accomplish this goal.

Microhomology-Mediated End Joining (MMEJ)

When the other recombination pathways fail or are not active, DSBs can be repaired by another, error-prone repair mechanism called microhomology-mediated end joining (MMEJ). This pathway is still needs to be fully characterized and is sometimes also referred to as alternative end-joining (alt-EJ), although it is unclear whether these two processes are based on the same mechanism. The most characteristic feature of this pathway, which distinguishes it from NHEJ, is the use of 5-25 bp microhomologies during the alignment of broken DNA strands (McVey and Lee, 2008).

MMEJ can occur at any time of the cell cycle and is independent of core NHEJ and HR factors, i.e. Ku70, Ligase IV and Rad52 genes (Boboila et al., 2010; Yu and McVey, 2010; Lee and Lee, 2007; Ma et al., 2003). Instead MMEJ initiation relies on its own set of proteins, the most important ones being the components of the MRN complex (MRX in yeast) comprising Mre11, Rad50 and Nbs1 (Xrs2 in yeast), also implicated in the first steps of HR (Ma et al., 2003). Apart from the MRN complex many other factors have been proposed to participate in MMEJ, e.g. CTBP-interacting protein (CtIP; Yun and Hiom, 2009), poly (ADP-ribose) polymerase 1 (PARP1), the ligase III/Xrcc1 complex, ligase I (Audebert et al., 2004), DNA polymerase θ (Yu and McVey, 2010), and the ERCC1/XPF complex (Ma et al., 2003). However, many more proteins are take part in is process.

It has been suggested that in the absence of other DNA-end binding proteins (like Ku or Rad51) the DSBs are recognized by PARP1 which then initiates their repair through MMEJ (McVey and Lee, 2008). The repair process, similarly to HR, starts with 5' to 3' end resection, which exposes short regions of homology on each side of the break. This processing step is conducted by the MRN complex and regulated by CtIP (Mladenov and Ilikakis, 2011). The complementary regions (present in the 3' ssDNA fragments) pair together and the non-complementary segments (flaps) are removed (Yu and McVey, 2010), probably by the ERCC1/XPF complex. Gaps (if any) are then filled in by a polymerase (e.g. DNA polymerase θ or δ (Yu and McVey, 2010; Lee and Lee, 2007)) and breaks joined by the ligase I or ligase III/Xrcc1 complex.

In the absence of immediate microhomology regions at the DNA ends, which is most often the case, a more distant fragment of the repaired molecule can be copied using an accurate DNA polymerase (e.g. polymerase θ). This duplicated region then participates in the alignment of DNA ends, which results in an insertion in the created junction. This more complex variant of microhomology-mediated repair has been termed synthesis-dependent MMEJ (SD-MMEJ) (Yu and McVey, 2010).

Although MMEJ was thought to act as an alternative recombination repair pathway, it has been shown to be very efficient in the process of IgH class switch recombination in B lymphocytes (Boboila et al., 2010), suggesting that it might be more than a backup mechanism. It is also possible that some DSBs, e.g. incompatible overhangs or blunt ends (which are poor NHEJ and/or HR targets) might be more efficiently repaired by MMEJ (Zhang and Paull, 2005).

TABLE D lists some of the key genes in each of the three pathways, which are therefore also key targets for influencing each of the three pathways (see also US Patent Publication 20120231449, which is incorporated herein by reference in its entirety). Also included in the table are DNA repair proteins such as MDC1 and MHS2. MDC1 is required to activate the intra-S phase and G2/M phase cell cycle checkpoints in response to DNA damage. However, MDC1 also functions in Rad51-mediated homologous recombination by retaining Rad51 in chromatin.

"Knock-down" in the context of the present invention conveys that expression of the target gene is reduced, such as by 10%, 20%, 30%, 40%, 50%, 60%, 70%, 80%, 90% or more. Complete knock-down means that there is no detectable expression of the target gene anymore. TABLE D shows also the results obtained with certain knock-down targets. As the person skilled in the art will appreciate there are variations in the nucleic acid sequences of the targets so that variants of the genes, in particular variants that display a sequence identity of 80%, 90% or 95% are part of the present invention.

Protein Processing and Metabolic Proteins

This category of proteins that can be used for cellular metabolic engineering neither belongs to the protein secretion pathway nor the recombination pathway but otherwise influence processes inherent in the expressing cell.

The protein processing or metabolic proteins are often enzymes such as chaperones (see definitions of chaperons above), proteins isomerases, sugar adding enzymes (e.g. sialyl or glycosyl transferases) or phosphatases, or control the cell energy level or mitochondrial function.

TABLE A sets forth a list of proteins that have been expressed (exp) and/or whose expression has been "knocked-down" (KD) under the subheading "protein processing and metabolic proteins".

Vector Design

Among non-viral vectors, transposons are particularly attractive because of their ability to integrate single copies of DNA sequences with high frequency at multiple loci within the host genome. Unlike viral vectors, some transposons were reported not to integrate preferentially close to cellular genes, and they are thus less likely to introduce deleterious mutations. Moreover, transposons are readily produced and handled, comprising generally of a transposon donor plasmid containing the cargo DNA flanked by inverted repeat sequences and of a transposase-expressing helper plasmid or mRNA. Several transposon systems were developed to mobilize DNA in a variety of cell lines without interfering with endogenous transposon copies. For instance, the PiggyBac (PB) transposon originally isolated from the cabbage looper moth efficiently transposes cargo DNA into a variety of mammalian cells.

Epigenetic regulatory elements can be used to protect the cargo DNA from unwanted epigenetic effects when placed near the transgene on plasmid vectors. For example, elements called matrix attachment region (MARs) were proposed to increase cargo DNA genomic integration and transcription while preventing heterochromatin silencing, as exemplified by the potent human MAR 1-68. They can also act as insulators and thereby prevent the activation of neighboring cellular genes. MAR elements have thus been used to mediate high and sustained expression in the context of plasmid or viral vectors.

As shown herein, with the proper vector design, the favorable properties of epigenetic regulators, in particular MAR elements, may be combined with those of transposable vectors.

Transposons and transposon based vectors of the present invention can be used in cellular metabolic engineering, for instance to express secretion proteins of different secretion pathways described herein. They are also particularly useful when multiple rounds of cargo DNA introduction are required. This was confirmed when testing multiple proteins of the cell's secretory pathway, where the transfection of multiple vectors and/or multiple successive transfection cycles may exhaust available antibiotic or other selection methods. The ability to quickly express therapeutic proteins without a need for antibiotic selection is also of particular interest, for instance when multiple therapeutic protein candidates must be expressed for screening purposes, since significant amounts of proteins can be obtained from unselected cell populations 2-3 weeks after transfection. In particular, MAR-containing transposon vectors are thus a promising addition to the currently available arsenal of expression vectors.

The experimental approaches chosen, allowed (as opposed to approaches that rely on antibiotic based assays), a distinction between effects based on (1) cargo DNA copy number and effects based on (2) cargo DNA expression levels.

MAR 1-68 was particularly efficient, when located centrally between the ITRs of the of a PiggyBac transposon as it did not decrease transposition efficiency. MAR X-29 also worked well at the edges of the transposon without decreasing transposition efficiency or expression.

Interestingly, the extent of the MAR-mediated activation of transposed genes was reduced when compared to that of spontaneous plasmid integration. Furthermore, the level of expression, when normalized to, e.g., transgene copies, was higher from the transposons than those obtained from the spontaneous integration of the plasmids in the absence of the transposase. This effect was observed irrespective of the size of the constructs, of the presence of the MAR or of promoter strength. This would be expected if transposition might often occur at genomic loci that are relatively permissive for expression, for instance because open chromatin structures may be more accessible to both the transposase and transcription factors. In this respect, previous studies have suggested that transposons may preferentially integrate within gene introns, at promoters, or at genomic loci with lower propensity for silencing, although this has remained a matter of debate. Alternatively, the co-integration of many plasmid copies at the same genomic locus, as elicited by spontaneous integration events, may lead to the formation of heterochromatin and to the silencing of repetitive sequences, which the MAR would oppose, whereas single-copy transposon integration may be less prone to such chromatin-mediated silencing. In addition, the integration of transposons at multiple independent genomic loci makes it likely that at least one copy landed in a favorable genomic environment and is expressed, whereas plasmid integration was found to occur predominantly at just one genomic locus.

The highest expression levels per cargo DNA, e.g., transgene/TER were obtained from a MAR-containing transposon when coupled to a strong promoter. It was surprising to find high expression levels could be obtained from a few transposed cargo DNA copies, e.g., not more than 20, 15, 10, or 5. If high productivities can nevertheless be obtained, fewer integrated, e.g., cargo DNA copies are advantageous, as it decreases the probability of point mutation occurrence in one or in a subset of the transgenes, as elicited from spontaneous mutagenic events. In addition, transposase-mediated integration events are less mutagenic than the DNA repair and recombination mechanisms involved in spontaneous plasmid integration, which can lead to incomplete or rearranged transgene copies.

The high efficiency of genomic integration by the piggyBac (PB) transposon is also be favorable when the amount of target cells is limiting, for instance for the non-viral transfer of therapeutic genes into primary stem cells to generate clonal populations for, e.g., cell-based therapies or regenerative medicine. In this context, physiological expression levels from a few transposed cargo DNA copies and the frequent occurrence of transposition events, thus obviating the need for antibiotic selection, is advantageous, since the use of antibiotic resistance genes and/or unreliable, e.g., transgene expression may raise safety concerns.

Effect of MAR Inclusion on Transposition Efficiency

As antibiotic resistance does not necessarily reflect efficient transgene expression, the green fluorescent protein (GFP) expressed from a strong GAPDH cellular promoter derivative was used as an indicator. To test whether adding a MAR element to the PB transposon may affect transposition efficiency and transgene expression, and to assess whether the location of the MAR in the construct had any influence on these effects, a series of transposon donor constructs were designed containing the GFP and puromycin resistance (Puro) gene, in which the MAR 1-68 or a control neutral spacer DNA sequence were inserted at different positions in the plasmid (FIG. 1). The parental Puro-GFP transposon plasmid without an insert was used as a control of transposition, to distinguish the impact of increased transposon size relative to effect of the MAR or spacer sequence addition.

In the presence of the transposase, the highest level of GFP expression from unselected cells was observed when the MAR was centrally located, but not when the MAR was placed downstream of the GFP coding sequence, nor when inserted outside of the transposed sequence as expected (FIG. 3A). In the presence of puromycin selection, the MAR-mediated activation was reduced, either with or without the transposase, while the GFP expression averages were increased by one order of magnitude (FIG. 3B). This confirmed that puromycin selection yielded only the minority of the cells that display the highest expression levels, as proposed above from the quantitation of transposition events. It further indicated that the transposable vectors containing a centrally located MAR yielded similar expression levels when compared to their plasmid counterpart transfected without the transposase.

Effect of MAR Inclusion on the Copy Number of Integrated Transposon

Higher GFP fluorescence levels may result from an increased transcription of the transgenes and/or by the integration of more transgene copies. This was assessed by quantifying the number of genome-integrated transgene copies resulting from the various types of vectors. Total genomic DNA was isolated from pooled populations of cells, either after cytofluorometric sorting of fluorescent cells from unselected populations or after selection for puromycin resistance. The transgene copy number was determined by quantitative polymerase chain reaction (qPCR) analysis of the GFP coding sequence relative to the cellular β2-microglobulin (B2M) gene. In the absence of antibiotic selection, the average number of transgenes integrated by either the transposase or by cellular recombination enzymes were similar, around 1-6 copies per genome, and they were not significantly affected by the MAR or control sequence (FIG. 4A). However, the lowest copy number was obtained when the MAR was included at the transposon edge, supporting our earlier conclusion that it decreases transposition at this location. After selection for highly expressing cells with puromycin, the number of transposed transgenes was in a similar 2-7 copy range (FIG. 4B). However, the number of transgenes copies integrated in the absence of the transposase was generally significantly higher, ranging from 6 to 14 copies. This can be readily explained by the fact that spontaneous integration usually results in the integration of concatemers of multiple plasmid copies at a single genomic locus (results not shown), and that higher transgene copy numbers should lead to higher expression levels when cells subjected to silencing effects have been removed by antibiotic selection. Taken together with the prior conclusion that antibiotic selection preferentially yields highly expressing cells, this also indicated that spontaneous plasmid integration results in a more variable number of transgene copies than transposable vectors.

GFP expression was then normalized to the gene copy number to assess the intrinsic expression potential of the vectors, independently from their propensity to integrate in the genome. Overall, lower expression per transgene copy was obtained from unselected cells, or from antibiotic-selected cells transfected without transposase or centrally-located MAR, indicating that transgene expression is influenced both by the inclusion of the epigenetic regulatory element and by the mode of transgene integration (FIG. 5). Expression per gene copy was generally increased by the transposase, when assessed from various vectors and combination of elements, and this was observed with or without antibiotic selection. The highest levels of expression per transgene copy were obtained after antibiotic selection from the cells generated with the transposon vector containing the MAR element centrally located and in presence of the transposase. Inclusion of the MAR immediately downstream of the GFP coding sequence did not increase transgene expression significantly, as noted earlier for the absolute levels of expression.

Finally, it was assessed whether the favorable effect of MAR 1-68 on expression may be specific to the strong human GAPDH promoter used here, or whether it would also occur with other promoters. Thus we replaced the human GAPDH promoter driving GFP expression by the weaker simian virus 40 (SV40) early promoter. Use of the weaker promoter yielded comparable numbers of GFP-positive cells and of integrated transgenes, indicating that the transposition efficiency is not altered by transgene expression (results not shown and FIG. 2A and FIG. 4B). However, the absolute levels of expression were lower with the SV40 promoter (not shown vs. FIG. 3B). In addition, expression normalized to the transposon copy number was decreased by 4.6-fold by the use of the SV40 promoter in the absence of the MAR, and by 3.1-fold with MAR 1-68 (results not shown). This indicated that the MAR could partially, but not fully prevent the decrease of expression resulting from the use of a weaker promoter, even in presence of the transposase. Overall, it could be shown that a few integrated copies are sufficient to obtain high transgene expression from transposons, and that the highest expression per transgene is obtained when, in this context, MAR-68, is placed upstream of the strong promoter.

CHO-M cells were electroporated once or twice with a single transgene MAR X_29-containing transposable vector. Transposition efficiency was highest after electroporation (30%-45% of the cells showed stable expression). However, transgene expression levels were similar to chemical transfection, which showed lower positive cells, ergo lower transposition efficiency. FIG. 7 shows the results with light and heavy chains of therapeutic Immunoglobulins inserted upstream of the MAR X_29 and titles ranging from 1 to 8 μg/ml were obtained. The levels were further increased to 23-55 μg/ml by sorting the expressing cells (FIG. 7C).

Expression of transgenes can also be substantially increased, often independent of the use of transposons by specific vector designs, in particular by the use of specific MAR element(s) at specific locations relative to the transgene and, preferably a combination of those MAR element(s) with promoters, enhances or fusions thereof.

Figure 18A:
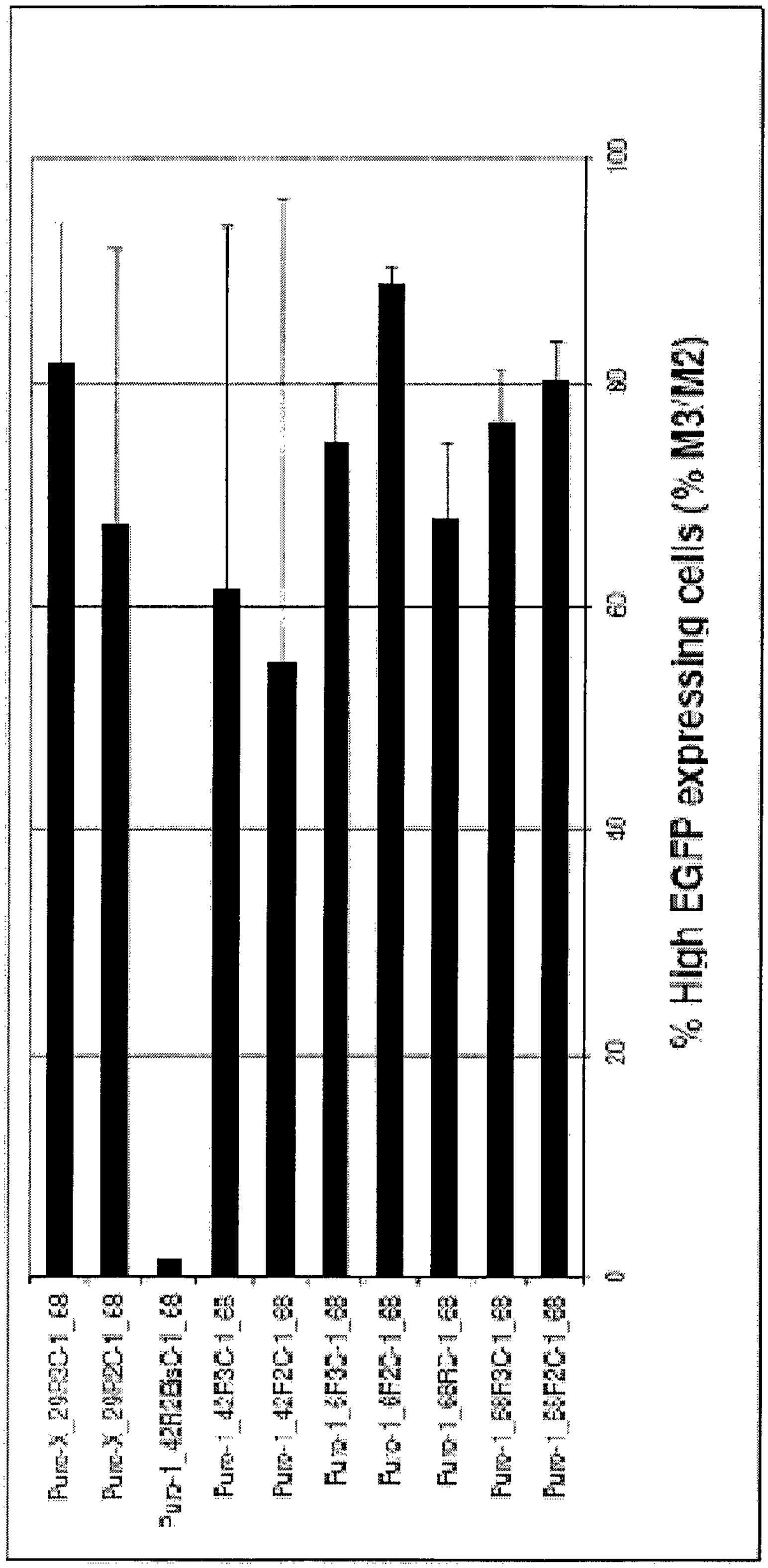
Figure 18B:
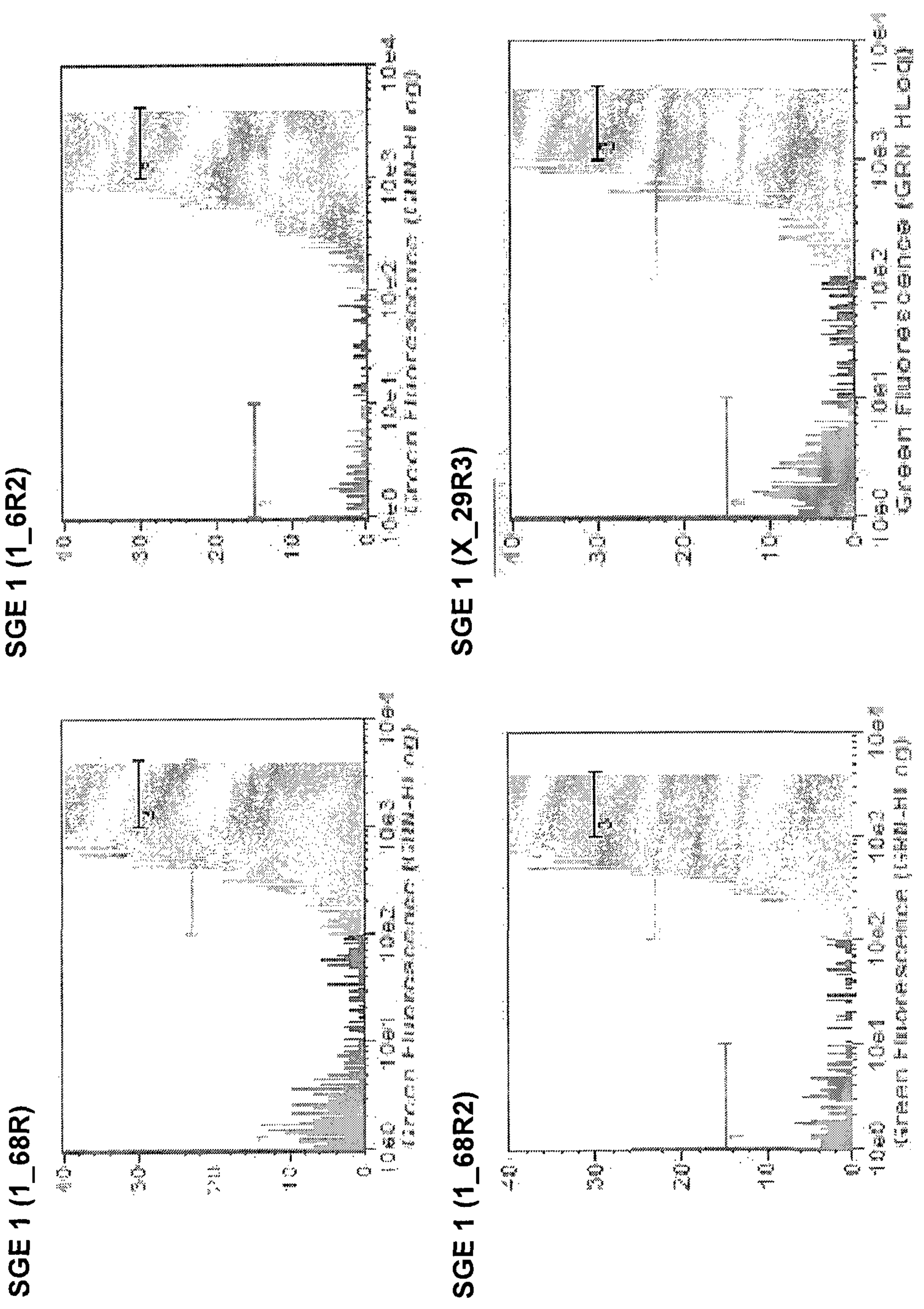

A respective vector may contain MARs that flank the transgene expression cassette. For example, the vector may contain, e.g., upstream MARs (one or more) and downstream MARs (one or more), e.g., one MAR positioned upstream and one MAR positioned downstream of a transgene expression cassette (FIG. 18A, FIG. 18B, FIG. 19). The vector may contain an integrated puromycin resistance gene under the control of the SV40 promoter. The transgene may be under the control of the human GAPDH promoter fused to the human cytomegalovirus (CMV) immediate-early genes enhancer (in particular the CGAPD fusion promoter as discussed above).

The highest percentile of high and very high producer cells (% M3/M2), as assessed for GFP fluorescence by FACS analysis and the least variability, could be obtained using are 1_6R2, 1_68R2 and X_29R3 as the upstream MAR (over 80%, 80% and over 80%). Thus, a percentile of high and very high producer cells (% M3/M2), of more than 70%, more than 75%, or more than 80%, are well within the scope of the present invention. As the person skilled in the art will understand, certain deviation from the specific sequence of theses MARs are permissible. Accordingly, vectors containing nucleic acid sequences having more than 80%, 85%, 90%, 95% sequence identities with SEQ ID Nos: 6, 7, 8, 9 and 10 are within the scope of the present invention (FIG. 18A, FIG. 18B).

Loss of expression in the bioreactor and/or in the absence of selection pressure often limits recovery of the protein of interest. Vectors containing the 1_68R2, 1_6R2 and X_29R3 MAR derivatives as the upstream MAR were tested over a period of 5 weeks of culture without selection, and GFP fluorescence was assessed weekly over this period. When considering the percentile of the M3 subpopulation, it was found that the 1_6R2 element as an upstream MAR and the unrearranged MAR 1-68 as a downstream MAR were the best tested combination in vectors with at least one upstream and one downstream two MARs (well above 80% after more than 2, 3, 4 weeks) (see, FIG. 19).

A similarly designed vector may also contain, e.g., just downstream MARs (one or more), e.g., one MAR positioned downstream of a transgenes expression cassette (FIGS. 20A, 20B, 21 and 22) and no upstream MAR. The vector may also in this case contain an integrated puromycin resistance gene under the control of the SV40 promoter. The transgene may be under the control of the human GAPDH promoter fused to the human cytomegalovirus (CMV) immediate-early genes enhancer. See, e.g., SEQ ID NO: 11 are others having sequence identities of more than 80%, 85%, 90% or 95%. Excellent results were achieved in such a single MAR constellation with X_29 as a MAR. The percentile of high GFP expressing cells (determined as above) and also the stability of expression over time (determined as above) is better then, e.g., that of high performing vectors in which MARs flanked the transgene expression cassette, namely a vector comprising a MAR 1_6R2 upstream and an unrearranged MAR 1-68 downstream (See FIG. 22). This finding contrast the well established assumptions that MARs are most effective when they flank the transgene (see U.S. Pat. No. 5,731,178). Stability of expression means that a DNA of interest, e.g., a transgene, is expressed by a cell population even after a certain period of time, e.g., after more than 4, 5, 6, 7, 8, 9, 10, 11, 12, 13 or 14 weeks at rate comparable (not more than 20%, 10 or 5% less) and particularly even higher as up to two weeks of the commencement of expression. Often stable expression is associated with a high percentile (e.g. more than 80%) or highly expressing subpopulation of cells.

Cellular Metabolic Engineering: Secretion Proteins

The secretion of heterologous proteins such as IgGs is dwarfed by improper polypeptide processing and low IgG production in cultured cells such as CHO cells.

It was observed that the expression of stress-induced chaperones like BiP is induced and that the chaperone is correctly localized in the ER and capable of interacting with the IgG precursor chains. However, IgGs containing particular variable sequences such as those found in Infliximab are nevertheless incorrectly processed and assembled, which leads to poor secretion. Therefore, the activation of the UPR response in these cells remains ineffective in rescuing significant level of immunoglobulin.

SRP14 was shown to be implicated in a molecular step of the secretion pathway that is limiting in CHO cells over-expressing an exogenous protein. Interestingly, this limiting step also occurs for the easy-to-express Trastuzumab that readily leads to high expressor clones. This conclusion followed the finding that expression of the human SRP14 readily restored expression of the LP clones, but that it also increased the secretion of the easily expressed IgG. SRP14 expression was found to increase the processing and availability of LC and HC precursors and to yield comparable levels of secretion for both types of IgGs. Overall, it demonstrated that SRP14 may be generally limiting when secreted proteins such as IgGs are over-expressed in CHO cells.

The strong effect obtained from the expression of SRP14 in CHO cells as observed in this study was unexpected and suggested that SRP14 causes an extended delay of the LC elongation in the difficult-to-produce IgG producer clones (FIG. 12B, point 1).

Prior work indicated that the signal peptide that emerges from a translating ribosome first interacts with the SRP54 subunit of the SRP particle, while association with SRP9 and SRP14 may block further elongation of the nascent polypeptide, resulting in translation arrest (Walter and Blobel 1981). In a second step, the ribosome-nascent polypeptide-SRP complex docks to the ER membrane through its interaction with the SR receptor (Gilmore et al., 1982; Walter et al., 1982). The SR may then coordinate the release of the SRP from the ribosome-nascent polypeptide complex and the association of the exit site of the ribosome with the translocon channel, through which the growing nascent polypeptide enters the ER (Lakkaraju et al., 2008). Then, the translation-coupled translocation may resume, leading to the removal of the signal peptide and to the synthesis of properly processed and secreted polypeptides.

Proper processing of the difficult-to-express IgGs might require an unusually long translational pausing, if the kinetics of docking onto the ER may be slower for particular combinations of IgG variable domain and signal peptide sequences, because of unfavorable structures of the nascent peptide. Thus, modulation of the translation arrest kinetic by expression of the exogenous human SRP14 component was considered in turn improve proper ER docking and the translocation of the pre-LC, and thus restore an efficient processing of the signal peptide (FIG. 12B, point 2). Consistently, the lowering of SRP14 levels in human cells lead to a lack of translation elongation delay in polysomes, which may result in the overextension of the nascent polypeptides beyond a critical length, after which the SRP may no longer properly target the The analysis of secretion intermediates and of possible cellular stress responses, followed by the systematic search of the upstream limiting activities that cause such stress response, and then finalized by the engineering of the CHO cell secretion metabolism has lead to a better understanding of the metabolic limitations of these cells and how to address them.

Heterologous Expression of SRP14 Restores Secretion and LC Processing

HP (high producer) and LP (Low producer) clones of IgG were co-transfected with a vector encoding the SRP14 component of SRP and with a neomycin resistance plasmid. Individual cells in the neomycin-resistant pool were separated by limiting dilution and subsequently tested for growth and immunoglobulin secretion in shaken culture dish batches. SRP14-expressing LP-derived subclones secreted significantly higher antibody amounts than their parental counterparts throughout the culture, and they yielded similar immunoglobulin titers as the HP SRP14-expressing subclones (FIGS. 8A and 8B, left panels).

Expression of SRP14 did not affect cell viability, but it appeared to slow down and prolong the growth of HP cell cultures up to similar cell densities (FIGS. 8A and 8B, right panels). Culture supernatants of the various subclones were collected and analyzed for antibody concentration. As shown in FIG. 8C, SRP14 expression enhanced the secretion from LP cells, leading to a 7-fold increase of the IgG specific productivity. Moreover, exogenous expression of SRP14 also improved IgG secretion from the HP subclones, leading to a 30% increase of the specific productivity. Interestingly, individual subclones expressing SRP14 secreted the difficult- and easy-to-express IgGs at essentially identical average rates, with median specific productivities exceeding 30 picogram per cell and per day (pcd). These very high IgG secretion levels were maintained for more than 6 months of culture, indicating that it is a stable property of SRP14-expressing cells.

To further investigate the relationship between SRP14 expression and IgG productivity, the SRP14 mRNA levels of the 5 individual SRP14-expressing LP subclones were analyzed by relative quantitative PCR. As shown in FIG. 8D, subclones overexpressed SRP14 at levels that ranged from 50 to nearly 200-fold over that of the endogenous CHO cell SRP14 mRNA. This was accompanied by an IgG secretion enhancement of 4 to 6-fold as compared to the LP control cell clone. Interestingly, the highest specific productivity was obtained from a subclone overexpressing SRP14 at an intermediate level, approximately 100-fold over the CHO cell secreted protein to the ER. Thus, CHO cells SRP14, and possibly also SRP54, would have a reduced affinity for signal sequences of the heterologous human Infliximab protein, leading to incorrect ER docking and/or to the elongation of the nascent peptide before proper docking has occurred. This would be corrected by the over-expression of human SRP14, lengthening of the time period during which the arrested ribosome-SRP complex may search for a properly organized docking site on the ER, despite the 'molecular jam' of over-expressed IgG proteins occurring at ER gates.

Consistently, overexpression of the SR and translocon, which may increase the ER capacity in terms of translocation, also resulted in an improvement of secretion, even in the absence of human SRP14 overexpression. Finally, it was demonstrated that the metabolic engineering of the secretory pathway, by the co-expression of combinations of human SRP, translocon and SR subunits, leads to further improvement of the protein secretion cellular capacity, yielding even higher secretion levels. Overall, it was concluded that SRP proteins, its receptor and the translocon may be generally limiting when secreted proteins such as human immunoglobulins are over-expressed by CHO cells.

Little has been known about the abundance of SRP and ER membrane components relative to secreted proteins and to ribosomes in different cell types, but translocation defects may conceivably arise in cells expressing high amounts of a recombinant protein. For instance, the SR and/or the translocon may become limiting when secreted proteins are expressed at abnormally high levels, or SRP14 may occur at sub-stoichiometric levels in CHO cells relative to other SRP subunits. Consistently, SRP9 and SRP14 are present in a 20-fold excess over other SRP proteins in primate cells but not in mouse cells, and over-expression of human SRP14 in normal human cells did not increase the efficiency of the secretion of the alkaline phosphatase. Furthermore, the human SRP14 is larger than its rodent counterpart, as it contains an alanine-rich tail at its C-terminus that is not found in the rodent SRP14. Thus, incorporation of the larger human SRP14 in the CHO SRP might lead to the formation of a functional SRP chimera of higher activity, in a dominant-positive effect.

The finding that the expression of cytosolic SRP components such as SRP14 leads to efficient processing and secretion of over-expressed proteins in CHO cells points to a bottleneck that can be used to improve recombinant protein yields. This bottleneck limits the expression of distinct and unrelated IgGs, and possibly also of the numerous other monoclonal antibodies and derivatives that constitute by far the most abundant class of recombinant therapeutic proteins.

endogenous SRP14 mRNA (SRP14-LP subclone E, not shown). This implied an interdependence of the level of SRP14 overexpression and IgG specific productivity up to a threshold level of SRP14 corresponding to a 100-fold increase over that of the endogenous expression level. This suggested that other components of the secretory pathway may in turn become limiting at very high levels of SRP14, and that balanced expression of the pathway components may be required for optimal IgG expression.

To test whether the increased specific productivity obtained during clonal cell line evaluation could be applied to a production process, the best HP and LP SRP14-expressing subclones were tested in shaken cultures dishes in fed-batch conditions (i.e. LP subclone E and HP subclone B of FIG. 8). The SRP14-expressing LP subclone yielded similarly high numbers of viable cells and immunoglobulin titers than the SRP14-expressing HP subclone, with a maximum of $8\times10^6$ cells/ml and above 2 g per liter at the end of the production run (FIGS. 9A and B).

The impact of SRP14 overexpression on immunoglobulin synthesis for these two subclones was next tested. This revealed that expression of human SRP14 in the LP-derived subclone led to normally processed and mature LC competent for folding and IgG assembly (FIG. 10A, LP lane S vs. lane-). Migration of the free HC was not affected, indicating that SRP14 expression acted specifically on the misprocessed LC of the difficult-to-express protein. Strikingly, SRP14 expression fully abolished the accumulation of aggregated LC in the Triton X-insoluble fraction (FIG. 9A, bottom panel). Expression of the control GFP protein did not improve protein solubility, nor did it restore proper processing of the LC (FIG. 10A, lane G of LP cells). Expression of SRP14 had no effect on the HC and LC migration pattern obtained from the HP subclone, and little effect was observed on the amount of the free chains and fully assembled IgG when compared to controls (FIG. 10A, lane G of HP cells).

Cycloheximide-based chase assays were performed to investigate the IgG folding and assembly kinetic as well as the fate of the IgG aggregates in the SRP14-expressing Infliximab producer subclone. In contrast to the parental LP cells exhibiting aggregated LC incompetent for IgG assembly, the SRP14-expressing LP subclone no longer accumulated Tx-100 insoluble LC (FIG. 9B, bottom panel). However, the free LC remained in small amounts relative to the free HC, as also noted for the HP cells, indicating that it was quickly incorporated into HC-LC dimers and the mature IgG and that it may be limiting IgG assembly (FIGS. 9A and 9B). Collectively, these results implied that SRP14 may play an essential role in LC processing by LP cells, and that additional SRP protein expression could improve the secretion of the difficult-to-express and easy-to-express IgGs up to similar levels.

Engineering of ER Translocation Improves Recombinant IgG Secretion

Given that overexpression of heterologous SRP14 increased IgG secretion up to a given threshold, it was reasoned that other components of the secretion pathway that interact directly or indirectly with SRP14 may become limiting in the SRP14-LP subclones. We therefore explored whether the overexpression of other components of the secretion pathway may also improve IgG expression, either alone or in combination with SRP14. These included the human SRP9 and SRP54 proteins that constitute the SRP complex together with SRP14, and subunits of the SRP receptor (SR) and the Sec61$\alpha$, $\beta$ and $\gamma$ subunits of the translocon.

In a first set of experiments, the best performing LP clone, namely LP clone E of FIG. 1, was transfected with expression vectors encoding SRP proteins or translocon proteins alone or in combinations. The resulting LP polyclonal cell pools were then evaluated for IgG production in batch cultivation. Expression of SRP components or of translocon proteins increased immunoglobulin secretion from these re-transfected LP polyclonal cell pools (FIG. 11A and data not shown). Compared to SRP14 expression alone, the overexpression of SRP protein combinations or of the translocon improved the specific productivity of transfected-LP polyclonal cell pools by an additional 20% to 40% (FIG. 11A, comparison of median values). These results clearly indicated that particular combinations were more potent to restore Infliximab secretion than the SRP14 expression alone, such as those consisting of the expression of the three SRP polypeptides and its receptor (SR), or the co-expression of the SR and of the translocon (FIG. 11A).

Whether the SRP14-expressing LP subclone E could be optimized further by the expression of SR and/or translocon combinations was also assessed. Compared to the 30 pcd of the SRP14-LP subclone E, polyclonal cell pools selected after transfection with the SR proteins and the translocon yielded specific productivities above 60 pcd for the difficult-to-express immunoglobulin (FIG. 10B). It was concluded that SR proteins and the translocon expressing vectors can also be used to generate clones with increased specific productivities as compared to SRP14-LP clone E, and that an approach based on series of consecutive transfection and selection cycles may be successfully applied.

Cellular Metabolic Engineering: Knock-Down of Recombination Pathways and Expression of TEPs and TEP Functional RNA To influence recombination, crucial DNA recombination genes can be silenced. Targets for knock-down are genes known from literature as crucial for particular recombination repair pathways in mammals (Table D). Since most of these genes are necessary for cell survival and development, their permanent silencing could result in reduced cell viability. Therefore, silencing these target genes transiently using RNA interference (RNAi) is preferred.

In cells treated with a mix of siRNAs against factors involved in the first steps of NHEJ, i.e. Ku 70, Ku80 and DNA-PKcs (one siRNA duplex per protein), the frequency of NHEJ events was significantly lower than in the untreated cells. Instead HR was more efficient in these cells, resulting in a reduced NHEJ to HR ratio (from 2.7:1 to 1.3:1). Conversely, in cells treated with siRNA targeted against an essential HR factor—Rad51, the HR-dependent GFP reconstitution was almost completely abolished, which increased the NHEJ:HR ratio to 5:1. These results seem to indicate that the HR and NHEJ reporter assay is sensitive enough to be used in the extrachromosomal form. They also further challenge the reliability of the previously used CHO mutant cell lines (notably the 51D1 cells, originally published as HR-negative cells, but seemingly capable of performing HR according to this assay—data not shown).

Increase of GFP expression and integration in the presence of MAR. In parallel experiments, CHO cells treated with different anti-HR or anti-NHEJ siRNAs were transfected with GFP or MAR-GFP containing plasmids. After two weeks of antibiotic selection the cells were assayed for GFP expression and integration by FACS and qPCR respectively. In all conditions tested the addition of the MAR resulted in a 4-5 fold increase of GFP expression compared to cells transfected with a plasmid without the MAR (FIG. 13, FIG. 14A), which is in line with previous reports (Grandjean et al., 2011). This increase was accompanied by an approx. 3-fold increase of integrated GFP copy number in cells transfected with the MAR-GFP plasmid as compared to cells that received the no-MAR vector (FIG. 13, FIG. 14A). There was also a 2-fold increase in the average GFP fluorescence per gene copy (FIG. 13, FIG. 14C), possibly due to a more favorable localization of the integration site (e.g. in a region rich in euchromatin). Therefore it could be hypothesized that MAR elements possess the ability to direct genes to genomic loci permissive for gene expression. A combination of antiHR siRNAs with MAR (siRNA: RAD51, Rad51C and Brca1) resulted in a fold change in mean GFP expression of above 11, while a singular antiHR-siRNA (si:RNA: Rad51 lead to a fold change of under 9. Other combinations such as a combination of siMMEJ siRNAs with MAR also led to improved expression relative to the singular siRNA (results not shown). Accordingly, combination of different siRNAs (2, 3, 4, 5, 6, 8, 9, 10) from targets in the same or different metabolic pathways, in particular the recombination pathway, are within the scope of the present invention.

No effect of NHEJ gene knock-down on transgene expression and integration. Treatment with siRNAs against the NHEJ proteins did not seem to significantly influence stable transgene expression. There was also no significant change in GFP copy number in the genome compared with the untreated cells (except in cells treated with the anti-53BP1 siRNAs, but only in the absence of the MAR, possibly pointing to an effect unlike recombination by the NHEJ pathway).

Increase of transgene expression and integration in the absence of HR factors. In contrast to the knock-down of NHEJ factors, the presence of siRNAs against HR proteins often resulted in a significant increase of stable GFP expression as compared to the untreated cells (except for Brca2, for which there was a significant decrease, but again only in the absence of the MAR) (FIG. 15A). As was the case with the silencing of NHEJ genes, the presence of the MAR resulted in an increased stable GFP expression and integration, as well as the expression per gene copy. This time however the silencing of HR factors enhanced this effect by 5 to 7-fold (the most striking being the knock-down of Rad51 reaching 7.4-fold higher GFP expression levels) (FIG. 15A), which could indicate that HR proteins counteract the positive effect of the MAR element on transgene expression. In the absence of the MAR, the increase in GFP expression was correlated with an elevated GFP copy number in the genome (results not shown). Surprisingly, this was not the case in the presence of MAR, indicating that the MAR-mediated increase in copy number was not affected by the HR protein knock-down (except for Rad51D siRNA). This seems to suggest that the absence of a functional HR repair pathway does not enhance the number of recombination events promoted by the MAR. Instead, it might stimulate the integration of the MAR and transgene in a more favorable locus allowing for its more efficient expression. This view is also supported by the elevated expression of individual GFP copies in the presence of the MAR in cells treated with the anti-HR siRNAs (FIG. 14C). Another possibility is that the number of plasmid copies integrated into the genome is already at its maximum in the control cells (with the amount of plasmid DNA used here) and cannot be further increased even in conditions more beneficial for the MAR.

Taken together these results suggest that the process of MAR-mediated transgene integration is preferentially mediated by a pathway opposed to homologous recombination, although likely not NHEJ since knock-down of its components had no effect on integration or expression. It could be hypothesized that this alternative pathway is less active in the presence of a functional HR pathway, but becomes more important if HR disabled.

Expression of Anti-HR shRNAS to Increase the Expression of Therapeutic Proteins

Three siRNA targeting Rad51 were converted into shRNA sequences that can form hairpin structures, and the shRNA coding sequence was inserted into a piggyBac transposon vector under the control of a GAPDH enhancer and CMV promoter fusion and followed by the MAR X-29, but devoid of an antibiotic selection gene. Suspension-adapted CHO-M cells were transfected three times with the transposon donor plasmid and the transposase expression vector, after which 30 individual cell clones were randomly picked using a ClonePix device. Parental cells as well as the pool of shRNA-expressing cell pool and clones were re-transfected with a GFP expression plasmid (namely the Puro-GFP-MAR X-29 construct), which was followed by puromycin selection of polyclonal pools of GFP-expressing cells. Comparison of the GFP fluorescence profile indicated that a higher proportion of medium to highly fluorescent cells (M2 cell population) or very highly fluorescent cells (M3 cell population) were obtained from the cell pool transfected with the shRNA vector as compared to the parental CHO-M cells (FIG. 17A).

Several shRNA-expressing clones mediated very high GFP levels, with over 80% of the antibiotic resistant cells being in the highly fluorescent M3 subpopulation 10 days after transfection, as exemplified by clone 16 and clone 26 (FIGS. 17A and B). High levels of GFP fluorescence were maintained in these two clones after 35 days of further culture without selection (FIG. 17C). In contrast, clone 17 did not express very high levels of GFP at day 10, and GFP expression appeared to be unstable (FIGS. 17B and C). Intermediate expression levels and stability were obtained from clone 8 and clone 22. These clones were also transfected with expression plasmids encoding the light and the heavy chain of the difficult-to-express Infliximab therapeutic antibody. As before, the clones 16 and 26 produced the highest levels of the antibody, followed by clones 8 and 22, whereas clone 17 expressed amounts of the immunoglobulin that were similar to the 0.5 to 1 pcd obtained from the parental CHO-M cells (FIG. 17D and data not shown). Cell clones displaying Rad51 mRNA levels that were most significantly reduced yielded high expression of both GFP and of the Infliximab immunoglobulin, indicating that increased transgene expression resulted from the decreased expression of the recombination protein (results not shown).

Thus, higher and more stable production levels of secreted therapeutic proteins such as Infliximab can be achieved from cells expressing a Rad51-targeting shRNA or from cell transiently transfected by siRNAs such as the Rad51-targeting siRNA.

Materials and Methods

Plasmids and DNA Vectors

The PB transposase expression vector pCS2+U5V5PBU3 contains the PB transposase coding sequence surrounded by the 5' and 3' untranslated terminal regions (UTR) of the *Xenopus laevis* β-globin gene. This plasmid was constructed as follows: the 3' UTR 317 bp fragment from pBSSK/SB10 (kindly provided by Dr S. Ivics) was inserted into pCS2+U5 (Invitrogen/Life Technologies, Paisley, UK) to yield pCS2+U5U3. The PB transposase coding sequence (2067 bp, GenBank accession number: EF587698) was synthesized by ATG:biosynthetic (Merzhausen, Germany) and cloned in the pCS2+U5U3 backbone between the two UTRs. The PB control vector corresponds to the unmodified pCS2+U5 plasmid (FIG. 1, left panel). The different transposons vectors used in this study were generated by introducing the PB 235 bp 3' and 310 bp 5' inverted terminal repeats (ITRs), synthesized by ATG:biosynthetic (Merzhausen, Germany), into the pBluescript SK-plasmid (pBSK ITR3'-ITR5', FIG. 1, right panel). The puromycin resistance gene ($Puro^R$), under the control of the SV40 promoter from pRc/RSV plasmid (Invitrogen/Life Technologies), was then inserted between the two ITRs. The MAR 1-68 and MAR X-29 elements, the puromycin resistance and GFP genes used in this study were as previously described. The immunoglobulin expression vectors and the SRP9, SRP14, SRP54, SRPRalpha, SRPRbeta, SEC61A1, SEC61B and SEC61G coding sequences were as described by Le Fourn et al. (*Metab. Eng., Epub* 2013 Feb. 1).

The GFP, immunoglobulin or secretion proteins were expressed using a eukaryotic expression cassette composed of a human CMV enhancer and human GAPDH promoter upstream of the coding sequence followed by a SV40 polyadenylation signal, the human gastrin terminator and a SV40 enhancer (see Le Fourn et al., 2013). Expression cassettes and/or MAR elements were inserted between the ITR sequences or in the bacterial vector backbone as illustrated in FIG. 1 and in figure legends using standard cloning methods.

Cell Culture and Transfection Analysis

The CHO DG44 cell line was cultivated in DMEM: F12 (Gibco) supplemented with Hypoxanthine/Thymidine (HT, Gibco) and 10% fetal bovine serum (FBS, Gibco). Transfections were performed using PEI (JetPRIME, Polyplus Transfection), according to the manufacturer's instructions. Cells were transfected with various amounts of pDNA sources of PB transposase (ranging from 0 to 1500 ng) for titration experiments or co-transfected with the optimal ratio of 300 ng of PB transposase expression plasmid and 300 ng of transposon donor plasmid. Two days after the transfection, cells were transferred to several Petri dishes depending on the experiment. For analysis of unselected transfected CHO cells, cells were replated without antibiotic selection for 3 weeks and the percentage of fluorescent cells and the fluorescence intensity of GFP positive cells were determined by FACS analysis using a CyAn ADP flow cytometer (Beckman Coulter). For gene copy number analysis of unselected cells, stable GFP positive CHO cells were sorted using a FACSAriaII. For antibiotic resistant colony-counting assays, 50,000 transfected cells were seeded in 100 mm plates and selected with 5 μg/ml puromycin for 2 weeks. Then, resistant colonies were fixed and stained in 70% EtOH 0.7% Methylene Blue for 10 min, and colonies >0.5 mm in diameter were counted. For GFP expression studies, cells were selected for two weeks before GFP fluorescence FACS analysis as described above.

CHO-M cells were maintained in suspension culture in SFM4CHO Hyclone serum-free medium (ThermoScientific) supplemented with L-glutamine (PAA, Austria) and HT supplement (Gibco, Invitrogen life sciences) at 37° C., 5% CO2 in humidified air. Transposon donor plasmids were transferred in these cells by electroporation according to the manufacturer's recommendations (Neon devices, Invitrogen). Quantification of immunoglobulin secretion was performed from batch cultures as described previously (see Le Fourn et al., 2013). Briefly, cell populations expressing immunoglobulins were evaluated in batch cultivation into 50 ml minibioreactor tubes (TPP, Switzerland) at 37° C. in 5% CO2 humidified incubator for 7 days. Immunoglobulin concentrations in cell culture supernatants were measured by sandwich ELISA.

qPCR Gene Copy Number Assays

Total DNA was isolated from CHO stable cell pools following transposition assays using the DNeasy Tissue Kit (Qiagen, Hilden, Germany) according to the manufacturer's protocol. The copy number of genome-integrated transgenes was assessed using 6 ng of genomic DNA by quantitative PCR using the SYBR Green-Taq polymerase kit from Eurogentec Inc and ABI Prism 7700 PCR machine (Applied Biosystems). The GFP-Forward: ACATTATGCCGGACAAAGCC, SEQ ID NO: 119 and GFP-Reverse: TTGTTTGGTAATGATCAGCAAGTTG, SEQ ID NO: 120 primers were used to quantify the GFP gene, while primers B2M-Forward: ACCACTCTGAAGGAGCCCA, SEQ ID NO: 121 and B2M-Reverse: GGAAGCTCTATCTGTGTCAA, SEQ ID NO: 122 were used to amplify the Beta-2 microglobulin gene. For the amplicon generated by the B2M primers, one hit was found per CHO haploid genome after alignment to our CHO genome assembly using NCBI BLAST software. As CHO are near-diploid cells, it was estimated that B2M is present at 2 copies per genome. The ratios of the GFP target gene copy number were calculated relative to that of the B2M reference gene, as described previously.

Sorting and Assay of Immunoglobulin-Expressing Cells

To magnetically sort IgG-expressing cells, transfected CHO-M cells were seeded at a cell density of $3\times10^5$ cells per ml in SFM4CHO medium (Thermo Scientific) supplemented with 8 mM L-glutamine and 1× HT supplement (both from Gibco), referred to as Complete Medium. After 4 days in culture, $2\times10^6$ cells were washed, re-suspended in PBS and incubated with a biotinylated human IgG (KPL216-1006) at a final concentration of 3 μg/ml, together with 30 μl pre-washed MyOne T1 streptavidin-coated Dynabeads (Invitrogen), on a rotary wheel for 30 minutes at room temperature. The cell and bead mix was then placed on a magnet to separate labeled cells from non-labeled cells. The beads were washed 4 times with a phosphate buffer saline (PBS) solution. After the final PBS wash, the beads and cells were re-suspended in 500 μl pre-warmed Complete Medium, transferred to a 24 well plate and incubated at 37° C. with 5% $CO_2$ After 24 h the magnetically-sorted polyclonal cells were separated from the beads and incubation was continued until the cells were of a sufficient density for expansion in 50 mL TPP spin tube bioreactors (TECHNO PLASTIC PRODUCTS AG, Switzerland).

Alternatively, two clones were isolated from non-sorted and non-selected populations expressing each of the three IgGs using a ClonePix device. Briefly, semi-solid media was used to immobilize single cells, and colonies secreting high amounts of IgG were picked ten days post-embedding. These cell lines were passaged every 3-4 days in spin tube bioreactors at a density of $3\times10^5$ cells/ml in a peptone-containing growth medium (Hyclone SFM4CHO supplemented with 8 mM glutamine) in a humidified incubator maintained at 37° C. and 5% CO2, with orbital shaking at 180 rpm.

IgG titers were determined from cells seeded at a cell density of $1\times10^5$ cells per ml and grown for 6 days in 5 ml of Complete Medium in 50 ml Spin tube bioreactors when assessing polyclonal cell populations. Alternatively, shake flask cultures of clonal populations were inoculated at a density of $3\times10^5$ cells/ml into SFM4CHO media to initiate the fed batch production process. Fed batch production assays were performed with 25 ml of culture volume in 125 ml shake flasks or 5 ml in 50 ml TPP culture tubes in humidified incubators maintained at 37° C. and 5% CO2 with shaking at 150 rpm (125 ml shake flask and spin tubes). The production was carried out for ten days by feeding 16%, of the initial culture volume of chemically defined concentrated feed (Hyclone, Cell Boost 5, 52 g/l) on days zero, three and six to eight. No glutamine and glucose feeding was applied during the culture run. The viability and viable cell density (VCD) of the culture was measured daily using a GUAVA machine (Millipore). A double sandwich ELISA assay was used to determine MAb concentrations secreted into the culture media.

Plasmids and Relative Quantitative PCR Analysis

Cloning vectors used in this study are the Selexis mammalian expression vectors SLXplasmid_082. The luciferase sequence of pGL3-Control Vector (Promega) was replaced by a eukaryotic expression cassette composed of a human CMV enhancer and human GAPDH promoter upstream of the EGFP coding sequence followed by a SV40 polyadenylation signal, the human gastrin terminator and a SV40 enhancer. Two human MAR-derived genetic elements are flanking the expression cassette and a puromycin resistance gene expressed from the SV40 promoter, whereas the SLX-plasmid_082 differ by the type of the MAR element located upstream of the expression cassette (hMAR 1-68 and hMAR X-29; Girod et al., 2007).

The trastuzumab and infliximab heavy and light chains cDNAs were cloned in a expression vector to replace EGFP. A vector carrying both the heavy and light chain expression cassette of each IgG was made by combining heavy and light chain expression cassettes together on one plasmid vector. The signal peptide sequence of all heavy and light chains are identical, as are the constant portions of the light chains. The constant portions of the heavy chains differ at several amino acid positions (DEL vs EEM variants).

PCR amplification primers and GenBank accession numbers of the SRP9, SRP14, SRP54, SRPRalpha, SRPRbeta, SEC61A1 and SEC61B cDNAs are listed elsewhere herein. The PCR products encoding secretion proteins were cloned into a vector to replace the EGFP sequence.

When multiple secretion proteins were co-expressed, the inverted terminal sequences of the piggyBac transposon were integrated into vectors to bracket the expression cassette, and the resulting vectors were co-transfected with a piggyBac transposase expression vector to improve transgene integration and obviate the need for antibiotic selection.

A typical PB transposase expression vector is pCS2+U5V5PBU3 which contains the PB transposase coding sequence surrounded by the 5' and 3' untranslated terminal regions (UTR) of the *Xenopus laevis* β-globin gene was used in related experiments. This plasmid was constructed as follows: the 3' UTR 317 bp fragment from pBSSK/SB10 was inserted into pCS2+U5 (Invitrogen/Life Technologies, Paisley, UK) to yield pCS2+U5U3. The PB transposase coding sequence (2067 bp, GenBank accession number: EF587698) was synthesized by ATG:biosynthetic (Merzhausen, Germany) and cloned in the pCS2+U5U3 backbone between the two UTRs. The PB control vector corresponds to the unmodified pCS2+U5 plasmid.

Different transposons vectors were generated by introducing the PB 235 bp 3' and 310 bp 5' inverted terminal repeats (ITRs), synthesized by ATG:biosynthetic (Merzhausen, Germany), into the pBluescript SK-plasmid (pBSK ITR3'-ITR5'). The neomycin phosphotransferase gene ($Neo^R$), under the control of the SV40 promoter from pRc/RSV plasmid (Invitrogen/Life Technologies), was then inserted between the two ITRs. The MAR 1-68 and MAR X-29 elements, the puromycin resistance and GFP genes used in this study were as previously described (Girod et al. 2007;

Grandjean et al. 2011; Hart and Laemmli 1998). The immunoglobulin expression vectors and the SRP9, SRP14, SRP54, SRPRalpha, SRPRbeta, SEC61A1 and SEC61B coding sequences are described herein. The secretion proteins were expressed using a eukaryotic expression cassette composed of a human CMV enhancer and human GAPDH promoter upstream of the coding sequence followed by a SV40 polyadenylation signal, the human gastrin terminator and a SV40 enhancer. Expression cassettes and/or MAR elements were inserted between the ITR sequences or in the bacterial vector backbone using standard cloning methods.

PiggyBac transposon systems including appropriate 3' and 5' ITRs as well as transposase are, e.g., available from SYSTEM BIOSCIENCE.

For relative quantitative PCR analysis, total RNA was extracted from 1.times.10.sup.5 cells and reverse transcribed into cDNA using the FastLane Cell cDNA Kit (Qiagen) according to the manufacturer's instructions. The expressions of SRP14 and GAPDH were quantified by qPCR using the Rotor Gene Q (Qiagen) and the LightCycler® 480 SYBR Green I Master (Roche) using primers. Messenger RNA levels of SRP14 were normalized to that of GAPDH using the Rotor-Gene Q Series Software (Qiagen).

Cell Culture, Stable Transfection and Subcloning of CHO Cell Lines

Suspension chinese hamster ovary cells (CHO-K1) were maintained in SFM4CHO Hyclone serum-free medium (ThermoScientific) supplemented with L-glutamine (PAA, Austria) and HT supplement (Gibco, Invitrogen life sciences) at 37° C., 5% CO2 in humidified air. CHO-K1 cells were transfected with trastuzumab or infliximab heavy and light chains expression vectors bearing puromycin resistance gene by electroporation according to the manufacturer's recommendations (Neon devices, Invitrogen). Two days later, the cells were transferred in T75 plates in medium containing 10 μg/ml of puromycin and the cells were further cultivated under selection for two weeks. Stable individual cell clones expressing Trastuzumab and Infliximab IgG were then generated by limiting dilution, expanded and analysed for growth performance and IgG production levels. Trastuzumab and Infliximab IgG-producing cell clones expressing the highest IgG levels were selected for further biochemical experiments. Some of these clones were then co-transfected with the SRP14 expressing vector and a plasmid bearing the neomycin resistance gene by electroporation. Cells were then cultivated in medium containing 300 μg/ml of G418 for two weeks as described above. Stable clones were isolated by limited dilution and SRP14 expression was confirmed by Q-PCR assays before culture expansion for biochemical analysis.

Batch and Fed-Batch Cultivation

Growth and production performances of individual clones expressing trastuzumab and infliximab were evaluated in batch cultivation into 50-ml minibioreactor (TPP, Switzerland) at 37° C. in 5% CO2 humidified incubator for 7 days. At day 3, day 4 and day 7 of the cell cultivation, cell density and viability were determined using the Guava EasyCyte flow cytometry system (Millipore). IgG titer in cell culture supernatants was measured by sandwich ELISA. Cell density ($Cv\cdot ml^{-1}$) and IgG titer values ($\mu g\cdot ml^{-1}$) were plotted at the indicated process time sampling day. The specific IgG productivity of the Trastuzumab and Infliximab expressing clones was determined as the slope of IgG concentration versus integral number of viable cell (IVCD) calculated from day 3 to day 7 (production phase), and expressed as pg per cell and per day (pcd).

For fed-batch production cultures, cells were seeded at 0.3×106 cells/ml into 125 ml shake flasks in 25 ml of SFM4CHO Hyclone serum-free medium. Cultures were maintained at 37° C. and 5% CO2 under agitation. Cultures were fed in a daily based with a commercial Hyclone Feed (ThermoScientific). Cell densities and IgG production were daily evaluated.

Proteins Expression and Aggregation Analysis

Soluble cytoplasmic proteins were extracted by permeabilizing cells with 1% Triton X-100 in PBS buffer in presence of a proteases inhibitor cocktail (Roche, inc). After incubation 30 min on ice, cells were centrifuged 10 min at 14,000 rpm. The supernatant was referred to as the "soluble cytosolic and ER proteins" fraction. The pellet was dissolved by sonication in urea Laemmli buffer (62.5 mM Tris, 2% SDS, 8 M Urea, 5% glycerol, bromophenol blue dye), yielding the aggregated and vesicular insoluble protein fraction. The soluble and insoluble fractions were then adjusted in Laemmli buffer containing or not 2-mercaptoethanol and boiled 8 min at 95° C. Reducing and non-reducing samples were separated on 10% or 4-10% gradient acrylamide gels by sodium dodecyl sulfate polyacrylamide gene electrophoresis (SDS-PAGE), respectively.

Proteins were then blotted onto a nitrocellulose membrane. After blocking in 5% milk diluted in TBS-Tween (20 mM Tris, 0.5 M NaCl, 0.1% Tween 20), membranes were analysed for different proteins using the following primary antibodies: anti-human IgG (H+L)-HRP conjugated donkey antibody (JK immunoresearch, #709 035 149, 1:5000), anti-human BiP rabbit polyclonal antibody (Cell signaling, BiP, C50B12, 1:2000), anti-human CHOP mouse monoclonal antibody (Cell signaling, CHOP, L63F7, 1:500), anti-human GAPDH goat polyclonal antibody. After overnight incubation at 4° C., each blot was probed with HRP conjugated anti-rabbit IgG or anti-mouse IgG (Cell signaling, 1:20000). Specific proteins recognized by each antibody were detected using ECL reagents and exposure to ECL film (Amersham Biosciences).

Cycloheximide-Based Proteins Chase Experiments

Cycloheximide-based chase experiments were carried out onto high (HP) and low (LP) IgG-producers CHO-K1 clones. Equal numbers of cells were plated into 6-wells plates in complete culture medium supplemented with 100 μM of cycloheximide (Sigma). At various time points, cells were harvested and lysed in PBS, 1% Triton X-100. The Tx-soluble and insoluble fractions were then resolved on 4-10% acrylamide non-reducing SDS-PAGE and immunoblotted with anti-human IgG antibody.

Differential Detergent Fractionation Assays

Fractionation of cytosolic from membrane proteins was performed by differential detergent extraction of cell pellet. Cells were first washed in 1 ml PBS, and the plasma membrane of Hp and LP cells was permeabilized in KHM buffer (110 mM KAc, 20 mM HEPES, 2 mM MgCl2, pH 7.2) containing 0.01% digitonin (Sigma) for 10 min in presence or not of 1% of Triton X-100. Semi-permeabilized cells were washed once in KHM buffer and Trypsin was added to 50 μg/ml 10 min at room temperature to digest the soluble proteins. Trypsin digestion was stopped by the addition of 1 mM PMSF and 4 mM AEBSF. Cells were collected by centrifugation and soluble proteins were extracted in presence of Triton X-100 and protease inhibitors as described in section 2.4. Reducing Laemmli buffer containing 2-mercaptoethanol was added to the pellet and supernatant fractions, which were then subjected to 8% SDS-PAGE. Immunoblotting was performed to detect IgG and BiP proteins.

Cross-Linking of Proteins and Western Blotting Analysis

Infliximab LP cells were washed once in PBS and incubated in with or without 1 mM of the dithiobis(succinimidyl propionate) (DSP) cross-linker (ThermoScientific) for 30 min on ice. Cross-linking was quenched by the addition of 50 mM of Tris-HCl (pH 7.4) for 10 min before protein extraction in 1% Triton X-100 containing PBS buffer. After centrifugation 10 min at 14,000 rpm in a microfuge, the Triton X-100 insoluble fraction or whole protein extract were analyzed by SDS-PAGE under reducing condition, immunoblotted and probed with anti-BiP and anti-LC antibodies. Equal amounts of Tx-insoluble fraction proteins were analyzed in parallel.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

TABLE A

TABLE A: EXEMPLARY LIST OF TEP PROTEINS EXPRESSED USING TRANSPOSON VECTORS

| | Name | Origin | Exp or KD[1] | NCBI Reference Sequence[2] | NCBI Reference Sequence[2] | Sequence variation[2] |
|---|---|---|---|---|---|---|
| Protein of protein secretion pathway | | | | | | |
| hSRP14 | *Homo sapiens* Signal Recognition Particle 14 kDa (Homologous Alu RNA Binding Protein) | Human | exp | NM_003134.4 | NP_003125.3 | C to G at CDS position 370 (Pro to Ala at aa position 124) [SEQ ID NO.: 12/13] |
| hSEC61A1 | *Homo sapiens* Sec61 alpha 1 subunit (*S. cerevisiae*) | Human | exp | NM_013336.3 | NP_037468.1 | [SEQ ID NO.: 14/15] |
| hSEC61B | *Homo sapiens* Sec61 beta subunit | Human | exp | NM_006808.2 | NP_006799.1 | [SEQ ID NO.: 16/17] |
| hSEC61G | *Homo sapiens* Sec61 gamma subunit | Human | exp | NM_014302.3 | NP_055117.1 | [SEQ ID NO.: 18/19] |
| hSRP54 | *Homo sapiens* signal recognition particle 54 kDa | Human | exp | NM_003136.3 | NP_003127.1 | [SEQ ID NO.: 20/21] IN LAST DOC |
| hSRP9 | *Homo sapiens* signal recognition particle 9 kDa | Human | exp | NM_001130440.1 | NP_001123912.1 | [SEQ ID NO.: 22/23] IN LAST DOC |
| hSRPRalpha | *Homo sapiens* Signal Recognition Particle Receptor, A Subunit | Human | exp | NM_003139.3 | NP_003130.2 | [SEQ ID NO.: 24/25] |
| hSRPRbeta | *Homo sapiens* Signal Recognition Particle Receptor, B Subunit | Human | exp | NM_021203.3 | NP_067026.3 | [SEQ ID NO.: 26/27] |
| hCANX | *Homo sapiens* calnexin | Human/ CHO | exp/ KD | NM_001746.3 | NP_001737.1 | [SEQ ID NO.: 28/29] |
| Proteins of one of the recombination pathways | | | | | | |
| hRAD51B | *Homo sapiens* RAD51 paralog B | Human/ CHO | exp/ KD | U84138.1 | AAC39723.1 | |
| Protein processing and metabolic proteins | | | | | | |
| hDerlin1 | *Homo sapiens* degradation in endoplasmic reticulum protein 1 | Human | exp | NM_024295.4 | NP_077271.1 | |
| hHNF-1a | Transcription Factor 1, Hepatic; LF-B1, Hepatic Nuclear Factor (HNF1), Albumin Proximal Factor | Human | exp | NM_000545.5 | NP_000536.5 | C to G at CDS position 51 (silent substitution), A to C at CDS position 79 (Ile to Leu at aa position 27), C to T at CDS position 1375 (silent substitution), G to A at CDS position 1460 (Ser to Asn at aa position 487) |
| hHNF-1b var1 | *Homo sapiens* HNF1 homeobox B (HNF1B) variant 1 | Human | exp | NM_000458.2 | NP_000449.1 | |
| hHNF-1b var2 | *Homo sapiens* HNF1 homeobox B (HNF1B) variant 2 | Human | exp | HM116553.1 | ADM43490.1 | |
| hHNF-4a | Hepatocyte Nuclear Factor 4, Alpha | Human | exp | NM_000457.3 | NP_000448.3 | |
| hVKORC1 | *Homo sapiens* Vitamin K Epoxide Reductase Complex, Subunit 1 | Human | exp | NM_024006.4 | NP_076869.1 | |
| hUCP2 | *Homo sapiens* uncoupling protein 2 (mitochondrial, proton carrier) | Human | exp | NM_003355.2 | NP_003346.2 | C to T at CDS position 164 (Ala to Val at aa position 55) |
| hUCP4 | *Homo sapiens* uncoupling protein 4 (mitochondrial, proton carrier) | Human | exp | NM_004277.3 | NP_004268.3 | [SEQ ID NO: 30/31] |

TABLE A-continued

| TABLE A: EXEMPLARY LIST OF TEP PROTEINS EXPRESSED USING TRANSPOSON VECTORS | | | | | | |
|---|---|---|---|---|---|---|
| | Name | Origin | Exp or KD[1] | NCBI Reference Sequence[2] | NCBI Reference Sequence[2] | Sequence variation[2] |
| hCMPSAT | *Homo sapiens* CMP-sialic acid transporter | Human | exp | NM_006416.4 | NP_006407.1 | [SEQ ID NO: 32/33] |
| hLMAN1 | *Homo sapiens* lectin, mannose-binding, 1 | Human | exp | NM_005570.3 | NP_005561.1 | |
| hMCFD2 | *Homo sapiens* multiple coagulation factor deficiency 2 | Human | exp | NM_001171506.2 | NP_001164977.1 | |
| CD-rST6Gal1 | Rat beta-galactoside alpha2,6-sialyltransferase-derived synthetic sequence | Selexis | exp | N/A | N/A | |
| rST6Gal1 | Rat beta-galactoside alpha2,6-sialyltransferase-derived synthetic sequence | Selexis | exp | N/A | NP_001106815.1 | [SEQ ID NO: 34/35] |
| hCOMSC | *Homo sapiens* C1GALT1-specific chaperone 1 (C1GALT1C1) variant 2 | Human | exp | NM_001011551.2 | NP_001011551.1 | [SEQ ID NO: 36/37] |
| hCIRP | *Homo sapiens* Cold Inducible RNA Binding Protein | Human | exp | NM_001280.2 | NP_001271.1 | T to C at CDS position 492 (silent substitution) |
| hGRP78 | *Homo sapiens* Immunoglobulin heavy chain binding protein | Human/ CHO | exp/ KD | NM_005347.4 | NP_005338.1 | |
| hTMX1 | *Homo sapiens* thioredoxin-related transmembrane protein 1 | Human | exp | NM_030755.4 | NP_110382.3 | T to G at CDS position 492 (silent substitution), G to A at CDS position 648 (silent substitution) |
| hp97 | *Homo sapiens* VCP valosin containing protein (predicted) | Human | exp | NM_007126.3 | NP_009057.1 | |
| hPEPD | *Homo sapiens* peptidase D (PEPD) variant 1 | Human | exp | NM_000285.3 | NP_000276.2 | C to T at CDS position 1131 (silent substitution |
| hT-Synthase | *Homo sapiens* core 1 synthase, glycoprotein-N-acetylgalactosamine 3-beta-galactosyltransferase, 1 (C1GALT1) | Human | exp | NM_020156.3 | NP_064541.1 | A to G at CDS position 107 (Asp to Gly at aa position 36) [SEQ ID NO: 38/39] |
| h4F2 | 4F2 heavy chain | Human | exp | AB018010.1 | BAA84649.1 | |
| hSPCA1 | *Homo sapiens* ATPase, Ca++ Transporting, Type 2C, Member 1 | Human | exp | NM_014382.2 | NP_055197.2 | |
| hST6Galnac5 | *Homo sapiens* ST6 (alpha-N-acetyl-neuraminyl-2,3-beta-galactosyl-1,3)-N-acetylgalactosaminide alpha-2,6-sialyltransferase 5 | Human | exp | NM_030965.1 | NP_112227.1 | |
| hDerlin2 | *Homo sapiens* degradation in endoplasmic reticulum protein 2 | Human | exp | NM_016041.3 | NP_057125.2 | |
| hMBTPS1 | *Homo sapiens* membrane-bound transcription factor peptidase, site 1 | Human | exp | NM_003791.2 | NP_003782.1 | C to T at CDS position 1317 (silent substitution) |
| hPRA1 | *Homo sapiens* Rab Acceptor 1 (Prenylated) | Human | exp | NM_006423.2 | NP_006414.2 | |
| hTPD52 | *Homo sapiens* tumor protein D52 | Human | exp | NM_001025252.1 | NP_001020423.1 | |
| hRAB1A var1 | *Homo sapiens* RAB1A (RAB1A) variant 1 | Human | exp | NM_004161.4 | NP_004152.1 | |
| hRAB1A var2 | *Homo sapiens* RAB1A (RAB1A) variant 2 | Human | exp | NM_015543.1 | NP_056358.1 | |
| hRAB1B | *Homo sapiens* RAB1B, member RAS oncogene family | Human | exp | NM_030981.2 | NP_112243.1 | |
| hP4HA1 | *Homo sapiens* prolyl 4-hydroxylase, alpha polypeptide | Human | exp | NM_000917.3 | NP_000908.2 | [SEQ ID NO: 40/41] |

TABLE A-continued

TABLE A: EXEMPLARY LIST OF TEP PROTEINS EXPRESSED USING TRANSPOSON VECTORS

| | Name | Origin | Exp or KD[1] | NCBI Reference Sequence[2] | NCBI Reference Sequence[2] | Sequence variation[2] |
|---|---|---|---|---|---|---|
| hP4HB | *Homo sapiens* prolyl 4-hydroxylase, beta polypeptide | Human | exp | NM_000918.3 | NP_000909.2 | [SEQ ID NO: 42/43] |
| hMGST1 | *Homo sapiens* microsomal glutathione S-transferase 1 | Human | exp | NM_145792.1 | NP_665735.1 | |
| hCRYAB | *Homo sapiens* crystallin, alpha B | Human | exp | NM_001885.1 | NP_001876.1 | |
| hGILZ | *Homo sapiens* TSC22 Domain Family, Member 3 | Human | exp | NM_198057.2 | NP_932174.1 | [SEQ ID NO: 44/45] |
| hCyPB | *Homo sapiens* Peptidylprolyl Isomerase B (Cyclophilin B) | Human | exp | NM_000942.4 | NP_000933.1 | [SEQ ID NO: 46/47] |
| hTIM21 | *Homo sapiens* translocase of inner mitochondrial membrane 21 homolog (TIMM21) | Human | exp | NM_014177.2 | NP_054896.2 | |
| hOGC | *Homo sapiens* Solute Carrier Family 25 (Mitochondrial Carrier; Oxoglutarate Carrier), Member 11 | Human | exp | NM_003562.4 | NP_003553.2 | |
| hNRF2 | nuclear factor, erythroid 2-like 2 | Human | exp | NM_006164.3 | NP_006155.2 | [SEQ ID NO: 48/49] |
| hHSP47 | *Homo sapiens* Serpin Peptidase Inhibitor, Clade H (Heat Shock Protein 47), Member 1, (Collagen Binding Protein 1) | Selexis | exp | N/A | NP_001226.2 | |
| hLAT1 | large neutral amino acid transporter | Human | exp | AB018009.1 | BAA84648.1 | |
| hPC | *Homo sapiens* pyruvate carboxylase | Human | exp | NM_000920.3 | NP_000911.2 | |
| hHK1 | *Homo sapiens* hexokinase 1 | Human | exp | NM_000188.2 | NP_000179.2 | G to A at CDS position 1443 (silent substitution) [SEQ ID NO: 50/51] |
| hPDI | *Homo sapiens* Protein disulfide isomerase family A, member 2 | Human | exp | NM_006849.2 | NP_006840.2 | G to A at CDS position 1347 (silent substitution) [SEQ ID NO: 52//53] |
| hBcl-xL | *Homo sapiens* BCL2-Associated Agonist Of Cell Death | Human | exp | NM_138578.1 | NP_612815.1 | |
| hTIM23 | *Homo sapiens* translocase of inner mitochondrial membrane 23 homolog (TIMM23) | Human | exp | NM_006327.2 | NP_006318.1 | |
| hPIN1 | *Homo sapiens* peptidylprolyl cis/trans isomerase, NIMA-interacting 1 | Human | exp | NM_006221.3 | NP_006212.1 | [SEQ ID NO: 54/55] |
| hSEPW1 | *Homo sapiens* selenoprotein W, 1 | Human | exp | NM_003009.2 | NP_003000.1 | [SEQ ID NO: 56/57] |
| hTOR1A | *Homo sapiens* torsin family 1, member A (torsin A) | Human | exp | NM_000113.2 | NP_000104.1 | |
| hHMGA1 | *Homo sapiens* high mobility group AT-hook 1 | Human | exp | NM_145899.2 | NP_665906.1 | |
| hP53 | Cellular tumor antigen p53 isoform a | Human | exp | NM_000546.5 | NP_000537.3 | |
| hNAP1 | *Homo sapiens* nucleosome assembly protein 1-like 1 | Human | exp | NM_004537.4 | NP_004528.1 | A to G at CDS position 471 (silent substitution) |
| hCOBRA1 | *Homo sapiens* Negative Elongation Factor Complex Member B | Human | exp | NM_015456.3 | NP_056271.2 | |
| NLS_DBD_PB | Synthetic DNA-binding protein | Selexis | exp | N/A | N/A | |
| NLS_DBD_VP16 | Synthetic DNA-binding protein | Selexis | exp | N/A | N/A | ] |

TABLE A-continued

TABLE A: EXEMPLARY LIST OF TEP PROTEINS EXPRESSED USING TRANSPOSON VECTORS

| | Name | Origin | Exp or KD[1] | NCBI Reference Sequence[2] | NCBI Reference Sequence[2] | Sequence variation[2] |
|---|---|---|---|---|---|---|
| hATF4 | *Homo sapiens* Activating Transcription Factor 4 | Human | exp | NM_001675.2 | NP_001666.2 | |
| hCALR | *Homo sapiens* calreticulin | Human | exp | NM_004343.3 | NP_004334.1 | [SEQ ID NO: 58/59] |
| hTAF-lalpha | *Homo sapiens* SET translocation (myeloid leukemia-associated) isoform 1 | Human | exp | NM_001122821.1 | NP_001116293.1 | |
| hCypA | *Homo sapiens* Peptidylprolyl Isomerase A (Cyclophilin A) | Human | exp | NM_021130.3 | NP_066953.1 | |
| hOct4 | *Homo sapiens* POU Class 5 Homeobox 1 | Human | exp | NM_002701.4 | NP_002692.2 | |
| hSox2 | *Homo sapiens* SRY (sex determining region Y)-box 2 | Human | exp | NM_003106.3 | NP_003097.1 | |
| hKlf4 | *Homo sapiens* Kruppel-like factor 4 (gut) | Human | exp | NM_004235.4 | NP_004226.3 | |
| hCAV1 | *Homo sapiens* caveolin 1, caveolae protein, 22 kDa | Human | exp | NM_001753.4 | NP_001744.2 | |
| hCHOP | *Homo sapiens* CHOP protein (product of DNA-damage-inducible transcript 3) | Human/ CHO | exp/ KD | NM_001195053.1 | NP_001181982.1 | |
| DroBiP | Synthetic BIP protein derivative | Selexis | exp | N/A | N/A | [SEQ ID NO: 60] Protein only |
| hDDOST | *Homo sapiens* dolichyl-diphosphooligosaccharide--protein glycosyltransferase subunit (non-catalytic) | Human | exp | NM_005216.4 | NP_005207.2 | [SEQ ID NO: 61/62] |
| hCDX1 | *Homo sapiens* caudal type homeobox 1 | Selexis | exp | N/A | NP_001795.2 | |
| hP5CS | *Homo sapiens* aldehyde dehydrogenase 18 family, member A1 (ALDH18A1) | Human | exp | NM_002860.3 | NP_002851.2 | |
| hHSP40 | *Homo sapiens* DnaJ (Hsp40) homolog, subfamily B, Member | Human | exp | NM_006145.1 | NP_006136.1 | [SEQ ID NO: 63/64] |
| helF4A1 | *Homo sapiens* eukaryotic translation initiation factor 4A1 | Human | exp | NM_001416.3 | NP_001407.1 | G to C at CDS position 147 (silent substitution) |
| hATP5A1 | *Homo sapiens* ATP synthase, H+ transporting, mitochondrial F1 complex, alpha subunit 1, cardiac muscle | Human | exp | NM_001001937.1 | NP_001001937.1 | [SEQ ID NO: 65/66] |
| hSERCA2 | *Homo sapiens* ATPase, Ca++ Transporting, Cardiac Muscle, Slow Twitch 2 | Human | exp | NM_170665.3 | NP_733765.1 | [SEQ ID NO: 67/68] |
| hPHB | *Homo sapiens* prohibitin | Human | exp | NM_002634.2 | NP_002625.1 | |
| hPDIA4 | *Homo sapiens* protein disulfide isomerase family A, member 4 | Human | exp | NM_004911.4 | NP_004902.1 | [SEQ ID NO: 69/70] |
| hPRPS/ MSMB | *Homo sapiens* beta-microseminoprotein isoform a precursor | Human | exp | NM_002443.3 | NP_002434.1 | |
| hH2AFZ | *Homo sapiens* H2A histone family, member Z | Human | exp | NM_002106.3 | NP_002097.1 | |
| hHSC70/ HSPA8 | *Homo sapiens* Heat shock cognate protein 70/heat shock protein 8 | Human | exp | NM_006597.4 | NP_006588.1 | [SEQ ID NO: 71/72] |
| hHYOU1 | *Homo sapiens* hypoxia up-regulated 1 | Human | exp | NM_006389.3 | NP_006380.1 | C to T at CDS position 543 (silent substitution), C to T at CDS position 1476 (silent substitution), A to G at CDS position 2235 (silent substitution) [SEQ ID NO: 73/74] |

TABLE A-continued

TABLE A: EXEMPLARY LIST OF TEP PROTEINS EXPRESSED USING TRANSPOSON VECTORS

| | Name | Origin | Exp or KD[1] | NCBI Reference Sequence[2] | NCBI Reference Sequence[2] | Sequence variation[2] |
|---|---|---|---|---|---|---|
| hST3GAL5_var1 | *Homo sapiens* ST3 beta-galactoside alpha-2,3-sialyltransferase 5 isoform 1 | Human | exp | NM_003896.3 | NP_003887.3 | |
| hST3GAL5_var2 | *Homo sapiens* ST3 beta-galactoside alpha-2,3-sialyltransferase 5 isoform 2 | Human | exp | NM_001042437.1 | NP_001035902.1 | |
| _NLS_DBD_CDX1_VP16 | Synthetic DNA-binding protein | Selexis | exp | N/A | N/A | |
| hc-Myc | *Homo sapiens* c-myc proto-oncogene protein | Human | exp | NM_002467.4 | NP_002458.2 | |
| hCG40346-ST3Gal1 | *Homo sapiens* ST3 beta-galactoside alpha-2,3-sialyltransferase 1 pseudogene 1 (ST3GAL1P1) on chromosome 4 | Human | exp | NG_025114.1 | N/A | |
| hXRCC5 | *Homo sapiens* X-ray repair complementing defective repair in Chinese hamster cells 5 (double-strand-break rejoining) | Human | exp | NM_021141.3 | NP_066964.1 | |
| hST3GAL1 | *Homo sapiens* ST3 beta-galactoside alpha-2,3-sialyltransferase 1 | Human | exp | NM_003033.3 | NP_003024.1 | G to A at CDS position 819 (silent substitution) |
| hCMP-SAS | cytidine monophosphate N-acetylneuraminic acid synthetase | Human | exp | NM_018686.4 | NP_061156.1 | C to T at CDS position 714 (silent substitution) [SEQ ID NO: 75/76] |
| hERO1-Lalpha | *Homo sapiens* ERO1-like (ERO1L) | Human | exp | NM_014584.1 | NP_055399.1 | |
| hXBP1_var1 | *Homo sapiens* X-box binding protein 1 (XBP1) variant 1 | Human | exp | NM_005080.3 | NP_005071.2 | |
| hASAH1 | *Homo sapiens* N-acylsphingosine amidohydrolase (acid ceramidase) 1 | Human | exp | NM_177924.3 | NP_808592.2 | T to C at CDS position 737 (Val to Ala at aa position 246) |
| hSPHK1 | *Homo sapiens* sphingosine kinase 1 | Human | exp | NM_021972.3 | NP_068807.2 | |
| hGadd45a | *Homo sapiens* Growth Arrest And DNA Damage-Inducible Protein GADD45 Alpha | Human | exp | NM_001924.3 | NP_001915.1 | |
| hASF1A | *Homo sapiens* anti-silencing function 1A histone chaperone | Human | exp | NM_014034.2 | NP_054753.1 | |
| hBeclin-1 | *Homo sapiens* Beclin 1, Autophagy Related | Human | exp | NM_003766.3 | NP_003757.1 | [SEQ ID NO: 77/78] |
| hRECQL5_var3 | *Homo sapiens* RecQ protein-like 5 (RECQL5), transcript variant 3 | Human | exp | NM_001003716.3 | NP_001003716.1 | |
| hMLH1 var 1 | *Homo sapiens* mutL homolog 1 (MLH1) variant 1 | Human | exp | NM_000249.3 | NP_000240.1 | T to Cat CDS position 1151 (Val to Asp at aa position 384) |
| hBlimp-1 | *Homo sapiens* PR Domain Containing 1, With ZNF Domain | Human | exp | NM_001198.3 | NP_001189.2 | |
| hMGMT | *Homo sapiens* O-6-methylguanine-DNA methyltransferase | Human | exp | NM_002412.3 | NP_002403.2 | |
| hERdj3 | *Homo sapiens* DnaJ (Hsp40) Homolog, Subfamily B, Member 11 | Human | exp | NM_016306.4 | NP_057390.1 | [SEQ ID NO: 79/80] |
| hRECQ1 | *Homo sapiens* RecQ Protein-Like (DNA Helicase Q1-Like) | Human | exp | NM_002907.3 | NP_002898.2 | |
| TAT_GyrA | Synthetic DNA-binding protein | Selexis | exp | N/A | N/A | |
| TAT_GyrB | Synthetic DNA-binding protein | Selexis | exp | N/A | N/A | |
| TAT_GyrB_EGFP | Synthetic DNA-binding protein | Selexis | exp | N/A | N/A | |

TABLE A-continued

TABLE A: EXEMPLARY LIST OF TEP PROTEINS EXPRESSED USING TRANSPOSON VECTORS

| | Name | Origin | Exp or KD[1] | NCBI Reference Sequence[2] | NCBI Reference Sequence[2] | Sequence variation[2] |
|---|---|---|---|---|---|---|
| NLS_GyrA | Synthetic DNA-binding protein | Selexis | exp | N/A | N/A | |
| NLS_GyrB | Synthetic DNA-binding protein | Selexis | exp | N/A | N/A | |
| hAC_Sc | *Homo sapiens* acid ceramidase isoform b | Selexis | exp | N/A | NP_004306.3 | |
| CHO_AGE | Chinese hamster Ovary N-acylglucosamine 2-epimerase-like | CHO | exp | XM_003497741.1 | XP_0003497789.1 | [SEQ ID NO: 81/82] |
| hWip1 | Wild-Type P53-Induced Phosphatase 1 | Human | exp | NM_003620.3 | NP_003611.1 | [SEQ ID NO: 83/84] |
| hRTP4 | *Homo sapiens* receptor (chemosensory) transporter protein 4 | Human | exp | NM_022147.2 | NP_071430.2 | C to T at CDS position 192 (silent substitution) [SEQ ID NO: 85/86] |
| hREEP2 | *Homo sapiens* receptor accessory protein 2 | Human | exp | NM_001271803.1 | NP_001258732.1 | [SEQ ID NO: 87/88] |
| hDPM1 | *Homo sapiens* dolichyl-phosphate mannosyltransferase polypeptide 1, catalytic subunit | Human | exp | NM_003859.1 | NP_003850.1 | [SEQ ID NO: 89/90] |
| hGS | *Homo sapiens* glutamate-ammonia ligase (glutamine synthetase) | Human | exp | NM_002065.5 | NP_002056.2 | |
| hDRiP78 | *Homo sapiens* DnaJ (Hsp40) Homolog, Subfamily C, Member 14 | Human | exp | XM_005269201.1 | XP_0005269258.1 | [SEQ ID NO: 91/92] |

[1]Exp indicates expression of the indicated human protein whereas KD indicates the knock down of the CHO protein. The term Selexis indicates a previously unknown sequence engineered by the applicants.
[2]The sequence of the expressed proteins is as indicated by the stated NCBI entry, unless variant sequences were expressed, and the variation are indicated under Sequence variations. N/A indicates a previously unknown sequence engineered by the applicants.

TABLE B

EXEMPLARY LIST OF shRNA EXPRESSED USING, E.G., SPECIFIC PIGGYBAC TRANSPOSON VECTORS

| | Vector-RNA placed between ITRs, MAR used | Size (bp) |
|---|---|---|
| 1 | pBSK_ITR_BT+_shRNA1_ccLDHA_X29_ITR claim 1 &25 | 8984 |
| 2 | pBSK_ITR_BT+_shRNA2_ccLDHA_X29_ITR | 8984 |
| 3 | pBSK_ITR_BT+_shRNA1_ccMEK1_X29_ITR | 8985 |
| 4 | pBSK_ITR_BT+_shRNA3_ccMEK1_X29_ITR | 8985 |
| 5 | pBSK_ITR_BT+_shRNA1_ccMEK2_X29_ITR | 8987 |
| 6 | pBSK_ITR_BT+_shRNA3_ccMEK2_X29_ITR | 8987 |
| 7 | pBSK_ITR_BT+_shRNA2_ccDNMT1_X29_ITR | 8987 |
| 8 | pBSK_ITR_BT+_shRNA3_ccDNMT1_X29_ITR | 8987 |
| 9 | pBSK_ITR_BT+_shRNA4_ccDNMT1_X29_ITR | 8987 |
| 10 | pBSK_ITR_BT+_shRNA1_ccDNMT3a_X29_ITR | 8987 |
| 11 | pBSK_ITR_BT+_shRNA2_ccDNMT3a_X29_ITR | 8987 |
| 12 | pBSK_ITR_BT+_shRNA3_ccDNMT3a_X29_ITR | 8987 |
| 13 | pBSK_ITR_BT+_shRNA1_ccRad51_X29_ITR | 8983 |
| 14 | pBSK_ITR_BT+_shRNA2_ccRad51_X29_ITR | 8983 |
| 15 | pBSK_ITR_BT+_shRNA3_ccRad51_X29_ITR | 8983 |
| 16 | pBSK_ITR_BT+_shRNA1_ccIFNAR1_X29_ITR | 8987 |
| 17 | pBSK_ITR_BT+_shRNA2_ccIFNAR1_X29_ITR | 8987 |
| 18 | pBSK_ITR_BT+_shRNA3_ccIFNAR1_X29_ITR | 8983 |
| 19 | pBSK_ITR_BT+_shRNA1_ccP2X7_X29_ITR | 8983 |
| 20 | pBSK_ITR_BT+_shRNA2_ccP2X7_X29_ITR | 8983 |
| 21 | pBSK_ITR_BT+_shRNA3_ccP2X7_X29_ITR | 8983 |
| 22 | pBSK_ITR_BT+_shRNA1_mPEPCK_X29_ITR | 8987 |
| 23 | pBSK_ITR_BT+_shRNA2_mPEPCK_X29_ITR | 8987 |
| 24 | pBSK_ITR_BT+_shRNA3_mPEPCK_X29_ITR | 8987 |
| 25 | pBSK_ITR_BT+_shRNA1_ccBiP_X29_ITR | 8983 |
| 26 | pBSK_ITR_BT+_shRNA2_ccBiP_X29_ITR | 8983 |
| 27 | pBSK_ITR_BT+_shRNA3_ccBiP_X29_ITR | 8983 |
| 28 | pBSK_ITR_BT+_shRNA1_ccP53_X29_ITR | 8987 |
| 29 | pBSK_ITR_BT+_shRNA2_ccP53_X29_ITR | 8987 |
| 30 | pBSK_ITR_BT+_shRNA3_ccP53_X29_ITR | 8987 |
| 31 | pBSK_ITR_BT+_shRNA1_pre-miR-466h-5p_X29_ITR | 8985 |
| 32 | pBSK_ITR_BT+_shRNA1_miR-466h-5p_X29_ITR | 8985 |

TABLE C

LIST OF EXAMPLES OF siRNAs (SENSE STRAND) AND EXAMPLES OF shRNAS CREATED FROM CORRESPONDING siRNAS

53BP1_1
UCAGAAUGAUGACAAAGUA (SEQ ID NO: 123)

53BP1_2
GAGCAAGGAGACAAUAAUA (SEQ ID NO: 124)

53BP1_3
CAAAGACAUCCCUGUUACA (SEQ ID NO: 125)

Brca1_1
CCACGUAACUGAAAUUAUA (SEQ ID NO: 126)

Brca1_2
AAGGCUGAGUUCUAUAAUA (SEQ ID NO: 127)

Brca1_3
AGAGCCAAAUGAACAAAGA (SEQ ID NO: 128)

Brca2_1
GAAGCUGUUUACAGAAUGA (SEQ ID NO: 129)

Brca2_2
CAAUGACUAUACAGACAAA (SEQ ID NO: 130)

Brca2_3
AACAGACGGUUGCCAUAAA (SEQ ID NO: 131)

cycD1_1
UGGAACUCCUUCUGGUGAA (SEQ ID NO: 132)

TABLE C-continued

LIST OF EXAMPLES OF siRNAs (SENSE STRAND) AND EXAMPLES OF shRNAS CREATED FROM CORRESPONDING siRNAS cycD1_2
CGCACUUUCUUUCCAGAGU (SEQ ID NO: 133)

cycD1_3
UGCCAGAGGCGGAUGAGAA (SEQ ID NO: 134)

DNA-PKcs_1
GGAUCGAGCUGUUCAGAAA (SEQ ID NO: 135)

DNA-PKcs_2
AGAUGAUGUUCACUCUAAA (SEQ ID NO: 136)

DNA-PKcs_3
AUCCAUCGGUAUCUUUAAA (SEQ ID NO: 137)

Ku70_1
GGUGCCCUUUACUGAGAAA (SEQ ID NO: 138)

Ku70_2
AAAGCCCAAGGUAGAGUUA (SEQ ID NO: 139)

Ku70_3
ACAUUUCCAAGACACAAUU (SEQ ID NO: 140)

Ku80_1
GAAACUGUCUAUUGCUUAA (SEQ ID NO: 141)

Ku80_2
CCAUAGGGAAGAAGUUUGA (SEQ ID NO: 142)

Ku80_3
GGAUUCCUAUGAGUGUUUA (SEQ ID NO: 143)

LigIV_1
AGAGCCUCCUUCAGUUAAU (SEQ ID NO: 144)

LigIV_2
CUAUACAGCAGGUAAAUGA (SEQ ID NO: 145)

LigIV_3
AGAGGUAUGAUAUCCUUAA (SEQ ID NO: 146)

Rad51_1
GUGCCAAUGAUGUGAAGAA (SEQ ID NO: 147)

*Corresponding Rad51 shRNA coding sequence:
ACAAGCTTGTGCCAATGATGTGAAGAATTCAAGAGATTCTTCACATCATTGGCACTCTAGAGTCGGGGCGGCCGGCC (SEQ ID NO: 148)

Rad51 _2
GGGAAUUAGUGAAGCCAAA (SEQ ID NO: 149)

**Corresponding Rad51 shRNA coding sequence:
ACAAGCTTGGGAATTAGTGAAGCCAAATTCAAGAGATTTGGCTTCACTAATTCCCTCTAGAGTCGGGGCGGCCGGCC (SEQ ID NO: 150)

Rad51_3
GGCGUUCAGAAAUCAUACA (SEQ ID NO: 151)

**Corresponding Rad51 shRNA coding sequence:
ACAAGCTTGGCGTTCAGAAATCATACATTCAAGAGATGTATGATTTCTGAACGCCTCTAGAGTCGGGGCGGCCGGCC (SEQ ID NO: 152)

Rad51b_1
ACAGCCUAUGAUAUAAAGA (SEQ ID NO: 153)

Rad51b_2
CAAGUUCUUGGCCAAACAA (SEQ ID NO: 154)

Rad51b_3
GUACCUGGCUGAGGAAUUU (SEQ ID NO: 155)

Rad51c_1
UGAUCAGCCUGGCAAAUAA (SEQ ID NO: 156)

TABLE C-continued

| LIST OF EXAMPLES OF siRNAs (SENSE STRAND) AND EXAMPLES OF shRNAS CREATED FROM CORRESPONDING siRNAS |
|---|
| Rad51c_2<br>AGAGGAAGCUUUAGAAACU (SEQ ID NO: 157) |
| Rad51c_3<br>GGAUGAAGAACACCAGAAA (SEQ ID NO: 158) |
| Rad51d_1<br>ACGGAGCAGACCUAUAUGA (SEQ ID NO: 159) |
| Rad51d_2<br>CCCAAGAUGAGGAGAAACA (SEQ ID NO: 160) |
| Rad51d_3<br>GCCUGGACAAACUACUUGA (SEQ ID NO: 161) |
| Rad52_1<br>UGAGAUGUUUGGUUACAAU (SEQ ID NO: 162) |
| Rad52_2<br>ACUGCAUUCUGGACAAAGA (SEQ ID NO: 163) |
| Rad52_3<br>CCCUGAAGACAACCUUGAA (SEQ ID NO: 164) |
| Rad54_1<br>AGAAGACCUGCUAUAUUUA (SEQ ID NO: 165) |
| Rad54_2<br>CAUCAGAUAUCCUCUCUAA (SEQ ID NO: 166) |
| Rad54_3<br>GAAGCUAUGUAACCAUCCA (SEQ ID NO: 167) |
| Xrcc2_1<br>GAAGUGUUCUCAGCUCCUA (SEQ ID NO: 168) |

TABLE C-continued

| LIST OF EXAMPLES OF siRNAs (SENSE STRAND) AND EXAMPLES OF shRNAS CREATED FROM CORRESPONDING siRNAS |
|---|
| Xrcc2_2<br>CAACACAAAGUCUAAUGCA (SEQ ID NO: 169) |
| Xrcc2_3<br>AUCAGAGGGUGGACUGCAA (SEQ ID NO: 170) |
| Xrcc3_1<br>CCACAUCUUCAUCGAGCAU (SEQ ID NO: 171) |
| Xrcc3_2<br>ACGGUGGAGGAGCAAGAGU (SEQ ID NO: 172) |
| Xrcc3_3<br>GAUCAGAUUCAGCAACCAC (SEQ ID NO: 173) |
| Xrcc4_1<br>AUAUGCUGAUGAAUUGAGA (SEQ ID NO: 174) |
| Xrcc4_2<br>CUGAAAGAUGUCUCAUUUA (SEQ ID NO: 175) |
| Xrcc4_3<br>AUGAGCACCUGCAGAAAGA (SEQ ID NO: 176) |
| Neg. Control 1<br>AGGUAGUGUAAUCGCCUUG (SEQ ID NO: 177) |
| Neg. Control 2<br>GACGACUCACAUACGUAAA (SEQ ID NO: 178) |
| Neg. Control 3<br>GAAUAUAUCGCGAAAUGUA (SEQ ID NO: 179) |

(*)()(*) illustrate the structure of a shRNA-encoding DNA sequence from the siRNA sequences listed using the Rad51-targeted molecules as examples. The DNA sequence corresponding to the shown siRNA strand is underlined, whereas the complementary sequence allowing hairpin formation is underlined twice.

TABLE D

SELECTED GENES OF CERTAIN RECOMBINATION PATHWAYS

| Recombination pathway | Target gene [sequence identifiers in brackets identify sequences of example genes] | Full name of target gene | Transfected vector GFP[1] | Transfected vector MAR-GFP[1] | No exp. |
|---|---|---|---|---|---|
| NHEJ | Xrcc4 | X-ray repair complementing defective repair in Chinese hamster cells 4 | 0 | 0 | 3 |
| | Ku70 | X-Ray Repair Complementing Defective Repair In Chinese Hamster Cells 6 | – | 0 | 3 |
| | Ku80 | X-ray repair complementing defective repair in Chinese hamster cells 5 (double-strand-break rejoining) | – | 0 | 3 |
| | LigIV | Ligase IV, DNA, ATP-Dependent | 0 | 0 | 3 |
| | DNA-PKcs | Protein Kinase, DNA-Activated, Catalytic Polypeptide | – | 0 | 3 |

TABLE D-continued

SELECTED GENES OF CERTAIN RECOMBINATION PATHWAYS

| Recombination pathway | Target gene [sequence identifiers in brackets identify sequences of example genes] | Full name of target gene | Transfected vector GFP[1] | MAR-GFP[1] | No exp. |
|---|---|---|---|---|---|
| | 53BP1 [SEQ ID NO.: 109] | Tumor suppressor p53-binding protein 1 | + | + | 3 |
| HR | Rad51 [SEQ ID NO.: 93] | RAD51 recombinase // DNA repair protein RAD51 | +++ | +++ | 14 |
| | Rad51B [SEQ ID NO.: 94] | RAD51 paralog B // DNA repair protein RAD51 homolog 2 | − | 0 | 3 |
| | Rad51C [SEQ ID NO.: 95] | RAD51 paralog C // DNA repair protein RAD51 homolog 3 | + | + | 4 |
| | Rad51D [SEQ ID NO.: 96] | RAD51 paralog D // DNA repair protein RAD51 homolog 4 | 0 | +++ | 4 |
| | Rad52 [SEQ ID NO.: 97] | RAD52 // DNA repair protein RAD52 | + | ++ | 3 |
| | Rad54 [SEQ ID NO.: 98] | RAD54 // DNA repair and recombination protein RAD54 | + | ++ | 3 |
| | Xrcc2 [SEQ ID NO.: 99] | X-ray repair complementing defective repair in Chinese hamster cells 2 // DNA repair protein XRCC2 | 0 | + | 3 |
| | Xrcc3 [SEQ ID NO.: 100] | X-ray repair complementing defective repair in Chinese hamster cells 3 // DNA repair protein XRCC3 | + | +++ | 3 |
| | Brca1 [SEQ ID NO.: 101] | breast cancer 1, early onset // breast cancer type 1 susceptibility protein | + | ++ | 3 |
| | Brca2 [SEQ ID NO.: 102] | breast cancer 2, early onset // breast cancer type 2 susceptibility protein | −− | 0 | 3 |
| | Cyclin D1 [SEQ ID NO.: 103] | Cyclin D1 | 0 | +++ | 3 |
| | Bard1 [SEQ ID NO.: 106] | BRCA1 associated RING domain 1 // BRCA1 associated RING domain 1 | + | ++ | 2 |
| MRN | Mre11 [SEQ ID NO.: 108] | Mre11 = meiotic recombination 11 // Double-strand break repair protein MRE11 | 0 | +++ | 6 |
| | Rad50 | RAD50 Homolog (*S. Cerevisiae*) | −− | + | 3 |
| | Nbs1 | Nibrin | −−− | + | 3 |

TABLE D-continued

| SELECTED GENES OF CERTAIN RECOMBINATION PATHWAYS | | | | | |
|---|---|---|---|---|---|
| Recombination pathway | Target gene [sequence identifiers in brackets identify sequences of example genes] | Full name of target gene | Transfected vector GFP[1] | MAR-GFP[1] | No exp. |
| MMEJ | Ercc1 [SEQ ID NO.: 104] | excision repair cross-complementing rodent repair deficiency, complementation group 1 // DNA excision repair protein ERCC-1 | + | + | 3 |
| | Xpf | excision repair cross-complementing rodent repair deficiency, complementation group 4 | 0 | 0 | 1 |
| | Pol theta | Polymerase (DNA directed), theta | 0 | 0 | 3 |
| | Ligase I [SEQ ID NO.: 107] | DNA ligase 1 // DNA ligase 1 | + | + | 1 |
| | Ligase III | Ligase III, DNA, ATP-Dependent | 0 | 0 | 5 |
| | Xrcc1 | X-ray repair complementing defective repair in Chinese hamster cells 1 | 0 | 0 | 3 |
| | CtIP | mediator of DNA-damage checkpoint 1 // Mediator of DNA damage checkpoint protein 1 | + | + | 1 |
| | PARP1 | mediator of DNA-damage checkpoint 1 // Mediator of DNA damage checkpoint protein 1 | + | + | 3 |
| | POLD3 | | 0 | 0 | 2 |
| DNA repair proteins | MDC1 [SEQ ID NO.: 105] | mediator of DNA-damage checkpoint 1 // Mediator of DNA damage checkpoint protein 1 | + | − | 1 |
| | MSH2 | mutS homolog 2 | 0 | 0 | 3 |

[1]Type of effect of the knock-down on GFP transgene expression; + positive effect, ++ statistically significant positive effect ($p < 0.05$), +++ statistically highly significant positive effect ($p < 0.01$), − negative effect, −− statistically significant negative effect ($p < 0.05$), −−− statistically highly significant negative effect ($p < 0.01$).

What we claim is:

1. A recombinant nucleic acid molecule that is part of a transposon vector comprising:

a) a 5' transposon-specific inverted terminal repeat (ITR) and a 3' ITR, and b) located between the 5' ITR and the 3' ITR:

(i) at least one nucleic acid sequence encoding a transgene expression processing (TEP) protein under the control of a promoter, wherein the TEP is selected from the group consisting of human Signal Recognition Particle 14 (hSRP14), human Protein Transport Protein 61α1 (hSec61α1), human Protein Transport Protein 61β (hSec61β), human Protein Transport Protein 61γ (hSec61γ), human Signal Recognition Particle 54 (hSRP54), human Signal Recognition Particle 9 (hSRP9), human Signal Recognition Particle Receptor α (hSRPRα), human Signal Recognition Particle β (hSRPβ), human Calnexin (hCANX), and combinations thereof, and (ii) a matrix attachment region (MAR) element, wherein the transposon vector increases an expression of a transgene encoding a product of interest in a mammalian cell by at least 10% relative to a plasmid vector comprising the TEP protein.

2. The recombinant nucleic acid molecule according to claim 1, wherein said MAR is a singular MAR element and is selected from SEQ ID Nos: 1 (MAR 1-68), or 3 (MAR X_S29), an engineered counterpart thereof, or has at least 80%, 90%, 95%, 98%, 99% or 100% sequence identity with any one of SEQ ID Nos: 1 or 3.

3. The recombinant nucleic acid molecule according to claim 2, wherein said singular MAR element is directly upstream of the 3' ITR.

4. The recombinant nucleic acid molecule according to claim 1, wherein said nucleic acid molecule is at least 5000, 6000, 7000, 8000, 90000 or 10000 base pairs (bps) long.

5. The recombinant nucleic acid molecule according to claim 1, wherein the transposon vector further comprises, between the 5' ITR and the 3' ITR (iii) an expression cassette, wherein the MAR element is located downstream of the expression cassette but not upstream of the expression cassette.

6. The recombinant nucleic acid molecule according to claim 5, wherein the expression cassette comprises a transgene promoter.

7. The recombinant nucleic acid molecule according to claim 6, further comprising, located between the 5' ITR and the 3' ITR at least one transgene encoding a product of interest under the control of the transgene promoter.

8. The recombinant nucleic acid molecule according to claim 7, wherein the MAR element is a singular MAR element.

9. The recombinant acid molecule of claim 7, wherein the product of interest is an antibiotic resistance protein or an immunoglobulin.

10. The recombinant nucleic acid molecule according to claim 7, further comprising a polyadenylation signal downstream of the transgene, and the MAR element is a singular MAR element downstream of the polyadenylation signal.

11. The recombinant nucleic acid molecule according to claim 8, wherein the singular MAR is a MAR 1-68 or a MAR X-S29 element, a MAR element that has at least 80%, 90%, 95%, 98%, 99% or 100% sequence identity with SEQ ID No: 1, or a MAR element that has at least 80%, 90%, 95%, 98%, 99% or 100% sequence identity with SEQ ID No: 3.

12. The recombinant nucleic acid molecule according to claim 8, wherein said product of interest is a therapeutic protein.

13. The recombinant nucleic acid molecule of claim 8, wherein the TEP protein corresponds to one or more of the following amino acid sequences: hSRP14 having SEQ ID NO: 13, hSec61α1 having SEQ ID NO:15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29, or amino acid sequences having more than 80%, 90%, 95% or 98% sequence identity with said sequences.

14. The recombinant nucleic acid molecule according to claim 11, wherein the singular MAR element has at least 80%, 90%, 95%, 98%, 99% or 100% sequence identity with SEQ ID NOs: 6, 7, 9 or 10.

15. The recombinant nucleic acid molecule according to claim 11, wherein the singular MAR element is a MAR X-S29 element or a MAR element that has at least 80%, 90%, 95%, 98%, 99% or 100% sequence identity with SEQ ID NO. 3.

16. The recombinant nucleic acid molecule according to claim 1, wherein the promoter of b) is a fusion promoter or a combination of promoters and enhancers, wherein the promoter or promoters are selected from the group consisting of Glyceraldehyde 3-phosphate dehydrogenase (GAPDH), cytosolic Glyceraldehyde 3-phosphate dehydrogenase (cGAPDH), Simian vacuolating virus 40 promoter (SV40p), Cytomegalovirus promoter (CMVp), Chinese Hamster Ovary elongation factor 1 α (CHO EF1α), Chinese Hamster Ovary Actin β (CHO Actβ), and Chinese Hamster Ovary Heat shock protein family A member 5 (CHO Hspa5), and are optionally followed by a Bovine Growth Hormone polyadenylation (BGH polyA) signal.

17. The recombinant nucleic acid molecule according to claim 1, wherein the promoter is a fusion promoter or a combination of promoters and enhancers, wherein the promoter or promoters are selected from the group consisting of GAPDH, cGAPDH, CHO Actβ, and CHO Hspa5.

18. The recombinant nucleic acid molecule of claim 1, wherein the TEP protein corresponds to one or more of the following amino acid sequences: hSRP14 having SEQ ID NO: 13, hSec61α1 having SEQ ID NO: 15, hSec61β having SEQ ID NO: 17, hSec61γ having SEQ ID NO: 19, hSRP54 having SEQ ID NO: 21, hSRP9 having SEQ ID NO: 23, hSRPRα having SEQ ID NO: 25, hSRPβ having SEQ ID NO: 27, and hCANX having SEQ ID NO: 29, or amino acid sequences having more than 80%, 90%, 95% or 98% sequence identity with said sequences.

19. The recombinant nucleic acid molecule according to claim 1, wherein said MAR is a singular MAR element.

20. The recombinant nucleic acid molecule according to claim 1, wherein the TEP protein is hSPR14.

21. A recombinant mammalian cell comprising:
- a) at least one first recombinant nucleic acid sequence encoding a TEP protein as part of the vector of claim 20, and
- b) a second recombinant nucleic acid molecule comprising:
  - (i) at least one transgene of interest, and
  - (ii) optionally, a MAR element.

22. The recombinant mammalian cell of claim 21, wherein the TEP protein is at least one TEP, wherein the TEP is one or more of hSRP14, hSec61α1, hSec61β, hSec61γ, hSRP54, hSRP9, hSRPRα, hSRPβ, and hCANX.

23. The recombinant mammalian cell of claim 21, wherein the at least one transgene of interest within the second recombinant nucleic acid molecule encodes a therapeutic protein.

24. The recombinant mammalian cell of claim 21, wherein the second recombinant nucleic acid molecule comprises a MAR element.

25. A kit comprising in one container the at least one transposon vector comprising the recombinant nucleic acid molecule according to claim 1, wherein the MAR is selected from any one of SEQ ID Nos:1 or 3, and in the same or a second container, a vector comprising at least one transgene and, in a third optional container a vector encoding a compatible transposase binding to the ITRs and in a further container instruction of how to use the vector or vectors.

26. The kit of claim 25, wherein more than one type of vector comprising the recombinant nucleic acid molecule is provided in one or more containers and wherein the TEP proteins of said more than one type of vector are at least two of the proteins selected from the group consisting of a chaperone, hSRP14, hSRP9, and hSRP54.

27. A method for expressing a TEP comprising:
- providing a recombinant mammalian cell comprising a transgene and a vector, and cultivating the mammalian cell, wherein the vector is the transposon vector according to claim 1 which expresses the TEP protein.

28. The method of claim 27, wherein the transposon vector comprises a singular MAR X-S29 element and/or a nucleic acid sequence having at least 80%, 90%, 95%, 98%, 99% or 100% sequence identity with SEQ ID NO. 3 and wherein, after more than 4, 5, 6, 7, 8, 9, 10, 11, 12, 13 or 14 weeks of cultivation, the TEP protein increases the expression of the transgene by at least 20%.

29. A recombinant mammalian cell comprising not more than 20, 15, 10 or 5 of the recombinant nucleic acid molecules of claim 1,
- wherein the recombinant nucleic acid molecules are optionally integrated into the genome of the cell as single copies and optionally, wherein the cell is a primary stem cell, a CHO cell, or a HEK293 cell.

30. The recombinant mammalian cell of claim 29, wherein said recombinant nucleic acid sequence encoding the TEP protein within said cell comprises nucleic acid sequences encoding:
- one or more of the following proteins of the protein secretion pathway hSRP14, hSec61α1, hSec61β, hSec61γ, hSRP54, hSRP9, hSRPRα, hSRPβ, and hCANX.

31. A method for transfecting mammalian cells comprising:

transfecting said mammalian cells with (i) at least one, at least two, at least three or at least four of said recombinant nucleic acid molecules of claim 1 each encoding a TEP protein; and (ii) a nucleic acid molecule encoding at least one transgene; and (iii) a nucleic acid molecule encoding a transposase; wherein the transposase recognizes the 5' and the 3' ITR.

32. The method of claim 31, wherein the cell is transfected with at least two of said recombinant nucleic acid molecules encoding one, two or three of the TEP proteins selected from the group consisting of hSRP14, hSec61α1, hSec61β, hSec61γ, hSRP54, hSRP9, hSRPRα, hSRPβ, hCANX, and combinations thereof.

33. The method of claim 31, wherein the vectors are co-transfected.

34. The method of claim 33, wherein the recombinant nucleic acid molecules encoding the TEP protein encode TEP proteins hSRP14, hSRP9 and hSRP54.

35. The method of claim 31, wherein said mammalian cells are transfected a second time.

36. The method of claim 31, wherein at least 30%, 40% or 45% of said mammalian cells express said protein of interest following transfection.

37. The method of claim 31, wherein said protein of interest is an immunoglobulin, hormone, cytokine or growth factor.

38. The method of claim 31, wherein said recombinant nucleic acid molecules encoding a TEP protein of (i) further comprise a selection marker; and wherein the nucleic acid molecule encoding at least one transgene of (ii) is expressed a) without selection for said marker, or b) with selection for said marker.

* * * * *

SEQUENCE LISTING

<160> NUMBER OF SEQ ID NOS: 179

<210> SEQ ID NO 1
<211> LENGTH: 3616
<212> TYPE: DNA
<213> ORGANISM: Homo sapiens
<220> FEATURE:
<221> NAME/KEY: MISC_BINDING
<222> LOCATION: (1)..(320)
<223> OTHER INFORMATION: MAR 1_68 OF CHROMOSOME 1

-continued

<400> SEQUENCE: 1

```
gactctagat tataccaacc tcataaaata agagcatata taaaagcaaa tgctcttatc      60
ttgcagatcc ctgaactgag gaggcaagat cagtttggca gttgaagcag ctggaatctg     120
caattcagag aatctaagaa aagacaaccc tgaagagaga gacccagaaa cctagcagga     180
gtttctccaa acattcaagg ctgagggata aatgttacat gcacagggtg agcctccaga     240
ggcttgtcca ttagcaactg ctacagtttc attatctcag ggatcacaga ttgtgctacc     300
tattgcctac catctgaaaa cagttgcttc ctatatttca tccagtttaa tatttattta     360
aaccaagaag gttaatctgg caccagctat tccgttgtga gtggatgtga aagtaccaat     420
tccattctgt tttactatta actatccttt gccttaatat gtatcagtag gtggcttgtt     480
gctaggaaat attaaatgaa tggcatgttt cataggttgt gtttaaagtt gttttttgag     540
ttaaatcttt ctttaataat actttctgat gtcaaaaaca cttagaagtc atggtgttga     600
acatctatat agggttggat ctaaaatagc ttcttaacct ttcctaacca ctgtttttgt     660
ttgtttgttt ttaactaagc atccagtttg ggaaattctg aattagggga atcataaaag     720
gtttcatttt agctgggcca cataaggaaa gtaagatatc aaattgtaaa aatcgttaag     780
aacttctatc ccatctgaag tgtgggttag gtgcctcttc tctgtgctcc cttaacatcc     840
tattttatct gtatatatat atattcttcc aaatatccat gcatgggaaa aaaaatctga     900
tcataaaaat attttaggct gggagtggtg gctcacgcct gtaatcccag cactttggga     960
ggctgaggtg ggcggatcat gaggtcaaga gatcgagacc atcctgacca atatggtgaa    1020
accccatctc tactaaagat acaaaactat tagctggacg tggtggcacg tgcctgtagt    1080
cccagctact cgggaggctg aggcaggaga acggcttgaa cccaggaggt ggaggttgca    1140
gtgagctgag atcgcgccac tgcactccag cctgggcgac agagcgagac tctgtctcaa    1200
aaaaaaaata tatatatata tatatataca catatatata taaaatatat atatatacac    1260
acatatatat ataaaatata tatatataca cacatatata taaaatatat atatatacac    1320
acatatatat aaaatatata tatacacaca tatatataaa atatatatat acacacatat    1380
atataaaata tatatataca cacatatata taaaatatat atatacacac atatatataa    1440
aatatatata tacacacata tatataaaat atatatatac acacatatat ataaaatata    1500
tatatacaca catatatata aaatatatat atacacacat atatataaaa tatatatata    1560
cacacatata tataaaatat atatatacac acatatataa aatatatata tacacacata    1620
tataaaatat atatatacac atatatataa aatatatata tacacatata tataaaatat    1680
atatacacac atatatataa aatatatata tacacacata tatataaaat atatatatac    1740
acatatatat aaaatatata tatacacata tatataaaat atatatatat acacatatat    1800
ataaaatata tatacacaca tatatataaa gtatatatat acacacatat atataaaata    1860
tatatataca catatatata aaatatatat atacacatat atataaaata tatatataca    1920
catatatata aaaatatata tatatatttt ttaaaatatt ccaattgtct cactttgtgg    1980
atgagaaaaa gaagtagtta gaggtcaagt aacttggcct acatcttttc tcaagattgt    2040
aaactcctag tgagcaataa ccacatcttc attttctttg tataaaacaa gaaagtttag    2100
catgaaaaag gtactcaatt acaaatgtgt tggattgaat tgaagaccct tggaagggga    2160
ttttgtacct gaggatctct ttcttttggc catattgttc aatggacaaa atttagcctt    2220
cgaaggcagg ccgatttgag gttaatacta cctttaccac ttgatagcta tgtgaccttg    2280
```

-continued

```
gccatgtggt ttcaacagtc tgaacctcat tttctctgtg tatgtgtggt cctccttaca   2340

agtttgtgaa aaatgtgaag tccttagcca tgatagccca atataacagg ctaaatgata   2400

ataggtttat gttcttttcc tttatattct cagataagca ctgtccaagt ttgaggtgtt   2460

ttgaggtctc gcctgatttg gattgtttga gtttatgcta ttctttgaat tctttgagct   2520

gttctgaagc agtgtatcat gaacaaaaac atccccagtt cagtccaaac ccctggttac   2580

atatcattct tatgccatgt tataaccagt ttgagagtgt tccctctgtt attgcattta   2640

agtttcagcc tcacacagaa attcagcagc caatttctaa gccctaagca taaaatctgg   2700

ggtggggggg ggggatggcc tgaagagcag cattatgaat agcaccatta taattaatga   2760

tctctcagga agatttacaa tcacaggtag cagataaaac aaatagtact gcttctgcac   2820

ttcccctcct tttattcgct atgaaatttt atgggaaatc agtccagtga aaaatgtaag   2880

ctcttaatct ttcccagaaa tcctacctca tttgatgaat actttgaggg aatgaattag   2940

agcatttttt tcttttatag tctacttcgc atttacgaag tgaggacggt agcttaggct   3000

gcctggccaa ctgatgagaa ggtcagaggc atttttagag acctctgttg tctttcattc   3060

atgttcattt tccacaaggc aagtaatttc caacaaatca gtgtcttcat tagtaataag   3120

attattaaca acaataatag tcatagtaac tattcagtga gagtccatta tatatcaggc   3180

attctacaag gtactttata tacatctgag taaacctcac acaattctac agggaggtat   3240

ttctatcccc atttaacaaa taaggaaacg aagtccaagt aaattaactt gcccaaggtc   3300

acacagatag tacctggcag aacaggaatt taaacctaaa tttgtccaac tccaaaagca   3360

gccttctatt tgttataaat gctgcctctc attatcacat attttattat taacaacaac   3420

aaacatacca attagcttaa gatacaatac aaccagataa tcatgatgac aacagtaatt   3480

gttatactat tataataaaa tagatgtttt gtatgttact ataatcttga atttgaatag   3540

aaatttgcat ttctgaaagc atgttcctgt catctaatat gattctgtat ctattaaaat   3600

agtactacat ctagag                                                   3616
```

```
<210> SEQ ID NO 2
<211> LENGTH: 4624
<212> TYPE: DNA
<213> ORGANISM: Homo sapiens
<220> FEATURE:
<221> NAME/KEY: MISC_BINDING
<222> LOCATION: (1)..(4624)
<223> OTHER INFORMATION: MAR 1_6 OF CHROMOSOME 1

<400> SEQUENCE: 2

ggatcttaaa tctattttat ttatttattt ttcatgtggc caataccctc cacccccttc     60

ttctgtctct ttcaacttat tgtggttacc ttgaggctac ctgagacagt aggcttgggt    120

ggggaagtat gcattctaag tgtaaagttt gatgagcttt gacaaatgtc aacccatgta    180

ccagaacatt ttcatcaccc ataaaatctc ccttgtgtca cttgccagtc agtgtctatt    240

ctagtatcca actcctggct ccaagaaacc attgaactgt tttctgtcac tataaattag    300

atttgtcttt tctagagttt catgtaaatg gaatcataca ctaagtactc tttgtgcctg    360

gcttctgctc agcataatgt ttttgagaat cattcatgct gctgcatgtt ttcagtagtt    420

catttttta aataggtgaa ttgtaactca ttctgtgaat ataccatatt ctgtcttcca    480

tttatctgtt agtggatctt taggtcgttt ctagttttgg gctattgcaa ataaagctgc    540

tgtaaatatt aatgcacaag ttttccatgt tcatatgttt catttcactt aggaaaatac    600

ctaagagagg aattgcacat attaaaaaaa ttttaaaaac tactaagctg ttctccaaaa    660
```

```
tggttgtaca atttttattc ccaagagcaa tatgagtgtt taattgctcc acattctcac    720
caacacttgg tgcttgttag ttttattttc attgttttca ttgttatgtc tgtgaggcag    780
cattgatgtg catgtctctg agtgtcatct tagcggtgat gctgagcatc agttcacgtc    840
cttataggcc gtttgtatat ctgctttgtg aaatgtctgt tcaaatcttt tgcctatttt    900
aaattgagtt gtgttcgtct tcttaggatt aagtaatgag ttaaaaatat ttctgataca    960
aatctttcat tatatatttc taatgctttc tcatctatag tttattttct catattcttt   1020
aactgtatct tttgaagagc aaattttact tttgattatg cccaatttat caagttttta   1080
tatggctctt ttgattatgc ccataatcac attagacttt gcctaaccca agtttgcaga   1140
gatttttct tttatgcttt tatctagaaa ttttgtagtt ttaggtttta aaaaagttta   1200
atttatttat ttgagacagg gtattgctct ttacatatac tggagtgcag tgatgcaatc   1260
atggctcact gcagcctcaa cctcttgggc tcaagcggtt ctcccatctc agagtcctga   1320
gtagctggcc aggtgcatgc cagcttcaat gtgtttttca tttgcatttc cctgataatt   1380
attgacgttg agcatttttt tcatatatca gttagctatt tgtacgtctt cttttgagaa   1440
acatctattc gggtcttttg cccattttaa agtcagatgg tttgtttgtc agctattgag   1500
ttgtttgagt tccttgtata ttctggatat taccatcttg tcagatgcac agtttgcaaa   1560
ttttttttt ctattttgta ggttgtctct ttctctgttg tttcctccgg tatgcagaag   1620
tttttagtg tgatgtaatt tcatttgtct gtttttgctt ttgttgcctg tactttctta   1680
ttcttatcca aaaaatcttt atctagatca atgtcacgaa gagtttctcc tctgttttct   1740
tcgagtagtt ttttataatt ttgggtatac atttaagtct ttaatctatt tggaattgat   1800
ttttgcatat ggtgagagat cagagtctaa tttcatactt ttggatgtgg aaagctagtt   1860
ttttcagcac catttattga agagactgtc tcttctccaa tgtgtgttct ttgtgccttc   1920
gtcaaaaatc agttggctgt gcgtggattt atttctgtgt tctctatttt gttccattgg   1980
tctagtttta gccttaaatt taggtctgca attttttttt ttttgtatat ggtgtgaagt   2040
aagagtcaaa gttcattatt tttcatatgg atatgtaatt actccagtac catcatttag   2100
tttgaatgga ctgtcctttc tccatggaat tacatgggca tcttttgtct gaaaccaatt   2160
atgtatgttt acgtatgtgt atgtttatgc atatgttata ggtttaatat atattaatat   2220
atataatata taatatataa atattaatat gtattatata atatatatta atatattata   2280
ttatattact atataaataa tattaatata ttatattaaa atattaataa atatatcata   2340
ttaaatatta tattaattaa atattaataa atatattata ttaatatatt tatatattaa   2400
acctataaca tatgcatata cttatttata tataacatgc atgtacttat ttatatatac   2460
aatatatatt tatatattat ataatatatt atatgtattt atatattata tatcatatat   2520
tatatgtatt tatatattat atatcatata atatatatat ttatattata tatattatat   2580
gatatataat attatataat gtattaatat atattaaacc tatatttata attctggact   2640
cactattttg tttcattggt gtctgtgtgt atctaaccct atgccaataa tgtactatct   2700
taattaccat agctttatag taagctttga aatcagatag tgtatttttt atcattgttt   2760
tttaaaataa tagtttatct ttttatttga atttgtaatc agctagtcag tttctgcaaa   2820
aagcttactg ggattttgct tggaattatg ttacatctgt agcatgtact atccaatatt   2880
ctagccttta tccacatgtg gctattaagg tttaaattaa ttaaattaaa atttaattaa   2940
ttaaaattaa aacttaataa ttggttcctc attcacacta ccatatgtca agtgttcaat   3000
```

-continued

```
agccacatat ggtcaatgtc ttggaaaagt caatacagta catttccatt attgcagtaa   3060

gttctgtcaa acagcactat cgtagaccga ttaggagaga actgacttaa cagtattgga   3120

tgctccagtc aatgaacatc tttttttttt tcatttattt cagtagtctc tgcagtatat   3180

tatagatttc agtttacata ttttgcatat attttattaa atgtataacg gtagaagtac   3240

tattattgga tgatgtgttc tatagatgta ttttaggtca agtttgttga tagtgttgtt   3300

taaatctcgt atacctcttg attttttat ttacttgttc tttgaattac tgagacagga   3360

atgttatatc cttaactata tttgtgaatt tattcacttc ttccttcagt tctgttaact   3420

tttgcttagg tgctttttaa aaatgaaact ttcaatctct gcctttttaat tgtagcattt   3480

agaccattta cattcaatgt aattatcaat atcagtttat ttaagtctga agttgtgcaa   3540

tttttcctct acctatatta taaatctttc tatatacaaa acacatgcta tgttttctgc   3600

atatgtttta aatgacaccc ggaaagcatt gacactattt ttgctttagg ttatctttca   3660

aagatgttaa aaatgagaaa gaaatattct gcatttatcc atacacttat tatttgcaaa   3720

ggttttttta aatacctttg tgtagatttc agttaccaac ttgtatttcc ttcagcttga   3780

agaacttaca atttcttgta ggacaggtct ctgacaacaa attatctcag cttttctttg   3840

tctaaaaaag ttattgcctt tatttttaaa atatattttc actggatatt gaattttagg   3900

tgataatctt tttttttttg ttagcacttt aaatatgtct tctaatgtcc tcttgctttc   3960

atagtttctg atgagaagtc tactgttatt agtatctctt tgtgtgtgtc tctctttttt   4020

ccctctctgc tattatggct attttttttt tttttttttt ttttggtcac tggtgtcagc   4080

aatttaatta tggtgtgcct tggtatgttt tgtgtgtgtg tgtgtgtgtg tgtgtgtgtg   4140

tgtgtgtgtg tagctgatgt tctttgagct ttagaatctg tgagtttgta gttttcatca   4200

attatttttt cttttcattc cttttattta ctcatgttcg tgttttattt tatattttta   4260

agaattttgt gcgtatttgt aataactgtt taaatgtcat ttgtgaattc cattgcttct   4320

aggtaggatt ctattgacag atatttttc cctgacgaga ggtcatactt tccttattct   4380

tcatgtatct agtggttttt ggttgaatac tggatatttt gaattttatg ggagtgctga   4440

attctacaat attccttaaa aatgtgttgg attttgtttt agcagatagc tatcttactt   4500

gaagatcaat ttcatatttt ttgatgttca ttttttcatt tattaaagaa taggtccatg   4560

gtagagttta ctgatatcaa cctttctggt gtctctaata aatgcaacat attcaataag   4620

atcc                                                                4624
```

<210> SEQ ID NO 3
<211> LENGTH: 3354
<212> TYPE: DNA
<213> ORGANISM: Homo sapiens
<220> FEATURE:
<221> NAME/KEY: MISC_BINDING
<222> LOCATION: (1)..(3354)
<223> OTHER INFORMATION: MAR X_S29 OF CHROMOSOME X

<400> SEQUENCE: 3

```
gatcccttta taaaaccaca atataatgga gtgctataat ttcaaacagt gtttggtctg     60

ctggcagagt ggtcattcta acagcagtca cagtagagta gaaataagac tgcagtatat    120

ctaaggcaaa aagctgaggt ttcaggagct tgaaggtaaa gaggaagaaa gaaatgggaa    180

tgggaattgg aaagacaaat atcgttaaga gaaaattgct tttaggagag gggaaagaat    240

ctatgtgtac ttaagactat ggaatcaatc ccatttaagc tgggaaacta gtttcatata    300

taactaataa attttattta cagaatatct atttacctga tctaggcttc aagccaaagg    360
```

-continued

```
gactgtgtga aaaaccatca gttctgtcat attcctaaaa aaaaattaaa aagttaaaaa    420
taaataaata ataaaacttc ttttctttca aaataatcaa ggtgcttatt cacatccatt    480
ccaatttggg gaaatactta ttttcctatg attagcgaag agaaaagtaa cttgcatttc    540
aattcaagtt gatacatgtc acttttaaga ggtcaactaa tatttgctag ttgagctaac    600
catataggct ttaaatactt tcatagtaga aagaaaatga aaatcattag tgaactgtat    660
aaaatagatc atacttttttg aaagaatcag actgaagttt ccgaaaaaaa gaagtaagct   720
tcaatgaaaa ggtaagtgaa tttagcattt actcagcatc tactatggac ttaacaccta    780
acagtagata atctgaaggc aaacatattt gtatagggac tgcagaatga tagatgataa    840
atatcatctc ttctatttga atgaatattt tttcaaatct ttcacacaca gtggtttgct    900
atggaaagat ttgtagtaca ttaaacaaat ctgaagatgg agttagaaag cttaggctat    960
gttttgagca caacatataa tttctctgtg attgtttctt catctttcaa atgaggttac   1020
tgtgaagatt aaatgagata actaaatgat gataaaataa tgtaatctta gcagcacctt   1080
atttaatctg tgcaacaact ctgtgaagtg agtagggctc agcttcagtc acttctctgc   1140
catttattaa ctaagatagt ttggaaagtt acccatctct tcagctgtaa aatgatgagg   1200
atcataccta ttttatgggg ctgcttttag gtacaaatat acaggcaagc actttgttaa   1260
tactaaagca ttacaccaat tagttttact cttttccatt cacacatgaa attaatgtaa   1320
tcagaattct gtagattacc taaatcttct gttaacacgt gatatgcagt tcaggttaaa   1380
tgtcagttga gttaccaaag cacatacata ctcaccaccc tatccaaatc tacaagcctc   1440
ccagtttgtc ttcactattt tggttaaatt aatatgaatt cctagatgaa aatttcactg   1500
atccaaatga aataaaaaat atattacaaa actcacacct gtaatctcaa cattttggga   1560
ggccaaggca ggtagatcac ttgaggccag gagttcaaga ccagcctgat caacatggtg   1620
aaaccctgtc tctactaaaa atacaaaaat tagccaggtg tggtggcatg tgcctgtagt   1680
cctacctact cgggaggctg aggcacaaga atcgcttgaa tgtgggaggt ggaggttgca   1740
gtgacctgag atcgtgccac tgcactccag cctaggcaac agagtgagat catgtgtcat   1800
atatatatat atatatatat atatatatat atatatatac acacacacac acatatatat   1860
atacacatat atatacgtat atatatatat gtatatatat acatatatat acatatatat   1920
atatacgtat atatatacgt atatatatat caatgtaaat tatttgggaa atttggtatg   1980
aatagtcttc cctgtgaaca cagatcataa aatcatatat caagcagaca aataagtagt   2040
agtcacttat atgcttatac ttgtaactta aagtaaaaga attacaaaag catatgacaa   2100
agactaattt taagatatcc taatttaaat tgttttctaa aagtgtgtat accattttac   2160
ctatcatatg aataatttag aaacatgttt ataaaattaa tgtccaaatc cattcaaaag   2220
ttttgtaatg cagatcaccc acaacaacaa agaatcctag cctattaaaa aagcaacacc   2280
acctacatat aatgaaatat tagcagcatc tatgtaacca aagttacaca gtgaatttgg   2340
gccatccaac actttgagca aagtgttgaa ttcatcaaat gaatgtgtaa tcatttactt   2400
actaatgcca atacacttta aggtaatctt aagtagaaga gatagagttt agaatttttt   2460
aaatttatct cttgttgtaa agcaatagac ttgaataaat aaattagaag aatcagtcat   2520
tcaagccacc agagtatttg atcgagattt cacaaactct aactttctga tacccattct   2580
cccaaaaacg tgtaacctcc tgtcgatagg aacaacccac tgcagggatg tttctcgtgg   2640
aaaaaggaaa tttcttttgc attggtttca gacctaactg gttacaagaa aaaccaaagg   2700
```

```
ccattgcaca atgctgaagt actttttttca aatttaaaat ttgaaagttg ttcttaaaat   2760

ctatcattta ttttaaaata cggatgaatg agaaagcata gatttgataa agtgaattct   2820

tttctgcaat ctacagacac ttccaaaaat cactacagac actacagaca ctacagaaaa   2880

tcataaataa acaagtgcta gtatcaatat ttttaccaaa aaatggcatt cttagaattt   2940

tttataggct agaaggtttg tacaaactaa tctgccacgg attttaaaat atgagtgaat   3000

aaattatatt gcaaaaaaaa tcaggttaca gagaactggc aaggaagact cttatgtaaa   3060

acacagaaaa catacaaaac gtatttttaa gacaaataaa aacagaactt gtacctcaga   3120

tgatactgga gattgtgttg acatattagc attatcactg tcttgctaaa acataaaaat   3180

aaaaagatgg aagatgaaat tacaatacaa atgatgattt aaacatataa aaggaaaata   3240

aaaattgttc tgaccaacta ctaaaggaag acctactaaa gatatgccat ccagcacatt   3300

gccactctac atgtggtctg taaaccagca gcatagggat cctctagcta gagt         3354
```

```
<210> SEQ ID NO 4
<211> LENGTH: 5463
<212> TYPE: DNA
<213> ORGANISM: Mus musculus
<220> FEATURE:
<221> NAME/KEY: MISC_FEATURE
<223> OTHER INFORMATION: S4_1-703_2328-5457 CONSTRUCT WITH FULL AVAI
      SITES

<400> SEQUENCE: 4
```

```
ctcgaggtct caagataaga atgactgctg taactcaaat ccaccaaagc tatttgtgtt     60

agaatgcttt cctttggtaa taacataata ccacagagtg agtgaatgta tcaagcaaag    120

tactcactca taatctctcc acccaaatga ctttgtcttc taaaattaaa cccttcccag    180

aggcctctcc ccttaatacc atattgggct cttcacactt cttccaacat cgccttccat    240

cctggccctt ccaacctccc ttctgtttgt gctaggaaca gctcaaggcc tcctatctac    300

cacagagtta catggcttgc cccttgccaa ccccccagta ccacacagtg agtgcaaaat    360

ctcaccacat tcagaaccca gtcactattc aaatcatatt ttaacctttg cagtactgac    420

tacttttgat tcatctaaac attactgaac tttattctag aaaacattta agaaatttgt    480

agttaggttc atcctttgag accttacatt taatttcttt ctatgtaaac ggaaagcatt    540

gttcagtccc acgctcatta tggcaaccca cttccaagta cttcgtttac tacgtgggct    600

ggaatcatac agttttctgt tgtgcttgtg ggagcagatc cccctaacct ctgctgattt    660

ttctcaccac ttatcataca tttattacat gcatgcactg ctgtgtgagt ttctaaatac    720

ttgggtagca attctctact attactttaa ttttcctact tgtctgcaaa tacgaaaagt    780

agcttgaaag aacttcagat ctttgttgtt atctgttgca aacactccat ttttctgttg    840

tagcaaaaaa aaaaaaaaag acatccatag ttgtcaatga gaatgcaaga tacatacatt    900

ctgcacctgt gtgctaacat aagtggctgc cctgtgactc agagattgct tgtccttctc    960

ctaagcctat cctttttgt tactttggat actttgttc aatgaatcca gaaaaagtgt   1020

ttttcagatt caccatgtga ccctcattta aaacctgtaa tccccctatg gttaagttcc   1080

tgcttttgtt tctgttttct ttctttcagt aaaaggaatt gaacccagtc cttccactta   1140

ctatctgagc atatggctct tttagattat gatgttggtg gtgttcattg gtctcaccaa   1200

aatgctaaag aagccttcat cttctacttg tgggtagtct ttacattcat tactgcaagt   1260

ttagtttatg tggtagtacc agatcctttg cttcttttga cttcatgcct acctaacagc   1320

agctctttcc tttagttaag cttatgaaat agtgtttctc tcatgtttcc tctatattct   1380
```

-continued

```
ctcttttgcc ttcctgtttc ttcctgttga ttccatccca ttggagtgaa atcttatgat   1440
cttttggcat caacaaagtg atctgcatcc aaataattcc acatctcatt ccatgttgac   1500
tgtggatcta tatatatata tatgtatata tgtatatatg tatatatgta tatatgtata   1560
tatgtatata tgtatatatg tatatatgta tatatgtata tatgtatata tgtatatatg   1620
tatatatgta tatatgtata tatgtatata tgtatatatg tatatatgta tatatgtata   1680
tatgtatata tgtatatatg tatatatgta tatatgtata tatgtatata tgtatatatg   1740
tatatatgta tatatgtata tatgtatata tgtatatatg tatatacgta tatatgcata   1800
tacgtatata tgtatatatg tatatatgta tatatgtata tatgtatata tgtatatatg   1860
tatatatgta tatatgtatg tatgtatgta tgtatgtata tatgtatata tgtatgtatg   1920
tatgtatgta tgtatgtatg tatatatgta tatatatatg tatgtatgta tgtatgtatg   1980
tatgtatatg tgtatatgtg tatatgtgta tatgtgtata tgtgtatata tgtatatatg   2040
tatatatgta tatatgtata tgtgtatatg tgtatatgtg tatatatgta tatatgtata   2100
tatgtatata tgtatatata taacatagta ttaaattata tatacatata taagtgaaat   2160
gtcacaatct tctagaactt gctctgtatg tccacttaac atggtagagt gagctatgtc   2220
agcattttct atttcctgtg aatcattctg tgtgttgcca agaagaaata tgatatattc   2280
tgaggttatg aaatgatatt ttggtcatca tgtttctcat cctattttca tattacctaa   2340
atacttttgc ttttaaaatt attattatta ataataatat aattatttat acaataatat   2400
ttaaataata tatttattta atataattat tatatttcac ataaaagcaa tagttccagt   2460
gttacaaatt gtaggcaact gggctgttct gattatctaa gttgggccca ggatatgtgc   2520
tgaatagtta aagcacatgc ccagcatgta tgagggtaaa aggatgggtg gatgtagtga   2580
cccatttgta atttaagcct tagcaggcag aggtgtgacc catagtgcaa agtacatagt   2640
cattataagg tcatctatat cacaatctct ggattagatt gattgaacct gctcagtgac   2700
caatgtgtta gcaatataca ggaggatgat aacatcaacg tcagaagaca cattgaaggg   2760
cttacaaata gtgcccattt actttaatac agaaaaattc aatgtaccct ctaggcaatt   2820
tcaactttta gtctcttggt aggatagtct acatttagaa tggctaattc ataaattaga   2880
aagcttcttc accccctact tttctggtta tttctctatg aatgtggtag gcatgagtta   2940
gtacacatgt ttccatgtac atgtgtttct atgtgtctgc atgcatatgg tagaatgtac   3000
tcatattcta tgtacagtta gaacaatatt tatattgtca aagaaatcaa aaggagtatt   3060
ataagcttca gaaataagga taagtttgaa atattcattg ttttattttt tacagtattt   3120
tttcctttga gaattctatg taaagtactt tgaacatatt tgccttcaac tcctccctca   3180
ctttcaccct ctcttcattc ctccctttcc tttccactca aagttgagat tcctttattt   3240
atttatttat ccttcaaata tcactggtac tatccacatg atctcaggat tgaggtctgc   3300
tctgacgtgt catcctgctt tcatgcaatg gccttatagg tggaacaaca ttatgaacta   3360
accagtaccc cggagctctt gactctagct gcatatatat caaaagatgg cctagtcggc   3420
catcactgga aagagaggct cattggactt gcaaacttta tatgccccag tacaggggaa   3480
caccagggcc aaaaaggggg agtgggtggg caggggagtg ggggtgggtg gatatggggg   3540
acttttggta tagcattgga aatgtaaatg agttaaatac ctaataaaaa atggaaaaaa   3600
aaagtttcta atgtgtgttt ctagaaactt cctctcttaa agcaacaaca tgtccatgag   3660
caatatagaa ttgaagatca ccatcaaatc ctctttattc ctcattgttt ccatcatgta   3720
```

-continued

```
ctaccagacc tctttaaagt gtagtacagt gtgttaggaa atgagcagat tatcctgggt   3780

atgtgctaaa ttagctactg agtcaaaata catttttttgc tgaacattaa gtgtttggtc   3840

atttctgggc aaaagaaaga aagaaagaaa gaaaagaaag aaagaaagga aggaaggaag   3900

gaaggaagga aggaaggaag gaaagaagga aggaaagaaa aaatggatgt aaattgttct   3960

gacagcatct gtctgagtca ggcagtggaa tgaaggagga atcctagaga atgcacagga   4020

aagcagccca aggagagtgt gggctgaaag gcatcatgtt agaaacatgc actcgatgac   4080

agaaccttga gaaaaaggaa ctcaagcaaa agcacttatt taaaattgta aaacgcactt   4140

tattcatagc catgggggat gtcaatattc caagcataag aatgatcagt ttccaatcac   4200

tgtgaacccc caaaacacaa agtgaaaacc cactacttta tttgatgaga tttggggttg   4260

ctctattaat ttataaaatc agagtaagac acgatataaa tgaaacgatt gtagttctaa   4320

agcagcggca cttccctgaa cagtgtcatt ttgacaagta actgctaaca tcttcaggtc   4380

acagcgactg aagaaaaagt agggaaagaa ggctggctgt gctgtttgac attttctttt   4440

cttatctggt gacatgaaga gaagctctgg gtccccctac tcttgttcat atatctgttg   4500

cttttatgct gcatcctgag gtttgaagaa atgcatttgg cactgagaaa agatgaggag   4560

agaatgcctt ggacatggtc ctaacatgct ttggtactga gaaaagagag cagaggagat   4620

gacatagaat aggagagata atttggccta ttttggcctt catctgagtg atagatttta   4680

cttaacaaat agaaacaaag ttttacttat aaacagaacc aatgacctgt gtcatctctg   4740

atatattgag ctttgaattc agtgaaatta tgaactaaat atatcactcc ataattttct   4800

aagagggcta tttgtatagt ttcagtgata gtgtgacaaa gtgtaatcta aatttctaaa   4860

aagtaaaata agtagataaa atagtaggta gaatagtata ataatagaat aagtataggt   4920

atggactaga ataaatagac aaaatagtag ataaaatgct aatgattttg ttgacagggt   4980

aatcatgaat atttttatta tttagctaaa gaaccaatgt tcatgtactc aagaagtgta   5040

ttgaggaact taggaaatta gtctgaacag gtgagagggt gcgccagaga acctgacagc   5100

ttctggaaca ggcggaagca cagaggcact gaggcagcac cctgtgtggg ccggggacag   5160

ccggccacct tccggaccgg aggacaggtg cccgcccggc tggggaggcg acctaagcca   5220

cagcagcagc ggtcgccatc ttggtccggg acccgccgaa cttaggaaat tagtctgaac   5280

aggtgagagg gtgcgccaga gaacctgaca gcttctggaa caggcagaag cacagaggcg   5340

ctgaggcagc accctgtgtg ggccggggac agccggccac cttccggacc ggaggacagg   5400

tgcccacccg gctggggagg cggcctaagc cacagcagca gcggtcgcca tcttggtccc   5460

ggg                                                                   5463
```

<210> SEQ ID NO 5
<211> LENGTH: 2957
<212> TYPE: DNA
<213> ORGANISM: Gallus gallus
<220> FEATURE:
<221> NAME/KEY: misc_feature
<222> LOCATION: (1)..(2957)
<223> OTHER INFORMATION: chicken lysozyme

<400> SEQUENCE: 5

```
tctagaaaac aatatatttc caaatgaaaa aaaaatctga taaaaagttg actttaaaaa     60

agtatcaata aatgtatgca tttctcacta gccttaaact ctgcatgaag tgtttgatga    120

gcagatgaag acaacatcat ttctagtttc agaaataata acagcatcaa aaccgcagct    180

gtaactccac tgagctcacg ttaagttttg atgtgtgaat atctgacaga actgacataa    240
```

-continued

```
tgagcactgc aaggatatca gacaagtcaa aatgaagaca gacaaaagta tttttttaata    300
taaaaatggt ctttatttct tcaatacaag gtaaactact attgcagttt aagaccaaca    360
caaaagttgg acagcaaatt gcttaacagt ctcctaaagg ctgaaaaaaa ggaacccatg    420
aaagctaaaa gttatgcagt atttcaagta taacatctaa aaatgatgaa acgatcccta    480
aaggtagaga ttaactaagt acttctgctg aaaatgtatt aaaatccgca gttgctagga    540
taccatctta ccttgttgag aaatacaggt ctccggcaac gcaacattca gcagactctt    600
tggcctgctg gaatcaggaa actgcttact atatacacat ataaatcctt tggagttggg    660
cattctgaga gacatccatt tcctgacatt ttgcagtgca actctgcatt ccaactcaga    720
caagctccca tgctgtattt caaagccatt tcttgaatag tttacccaga catccttgtg    780
caaattggga atgaggaaat gcaatggtac aggaagacaa tacagcctta tgtttagaaa    840
gtcagcagcg ctggtaatct tcataaaaat gtaactgttt tccaaatagg aatgtatttc    900
acttgtaaaa cacctggtcc tttttatatt actttttttt tttttaagg acacctgcac    960
taatttgcaa tcacttgtat ttataaaagc acacgcactc ctcattttct tacatttgaa   1020
gatcagcaga atgtctcttt cataatgtaa taatcatatg cacagtttaa aatattttct   1080
attacaaaat acagtacaca agagggtgag gccaaagtct attacttgaa tatattccaa   1140
agtgtcagca ctgggggtgt aaaattacat tacatggtat gaataggcgg aattctttta   1200
caactgaaat gctcgatttc attgggatca aaggtaagta ctgtttacta tcttcaagag   1260
acttcaatca agtcggtgta tttccaaaga agcttaaaag attgaagcac agacacaggc   1320
cacaccagag cctacacctg ctgcaataag tggtgctata gaaaggattc aggaactaac   1380
aagtgcataa tttacaaata gagatgcttt atcatacttt gcccaacatg ggaaaaaaga   1440
catcccatga gaatatccaa ctgaggaact tctctgtttc atagtaactc atctactact   1500
gctaagatgg tttgaaaagt acccagcagg tgagatatgt tcgggaggtg gctgtgtggc   1560
agcgtgtccc aacacgacac aaagcacccc acccctatct gcaatgctca ctgcaaggca   1620
gtgccgtaaa cagctgcaac aggcatcact tctgcataaa tgctgtgact cgttagcatg   1680
ctgcaactgt gtttaaaacc tatgcactcc gttaccaaaa taatttaagt cccaaataaa   1740
tccatgcagc ttgcttccta tgccaacata ttttagaaag tattcattct tctttaagaa   1800
tatgcacgtg gatctacact tcctgggatc tgaagcgatt tatacctcag ttgcagaagc   1860
agtttagtgt cctggatctg ggaaggcagc agcaaacgtg cccgttttac atttgaaccc   1920
atgtgacaac ccgccttact gagcatcgct ctaggaaatt taaggctgta tccttacaac   1980
acaagaacca acgacagact gcatataaaa ttctataaat aaaaatagga gtgaagtctg   2040
tttgacctgt acacacagag catagagata aaaaaaaaag gaaatcagga attacgtatt   2100
tctataaatg ccatatattt ttactagaaa cacagatgac aagtatatac aacatgtaaa   2160
tccgaagtta tcaacatgtt aactaggaaa acatttacaa gcatttgggt atgcaactag   2220
atcatcaggt aaaaaatccc attagaaaaa tctaagcctc gccagtttca aaggaaaaaa   2280
accagagaac gctcactact tcaaaggaaa aaaaataaag catcaagctg gcctaaactt   2340
aataaggtat ctcatgtaac aacagctatc caagctttca agccacacta taaataaaaa   2400
cctcaagttc cgatcaacgt tttccataat gcaatcagaa ccaaaggcat tggcacagaa   2460
agcaaaaagg gaatgaaaga aaagggctgt acagtttcca aaaggttctt cttttgaaga   2520
aatgtttctg acctgtcaaa acatacagtc cagtagaaat tttactaaga aaaaagaaca   2580
```

-continued

```
ccttacttaa aaaaaaaaaa caacaaaaaa aacaggcaaa aaaacctctc ctgtcactga   2640

gctgccacca cccaaccacc acctgctgtg ggctttgtct cccaagacaa aggacacaca   2700

gccttatcca atattcaaca ttacttataa aaacgctgat cagaagaaat accaagtatt   2760

tcctcagaga ctgttatatc ctttcatcgg caacaagaga tgaaatacaa cagagtgaat   2820

atcaaagaag gcggcaggag ccaccgtggc accatcaccg ggcagtgcag tgcccaactg   2880

ccgttttctg agcacgcata ggaagccgtc agtcacatgt aataaaccaa aacctggtac   2940

agttatatta tggatcc                                                  2957
```

<210> SEQ ID NO 6
<211> LENGTH: 3659
<212> TYPE: DNA
<213> ORGANISM: Homo sapiens
<220> FEATURE:
<221> NAME/KEY: MISC_FEATURE
<223> OTHER INFORMATION: 1_68R(NcoI+XbaI filled)

<400> SEQUENCE: 6

```
gtacccccaa aagaaagaga tcctcaggta caaaatcccc ttccaagggt cttcaattca     60

atccaacaca tttgtaattg agtacctttt tcatgctaaa ctttcttgtt ttatacaaag    120

aaaatgaaga tgtggttatt gctcactagg agtttacaat cttgagaaaa gatgtaggcc    180

aagttacttg acctctaact acttcttttt ctcatccaca aagtgagaca attggaatat    240

tttaaaaaat atatatatat atttttatat atatgtgtat atatatattt tatatatatg    300

tgtatatata tattttatat atatgtgtat atatatattt tatatatatg tgtgtatata    360

tatactttat atatatgtgt gtatatatat tttatatata tgtgtatata tatatatttt    420

atatatatgt gtatatatat attttatata tatgtgtata tatatatttt atatatatgt    480

gtgtatatat atattttata tatatgtgtg tatatatatt ttatatatat gtgtatatat    540

atattttata tatatgtgta tatatatatt ttatatatgt gtgtatatat atattttata    600

tatgtgtgta tatatatatt ttatatatat gtgtgtatat atatatttta tatatatgtg    660

tgtatatata tattttatat atatgtgtgt atatatatat tttatatata tgtgtgtata    720

tatatatttt atatatatgt gtgtatatat atattttata tatatgtgtg tatatatata    780

ttttatatat atgtgtgtat atatatattt tatatatatg tgtgtatata tatattttat    840

atatatgtgt gtatatatat attttatata tatgtgtgta tatatatata ttttatatat    900

atgtgtgtat atatatatat tttatatata tatgtgtgta tatatatata ttttatatat    960

atatgtgtat atatatatat atatatattt tttttttgag acagagtctc gctctgtcgc   1020

ccaggctgga gtgcagtggc gcgatctcag ctcactgcaa cctccacctc ctgggttcaa   1080

gccgttctcc tgcctcagcc tcccgagtag ctgggactac aggcacgtgc caccacgtcc   1140

agctaatagt tttgtatctt tagtagagat ggggtttcac catattggtc aggatggtct   1200

cgatctcttg acctcatgat ccgcccacct cagcctccca aagtgctggg attacaggcg   1260

tgagccacca ctcccagcct aaaatatttt tatgatcaga tttttttttcc catgcatgga   1320

tatttggaag aatatatata tatacagata aaataggatg ttaagggagc acagagaaga   1380

ggcacctaac ccacacttca gatgggatag aagttcttaa cgatttttac aatttgatat   1440

cttactttcc ttatgtggcc cagctaaaat gaaacctttt atgattcccc taattcagaa   1500

tttcccaaac tggatgctta gttaaaaaca aacaaacaaa aacagtggtt aggaaaggtt   1560

aagaagctat tttagatcca accctatata gatgttcaac accatgactt ctaagtgttt   1620
```

-continued

```
ttgacatcag aaagtattat taaagaaaga tttaactcaa aaaacaactt taaacacaac   1680
ctatgaaaca tgccattcat ttaatatttc ctagcaacaa gccacctact gatacatatt   1740
aaggcaaagg atagttaata gtaaaacaga atggaattgg tactttcaca tccactcaca   1800
acggaatagc tggtgccaga ttaaccttct tggtttaaat aaatattaaa ctggatgaaa   1860
tataggaagc aactgttttc agatggtagg caataggtag cacaatctgt gatccctgag   1920
ataatgaaac tgtagcagtt gctaatggac aagcctctgg aggctcaccc tgtgcatgta   1980
acatttatcc ctcagccttg aatgtttgga gaaactcctg ctaggtttct gggtctctct   2040
cttcagggtt gtcttttctt agattctctg aattgcagat tccagctgct tcaactgcca   2100
aactgatctt gcctcctcag ttcagggatc tgcaagataa gagcatttgc ttttatatat   2160
gctcttattt tatgaggttg gtataatcta gctagagtcg agatctttgg ccatattgtt   2220
caatggacaa aatttagcct tcgaaggcag gccgatttga ggttaatact acctttacca   2280
cttgatagct atgtgacctt ggccatgtgg tttcaacagt ctgaacctca ttttctctgt   2340
gtatgtgtgg tcctccttac aagtttgtga aaaatgtgaa gtccttagcc atgatagccc   2400
aatataacag gctaaatgat aataggttta tgttcttttc ctttatattc tcagataagc   2460
actgtccaag tttgaggtgt tttgaggtct cgcctgattt ggattgtttg agtttatgct   2520
attctttgaa ttctttgagc tgttctgaag cagtgtatca tgaacaaaaa catccccagt   2580
tcagtccaaa cccctggtta catatcattc ttatgccatg ttataaccag tttgagagtg   2640
ttccctctgt tattgcattt aagtttcagc ctcacacaga aattcagcag ccaatttcta   2700
agccctaagc ataaaatctg ggtgggggg ggggggatggc ctgaagagca gcattatgaa   2760
tagcaccatt ataattaatg atctctcagg aagatttaca atcacaggta gcagataaaa   2820
caaatagtac tgcttctgca cttcccctcc ttttattcgc tatgaaattt tatgggaaat   2880
cagtccagtg aaaaatgtaa gctcttaatc tttcccagaa atcctacctc atttgatgaa   2940
tactttgagg gaatgaatta gagcattttt ttcttttata gtctacttcg catttacgaa   3000
gtgaggacgg tagcttaggc tgcctggcca actgatgaga aggtcagagg catttttaga   3060
gacctctgtt gtctttcatt catgttcatt ttccacaagg caagtaattt ccaacaaatc   3120
agtgtcttca ttagtaataa gattattaac aacaataata gtcatagtaa ctattcagtg   3180
agagtccatt atatatcagg cattctacaa ggtactttat atacatctga gtaaacctca   3240
cacaattcta cagggaggta tttctatccc catttaacaa ataaggaaac gaagtccaag   3300
taaattaact tgcccaaggt cacacagata gtacctggca gaacaggaat ttaaacctaa   3360
atttgtccaa ctccaaaagc agccttctat ttgttataaa tgctgcctct cattatcaca   3420
tattttatta ttaacaacaa caaacatacc aattagctta agatacaata caaccagata   3480
atcatgatga caacagtaat tgttatacta ttataataaa atagatgttt tgtatgttac   3540
tataatcttg aatttgaata gaaatttgca tttctgaaag catgttcctg tcatctaata   3600
tgattctgta tctattaaaa tagtactaca tctagcccgg gctcgacatt gattattga    3659
```

<210> SEQ ID NO 7
<211> LENGTH: 2751
<212> TYPE: DNA
<213> ORGANISM: Homo sapiens
<220> FEATURE:
<221> NAME/KEY: MISC_FEATURE
<223> OTHER INFORMATION: 1_68R2 (NcoI + XbaI filled)

<400> SEQUENCE: 7

-continued

```
gtacccccaa aagaaagaga tcctcaggta caaaatcccc ttccaagggt cttcaattca     60
atccaacaca tttgtaattg agtacctttt tcatgctaaa ctttcttgtt ttatacaaag    120
aaaatgaaga tgtggttatt gctcactagg agtttacaat cttgagaaaa gatgtaggcc    180
aagttacttg acctctaact acttcttttt ctcatccaca aagtgagaca attggaatat    240
tttaaaaaat atatatatat atttttatat atatgtgtat atatatattt tatatatatg    300
tgtatatata tattttatat atatgtgtat atatatattt tatatatatg tgtgtatata    360
tatactttat atatatgtgt gtatatatat tttatatata tgtgtatata tatatatttt    420
atatatatgt gtatatatat attttatata tatgtgtata tatatatttt atatatatgt    480
gtgtatatat atattttata tatatgtgtg tatatatatt ttatatatat gtgtatatat    540
atattttata tatatgtgta tatatatatt ttatatatgt gtgtatatat atattttata    600
tatgtgtgta tatatatatt ttatatatat gtgtgtatat atatatttta tatatatgtg    660
tgtatatata tattttatat atatgtgtgt atatatatat tttatatata tgtgtgtata    720
tatatatttt atatatatgt gtgtatatat atattttata tatatgtgtg tatatatata    780
ttttatatat atgtgtgtat atatatattt tatatatatg tgtgtatata tatattttat    840
atatatgtgt gtatatatat attttatata tatgtgtgta tatatatata ttttatatat    900
atgtgtgtat atatatatat tttatatata tatgtgtgta tatatatata ttttatatat    960
atatgtgtat atatatatat atatatattt ttttttgag acagagtctc gctctgtcgc   1020
ccaggctgga gtgcagtggc gcgatctcag ctcactgcaa cctccacctc ctgggttcaa   1080
gccgttctcc tgcctcagcc tcccgagtag ctgggactac aggcacgtgc caccacgtcc   1140
agctaatagt tttgtatctt tagtagagat ggggtttcac catattggtc aggatggtct   1200
cgatctcttg acctcatgat ccgcccacct cagcctccca aagtgctggg attacaggcg   1260
tgagccacca ctcccagcct aaaatatttt tatgatcttt ggccatattg ttcaatggac   1320
aaaatttagc cttcgaaggc aggccgattt gaggttaata ctacctttac cacttgatag   1380
ctatgtgacc ttggccatgt ggtttcaaca gtctgaacct cattttctct gtgtatgtgt   1440
ggtcctcctt acaagtttgt gaaaaatgtg aagtccttag ccatgatagc ccaatataac   1500
aggctaaatg ataataggtt tatgttcttt tcctttatat tctcagataa gcactgtcca   1560
agtttgaggt gttttgaggt ctcgcctgat ttggattgtt tgagtttatg ctattctttg   1620
aattctttga gctgttctga agcagtgtat catgaacaaa aacatcccca gttcagtcca   1680
aacccctggt tacatatcat tcttatgcca tgttataacc agtttgagag tgttccctct   1740
gttattgcat ttaagtttca gcctcacaca gaaattcagc agccaatttc taagccctaa   1800
gcataaaatc tggggtgggg gggggggatg gcctgaagag cagcattatg aatagcacca   1860
ttataattaa tgatctctca ggaagattta caatcacagg tagcagataa aacaaatagt   1920
actgcttctg cacttcccct ccttttattc gctatgaaat tttatgggaa atcagtccag   1980
tgaaaaatgt aagctcttaa tctttcccag aaatcctacc tcatttgatg aatactttga   2040
gggaatgaat tagagcattt ttttctttta tagtctactt cgcatttacg aagtgaggac   2100
ggtagcttag gctgcctggc caactgatga gaaggtcaga ggcattttta gagacctctg   2160
ttgtctttca ttcatgttca ttttccacaa ggcaagtaat ttccaacaaa tcagtgtctt   2220
cattagtaat aagattatta acaacaataa tagtcatagt aactattcag tgagagtcca   2280
ttatatatca ggcattctac aaggtacttt atatacatct gagtaaacct cacacaattc   2340
tacagggagg tatttctatc cccatttaac aaataaggaa acgaagtcca agtaaattaa   2400
```

-continued cttgcccaag gtcacacaga tagtacctgg cagaacagga atttaaacct aaatttgtcc 2460
aactccaaaa gcagccttct atttgttata aatgctgcct ctcattatca catattttat 2520
tattaacaac aacaaacata ccaattagct taagatacaa tacaaccaga taatcatgat 2580
gacaacagta attgttatac tattataata aaatagatgt tttgtatgtt actataatct 2640
tgaatttgaa tagaaatttg catttctgaa agcatgttcc tgtcatctaa tatgattctg 2700
tatctattaa aatagtacta catctagccc gggctcgaca ttgattattg a 2751

<210> SEQ ID NO 8
<211> LENGTH: 2082
<212> TYPE: DNA
<213> ORGANISM: Homo sapiens
<220> FEATURE:
<221> NAME/KEY: MISC_FEATURE
<223> OTHER INFORMATION: 1_6R2(HindIII filled)

<400> SEQUENCE: 8
tcgacatgga attacatggg catcttttgt ctgaaaccaa ttatgtatgt ttacgtatgt 60
gtatgtttat gcatatgtta taggtttaat atatattaat atatataata tataatatat 120
aaatattaat atgtattata taatatatat taatatatta tattatatta ctatataaat 180
aatattaata tattatatta aaatattaat aaatatatca tattaaatat tatattaatt 240
aaatattaat aaatatatta tattaatata tttatatatt aaacctataa catatgcata 300
tacttattta tatataacat gcatgtactt atttatatat acaatatata tttatatatt 360
atataatata ttatatgtat ttatatatta tatatcatat attatatgta tttatatatt 420
atatatcata taatatatat atttatatta tatatattat atgatatata atattatata 480
atgtattaat atatattaaa cctatattta taattctgga ctcactattt tgtttcattg 540
gtgtctgtgt gtatctaacc ctatgccaat aatgtactat cttaattacc atagctttat 600
agtaagctag cttgatatcg aattcctgca gcccggggga tccactagat ttggccatat 660
tgttcaatgg acaaaattta gccttcgaag gcaggccgat ttgaggttaa tactaccttt 720
accacttgat agctatgtga ccttggccat gtggtttcaa cagtctgaac ctcattttct 780
ctgtgtatgt gtggtcctcc ttacaagttt gtgaaaaatg tgaagtcctt agccatgata 840
gcccaatata acaggctaaa tgataatagg tttatgttct tttcctttat attctcagat 900
aagcactgtc caagtttgag gtgttttgag gtctcgcctg atttggattg tttgagttta 960
tgctattctt tgaattcttt gagctgttct gaagcagtgt atcatgaaca aaaacatccc 1020
cagttcagtc caaacccctg gttacatatc attcttatgc catgttataa ccagtttgag 1080
agtgttccct ctgttattgc atttaagttt cagcctcaca cagaaattca gcagccaatt 1140
tctaagccct aagcataaaa tctggggtgg ggggggggga tggcctgaag agcagcatta 1200
tgaatagcac cattataatt aatgatctct caggaagatt tacaatcaca ggtagcagat 1260
aaaacaaata gtactgcttc tgcacttccc ctccttttat tcgctatgaa attttatggg 1320
aaatcagtcc agtgaaaaat gtaagctctt aatctttccc agaaatccta cctcatttga 1380
tgaatacttt gagggaatga attagagcat ttttttcttt tatagtctac ttcgcattta 1440
cgaagtgagg acggtagctt aggctgcctg gccaactgat gagaaggtca gaggcatttt 1500
tagagacctc tgttgtcttt cattcatgtt cattttccac aaggcaagta atttccaaca 1560
aatcagtgtc ttcattagta ataagattat taacaacaat aatagtcata gtaactattc 1620
agtgagagtc cattatatat caggcattct acaaggtact ttatatacat ctgagtaaac 1680

```
ctcacacaat tctacaggga ggtatttcta tccccattta acaaataagg aaacgaagtc   1740
caagtaaatt aacttgccca aggtcacaca gatagtacct ggcagaacag gaatttaaac   1800
ctaaatttgt ccaactccaa aagcagcctt ctatttgtta taaatgctgc ctctcattat   1860
cacatatttt attattaaca acaacaaaca taccaattag cttaagatac aatacaacca   1920
gataatcatg atgacaacag taattgttat actattataa taaaatagat gttttgtatg   1980
ttactataat cttgaatttg aatagaaatt tgcatttctg aaagcatgtt cctgtcatct   2040
aatatgattc tgtatctatt aaaatagtac tacatctagc cc                      2082
```

<210> SEQ ID NO 9
<211> LENGTH: 3345
<212> TYPE: DNA
<213> ORGANISM: Homo sapiens
<220> FEATURE:
<221> NAME/KEY: X_S29(2*HindIII, SalI filled)
<222> LOCATION: (1)..(3345)
<220> FEATURE:
<221> NAME/KEY: misc_feature
<222> LOCATION: (1)..(3345)

<400> SEQUENCE: 9

```
gatcccttta taaaaccaca atataatgga gtgctataat ttcaaacagt gtttggtctg     60
ctggcagagt ggtcattcta acagcagtca cagtagagta gaaataagac tgcagtatat    120
ctaaggcaaa aagctgaggt ttcaggagct tgaaggtaaa gaggaagaaa gaaatgggaa    180
tgggaattgg aaagacaaat atcgttaaga gaaaattgct tttaggagag gggaaagaat    240
ctatgtgtac ttaagactat ggaatcaatc ccatttaagc tgggaaacta gtttcatata    300
taactaataa attttattta cagaatatct atttacctga tctaggcttc aagccaaagg    360
gactgtgtga aaaaccatca gttctgtcat attcctaaaa aaaaattaaa aagttaaaaa    420
taaataaata ataaaacttc ttttctttca aaataatcaa ggtgcttatt cacatccatt    480
ccaatttggg gaaatactta ttttcctatg attagcgaag agaaaagtaa cttgcatttc    540
aattcaagtt gatacatgtc acttttaaga ggtcaactaa tatttgctag ttgagctaac    600
catataggct ttaaatactt tcatagtaga aagaaaatga aaatcattag tgaactgtat    660
aaaatagatc atacttttg aaagaatcag actgaagttt ccgaaaaaaa gaagtaagct    720
agcttcaatg aaaaggtaag tgaatttagc atttactcag catctactat ggacttaaca    780
cctaacagta gataatctga aggcaaacat atttgtatag ggactgcaga atgatagatg    840
ataaatatca tctcttctat ttgaatgaat attttttcaa atctttcaca cacagtggtt    900
tgctatggaa agatttgtag tacattaaac aaatctgaag atggagttag aaagctagct    960
taggctatgt tttgagcaca acatataatt tctctgtgat tgtttcttca tctttcaaat   1020
gaggttactg tgaagattaa atgagataac taaatgatga taaaataatg taatcttagc   1080
agcaccttat ttaatctgtg caacaactct gtgaagtgag tagggctcag cttcagtcac   1140
ttctctgcca tttattaact aagatagttt ggaaagttac ccatctcttc agctgtaaaa   1200
tgatgaggat catacctatt ttatggggct gcttttaggt acaaatatac aggcaagcac   1260
tttgttaata ctaaagcatt acaccaatta gttttactct tttccattca cacatgaaat   1320
taatgtaatc agaattctgt agattaccta aatcttctgt taacacgtga tatgcagttc   1380
aggttaaatg tcagttgagt taccaaagca catacatact caccacccta tccaaatcta   1440
caagcctccc agtttgtctt cactattttg gttaaattaa tatgaattcc tagatgaaaa   1500
```

-continued

```
tttcactgat ccaaatgaaa taaaaaatat attacaaaac tcacacctgt aatctcaaca   1560

ttttgggagg ccaaggcagg tagatcactt gaggccagga gttcaagacc agcctgatca   1620

acatggtgaa accctgtctc tactaaaaat acaaaaatta gccaggtgtg gtggcatgtg   1680

cctgtagtcc tacctactcg ggaggctgag gcacaagaat cgcttgaatg tgggaggtgg   1740

aggttgcagt gacctgagat cgtgccactg cactccagcc taggcaacag agtgagatca   1800

tgtgtcatat atatatatat atatatatat atatatatat atatatacac acacacacac   1860

atatatatat acacatatat atacgtatat atatatatgt atatatatac atatatatac   1920

atatatatat atacgtatat atatacgtat atatatatca atgtaaatta tttgggaaat   1980

ttggtatgaa tagtcttccc tgtgaacaca gatcataaaa tcatatatca agcagacaaa   2040

taagtagtag tcacttatat gcttatactt gtaacttaaa gtaaaagaat tacaaaagca   2100

tatgacaaag actaatttta agatatccta atttaaattg ttttctaaaa gtgtgtatac   2160

cattttacct atcatatgaa taatttagaa acatgtttat aaaattaatg tccaaatcca   2220

ttcaaaagtt ttgtaatgca gatcacccac aacaacaaag aatcctagcc tattaaaaaa   2280

gcaacaccac ctacatataa tgaaatatta gcagcatcta tgtaaccaaa gttacacagt   2340

gaatttgggc catccaacac tttgagcaaa gtgttgaatt catcaaatga atgtgtaatc   2400

atttacttac taatgccaat acactttaag gtaatcttaa gtagaagaga tagagtttag   2460

aattttttaa atttatctct tgttgtaaag caatagactt gaataaataa attagaagaa   2520

tcagtcattc aagccaccag agtatttgat cgagatttca caaactctaa ctttctgata   2580

cccattctcc caaaaacgtg taacctcctg tcgataggaa caacccactg cagggatgtt   2640

tctcgtggaa aaaggaaatt tcttttgcat tggtttcaga cctaactggt tacaagaaaa   2700

accaaaggcc attgcacaat gctgaagtac tttttcaaa tttaaaattt gaaagttgtt   2760

cttaaaatct atcatttatt ttaaaatacg gatgaatgag aaagcataga tttgataaag   2820

tgaattcttt tctgcaatct acagacactt ccaaaaatca ctacagacac tacagacact   2880

acagaaaatc ataaataaac aagtgctagt atcaatattt ttaccaaaaa atggcattct   2940

tagaattttt tataggctag aaggtttgta caaactaatc tgccacggat tttaaaatat   3000

gagtgaataa attatattgc aaaaaaaatc aggttacaga gaactggcaa ggaagactct   3060

tatgtaaaac acagaaaaca tacaaaacgt atttttaaga caaataaaaa cagaacttgt   3120

acctcagatg atactggaga ttgtgttgac atattagcat tatcactgtc ttgctaaaac   3180

ataaaaataa aaagatggaa gatgaaatta caatacaaat gatgatttaa acatataaaa   3240

ggaaaataaa aattgttctg accaactact aaaggaagac ctactaaaga tatgccatcc   3300

agcacattgc cactctacat gtggtctgta aaccagcagc atagg                   3345
```

```
<210> SEQ ID NO 10
<211> LENGTH: 892
<212> TYPE: DNA
<213> ORGANISM: Homo sapiens
<220> FEATURE:
<221> NAME/KEY: misc_feature
<222> LOCATION: (1)..(892)
<223> OTHER INFORMATION: X_S29R3

<400> SEQUENCE: 10

aattcaacac tttgctcaaa gtgttggatg gcccaaattc actgtgtaac tttggttaca     60

tagatgctgc taatatttca ttatatgtag gtggtgttgc ttttttaata ggctaggatt    120

ctttgttgtt gtgggtgatc tgcattacaa aacttttgaa tggatttgga cattaatttt    180
```

-continued ataaacatgt ttctaaatta ttcatatgat aggtaaaatg gtatacacac ttttagaaaa 240
caatttaaat taggatatct taaaattagt ctttgtcata tgcttttgta attcttttac 300
tttaagttac aagtataagc atataagtga ctactactta tttgtctgct tgatatatga 360
ttttatgatc tgtgttcaca gggaagacta ttcataccaa atttcccaaa taatttacat 420
tgatatatat atacgtatat atatacgtat atatatatat gtatatatat gtatatatat 480
acatatatat atatacgtat atatatgtgt atatatatat gtgtgtgtgt gtgtatatat 540
atatatatat atatatatat atatatatat atatgacaca tgatctcact ctgttgccta 600
ggctggagtg cagtggcacg atctcaggtc actgcaacct ccacctccca cattcaagcg 660
attcttgtgc ctcagcctcc cgagtaggta ggactacagg cacatgccac cacacctggc 720
taatttttgt atttttagta gagacagggt ttcaccatgt tgatcaggct ggtcttgaac 780
tcctggcctc aagtgatcta cctgccttgg cctcccaaaa tgttgagatt acaggtgtga 840
gttttgtaat atatttttta tttcatttgg atcagtgaaa ttttcatcta gg 892

<210> SEQ ID NO 11
<211> LENGTH: 1173
<212> TYPE: DNA
<213> ORGANISM: Homo sapiens
<220> FEATURE:
<221> NAME/KEY: C_GAPDH promoter
<222> LOCATION: (1)..(363)
<223> OTHER INFORMATION: Human CMV IE gene enhancer

<400> SEQUENCE: 11
ctagttatta atagtaatca attacggggt cattagttca tagcccatat atggagttcc 60
gcgttacata acttacggta aatggcccgc ctggctgacc gcccaacgac ccccgcccat 120
tgacgtcaat aatgacgtat gttcccatag taacgccaat agggactttc cattgacgtc 180
aatgggtgga ctatttacgg taaactgccc acttggcagt acatcaagtg tatcatatgc 240
caagtacgcc ccctattgac gtcaatgacg gtaaatggcc cgcctggcat tatgcccagt 300
acatgacctt atgggacttt cctacttggc agtacatcta cgtattagtc atcgctatta 360
ccatgacctc gaggagaagt tccccaactt tcccgcctct cagcctttga aagaaagaaa 420
ggggaggggg caggccgcgt gcagccgcga gcggtgctgg gctccggctc caattcccca 480
tctcagtcgt tcccaaagtc ctcctgtttc atccaagcgt gtaagggtcc ccgtccttga 540
ctccctagtg tcctgctgcc cacagtccag tcctgggaac cagcaccgat cacctcccat 600
cgggccaatc tcagtccctt ccccccctacg tcggggccca cacgctcggt gcgtgcccag 660
ttgaaccagg cggctgcgga aaaaaaaaag cggggagaaa gtagggcccg gctactagcg 720
gttttacggg cgcacgtagc tcaggcctca agaccttggg ctgggactgg ctgagcctgg 780
cgggaggcgg ggtccgagtc accgcctgcc gccgcgcccc cggtttctat aaattgagcc 840
cgcagcctcc cgcttcgctc tctgctcctc ctgttcgaca gtcagccgca tcttcttttg 900
cgtcgccagg tgaagacggg cggagagaaa cccgggaggc tagggacggc ctgaaggcgg 960
caggggcggg cgcaggccgg atgtgttcgc gccgctgcgg ggtgggcccg ggcggcctcc 1020
gcattgcagg ggcgggcgga ggacgtgatg cggcgcgggc tgggcatgga ggcctggtgg 1080
gggaggggag gggaggcgtg tgtgtcggcc ggggccacta ggcgctcact gttctctccc 1140
tccgcgcagc cgagccacat cgctcagaca cca 1173

<210> SEQ ID NO 12

<211> LENGTH: 411
<212> TYPE: DNA
<213> ORGANISM: Homo sapiens
<220> FEATURE:
<221> NAME/KEY: misc_feature
<223> OTHER INFORMATION: hSRP14

<400> SEQUENCE: 12
atggtgttgt tggagagcga gcagttcctg acggagctga ccagactttt ccagaagtgc 60
cggacgtcgg gcagcgtcta tatcaccttg aagaagtatg acggtcgaac caaacccatt 120
ccaaagaagg gtactgtgga gggctttgag cccgcagaca acaagtgtct gttaagagct 180
accgatggga agaagaagat cagcactgtg gtgagctcca aggaagtgaa taagtttcag 240
atggcttatt caaacctcct tagagctaac atggatgggc tgaagaagag agacaaaaag 300
aacaaaacta agaagaccaa agcagcagca gcagcagcag cagcagcacc tgccgcagca 360
gcaacagcac caacaacagc agcaacaaca gcagcaacag cagcacagta a 411

<210> SEQ ID NO 13
<211> LENGTH: 136
<212> TYPE: PRT
<213> ORGANISM: Homo sapiens
<220> FEATURE:
<221> NAME/KEY: MISC_FEATURE
<223> OTHER INFORMATION: hSRP14

<400> SEQUENCE: 13

Met Val Leu Leu Glu Ser Glu Gln Phe Leu Thr Glu Leu Thr Arg Leu
1 5 10 15

Phe Gln Lys Cys Arg Thr Ser Gly Ser Val Tyr Ile Thr Leu Lys Lys
20 25 30

Tyr Asp Gly Arg Thr Lys Pro Ile Pro Lys Lys Gly Thr Val Glu Gly
35 40 45

Phe Glu Pro Ala Asp Asn Lys Cys Leu Leu Arg Ala Thr Asp Gly Lys
50 55 60

Lys Lys Ile Ser Thr Val Val Ser Ser Lys Glu Val Asn Lys Phe Gln
65 70 75 80

Met Ala Tyr Ser Asn Leu Leu Arg Ala Asn Met Asp Gly Leu Lys Lys
85 90 95

Arg Asp Lys Lys Asn Lys Thr Lys Lys Thr Lys Ala Ala Ala Ala Ala
100 105 110

Ala Ala Ala Ala Pro Ala Ala Ala Ala Thr Ala Pro Thr Thr Ala Ala
115 120 125

Thr Thr Ala Ala Thr Ala Ala Gln
130 135

<210> SEQ ID NO 14
<211> LENGTH: 1431
<212> TYPE: DNA
<213> ORGANISM: Homo sapiens
<220> FEATURE:
<221> NAME/KEY: misc_feature
<223> OTHER INFORMATION: hSEC61A1

<400> SEQUENCE: 14
atggcaatca aatttctgga agtcatcaag cccttctgtg tcatcctgcc ggaaattcag 60
aagccagaga ggaagattca gtttaaggag aaagtgctgt ggaccgctat caccctcttt 120
atcttcttag tgtgctgcca gattcccctg tttgggatca tgtcttcaga ttcagctgac 180
cctttctatt ggatgagagt gattctagcc tctaacagag gcacattgat ggagctaggg 240
atctctccta ttgtcacgtc tggccttata atgcaactct tggctggcgc caagataatt 300
gaagttggtg acaccccaaa agaccgagct ctcttcaacg gagcccaaaa gttatttggc 360
atgatcatta ctatcggcca gtctatcgtg tatgtgatga ccgggatgta tggggaccct 420
tctgaaatgg gtgctggaat ttgcctgcta atcaccattc agctctttgt tgctggctta 480
attgtcctac ttttggatga actcctgcaa aaaggatatg gccttggctc tggtatttct 540
ctcttcattg caactaacat ctgtgaaacc atcgtatgga aggcattcag ccccactact 600
gtcaacactg gccgaggaat ggaatttgaa ggtgctatca tcgcactttt ccatctgctg 660
gccacacgca cagacaaggt ccgagccctt cgggaggcgt tctaccgcca gaatcttccc 720
aacctcatga atctcatcgc caccatcttt gtctttgcag tggtcatcta tttccagggc 780
ttccgagtgg acctgccaat caagtcggcc cgctaccgtg gccagtacaa cacctatccc 840
atcaagctct tctatacgtc caacatcccc atcatcctgc agtctgccct ggtgtccaac 900
ctttatgtca tctcccaaat gctctcagct cgcttcagtg gcaacttgct ggtcagcctg 960
ctgggcacct ggtcggacac gtcttctggg ggcccagcac gtgcttatcc agttggtggc 1020
ctttgctatt acctgtcccc tccagaatct tttggctccg tgttagaaga cccggtccat 1080
gcagttgtat acatagtgtt catgctgggc tcctgtgcat tcttctccaa aacgtggatt 1140
gaggtctcag gttcctctgc caaagatgtt gcaaagcagc tgaaggagca gcagatggtg 1200
atgagaggcc accgagagac ctccatggtc catgaactca accggtacat ccccacagcc 1260
gcggcctttg gtgggctgtg catcggggcc ctctcggtcc tggctgactt cctaggcgcc 1320
attgggtctg gaaccgggat cctgctcgca gtcacaatca tctaccagta ctttgagatc 1380
ttcgttaagg agcaaagcga ggttggcagc atgggggccc tgctcttctg a 1431

<210> SEQ ID NO 15
<211> LENGTH: 476
<212> TYPE: PRT
<213> ORGANISM: Homo sapiens
<220> FEATURE:
<221> NAME/KEY: MISC_FEATURE
<223> OTHER INFORMATION: hSEC61A1

<400> SEQUENCE: 15

Met Ala Ile Lys Phe Leu Glu Val Ile Lys Pro Phe Cys Val Ile Leu
1 5 10 15

Pro Glu Ile Gln Lys Pro Glu Arg Lys Ile Gln Phe Lys Glu Lys Val
20 25 30

Leu Trp Thr Ala Ile Thr Leu Phe Ile Phe Leu Val Cys Cys Gln Ile
35 40 45

Pro Leu Phe Gly Ile Met Ser Ser Asp Ser Ala Asp Pro Phe Tyr Trp
50 55 60

Met Arg Val Ile Leu Ala Ser Asn Arg Gly Thr Leu Met Glu Leu Gly
65 70 75 80

Ile Ser Pro Ile Val Thr Ser Gly Leu Ile Met Gln Leu Leu Ala Gly
85 90 95

Ala Lys Ile Ile Glu Val Gly Asp Thr Pro Lys Asp Arg Ala Leu Phe
100 105 110

Asn Gly Ala Gln Lys Leu Phe Gly Met Ile Ile Thr Ile Gly Gln Ser
115 120 125

Ile Val Tyr Val Met Thr Gly Met Tyr Gly Asp Pro Ser Glu Met Gly
130 135 140

-continued

```
Ala Gly Ile Cys Leu Leu Ile Thr Ile Gln Leu Phe Val Ala Gly Leu
145                 150                 155                 160

Ile Val Leu Leu Leu Asp Glu Leu Leu Gln Lys Gly Tyr Gly Leu Gly
                165                 170                 175

Ser Gly Ile Ser Leu Phe Ile Ala Thr Asn Ile Cys Glu Thr Ile Val
            180                 185                 190

Trp Lys Ala Phe Ser Pro Thr Thr Val Asn Thr Gly Arg Gly Met Glu
        195                 200                 205

Phe Glu Gly Ala Ile Ile Ala Leu Phe His Leu Leu Ala Thr Arg Thr
    210                 215                 220

Asp Lys Val Arg Ala Leu Arg Glu Ala Phe Tyr Arg Gln Asn Leu Pro
225                 230                 235                 240

Asn Leu Met Asn Leu Ile Ala Thr Ile Phe Val Phe Ala Val Val Ile
                245                 250                 255

Tyr Phe Gln Gly Phe Arg Val Asp Leu Pro Ile Lys Ser Ala Arg Tyr
            260                 265                 270

Arg Gly Gln Tyr Asn Thr Tyr Pro Ile Lys Leu Phe Tyr Thr Ser Asn
        275                 280                 285

Ile Pro Ile Ile Leu Gln Ser Ala Leu Val Ser Asn Leu Tyr Val Ile
    290                 295                 300

Ser Gln Met Leu Ser Ala Arg Phe Ser Gly Asn Leu Leu Val Ser Leu
305                 310                 315                 320

Leu Gly Thr Trp Ser Asp Thr Ser Ser Gly Gly Pro Ala Arg Ala Tyr
                325                 330                 335

Pro Val Gly Gly Leu Cys Tyr Tyr Leu Ser Pro Pro Glu Ser Phe Gly
            340                 345                 350

Ser Val Leu Glu Asp Pro Val His Ala Val Val Tyr Ile Val Phe Met
        355                 360                 365

Leu Gly Ser Cys Ala Phe Phe Ser Lys Thr Trp Ile Glu Val Ser Gly
    370                 375                 380

Ser Ser Ala Lys Asp Val Ala Lys Gln Leu Lys Glu Gln Gln Met Val
385                 390                 395                 400

Met Arg Gly His Arg Glu Thr Ser Met Val His Glu Leu Asn Arg Tyr
                405                 410                 415

Ile Pro Thr Ala Ala Ala Phe Gly Gly Leu Cys Ile Gly Ala Leu Ser
            420                 425                 430

Val Leu Ala Asp Phe Leu Gly Ala Ile Gly Ser Gly Thr Gly Ile Leu
        435                 440                 445

Leu Ala Val Thr Ile Ile Tyr Gln Tyr Phe Glu Ile Phe Val Lys Glu
    450                 455                 460

Gln Ser Glu Val Gly Ser Met Gly Ala Leu Leu Phe
465                 470                 475
```

<210> SEQ ID NO 16
<211> LENGTH: 291
<212> TYPE: DNA
<213> ORGANISM: Homo sapiens
<220> FEATURE:
<221> NAME/KEY: misc_feature
<223> OTHER INFORMATION: hSEC61B

<400> SEQUENCE: 16

```
atgcctggtc cgacccccag tggcactaac gtgggatcct cagggcgctc tcccagcaaa     60

gcagtggccg cccgggcggc gggatccact gtccggcaga ggaaaaatgc cagctgtggg    120

acaaggagtg caggccgcac aacctcggca ggcaccgggg ggatgtggcg attctacaca    180
```

-continued gaagattcac ctgggctcaa agttggccct gttccagtat tggttatgag tcttctgttc 240
atcgcttctg tatttatgtt gcacatttgg ggcaagtaca ctcgttcgta g 291

<210> SEQ ID NO 17
<211> LENGTH: 96
<212> TYPE: PRT
<213> ORGANISM: Homo sapiens
<220> FEATURE:
<221> NAME/KEY: MISC_FEATURE
<223> OTHER INFORMATION: hSEC61B

<400> SEQUENCE: 17

```
Met Pro Gly Pro Thr Pro Ser Gly Thr Asn Val Gly Ser Ser Gly Arg
1               5                   10                  15

Ser Pro Ser Lys Ala Val Ala Ala Arg Ala Ala Gly Ser Thr Val Arg
            20                  25                  30

Gln Arg Lys Asn Ala Ser Cys Gly Thr Arg Ser Ala Gly Arg Thr Thr
        35                  40                  45

Ser Ala Gly Thr Gly Gly Met Trp Arg Phe Tyr Thr Glu Asp Ser Pro
    50                  55                  60

Gly Leu Lys Val Gly Pro Val Pro Val Leu Val Met Ser Leu Leu Phe
65                  70                  75                  80

Ile Ala Ser Val Phe Met Leu His Ile Trp Gly Lys Tyr Thr Arg Ser
                85                  90                  95
```

<210> SEQ ID NO 18
<211> LENGTH: 207
<212> TYPE: DNA
<213> ORGANISM: Homo sapiens
<220> FEATURE:
<221> NAME/KEY: misc_feature
<223> OTHER INFORMATION: hSEC61G

<400> SEQUENCE: 18
atggatcagg taatgcagtt tgttgagcca agtcggcagt ttgtaaagga ctccattcgg 60
ctggttaaaa gatgcactaa acctgataga aaagaattcc agaagattgc catggcaaca 120
gcaataggat ttgctataat gggattcatt ggcttctttg tgaaattgat ccatattcct 180
attaataaca tcattgttgg tggctga 207

<210> SEQ ID NO 19
<211> LENGTH: 68
<212> TYPE: PRT
<213> ORGANISM: Homo sapiens
<220> FEATURE:
<221> NAME/KEY: MISC_FEATURE
<223> OTHER INFORMATION: hSEC61G

<400> SEQUENCE: 19

```
Met Asp Gln Val Met Gln Phe Val Glu Pro Ser Arg Gln Phe Val Lys
1               5                   10                  15

Asp Ser Ile Arg Leu Val Lys Arg Cys Thr Lys Pro Asp Arg Lys Glu
            20                  25                  30

Phe Gln Lys Ile Ala Met Ala Thr Ala Ile Gly Phe Ala Ile Met Gly
        35                  40                  45

Phe Ile Gly Phe Phe Val Lys Leu Ile His Ile Pro Ile Asn Asn Ile
    50                  55                  60

Ile Val Gly Gly
65
```

<210> SEQ ID NO 20
<211> LENGTH: 1515
<212> TYPE: DNA
<213> ORGANISM: Homo sapiens
<220> FEATURE:
<221> NAME/KEY: misc_feature
<223> OTHER INFORMATION: hSRP54

<400> SEQUENCE: 20
atggttctag cagaccttgg aagaaaaata acatcagcat tacgctcgtt gagcaatgcc 60
accattatca atgaagaggt attgaatgct atgctaaaag aagtctgtac cgctttgttg 120
gaagcagatg ttaatattaa actagtgaag caactaagag aaaatgttaa gtctgctatt 180
gatcttgaag agatggcatc tggtcttaac aaaagaaaaa tgattcagca tgctgtattt 240
aaagaacttg tgaagcttgt agaccctgga gttaaggcat ggacacccac taaaggaaaa 300
caaaatgtga ttatgtttgt tggattgcaa gggagtggta aaacaacaac atgttcaaag 360
ctagcatatt attaccagag gaaaggttgg aagacctgtt taatatgtgc agacacattc 420
agagcagggg cttttgacca actaaaacag aatgctacca aagcaagaat tccattttat 480
ggaagctata cagaaatgga tcctgtcatc attgcttctg aaggagtaga gaaatttaaa 540
aatgaaaatt ttgaaattat tattgttgat acaagtggcc gccacaaaca agaagactct 600
ttgtttgaag aaatgcttca agttgctaat gctatacaac ctgataacat tgtttatgtg 660
atggatgcct ccattgggca ggcttgtgaa gcccaggcta aggcttttaa agataaagta 720
gatgtagcct cagtaatagt gacaaaactt gatggccatg caaaaggagg tggtgcactc 780
agtgcagtcg ctgccacaaa aagtccgatt attttcattg gtacagggga acatatagat 840
gactttgaac ctttcaaaac acagcctttt attagcaaac ttcttggtat gggcgacatt 900
gaaggactga tagataaagt caacgagttg aagttggatg acaatgaagc acttatagag 960
aagttgaaac atggtcagtt tacgttgcga gacatgtatg agcaatttca aaatatcatg 1020
aaaatgggcc ccttcagtca gatcttgggg atgatccctg gttttgggac agattttatg 1080
agcaaaggaa atgaacagga gtcaatggca aggctaaaga aattaatgac aataatggat 1140
agtatgaatg atcaagaact agacagtacg gatggtgcca aagtttttag taaacaacca 1200
ggaagaatcc aaagagtagc aagaggatcg ggtgtatcaa caagagatgt tcaagaactt 1260
ttgacacaat ataccaagtt tgcacagatg gtaaaaaaga tgggaggtat caaaggactt 1320
ttcaaaggtg gcgacatgtc taagaatgtg agccagtcac agatggcaaa attgaaccaa 1380
caaatggcca aaatgatgga tcctagggtt cttcatcaca tgggtggtat ggcaggactt 1440
cagtcaatga tgaggcagtt tcaacagggt gctgctggca acatgaaagg catgatggga 1500
ttcaataata tgtaa 1515

<210> SEQ ID NO 21
<211> LENGTH: 504
<212> TYPE: PRT
<213> ORGANISM: Homo sapiens
<220> FEATURE:
<221> NAME/KEY: MISC_FEATURE
<223> OTHER INFORMATION: hSRP54

<400> SEQUENCE: 21

Met Val Leu Ala Asp Leu Gly Arg Lys Ile Thr Ser Ala Leu Arg Ser
1 5 10 15

Leu Ser Asn Ala Thr Ile Ile Asn Glu Glu Val Leu Asn Ala Met Leu
20 25 30

-continued

```
Lys Glu Val Cys Thr Ala Leu Leu Glu Ala Asp Val Asn Ile Lys Leu
        35                  40                  45

Val Lys Gln Leu Arg Glu Asn Val Lys Ser Ala Ile Asp Leu Glu Glu
    50                  55                  60

Met Ala Ser Gly Leu Asn Lys Arg Lys Met Ile Gln His Ala Val Phe
65                  70                  75                  80

Lys Glu Leu Val Lys Leu Val Asp Pro Gly Val Lys Ala Trp Thr Pro
                85                  90                  95

Thr Lys Gly Lys Gln Asn Val Ile Met Phe Val Gly Leu Gln Gly Ser
            100                 105                 110

Gly Lys Thr Thr Thr Cys Ser Lys Leu Ala Tyr Tyr Tyr Gln Arg Lys
        115                 120                 125

Gly Trp Lys Thr Cys Leu Ile Cys Ala Asp Thr Phe Arg Ala Gly Ala
    130                 135                 140

Phe Asp Gln Leu Lys Gln Asn Ala Thr Lys Ala Arg Ile Pro Phe Tyr
145                 150                 155                 160

Gly Ser Tyr Thr Glu Met Asp Pro Val Ile Ile Ala Ser Glu Gly Val
                165                 170                 175

Glu Lys Phe Lys Asn Glu Asn Phe Glu Ile Ile Ile Val Asp Thr Ser
            180                 185                 190

Gly Arg His Lys Gln Glu Asp Ser Leu Phe Glu Glu Met Leu Gln Val
        195                 200                 205

Ala Asn Ala Ile Gln Pro Asp Asn Ile Val Tyr Val Met Asp Ala Ser
    210                 215                 220

Ile Gly Gln Ala Cys Glu Ala Gln Ala Lys Ala Phe Lys Asp Lys Val
225                 230                 235                 240

Asp Val Ala Ser Val Ile Val Thr Lys Leu Asp Gly His Ala Lys Gly
                245                 250                 255

Gly Gly Ala Leu Ser Ala Val Ala Ala Thr Lys Ser Pro Ile Ile Phe
            260                 265                 270

Ile Gly Thr Gly Glu His Ile Asp Asp Phe Glu Pro Phe Lys Thr Gln
        275                 280                 285

Pro Phe Ile Ser Lys Leu Leu Gly Met Gly Asp Ile Glu Gly Leu Ile
    290                 295                 300

Asp Lys Val Asn Glu Leu Lys Leu Asp Asp Asn Glu Ala Leu Ile Glu
305                 310                 315                 320

Lys Leu Lys His Gly Gln Phe Thr Leu Arg Asp Met Tyr Glu Gln Phe
                325                 330                 335

Gln Asn Ile Met Lys Met Gly Pro Phe Ser Gln Ile Leu Gly Met Ile
            340                 345                 350

Pro Gly Phe Gly Thr Asp Phe Met Ser Lys Gly Asn Glu Gln Glu Ser
        355                 360                 365

Met Ala Arg Leu Lys Lys Leu Met Thr Ile Met Asp Ser Met Asn Asp
    370                 375                 380

Gln Glu Leu Asp Ser Thr Asp Gly Ala Lys Val Phe Ser Lys Gln Pro
385                 390                 395                 400

Gly Arg Ile Gln Arg Val Ala Arg Gly Ser Gly Val Ser Thr Arg Asp
                405                 410                 415

Val Gln Glu Leu Leu Thr Gln Tyr Thr Lys Phe Ala Gln Met Val Lys
            420                 425                 430

Lys Met Gly Gly Ile Lys Gly Leu Phe Lys Gly Gly Asp Met Ser Lys
        435                 440                 445
```

```
Asn Val Ser Gln Ser Gln Met Ala Lys Leu Asn Gln Gln Met Ala Lys
    450                 455                 460

Met Met Asp Pro Arg Val Leu His His Met Gly Gly Met Ala Gly Leu
465                 470                 475                 480

Gln Ser Met Met Arg Gln Phe Gln Gln Gly Ala Ala Gly Asn Met Lys
                485                 490                 495

Gly Met Met Gly Phe Asn Asn Met
            500


<210> SEQ ID NO 22
<211> LENGTH: 249
<212> TYPE: DNA
<213> ORGANISM: Homo sapiens
<220> FEATURE:
<221> NAME/KEY: misc_feature
<223> OTHER INFORMATION: hSRP9

<400> SEQUENCE: 22

atgccgcagt accagacctg ggaggagttc agccgcgctg ccgagaagct ttacctcgct      60

gaccctatga aggcacgtgt ggttctcaaa tataggcatt ctgatgggaa cttgtgtgtt     120

aaagtaacag atgatttagt tagacagtgt cttgctctat tgctcaggct gcagtgcagt     180

ggcatgatca tagctcactg catcctcgac ctcctgggct caagcggtcc tcttgcttca     240

gcctcctga                                                             249


<210> SEQ ID NO 23
<211> LENGTH: 82
<212> TYPE: PRT
<213> ORGANISM: Homo sapiens
<220> FEATURE:
<221> NAME/KEY: MISC_FEATURE
<223> OTHER INFORMATION: hSRP9

<400> SEQUENCE: 23

Met Pro Gln Tyr Gln Thr Trp Glu Glu Phe Ser Arg Ala Ala Glu Lys
1               5                   10                  15

Leu Tyr Leu Ala Asp Pro Met Lys Ala Arg Val Val Leu Lys Tyr Arg
            20                  25                  30

His Ser Asp Gly Asn Leu Cys Val Lys Val Thr Asp Asp Leu Val Arg
        35                  40                  45

Gln Cys Leu Ala Leu Leu Leu Arg Leu Gln Cys Ser Gly Met Ile Ile
    50                  55                  60

Ala His Cys Ile Leu Asp Leu Leu Gly Ser Ser Gly Pro Leu Ala Ser
65                  70                  75                  80

Ala Ser


<210> SEQ ID NO 24
<211> LENGTH: 1917
<212> TYPE: DNA
<213> ORGANISM: Homo sapiens
<220> FEATURE:
<221> NAME/KEY: misc_feature
<223> OTHER INFORMATION: hSRPRalpha

<400> SEQUENCE: 24

atgctcgact tcttcaccat tttctccaag ggcgggcttg tgctctggtg cttccagggc      60

gttagcgact catgcaccgg acccgttaac gcgttgattc gttccgtgct gctgcaggaa     120

cggggaggta acaactcctt cacccatgag gcactcacac tcaagtataa actggacaac     180

cagtttgagc tggtgtttgt ggttggtttt cagaagatcc tgacactgac atatgtagac     240
```

aaattgatag atgacgtgca tcggctgttt cgggacaagt accgcacaga gatccaacag 300
caaagtgctt taagtttatt aaatggcact tttgatttcc aaaatgactt cctgcggctc 360
cttcgtgaag cagaggagag cagtaagatc cgtgctccca ctaccatgaa gaaatttgaa 420
gattctgaaa aggccaagaa acctgtgagg tccatgattg agacacgggg ggaaaagccc 480
aaggaaaaag caaagaatag caaaaaaaag ggggccaaga aggaaggttc tgatggtcct 540
ttggctacca gcaaaccagt ccctgcagaa aagtcaggtc ttccagtggg tcctgagaac 600
ggagtagaac tttccaaaga ggagctgatc cgcaggaagc gcgaggagtt cattcagaag 660
catgggaggg gtatggagaa gtccaacaag tccacgaagt cagatgctcc aaaggagaag 720
ggcaaaaaag caccccgggt gtgggaactg ggtggctgtg ctaacaaaga agtgttggat 780
tacagtactc ccaccaccaa tggaacccct gaggctgcct tgtctgagga catcaacctg 840
attcgaggga ctgggtctgg ggggcagctt caggatctgg actgcagcag ctctgatgac 900
gaaggggctg ctcaaaactc taccaaacct agtgcgacca agggaacact gggtggcatg 960
tttggtatgc tgaagggcct tgtgggttca aagagcttga gtcgtgaaga catggaatct 1020
gtgctggaca agatgcgtga tcatctcatt gctaagaacg tggctgcaga cattgccgtc 1080
cagctctgtg aatctgttgc caacaagttg gaagggaagg tgatggggac gttcagcacg 1140
gtgacttcca cagtaaagca agccctacag gagtccctgg tgcagattct gcagccacag 1200
cgtcgtgtag acatgctccg ggacatcatg gatgcccagc gtcgccagcg cccttatgtc 1260
gtcaccttct gcggcgttaa tggagtgggg aaatctacta atcttgccaa gatttccttc 1320
tggttgttag agaatggctt cagtgtcctc attgctgcct gtgatacatt tcgtgctggg 1380
gccgtggagc agctgcgtac acacacccgg cgtttgagtg ccctacaccc tccagagaag 1440
catggtggcc gcaccatggt gcagttgttt gaaaagggct atggcaagga tgctgctggc 1500
attgccatgg aagccattgc ttttgcacgt aaccaaggct ttgacgtggt gctggtggac 1560
acggcaggcc gcatgcaaga caatgcccct ctgatgactg ccctggccaa actcattact 1620
gtcaatacac ctgatttggt gctgtttgta ggagaagcct tagtaggcaa tgaagccgtg 1680
gaccagctgg tcaagttcaa cagagccttg gctgaccatt ctatggctca gacacctcgg 1740
ctcattgatg gcattgttct taccaaattt gataccattg atgacaaggt gggagctgct 1800
atttctatga cgtacatcac aagcaaaccc atcgtctttg tgggcaccgg ccagacctac 1860
tgtgacctac gcagcctcaa tgccaaggct gtggtggctg ccctcatgaa ggcttaa 1917

<210> SEQ ID NO 25
<211> LENGTH: 638
<212> TYPE: PRT
<213> ORGANISM: Homo sapiens
<220> FEATURE:
<221> NAME/KEY: MISC_FEATURE
<223> OTHER INFORMATION: hSRPRalpha

<400> SEQUENCE: 25

Met Leu Asp Phe Phe Thr Ile Phe Ser Lys Gly Gly Leu Val Leu Trp
1 5 10 15

Cys Phe Gln Gly Val Ser Asp Ser Cys Thr Gly Pro Val Asn Ala Leu
20 25 30

Ile Arg Ser Val Leu Leu Gln Glu Arg Gly Gly Asn Asn Ser Phe Thr
35 40 45

His Glu Ala Leu Thr Leu Lys Tyr Lys Leu Asp Asn Gln Phe Glu Leu
50 55 60

-continued

```
Val Phe Val Val Gly Phe Gln Lys Ile Leu Thr Leu Thr Tyr Val Asp
65                  70                  75                  80

Lys Leu Ile Asp Asp Val His Arg Leu Phe Arg Asp Lys Tyr Arg Thr
                85                  90                  95

Glu Ile Gln Gln Gln Ser Ala Leu Ser Leu Leu Asn Gly Thr Phe Asp
            100                 105                 110

Phe Gln Asn Asp Phe Leu Arg Leu Leu Arg Glu Ala Glu Glu Ser Ser
        115                 120                 125

Lys Ile Arg Ala Pro Thr Thr Met Lys Lys Phe Glu Asp Ser Glu Lys
    130                 135                 140

Ala Lys Lys Pro Val Arg Ser Met Ile Glu Thr Arg Gly Glu Lys Pro
145                 150                 155                 160

Lys Glu Lys Ala Lys Asn Ser Lys Lys Lys Gly Ala Lys Lys Glu Gly
                165                 170                 175

Ser Asp Gly Pro Leu Ala Thr Ser Lys Pro Val Pro Ala Glu Lys Ser
            180                 185                 190

Gly Leu Pro Val Gly Pro Glu Asn Gly Val Glu Leu Ser Lys Glu Glu
        195                 200                 205

Leu Ile Arg Arg Lys Arg Glu Glu Phe Ile Gln Lys His Gly Arg Gly
    210                 215                 220

Met Glu Lys Ser Asn Lys Ser Thr Lys Ser Asp Ala Pro Lys Glu Lys
225                 230                 235                 240

Gly Lys Lys Ala Pro Arg Val Trp Glu Leu Gly Gly Cys Ala Asn Lys
                245                 250                 255

Glu Val Leu Asp Tyr Ser Thr Pro Thr Thr Asn Gly Thr Pro Glu Ala
            260                 265                 270

Ala Leu Ser Glu Asp Ile Asn Leu Ile Arg Gly Thr Gly Ser Gly Gly
        275                 280                 285

Gln Leu Gln Asp Leu Asp Cys Ser Ser Ser Asp Asp Glu Gly Ala Ala
    290                 295                 300

Gln Asn Ser Thr Lys Pro Ser Ala Thr Lys Gly Thr Leu Gly Gly Met
305                 310                 315                 320

Phe Gly Met Leu Lys Gly Leu Val Gly Ser Lys Ser Leu Ser Arg Glu
                325                 330                 335

Asp Met Glu Ser Val Leu Asp Lys Met Arg Asp His Leu Ile Ala Lys
            340                 345                 350

Asn Val Ala Ala Asp Ile Ala Val Gln Leu Cys Glu Ser Val Ala Asn
        355                 360                 365

Lys Leu Glu Gly Lys Val Met Gly Thr Phe Ser Thr Val Thr Ser Thr
    370                 375                 380

Val Lys Gln Ala Leu Gln Glu Ser Leu Val Gln Ile Leu Gln Pro Gln
385                 390                 395                 400

Arg Arg Val Asp Met Leu Arg Asp Ile Met Asp Ala Gln Arg Arg Gln
                405                 410                 415

Arg Pro Tyr Val Val Thr Phe Cys Gly Val Asn Gly Val Gly Lys Ser
            420                 425                 430

Thr Asn Leu Ala Lys Ile Ser Phe Trp Leu Leu Glu Asn Gly Phe Ser
        435                 440                 445

Val Leu Ile Ala Ala Cys Asp Thr Phe Arg Ala Gly Ala Val Glu Gln
    450                 455                 460

Leu Arg Thr His Thr Arg Arg Leu Ser Ala Leu His Pro Pro Glu Lys
465                 470                 475                 480
```

```
His Gly Gly Arg Thr Met Val Gln Leu Phe Glu Lys Gly Tyr Gly Lys
                485                 490                 495

Asp Ala Ala Gly Ile Ala Met Glu Ala Ile Ala Phe Ala Arg Asn Gln
            500                 505                 510

Gly Phe Asp Val Val Leu Val Asp Thr Ala Gly Arg Met Gln Asp Asn
        515                 520                 525

Ala Pro Leu Met Thr Ala Leu Ala Lys Leu Ile Thr Val Asn Thr Pro
    530                 535                 540

Asp Leu Val Leu Phe Val Gly Glu Ala Leu Val Gly Asn Glu Ala Val
545                 550                 555                 560

Asp Gln Leu Val Lys Phe Asn Arg Ala Leu Ala Asp His Ser Met Ala
                565                 570                 575

Gln Thr Pro Arg Leu Ile Asp Gly Ile Val Leu Thr Lys Phe Asp Thr
            580                 585                 590

Ile Asp Asp Lys Val Gly Ala Ala Ile Ser Met Thr Tyr Ile Thr Ser
        595                 600                 605

Lys Pro Ile Val Phe Val Gly Thr Gly Gln Thr Tyr Cys Asp Leu Arg
    610                 615                 620

Ser Leu Asn Ala Lys Ala Val Val Ala Ala Leu Met Lys Ala
625                 630                 635
```

<210> SEQ ID NO 26
<211> LENGTH: 816
<212> TYPE: DNA
<213> ORGANISM: Homo sapiens
<220> FEATURE:
<221> NAME/KEY: misc_feature
<223> OTHER INFORMATION: hSRPRbeta

<400> SEQUENCE: 26

```
atggcttccg cggactcgcg ccgggtggca gatggcggcg gtgccggggg caccttccag      60

ccctacctag acaccttgcg gcaggagctg cagcagacgg acccaacgct gttgtcagta     120

gtggtggcgg ttcttgcggt gctgctgacg ctagtcttct ggaagttaat ccggagcaga     180

aggagcagtc agagagctgt tcttcttgtt ggcctttgtg attccgggaa aacgttgctc     240

tttgtcaggt tgttaacagg cctttataga gacactcaga cgtccattac tgacagctgt     300

gctgtataca gagtcaacaa taacaggggc aatagtctga ccttgattga ccttcccggc     360

catgagagtt tgaggcttca gttcttagag cggtttaagt cttcagccag ggctattgtg     420

tttgttgtgg atagtgcagc attccagcga gaggtgaaag atgtggctga gtttctgtat     480

caagtcctca ttgacagtat gggtctgaag aatacaccat cattcttaat agcctgcaat     540

aagcaagata ttgcaatggc aaaatcagca aagttaattc aacagcagct ggagaaagaa     600

ctcaacacct tacgagttac ccgttctgct gcccccagca cactggacag ttccagcact     660

gcccctgctc agctggggaa gaaaggcaaa gagtttgaat tctcacagtt gcccctcaaa     720

gtggagttcc tggagtgcag tgccaagggt ggaagagggg acgtgggctc tgctgacatc     780

caggacttgg agaaatggct ggctaaaatt gcctga                               816
```

<210> SEQ ID NO 27
<211> LENGTH: 271
<212> TYPE: PRT
<213> ORGANISM: Homo sapiens
<220> FEATURE:
<221> NAME/KEY: MISC_FEATURE
<223> OTHER INFORMATION: hSRPRbeta

<400> SEQUENCE: 27

```
Met Ala Ser Ala Asp Ser Arg Arg Val Ala Asp Gly Gly Gly Ala Gly
1               5                   10                  15

Gly Thr Phe Gln Pro Tyr Leu Asp Thr Leu Arg Gln Glu Leu Gln Gln
            20                  25                  30

Thr Asp Pro Thr Leu Leu Ser Val Val Val Ala Val Leu Ala Val Leu
        35                  40                  45

Leu Thr Leu Val Phe Trp Lys Leu Ile Arg Ser Arg Arg Ser Ser Gln
    50                  55                  60

Arg Ala Val Leu Leu Val Gly Leu Cys Asp Ser Gly Lys Thr Leu Leu
65                  70                  75                  80

Phe Val Arg Leu Leu Thr Gly Leu Tyr Arg Asp Thr Gln Thr Ser Ile
                85                  90                  95

Thr Asp Ser Cys Ala Val Tyr Arg Val Asn Asn Asn Arg Gly Asn Ser
            100                 105                 110

Leu Thr Leu Ile Asp Leu Pro Gly His Glu Ser Leu Arg Leu Gln Phe
        115                 120                 125

Leu Glu Arg Phe Lys Ser Ser Ala Arg Ala Ile Val Phe Val Val Asp
    130                 135                 140

Ser Ala Ala Phe Gln Arg Glu Val Lys Asp Val Ala Glu Phe Leu Tyr
145                 150                 155                 160

Gln Val Leu Ile Asp Ser Met Gly Leu Lys Asn Thr Pro Ser Phe Leu
                165                 170                 175

Ile Ala Cys Asn Lys Gln Asp Ile Ala Met Ala Lys Ser Ala Lys Leu
            180                 185                 190

Ile Gln Gln Gln Leu Glu Lys Glu Leu Asn Thr Leu Arg Val Thr Arg
        195                 200                 205

Ser Ala Ala Pro Ser Thr Leu Asp Ser Ser Ser Thr Ala Pro Ala Gln
    210                 215                 220

Leu Gly Lys Lys Gly Lys Glu Phe Glu Phe Ser Gln Leu Pro Leu Lys
225                 230                 235                 240

Val Glu Phe Leu Glu Cys Ser Ala Lys Gly Gly Arg Gly Asp Val Gly
                245                 250                 255

Ser Ala Asp Ile Gln Asp Leu Glu Lys Trp Leu Ala Lys Ile Ala
            260                 265                 270
```

<210> SEQ ID NO 28
<211> LENGTH: 1779
<212> TYPE: DNA
<213> ORGANISM: Homo sapiens
<220> FEATURE:
<221> NAME/KEY: misc_feature
<223> OTHER INFORMATION: hCANX

<400> SEQUENCE: 28

```
atggaaggga agtggttgct gtgtatgtta ctggtgcttg gaactgctat tgttgaggct      60

catgatggac atgatgatga tgtgattgat attgaggatg accttgacga tgtcattgaa     120

gaggtagaag actcaaaacc agataccact gctcctcctt catctcccaa ggttacttac     180

aaagctccag ttccaacagg ggaagtatat tttgctgatt cttttgacag aggaactctg     240

tcagggtgga ttttatccaa agccaagaaa gacgataccg atgatgaaat tgccaaatat     300

gatggaaagt gggaggtaga ggaaatgaag gagtcaaagc ttccaggtga taaaggactt     360

gtgttgatgt ctcgggccaa gcatcatgcc atctctgcta aactgaacaa gcccttcctg     420

tttgacacca agcctctcat tgttcagtat gaggttaatt tccaaaatgg aatagaatgt     480
```

-continued

```
ggtggtgcct atgtgaaact gctttctaaa acaccagaac tcaacctgga tcagttccat    540

gacaagaccc cttatacgat tatgtttggt ccagataaat gtggagagga ctataaactg    600

cacttcatct tccgacacaa aaaccccaaa acgggtatct atgaagaaaa acatgctaag    660

aggccagatg cagatctgaa gacctatttt actgataaga aaacacatct ttacacacta    720

atcttgaatc cagataatag ttttgaaata ctggttgacc aatctgtggt gaatagtgga    780

aatctgctca atgacatgac tcctcctgta aatccttcac gtgaaattga ggacccagaa    840

gaccggaagc ccgaggattg ggatgaaaga ccaaaaatcc cagatccaga agctgtcaag    900

ccagatgact gggatgaaga tgcccctgct aagattccag atgaagaggc cacaaaaccc    960

gaaggctggt tagatgatga gcctgagtac gtacctgatc cagacgcaga gaaacctgag   1020

gattgggatg aagacatgga tggagaatgg gaggctcctc agattgccaa ccctagatgt   1080

gagtcagctc ctggatgtgg tgtctggcag cgacctgtga ttgacaaccc caattataaa   1140

ggcaaatgga agcctcctat gattgacaat cccagttacc agggaatctg gaaacccagg   1200

aaaataccaa atccagattt ctttgaagat ctggaacctt tcagaatgac tccttttagt   1260

gctattggtt tggagctgtg gtccatgacc tctgacattt tttttgacaa ctttatcatt   1320

tgtgctgatc gaagaatagt tgatgattgg gccaatgatg gatggggcct gaagaaagct   1380

gctgatgggg ctgctgagcc aggcgttgtg gggcagatga tcgaggcagc tgaagagcgc   1440

ccgtggctgt gggtagtcta tattctaact gtagcccttc ctgtgttcct ggttatcctc   1500

ttctgctgtt ctggaaagaa acagaccagt ggtatggagt ataagaaaac tgatgcacct   1560

caaccggatg tgaaggaaga ggaagaagag aaggaagagg aaaaggacaa gggagatgag   1620

gaggaggaag gagaagagaa acttgaagag aaacagaaaa gtgatgctga agaagatggt   1680

ggcactgtca gtcaagagga ggaagacaga aaacctaaag cagaggagga tgaaattttg   1740

aacagatcac caagaaacag aaagccacga agagagtga                          1779
```

<210> SEQ ID NO 29
<211> LENGTH: 592
<212> TYPE: PRT
<213> ORGANISM: Homo sapiens
<220> FEATURE:
<221> NAME/KEY: MISC_FEATURE
<223> OTHER INFORMATION: hCANX

<400> SEQUENCE: 29

```
Met Glu Gly Lys Trp Leu Leu Cys Met Leu Leu Val Leu Gly Thr Ala
1               5                   10                  15

Ile Val Glu Ala His Asp Gly His Asp Asp Val Ile Asp Ile Glu
            20                  25                  30

Asp Asp Leu Asp Asp Val Ile Glu Glu Val Glu Asp Ser Lys Pro Asp
        35                  40                  45

Thr Thr Ala Pro Pro Ser Ser Pro Lys Val Thr Tyr Lys Ala Pro Val
    50                  55                  60

Pro Thr Gly Glu Val Tyr Phe Ala Asp Ser Phe Asp Arg Gly Thr Leu
65                  70                  75                  80

Ser Gly Trp Ile Leu Ser Lys Ala Lys Lys Asp Asp Thr Asp Asp Glu
                85                  90                  95

Ile Ala Lys Tyr Asp Gly Lys Trp Glu Val Glu Glu Met Lys Glu Ser
            100                 105                 110

Lys Leu Pro Gly Asp Lys Gly Leu Val Leu Met Ser Arg Ala Lys His
        115                 120                 125
```

-continued

```
His Ala Ile Ser Ala Lys Leu Asn Lys Pro Phe Leu Phe Asp Thr Lys
    130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
            180                 185                 190

Lys Cys Gly Glu Asp Tyr Lys Leu His Phe Ile Phe Arg His Lys Asn
        195                 200                 205

Pro Lys Thr Gly Ile Tyr Glu Glu Lys His Ala Lys Arg Pro Asp Ala
    210                 215                 220

Asp Leu Lys Thr Tyr Phe Thr Asp Lys Lys Thr His Leu Tyr Thr Leu
225                 230                 235                 240

Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
            260                 265                 270

Ser Arg Glu Ile Glu Asp Pro Glu Asp Arg Lys Pro Glu Asp Trp Asp
        275                 280                 285

Glu Arg Pro Lys Ile Pro Asp Pro Glu Ala Val Lys Pro Asp Asp Trp
    290                 295                 300

Asp Glu Asp Ala Pro Ala Lys Ile Pro Asp Glu Glu Ala Thr Lys Pro
305                 310                 315                 320

Glu Gly Trp Leu Asp Asp Glu Pro Glu Tyr Val Pro Asp Pro Asp Ala
                325                 330                 335

Glu Lys Pro Glu Asp Trp Asp Glu Asp Met Asp Gly Glu Trp Glu Ala
            340                 345                 350

Pro Gln Ile Ala Asn Pro Arg Cys Glu Ser Ala Pro Gly Cys Gly Val
        355                 360                 365

Trp Gln Arg Pro Val Ile Asp Asn Pro Asn Tyr Lys Gly Lys Trp Lys
    370                 375                 380

Pro Pro Met Ile Asp Asn Pro Ser Tyr Gln Gly Ile Trp Lys Pro Arg
385                 390                 395                 400

Lys Ile Pro Asn Pro Asp Phe Phe Glu Asp Leu Glu Pro Phe Arg Met
                405                 410                 415

Thr Pro Phe Ser Ala Ile Gly Leu Glu Leu Trp Ser Met Thr Ser Asp
            420                 425                 430

Ile Phe Phe Asp Asn Phe Ile Ile Cys Ala Asp Arg Arg Ile Val Asp
        435                 440                 445

Asp Trp Ala Asn Asp Gly Trp Gly Leu Lys Lys Ala Ala Asp Gly Ala
    450                 455                 460

Ala Glu Pro Gly Val Val Gly Gln Met Ile Glu Ala Ala Glu Glu Arg
465                 470                 475                 480

Pro Trp Leu Trp Val Val Tyr Ile Leu Thr Val Ala Leu Pro Val Phe
                485                 490                 495

Leu Val Ile Leu Phe Cys Cys Ser Gly Lys Lys Gln Thr Ser Gly Met
            500                 505                 510

Glu Tyr Lys Lys Thr Asp Ala Pro Gln Pro Asp Val Lys Glu Glu Glu
        515                 520                 525

Glu Glu Lys Glu Glu Glu Lys Asp Lys Gly Asp Glu Glu Glu Glu Gly
    530                 535                 540

Glu Glu Lys Leu Glu Glu Lys Gln Lys Ser Asp Ala Glu Glu Asp Gly
```

-continued 545 550 555 560

Gly Thr Val Ser Gln Glu Glu Glu Asp Arg Lys Pro Lys Ala Glu Glu
565 570 575

Asp Glu Ile Leu Asn Arg Ser Pro Arg Asn Arg Lys Pro Arg Arg Glu
580 585 590

<210> SEQ ID NO 30
<211> LENGTH: 972
<212> TYPE: DNA
<213> ORGANISM: Homo sapiens
<220> FEATURE:
<221> NAME/KEY: misc_feature
<223> OTHER INFORMATION: hUCP4

<400> SEQUENCE: 30
atgtccgtcc cggaggagga ggagaggctt ttgccgctga cccagagatg gccccgagcg 60
agcaaattcc tactgtccgg ctgcgcggct accgtggccg agctagcaac ctttcccctg 120
gatctcacaa aaactcgact ccaaatgcaa ggagaagcag ctcttgctcg gttgggagac 180
ggtgcaagag aatctgcccc ctatagggga atggtgcgca cagccctagg gatcattgaa 240
gaggaaggct ttctaaagct ttggcaagga gtgacacccg ccatttacag acacgtagtg 300
tattctggag gtcgaatggt cacatatgaa catctccgag aggttgtgtt tggcaaaagt 360
gaagatgagc attatcccct ttggaaatca gtcattggag ggatgatggc tggtgttatt 420
ggccagtttt tagccaatcc aactgaccta gtgaaggttc agatgcaaat ggaaggaaaa 480
aggaaactgg aaggaaaacc attgcgattt cgtggtgtac atcatgcatt tgcaaaaatc 540
ttagctgaag gaggaatacg agggctttgg gcaggctggg tacccaatat acaaagagca 600
gcactggtga atatgggaga tttaaccact tatgatacag tgaaacacta cttggtattg 660
aatacaccac ttgaggacaa tatcatgact cacggtttat caagtttatg ttctggactg 720
gtagcttcta ttctgggaac accagccgat gtcatcaaaa gcagaataat gaatcaacca 780
cgagataaac aaggaagggg acttttgtat aaatcatcga ctgactgctt gattcaggct 840
gttcaaggtg aaggattcat gagtctatat aaaggctttt taccatcttg gctgagaatg 900
accccttggt caatggtgtt ctggcttact tatgaaaaaa tcagagagat gagtggagtc 960
agtccatttt aa 972

<210> SEQ ID NO 31
<211> LENGTH: 323
<212> TYPE: PRT
<213> ORGANISM: Homo sapiens
<220> FEATURE:
<221> NAME/KEY: MISC_FEATURE
<223> OTHER INFORMATION: hUCP4

<400> SEQUENCE: 31

Met Ser Val Pro Glu Glu Glu Glu Arg Leu Leu Pro Leu Thr Gln Arg
1 5 10 15

Trp Pro Arg Ala Ser Lys Phe Leu Leu Ser Gly Cys Ala Ala Thr Val
20 25 30

Ala Glu Leu Ala Thr Phe Pro Leu Asp Leu Thr Lys Thr Arg Leu Gln
35 40 45

Met Gln Gly Glu Ala Ala Leu Ala Arg Leu Gly Asp Gly Ala Arg Glu
50 55 60

Ser Ala Pro Tyr Arg Gly Met Val Arg Thr Ala Leu Gly Ile Ile Glu
65 70 75 80

```
Glu Glu Gly Phe Leu Lys Leu Trp Gln Gly Val Thr Pro Ala Ile Tyr
                85                  90                  95

Arg His Val Val Tyr Ser Gly Gly Arg Met Val Thr Tyr Glu His Leu
            100                 105                 110

Arg Glu Val Val Phe Gly Lys Ser Glu Asp Glu His Tyr Pro Leu Trp
        115                 120                 125

Lys Ser Val Ile Gly Gly Met Met Ala Gly Val Ile Gly Gln Phe Leu
    130                 135                 140

Ala Asn Pro Thr Asp Leu Val Lys Val Gln Met Gln Met Glu Gly Lys
145                 150                 155                 160

Arg Lys Leu Glu Gly Lys Pro Leu Arg Phe Arg Gly Val His His Ala
                165                 170                 175

Phe Ala Lys Ile Leu Ala Glu Gly Gly Ile Arg Gly Leu Trp Ala Gly
            180                 185                 190

Trp Val Pro Asn Ile Gln Arg Ala Ala Leu Val Asn Met Gly Asp Leu
        195                 200                 205

Thr Thr Tyr Asp Thr Val Lys His Tyr Leu Val Leu Asn Thr Pro Leu
    210                 215                 220

Glu Asp Asn Ile Met Thr His Gly Leu Ser Ser Leu Cys Ser Gly Leu
225                 230                 235                 240

Val Ala Ser Ile Leu Gly Thr Pro Ala Asp Val Ile Lys Ser Arg Ile
                245                 250                 255

Met Asn Gln Pro Arg Asp Lys Gln Gly Arg Gly Leu Leu Tyr Lys Ser
            260                 265                 270

Ser Thr Asp Cys Leu Ile Gln Ala Val Gln Gly Glu Gly Phe Met Ser
        275                 280                 285

Leu Tyr Lys Gly Phe Leu Pro Ser Trp Leu Arg Met Thr Pro Trp Ser
    290                 295                 300

Met Val Phe Trp Leu Thr Tyr Glu Lys Ile Arg Glu Met Ser Gly Val
305                 310                 315                 320

Ser Pro Phe
```

<210> SEQ ID NO 32
<211> LENGTH: 1014
<212> TYPE: DNA
<213> ORGANISM: Homo sapiens
<220> FEATURE:
<221> NAME/KEY: misc_feature
<223> OTHER INFORMATION: hCMPSAT

<400> SEQUENCE: 32

```
atggctgccc cgagagacaa tgtcacttta ttattcaagt tatactgctt ggcagtgatg      60

accctgatgg ctgcagtcta taccatagct ttaagataca caaggacatc agacaaagaa     120

ctctactttt caaccacagc cgtgtgtatc acagaagtta taaagttatt gctaagtgtg     180

ggaattttag ctaaagaaac tggtagtctg ggtagattca aagcatcttt aagagaaaat     240

gtcttgggga gccccaagga actgttgaag ttaagtgtgc catcgttagt gtatgctgtt     300

cagaacaaca tggctttcct agctcttagc aatctggatg cagcagtgta ccaggtgacc     360

taccagttga agattccgtg tactgcttta tgcactgttt taatgttaaa ccggacactc     420

agcaaattac agtgggtttc agtttttatg ctgtgtgctg gagttacgct tgtacagtgg     480

aaaccagccc aagctacaaa agtggtggtg gaacaaaatc cattattagg gtttggcgct     540

atagctattg ctgtattgtg ctcaggattt gcaggagtat attttgaaaa agttttaaag     600

agttcagata cttctctttg ggtgagaaac attcaaatgt atctatcagg gattattgtg     660
```

acattagctg gcgtctactt gtcagatgga gctgaaatta aagaaaaagg atttttctat 720
ggttacacat attatgtctg gtttgtcatc tttcttgcaa gtgttggtgg cctctacact 780
tctgttgtgg ttaagtacac agacaacatc atgaaaggct tttctgcagc agcggccatt 840
gtcctttcca ccattgcttc agtaatgctg tttggattac agataacact cacctttgcc 900
ctgggtactc ttcttgtatg tgtttccata tatctctatg gattacccag acaagacact 960
acatccatcc aacaaggaga aacagcttca aaggagagag ttattggtgt gtga 1014

<210> SEQ ID NO 33
<211> LENGTH: 337
<212> TYPE: PRT
<213> ORGANISM: Homo sapiens
<220> FEATURE:
<221> NAME/KEY: MISC_FEATURE
<223> OTHER INFORMATION: hCMPSAT

<400> SEQUENCE: 33

Met Ala Ala Pro Arg Asp Asn Val Thr Leu Leu Phe Lys Leu Tyr Cys
1 5 10 15

Leu Ala Val Met Thr Leu Met Ala Ala Val Tyr Thr Ile Ala Leu Arg
20 25 30

Tyr Thr Arg Thr Ser Asp Lys Glu Leu Tyr Phe Ser Thr Thr Ala Val
35 40 45

Cys Ile Thr Glu Val Ile Lys Leu Leu Leu Ser Val Gly Ile Leu Ala
50 55 60

Lys Glu Thr Gly Ser Leu Gly Arg Phe Lys Ala Ser Leu Arg Glu Asn
65 70 75 80

Val Leu Gly Ser Pro Lys Glu Leu Leu Lys Leu Ser Val Pro Ser Leu
85 90 95

Val Tyr Ala Val Gln Asn Asn Met Ala Phe Leu Ala Leu Ser Asn Leu
100 105 110

Asp Ala Ala Val Tyr Gln Val Thr Tyr Gln Leu Lys Ile Pro Cys Thr
115 120 125

Ala Leu Cys Thr Val Leu Met Leu Asn Arg Thr Leu Ser Lys Leu Gln
130 135 140

Trp Val Ser Val Phe Met Leu Cys Ala Gly Val Thr Leu Val Gln Trp
145 150 155 160

Lys Pro Ala Gln Ala Thr Lys Val Val Val Glu Gln Asn Pro Leu Leu
165 170 175

Gly Phe Gly Ala Ile Ala Ile Ala Val Leu Cys Ser Gly Phe Ala Gly
180 185 190

Val Tyr Phe Glu Lys Val Leu Lys Ser Ser Asp Thr Ser Leu Trp Val
195 200 205

Arg Asn Ile Gln Met Tyr Leu Ser Gly Ile Ile Val Thr Leu Ala Gly
210 215 220

Val Tyr Leu Ser Asp Gly Ala Glu Ile Lys Glu Lys Gly Phe Phe Tyr
225 230 235 240

Gly Tyr Thr Tyr Tyr Val Trp Phe Val Ile Phe Leu Ala Ser Val Gly
245 250 255

Gly Leu Tyr Thr Ser Val Val Val Lys Tyr Thr Asp Asn Ile Met Lys
260 265 270

Gly Phe Ser Ala Ala Ala Ala Ile Val Leu Ser Thr Ile Ala Ser Val
275 280 285

Met Leu Phe Gly Leu Gln Ile Thr Leu Thr Phe Ala Leu Gly Thr Leu

```
    290                 295                 300

Leu Val Cys Val Ser Ile Tyr Leu Tyr Gly Leu Pro Arg Gln Asp Thr
305                 310                 315                 320

Thr Ser Ile Gln Gln Gly Glu Thr Ala Ser Lys Glu Arg Val Ile Gly
                325                 330                 335

Val
```

<210> SEQ ID NO 34
<211> LENGTH: 1212
<212> TYPE: DNA
<213> ORGANISM: Artificial Sequence
<220> FEATURE:
<223> OTHER INFORMATION: Optimized Sequence
<220> FEATURE:
<221> NAME/KEY: misc_feature
<223> OTHER INFORMATION: rST6Gal1

<400> SEQUENCE: 34

```
atgatccaca ccaacctgaa gaagaagttc tccctgttca tcctggtgtt tctgctgttc     60

gccgtgatct gcgtgtggaa gaagggctcc gactacgagg ctctgaccct gcaggccaaa    120

gaattccaga tgcccaagtc ccaagaaaag gtggcaatgg gctccgccag ccaggtggtg    180

ttctccaact ccaagcagga ccctaaagag gacatcccta tcctgtccta ccacagagtg    240

accgccaaag tgaagcctca gcctagcttc caggtctggg acaaggactc cacctacagc    300

aagctgaacc ctcggctgct gaagatctgg cggaactacc tgaacatgaa caagtacaag    360

gtgtcctaca agggccctgg ccctggcgtg aagttctccg tggaggccct gaggtgccac    420

ctgagggacc acgtgaacgt gtccatgatc gaggccaccg acttcccatt caacaccacc    480

gagtgggagg gctacctgcc taaagagaac ttccggacca aagtgggccc ttggcagaga    540

tgcgccgtgg tgtcctccgc cggctccctg aagaactctc agctgggccg ggagatcgac    600

aaccacgacg ccgtgctgag gttcaacggc gctcctaccg acaacttcca gcaggacgtg    660

ggctccaaga ccaccatcag actgatgaac agccagctgg tgaccaccga gaagcggttt    720

ctgaaggact ccctgtacac cgagggcatc ctgatcgtgt gggacccttc cgtgtaccac    780

gccgacatcc ctaagtggta tcagaagccc gactacaact tcttcgagac atacaagtcc    840

taccggcggc tgaacccttc ccagcctttc tacatcctga agccccagat gccttgggag    900

ctgtgggaca tcatccagga aatctccgcc gacctgatcc agcctaaccc tccttcctcc    960

ggcatgctgg gcatcatcat catgatgacc ctgtgcgacc aggtggacat ctacgagttt   1020

ctgccttcca agagaaagac cgacgtgtgc tactaccacc agaagttctt cgactccgcc   1080

tgcacaatgg gcgcctacca ccccctgctg ttcgagaaga acatggtgaa gcacctgaac   1140

gagggcaccg acgaggacat ctacctgttc ggcaaggcca ccctgtccgg cttccggaac   1200

atccggtgct ga                                                        1212
```

<210> SEQ ID NO 35
<211> LENGTH: 403
<212> TYPE: PRT
<213> ORGANISM: Rattus norvegicus
<220> FEATURE:
<221> NAME/KEY: MISC_FEATURE
<223> OTHER INFORMATION: rST6Gal1

<400> SEQUENCE: 35

```
Met Ile His Thr Asn Leu Lys Lys Lys Phe Ser Leu Phe Ile Leu Val
1               5                   10                  15
```

-continued

```
Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Pro Lys Ser Gln
        35                  40                  45

Glu Lys Val Ala Met Gly Ser Ala Ser Gln Val Val Phe Ser Asn Ser
    50                  55                  60

Lys Gln Asp Pro Lys Glu Asp Ile Pro Ile Leu Ser Tyr His Arg Val
65                  70                  75                  80

Thr Ala Lys Val Lys Pro Gln Pro Ser Phe Gln Val Trp Asp Lys Asp
                85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Pro
        115                 120                 125

Gly Val Lys Phe Ser Val Glu Ala Leu Arg Cys His Leu Arg Asp His
    130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Val Gly
                165                 170                 175

Pro Trp Gln Arg Cys Ala Val Val Ser Ser Ala Gly Ser Leu Lys Asn
            180                 185                 190

Ser Gln Leu Gly Arg Glu Ile Asp Asn His Asp Ala Val Leu Arg Phe
        195                 200                 205

Asn Gly Ala Pro Thr Asp Asn Phe Gln Gln Asp Val Gly Ser Lys Thr
    210                 215                 220

Thr Ile Arg Leu Met Asn Ser Gln Leu Val Thr Thr Glu Lys Arg Phe
225                 230                 235                 240

Leu Lys Asp Ser Leu Tyr Thr Glu Gly Ile Leu Ile Val Trp Asp Pro
                245                 250                 255

Ser Val Tyr His Ala Asp Ile Pro Lys Trp Tyr Gln Lys Pro Asp Tyr
            260                 265                 270

Asn Phe Phe Glu Thr Tyr Lys Ser Tyr Arg Arg Leu Asn Pro Ser Gln
        275                 280                 285

Pro Phe Tyr Ile Leu Lys Pro Gln Met Pro Trp Glu Leu Trp Asp Ile
    290                 295                 300

Ile Gln Glu Ile Ser Ala Asp Leu Ile Gln Pro Asn Pro Pro Ser Ser
305                 310                 315                 320

Gly Met Leu Gly Ile Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr
            340                 345                 350

His Gln Lys Phe Phe Asp Ser Ala Cys Thr Met Gly Ala Tyr His Pro
        355                 360                 365

Leu Leu Phe Glu Lys Asn Met Val Lys His Leu Asn Glu Gly Thr Asp
    370                 375                 380

Glu Asp Ile Tyr Leu Phe Gly Lys Ala Thr Leu Ser Gly Phe Arg Asn
385                 390                 395                 400

Ile Arg Cys
```

<210> SEQ ID NO 36
<211> LENGTH: 957
<212> TYPE: DNA
<213> ORGANISM: Homo sapiens
<220> FEATURE:
<221> NAME/KEY: misc_feature
<223> OTHER INFORMATION: hCOMSC

<400> SEQUENCE: 36

```
atgctttctg aaagcagctc ctttttgaag ggtgtgatgc ttggaagcat tttctgtgct     60

ttgatcacta tgctaggaca cattaggatt ggtcatggaa atagaatgca ccaccatgag    120

catcatcacc tacaagctcc taacaaagaa gatatcttga aaatttcaga ggatgagcgc    180

atggagctca gtaagagctt tcgagtatac tgtattatcc ttgtaaaacc caaagatgtg    240

agtctttggg ctgcagtaaa ggagacttgg accaaacact gtgacaaagc agagttcttc    300

agttctgaaa atgttaaagt gtttgagtca attaatatgg acacaaatga catgtggtta    360

atgatgagaa aagcttacaa atacgccttt gataagtata gagaccaata caactggttc    420

ttccttgcac gccccactac gtttgctatc attgaaaacc taaagtattt tttgttaaaa    480

aaggatccat cacagccttt ctatctaggc cacactataa aatctggaga ccttgaatat    540

gtgggtatgg aaggaggaat tgtcttaagt gtagaatcaa tgaaaagact taacagcctt    600

ctcaatatcc cagaaaagtg tcctgaacag ggagggatga tttggaagat atctgaagat    660

aaacagctag cagtttgcct gaaatatgct ggagtatttg cagaaaatgc agaagatgct    720

gatggaaaag atgtatttaa taccaaatct gttgggcttt ctattaaaga ggcaatgact    780

tatcacccca accaggtagt agaaggctgt tgttcagata tggctgttac ttttaatgga    840

ctgactccaa atcagatgca tgtgatgatg tatggggtat accgccttag ggcatttggg    900

catattttca atgatgcatt ggttttctta cctccaaatg gttctgacaa tgactga       957
```

<210> SEQ ID NO 37
<211> LENGTH: 318
<212> TYPE: PRT
<213> ORGANISM: Homo sapiens
<220> FEATURE:
<221> NAME/KEY: MISC_FEATURE
<223> OTHER INFORMATION: hCOMSC

<400> SEQUENCE: 37

```
Met Leu Ser Glu Ser Ser Ser Phe Leu Lys Gly Val Met Leu Gly Ser
1               5                   10                  15

Ile Phe Cys Ala Leu Ile Thr Met Leu Gly His Ile Arg Ile Gly His
            20                  25                  30

Gly Asn Arg Met His His His Glu His His His Leu Gln Ala Pro Asn
        35                  40                  45

Lys Glu Asp Ile Leu Lys Ile Ser Glu Asp Glu Arg Met Glu Leu Ser
    50                  55                  60

Lys Ser Phe Arg Val Tyr Cys Ile Ile Leu Val Lys Pro Lys Asp Val
65                  70                  75                  80

Ser Leu Trp Ala Ala Val Lys Glu Thr Trp Thr Lys His Cys Asp Lys
                85                  90                  95

Ala Glu Phe Phe Ser Ser Glu Asn Val Lys Val Phe Glu Ser Ile Asn
            100                 105                 110

Met Asp Thr Asn Asp Met Trp Leu Met Met Arg Lys Ala Tyr Lys Tyr
        115                 120                 125

Ala Phe Asp Lys Tyr Arg Asp Gln Tyr Asn Trp Phe Phe Leu Ala Arg
    130                 135                 140

Pro Thr Thr Phe Ala Ile Ile Glu Asn Leu Lys Tyr Phe Leu Leu Lys
145                 150                 155                 160
```

```
Lys Asp Pro Ser Gln Pro Phe Tyr Leu Gly His Thr Ile Lys Ser Gly
                165                 170                 175

Asp Leu Glu Tyr Val Gly Met Glu Gly Gly Ile Val Leu Ser Val Glu
            180                 185                 190

Ser Met Lys Arg Leu Asn Ser Leu Leu Asn Ile Pro Glu Lys Cys Pro
        195                 200                 205

Glu Gln Gly Gly Met Ile Trp Lys Ile Ser Glu Asp Lys Gln Leu Ala
    210                 215                 220

Val Cys Leu Lys Tyr Ala Gly Val Phe Ala Glu Asn Ala Glu Asp Ala
225                 230                 235                 240

Asp Gly Lys Asp Val Phe Asn Thr Lys Ser Val Gly Leu Ser Ile Lys
                245                 250                 255

Glu Ala Met Thr Tyr His Pro Asn Gln Val Val Glu Gly Cys Cys Ser
            260                 265                 270

Asp Met Ala Val Thr Phe Asn Gly Leu Thr Pro Asn Gln Met His Val
        275                 280                 285

Met Met Tyr Gly Val Tyr Arg Leu Arg Ala Phe Gly His Ile Phe Asn
    290                 295                 300

Asp Ala Leu Val Phe Leu Pro Pro Asn Gly Ser Asp Asn Asp
305                 310                 315


<210> SEQ ID NO 38
<211> LENGTH: 1092
<212> TYPE: DNA
<213> ORGANISM: Homo sapiens
<220> FEATURE:
<221> NAME/KEY: misc_feature
<223> OTHER INFORMATION: hT-Synthase

<400> SEQUENCE: 38

atggcctcta aatcctggct gaattttta accttcctct gtggatcagc aataggattt      60

cttttatgtt ctcagctatt tagtattttg ttgggagaaa aggttgacac ccagcctaat     120

gttcttcata atgatcctca tgcaaggcat tcagatgata atggacagaa tcatctagaa     180

ggacaaatga acttcaatgc agattctagc caacataaag atgagaacac agacattgct     240

gaaaacctct atcagaaagt tagaattctt tgctgggtta tgaccggccc tcaaaaccta     300

gagaaaaagg ccaaacacgt caaagctact tgggcccagc gttgtaacaa agtgttgttt     360

atgagttcag aagaaaataa agacttccct gctgtgggac tgaaaaccaa agaaggcaga     420

gatcaactat actggaaaac aattaaagct tttcagtatg ttcatgaaca ttatttagaa     480

gatgctgatt ggtttttgaa agcagatgat gacacgtatg tcatactaga caatttgagg     540

tggcttcttt caaaatacga ccctgaagaa cccatttact ttgggagaag atttaagcct     600

tatgtaaagc agggctacat gagtggagga gcaggatatg tactaagcaa agaagccttg     660

aaaagatttg ttgatgcatt taaaacagac aagtgtacac atagttcctc cattgaagac     720

ttagcactgg ggagatgcat ggaaattatg aatgtagaag caggagattc cagagatacc     780

attggaaaag aaacttttca tccctttgtg ccagaacacc atttaattaa aggttatcta     840

cctagaacgt tttggtactg gaattacaac tattatcctc ctgtagaggg tcctggttgc     900

tgctctgatc ttgcagtttc ttttcactat gttgattcta caaccatgta tgagttagaa     960

tacctcgttt atcatcttcg tccatatggt tatttataca gatatcaacc taccttacct    1020

gaacgtatac taaaggaaat tagtcaagca aacaaaaatg aagatacaaa agtgaagtta    1080

ggaaatcctt ga                                                        1092
```

<210> SEQ ID NO 39
<211> LENGTH: 363
<212> TYPE: PRT
<213> ORGANISM: Homo sapiens
<220> FEATURE:
<221> NAME/KEY: MISC_FEATURE
<223> OTHER INFORMATION: hT-Synthase

<400> SEQUENCE: 39

```
Met Ala Ser Lys Ser Trp Leu Asn Phe Leu Thr Phe Leu Cys Gly Ser
1               5                   10                  15

Ala Ile Gly Phe Leu Leu Cys Ser Gln Leu Phe Ser Ile Leu Leu Gly
            20                  25                  30

Glu Lys Val Asp Thr Gln Pro Asn Val Leu His Asn Asp Pro His Ala
        35                  40                  45

Arg His Ser Asp Asp Asn Gly Gln Asn His Leu Glu Gly Gln Met Asn
    50                  55                  60

Phe Asn Ala Asp Ser Ser Gln His Lys Asp Glu Asn Thr Asp Ile Ala
65                  70                  75                  80

Glu Asn Leu Tyr Gln Lys Val Arg Ile Leu Cys Trp Val Met Thr Gly
                85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
        115                 120                 125

Phe Pro Ala Val Gly Leu Lys Thr Lys Glu Gly Arg Asp Gln Leu Tyr
    130                 135                 140

Trp Lys Thr Ile Lys Ala Phe Gln Tyr Val His Glu His Tyr Leu Glu
145                 150                 155                 160

Asp Ala Asp Trp Phe Leu Lys Ala Asp Asp Asp Thr Tyr Val Ile Leu
                165                 170                 175

Asp Asn Leu Arg Trp Leu Leu Ser Lys Tyr Asp Pro Glu Glu Pro Ile
            180                 185                 190

Tyr Phe Gly Arg Arg Phe Lys Pro Tyr Val Lys Gln Gly Tyr Met Ser
        195                 200                 205

Gly Gly Ala Gly Tyr Val Leu Ser Lys Glu Ala Leu Lys Arg Phe Val
    210                 215                 220

Asp Ala Phe Lys Thr Asp Lys Cys Thr His Ser Ser Ser Ile Glu Asp
225                 230                 235                 240

Leu Ala Leu Gly Arg Cys Met Glu Ile Met Asn Val Glu Ala Gly Asp
                245                 250                 255

Ser Arg Asp Thr Ile Gly Lys Glu Thr Phe His Pro Phe Val Pro Glu
            260                 265                 270

His His Leu Ile Lys Gly Tyr Leu Pro Arg Thr Phe Trp Tyr Trp Asn
        275                 280                 285

Tyr Asn Tyr Tyr Pro Pro Val Glu Gly Pro Gly Cys Cys Ser Asp Leu
    290                 295                 300

Ala Val Ser Phe His Tyr Val Asp Ser Thr Thr Met Tyr Glu Leu Glu
305                 310                 315                 320

Tyr Leu Val Tyr His Leu Arg Pro Tyr Gly Tyr Leu Tyr Arg Tyr Gln
                325                 330                 335

Pro Thr Leu Pro Glu Arg Ile Leu Lys Glu Ile Ser Gln Ala Asn Lys
            340                 345                 350

Asn Glu Asp Thr Lys Val Lys Leu Gly Asn Pro
        355                 360
```

<210> SEQ ID NO 40
<211> LENGTH: 1605
<212> TYPE: DNA
<213> ORGANISM: Homo sapiens
<220> FEATURE:
<221> NAME/KEY: misc_feature
<223> OTHER INFORMATION: hP4HA1

<400> SEQUENCE: 40
atgatctggt atatattaat tataggaatt ctgcttcccc agtctttggc tcatccaggc 60
ttttttactt caattggtca gatgactgat ttgatccata ctgagaaaga tctggtgact 120
tctctgaaag attatattaa ggcagaagag gacaagttag aacaaataaa aaaatgggca 180
gagaagttag atcggctaac tagtacagcg acaaaagatc cagaaggatt tgttgggcat 240
ccagtaaatg cattcaaatt aatgaaacgt ctgaatactg agtggagtga gttggagaat 300
ctggtcctta aggatatgtc agatggcttt atctctaacc taaccattca gagacagtac 360
tttcctaatg atgaagatca ggttggggca gccaaagctc tgttacgtct ccaggatacc 420
tacaatttgg atacagatac catctcaaag ggtaatcttc caggagtgaa acacaaatct 480
tttctaacgg ctgaggactg ctttgagttg ggcaaagtgg cctatacaga agcagattat 540
taccatacgg aactgtggat ggaacaagcc ctaaggcaac tggatgaagg cgagatttct 600
accatagata aagtctctgt tctagattat ttgagctatg cggtatatca gcagggagac 660
ctggataagg cacttttgct cacaaagaag cttcttgaac tagatcctga acatcagaga 720
gctaatggta acttaaaata ttttgagtat ataatggcta aagaaaaaga tgtcaataag 780
tctgcttcag atgaccaatc tgatcagaaa actacaccaa agaaaaaagg ggttgctgtg 840
gattacctgc cagagagaca gaagtacgaa atgctgtgcc gtggggaggg tatcaaaatg 900
acccctcgga gacagaaaaa actcttttgc cgctaccatg atggaaaccg taatcctaaa 960
tttattctgg ctccagctaa acaggaggat gaatgggaca agcctcgtat tattcgcttc 1020
catgatatta tttctgatgc agaaattgaa atcgtcaaag acctagcaaa accaaggctg 1080
agccgagcta cagtacatga ccctgagact ggaaaattga ccacagcaca gtacagagta 1140
tctaagagtg cctggctctc tggctatgaa aatcctgtgg tgtctcgaat taatatgaga 1200
atacaagatc taacaggact agatgtttcc acagcagagg aattacaggt agcaaattat 1260
ggagttggag gacagtatga accccatttt gactttgcac ggaaagatga gccagatgct 1320
ttcaaagagc tggggacagg aaatagaatt gctacatggc tgttttatat gagtgatgtg 1380
tctgcaggag gagccactgt ttttcctgaa gttggagcta gtgtttggcc caaaaaagga 1440
actgctgttt tctggtataa tctgtttgcc agtggagaag gagattatag tacacggcat 1500
gcagcctgtc cagtgctagt tggcaacaaa tgggtatcca ataaatggct ccatgaacgt 1560
ggacaagaat ttcgaagacc ttgtacgttg tcagaattgg aatga 1605

<210> SEQ ID NO 41
<211> LENGTH: 534
<212> TYPE: PRT
<213> ORGANISM: Homo sapiens
<220> FEATURE:
<221> NAME/KEY: MISC_FEATURE
<223> OTHER INFORMATION: hP4HA1

<400> SEQUENCE: 41

Met Ile Trp Tyr Ile Leu Ile Ile Gly Ile Leu Leu Pro Gln Ser Leu
1 5 10 15

```
Ala His Pro Gly Phe Phe Thr Ser Ile Gly Gln Met Thr Asp Leu Ile
            20                  25                  30

His Thr Glu Lys Asp Leu Val Thr Ser Leu Lys Asp Tyr Ile Lys Ala
        35                  40                  45

Glu Glu Asp Lys Leu Glu Gln Ile Lys Lys Trp Ala Glu Lys Leu Asp
    50                  55                  60

Arg Leu Thr Ser Thr Ala Thr Lys Asp Pro Glu Gly Phe Val Gly His
65                  70                  75                  80

Pro Val Asn Ala Phe Lys Leu Met Lys Arg Leu Asn Thr Glu Trp Ser
                85                  90                  95

Glu Leu Glu Asn Leu Val Leu Lys Asp Met Ser Asp Gly Phe Ile Ser
            100                 105                 110

Asn Leu Thr Ile Gln Arg Gln Tyr Phe Pro Asn Asp Glu Asp Gln Val
        115                 120                 125

Gly Ala Ala Lys Ala Leu Leu Arg Leu Gln Asp Thr Tyr Asn Leu Asp
    130                 135                 140

Thr Asp Thr Ile Ser Lys Gly Asn Leu Pro Gly Val Lys His Lys Ser
145                 150                 155                 160

Phe Leu Thr Ala Glu Asp Cys Phe Glu Leu Gly Lys Val Ala Tyr Thr
                165                 170                 175

Glu Ala Asp Tyr Tyr His Thr Glu Leu Trp Met Glu Gln Ala Leu Arg
            180                 185                 190

Gln Leu Asp Glu Gly Glu Ile Ser Thr Ile Asp Lys Val Ser Val Leu
        195                 200                 205

Asp Tyr Leu Ser Tyr Ala Val Tyr Gln Gln Gly Asp Leu Asp Lys Ala
    210                 215                 220

Leu Leu Leu Thr Lys Lys Leu Leu Glu Leu Asp Pro Glu His Gln Arg
225                 230                 235                 240

Ala Asn Gly Asn Leu Lys Tyr Phe Glu Tyr Ile Met Ala Lys Glu Lys
                245                 250                 255

Asp Val Asn Lys Ser Ala Ser Asp Asp Gln Ser Asp Gln Lys Thr Thr
            260                 265                 270

Pro Lys Lys Lys Gly Val Ala Val Asp Tyr Leu Pro Glu Arg Gln Lys
        275                 280                 285

Tyr Glu Met Leu Cys Arg Gly Glu Gly Ile Lys Met Thr Pro Arg Arg
    290                 295                 300

Gln Lys Lys Leu Phe Cys Arg Tyr His Asp Gly Asn Arg Asn Pro Lys
305                 310                 315                 320

Phe Ile Leu Ala Pro Ala Lys Gln Glu Asp Glu Trp Asp Lys Pro Arg
                325                 330                 335

Ile Ile Arg Phe His Asp Ile Ile Ser Asp Ala Glu Ile Glu Ile Val
            340                 345                 350

Lys Asp Leu Ala Lys Pro Arg Leu Ser Arg Ala Thr Val His Asp Pro
        355                 360                 365

Glu Thr Gly Lys Leu Thr Thr Ala Gln Tyr Arg Val Ser Lys Ser Ala
    370                 375                 380

Trp Leu Ser Gly Tyr Glu Asn Pro Val Val Ser Arg Ile Asn Met Arg
385                 390                 395                 400

Ile Gln Asp Leu Thr Gly Leu Asp Val Ser Thr Ala Glu Glu Leu Gln
                405                 410                 415

Val Ala Asn Tyr Gly Val Gly Gly Gln Tyr Glu Pro His Phe Asp Phe
            420                 425                 430
```

-continued

```
Ala Arg Lys Asp Glu Pro Asp Ala Phe Lys Glu Leu Gly Thr Gly Asn
        435                 440                 445

Arg Ile Ala Thr Trp Leu Phe Tyr Met Ser Asp Val Ser Ala Gly Gly
    450                 455                 460

Ala Thr Val Phe Pro Glu Val Gly Ala Ser Val Trp Pro Lys Lys Gly
465                 470                 475                 480

Thr Ala Val Phe Trp Tyr Asn Leu Phe Ala Ser Gly Glu Gly Asp Tyr
                485                 490                 495

Ser Thr Arg His Ala Ala Cys Pro Val Leu Val Gly Asn Lys Trp Val
            500                 505                 510

Ser Asn Lys Trp Leu His Glu Arg Gly Gln Glu Phe Arg Arg Pro Cys
        515                 520                 525

Thr Leu Ser Glu Leu Glu
    530
```

<210> SEQ ID NO 42
<211> LENGTH: 1527
<212> TYPE: DNA
<213> ORGANISM: Homo sapiens
<220> FEATURE:
<221> NAME/KEY: misc_feature
<223> OTHER INFORMATION: hP4HB

<400> SEQUENCE: 42

```
atgctgcgcc gcgctctgct gtgcctggcc gtggccgccc tggtgcgcgc cgacgccccc     60

gaggaggagg accacgtcct ggtgctgcgg aaaagcaact tcgcggaggc gctggcggcc    120

cacaagtacc tgctggtgga gttctatgcc ccttggtgtg gccactgcaa ggctctggcc    180

cctgagtatg ccaaagccgc tgggaagctg aaggcagaag gttccgagat caggttggcc    240

aaggtggacg ccacggagga gtctgacctg gcccagcagt acggcgtgcg cggctatccc    300

accatcaagt tcttcaggaa tggagacacg gcttccccca aggaatatac agctggcaga    360

gaggctgatg acatcgtgaa ctggctgaag aagcgcacgg gcccggctgc caccaccctg    420

cctgacggcg cagctgcaga gtccttggtg gagtccagcg aggtggctgt catcggcttc    480

ttcaaggacg tggagtcgga ctctgccaag cagtttttgc aggcagcaga ggccatcgat    540

gacataccat ttgggatcac ttccaacagt gacgtgttct ccaaatacca gctcgacaaa    600

gatggggttg tcctctttaa gaagtttgat gaaggccgga acaactttga aggggaggtc    660

accaaggaga acctgctgga ctttatcaaa cacaaccagc tgccccttgt catcgagttc    720

accgagcaga cagccccgaa gatttttgga ggtgaaatca agactcacat cctgctgttc    780

ttgcccaaga gtgtgtctga ctatgacggc aaactgagca acttcaaaac agcagccgag    840

agcttcaagg gcaagatcct gttcatcttc atcgacagcg accacaccga caaccagcgc    900

atcctcgagt tctttggcct gaagaaggaa gagtgcccgg ccgtgcgcct catcaccctg    960

gaggaggaga tgaccaagta caagcccgaa tcggaggagc tgacggcaga gaggatcaca   1020

gagttctgcc accgcttcct ggagggcaaa atcaagcccc acctgatgag ccaggagctg   1080

ccggaggact gggacaagca gcctgtcaag gtgcttgttg ggaagaactt tgaagacgtg   1140

gcttttgatg agaaaaaaaa cgtctttgtg gagttctatg ccccatggtg tggtcactgc   1200

aaacagttgg ctcccatttg ggataaactg ggagagacgt acaaggacca tgagaacatc   1260

gtcatcgcca agatggactc gactgccaac gaggtggagg ccgtcaaagt gcacagcttc   1320

cccacactca agttctttcc tgccagtgcc gacaggacgg tcattgatta caacggggaa   1380

cgcacgctgg atggttttaa gaaattcctg gagagcggtg gccaggatgg ggcaggggat   1440
```

gatgacgatc tcgaggacct ggaagaagca gaggagccag acatggagga agacgatgat 1500
cagaaagctg tgaaagatga actgtaa 1527

<210> SEQ ID NO 43
<211> LENGTH: 508
<212> TYPE: PRT
<213> ORGANISM: Homo sapiens
<220> FEATURE:
<221> NAME/KEY: MISC_FEATURE
<223> OTHER INFORMATION: hP4HB

<400> SEQUENCE: 43

```
Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335
```

```
Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
            500                 505


<210> SEQ ID NO 44
<211> LENGTH: 603
<212> TYPE: DNA
<213> ORGANISM: Homo sapiens
<220> FEATURE:
<221> NAME/KEY: misc_feature
<223> OTHER INFORMATION: hGILZ

<400> SEQUENCE: 44

atggcccagt ccaagctcga ttgccgctca cctgtcggcc tcgactgctg caactgctgc      60

ctggacctgg cccatcggag tgggctccag cgaggcagca gcggggagaa caacaacccg     120

ggcagcccta cagtgagcaa ctttcggcag ctgcaggaaa agctggtctt tgagaacctc     180

aataccgaca agctcaacag cataatgcgg caggattcgc tagagccggt gctgcgggac     240

ccctgctacc tgatcaacga gggcatctgc aaccgcaaca tcgaccagac catgctctcc     300

atcctgctct tcttccacag tgcctccgga gccagcgtgg tggccataga caacaagatc     360

gaacaggcca tggatctggt gaagaatcat ctgatgtatg ctgtgagaga ggaggtggag     420

atcctgaagg agcagatccg agagctggtg gagaagaact cccagctaga gcgtgagaac     480

accctgttga agaccctggc aagcccagag cagctggaga agttccagtc ctgtctgagc     540

cctgaagagc cagctcccga atccccacaa gtgcccgagg cccctggtgg ttctgcggtg     600

taa                                                                   603


<210> SEQ ID NO 45
<211> LENGTH: 200
<212> TYPE: PRT
<213> ORGANISM: Homo sapiens
<220> FEATURE:
<221> NAME/KEY: MISC_FEATURE
<223> OTHER INFORMATION: hGILZ

<400> SEQUENCE: 45

Met Ala Gln Ser Lys Leu Asp Cys Arg Ser Pro Val Gly Leu Asp Cys
1               5                   10                  15
```

```
Cys Asn Cys Cys Leu Asp Leu Ala His Arg Ser Gly Leu Gln Arg Gly
            20                  25                  30

Ser Ser Gly Glu Asn Asn Asn Pro Gly Ser Pro Thr Val Ser Asn Phe
        35                  40                  45

Arg Gln Leu Gln Glu Lys Leu Val Phe Glu Asn Leu Asn Thr Asp Lys
    50                  55                  60

Leu Asn Ser Ile Met Arg Gln Asp Ser Leu Glu Pro Val Leu Arg Asp
65                  70                  75                  80

Pro Cys Tyr Leu Ile Asn Glu Gly Ile Cys Asn Arg Asn Ile Asp Gln
                85                  90                  95

Thr Met Leu Ser Ile Leu Leu Phe Phe His Ser Ala Ser Gly Ala Ser
            100                 105                 110

Val Val Ala Ile Asp Asn Lys Ile Glu Gln Ala Met Asp Leu Val Lys
        115                 120                 125

Asn His Leu Met Tyr Ala Val Arg Glu Glu Val Glu Ile Leu Lys Glu
    130                 135                 140

Gln Ile Arg Glu Leu Val Glu Lys Asn Ser Gln Leu Glu Arg Glu Asn
145                 150                 155                 160

Thr Leu Leu Lys Thr Leu Ala Ser Pro Glu Gln Leu Glu Lys Phe Gln
                165                 170                 175

Ser Cys Leu Ser Pro Glu Glu Pro Ala Pro Glu Ser Pro Gln Val Pro
            180                 185                 190

Glu Ala Pro Gly Gly Ser Ala Val
        195                 200
```

<210> SEQ ID NO 46
<211> LENGTH: 651
<212> TYPE: DNA
<213> ORGANISM: Homo sapiens
<220> FEATURE:
<221> NAME/KEY: misc_feature
<223> OTHER INFORMATION: hCyPB

<400> SEQUENCE: 46

```
atgctgcgcc tctccgaacg caacatgaag gtgctccttg ccgccgccct catcgcgggg     60

tccgtcttct tcctgctgct gccgggacct tctgcggccg atgagaagaa gaaggggccc    120

aaagtcaccg tcaaggtgta ttttgaccta cgaattggag atgaagatgt aggccgggtg    180

atctttggtc tcttcggaaa gactgttcca aaaacagtgg ataattttgt ggccttagct    240

acaggagaga aaggatttgg ctacaaaaac agcaaattcc atcgtgtaat caaggacttc    300

atgatccagg gcggagactt caccagggga gatggcacag gaggaaagag catctacggt    360

gagcgcttcc ccgatgagaa cttcaaactg aagcactacg ggcctggctg ggtgagcatg    420

gccaacgcag gcaaagacac caacggctcc cagttcttca tcacgacagt caagacagcc    480

tggctagatg gcaagcatgt ggtgtttggc aaagttctag agggcatgga ggtggtgcgg    540

aaggtggaga gcaccaagac agacagccgg gataaacccc tgaaggatgt gatcatcgca    600

gactgcggca agatcgaggt ggagaagccc tttgccatcg ccaaggagta g             651
```

<210> SEQ ID NO 47
<211> LENGTH: 216
<212> TYPE: PRT
<213> ORGANISM: Homo sapiens
<220> FEATURE:
<221> NAME/KEY: MISC_FEATURE
<223> OTHER INFORMATION: hCyPB

<400> SEQUENCE: 47

Met Leu Arg Leu Ser Glu Arg Asn Met Lys Val Leu Leu Ala Ala Ala
1 5 10 15

Leu Ile Ala Gly Ser Val Phe Phe Leu Leu Leu Pro Gly Pro Ser Ala
20 25 30

Ala Asp Glu Lys Lys Lys Gly Pro Lys Val Thr Val Lys Val Tyr Phe
35 40 45

Asp Leu Arg Ile Gly Asp Glu Asp Val Gly Arg Val Ile Phe Gly Leu
50 55 60

Phe Gly Lys Thr Val Pro Lys Thr Val Asp Asn Phe Val Ala Leu Ala
65 70 75 80

Thr Gly Glu Lys Gly Phe Gly Tyr Lys Asn Ser Lys Phe His Arg Val
85 90 95

Ile Lys Asp Phe Met Ile Gln Gly Gly Asp Phe Thr Arg Gly Asp Gly
100 105 110

Thr Gly Gly Lys Ser Ile Tyr Gly Glu Arg Phe Pro Asp Glu Asn Phe
115 120 125

Lys Leu Lys His Tyr Gly Pro Gly Trp Val Ser Met Ala Asn Ala Gly
130 135 140

Lys Asp Thr Asn Gly Ser Gln Phe Phe Ile Thr Thr Val Lys Thr Ala
145 150 155 160

Trp Leu Asp Gly Lys His Val Val Phe Gly Lys Val Leu Glu Gly Met
165 170 175

Glu Val Val Arg Lys Val Glu Ser Thr Lys Thr Asp Ser Arg Asp Lys
180 185 190

Pro Leu Lys Asp Val Ile Ile Ala Asp Cys Gly Lys Ile Glu Val Glu
195 200 205

Lys Pro Phe Ala Ile Ala Lys Glu
210 215

<210> SEQ ID NO 48
<211> LENGTH: 1818
<212> TYPE: DNA
<213> ORGANISM: Homo sapiens
<220> FEATURE:
<221> NAME/KEY: misc_feature
<223> OTHER INFORMATION: hNRF2

<400> SEQUENCE: 48
atgatggact tggagctgcc gccgccggga ctcccgtccc agcaggacat ggatttgatt 60
gacatacttt ggaggcaaga tatagatctt ggagtaagtc gagaagtatt tgacttcagt 120
cagcgacgga aagagtatga gctggaaaaa cagaaaaaac ttgaaaagga aagacaagaa 180
caactccaaa aggagcaaga gaaagccttt ttcgctcagt tacaactaga tgaagagaca 240
ggtgaatttc tcccaattca gccagcccag cacatccagt cagaaaccag tggatctgcc 300
aactactccc aggttgccca cattcccaaa tcagatgctt tgtactttga tgactgcatg 360
cagcttttgg cgcagacatt cccgtttgta gatgacaatg aggtttcttc ggctacgttt 420
cagtcacttg ttcctgatat tcccggtcac atcgagagcc cagtcttcat tgctactaat 480
caggctcagt cacctgaaac ttctgttgct caggtagccc ctgttgattt agacggtatg 540
caacaggaca ttgagcaagt ttgggaggag ctattatcca ttcctgagtt acagtgtctt 600
aatattgaaa atgacaagct ggttgagact accatggttc caagtccaga agccaaactg 660
acagaagttg acaattatca tttttactca tctataccct caatggaaaa agaagtaggt 720

```
aactgtagtc cacattttct taatgctttt gaggattcct tcagcagcat cctctccaca    780

gaagacccca accagttgac agtgaactca ttaaattcag atgccacagt caacacagat    840

tttggtgatg aattttattc tgctttcata gctgagccca gtatcagcaa cagcatgccc    900

tcacctgcta ctttaagcca ttcactctct gaacttctaa atgggcccat tgatgtttct    960

gatctatcac tttgcaaagc tttcaaccaa aaccaccctg aaagcacagc agaattcaat   1020

gattctgact ccggcatttc actaaacaca agtcccagtg tggcatcacc agaacactca   1080

gtggaatctt ccagctatgg agacacacta cttggcctca gtgattctga agtggaagag   1140

ctagatagtg cccctggaag tgtcaaacag aatggtccta aaacaccagt acattcttct   1200

ggggatatgg tacaaccctt gtcaccatct caggggcaga gcactcacgt gcatgatgcc   1260

caatgtgaga acacaccaga gaaagaattg cctgtaagtc ctggtcatcg gaaaacccca   1320

ttcacaaaag acaaacattc aagccgcttg gaggctcatc tcacaagaga tgaacttagg   1380

gcaaaagctc tccatatccc attccctgta gaaaaaatca ttaacctccc tgttgttgac   1440

ttcaacgaaa tgatgtccaa agagcagttc aatgaagctc aacttgcatt aattcgggat   1500

atacgtagga ggggtaagaa taaagtggct gctcagaatt gcagaaaaag aaaactggaa   1560

aatatagtag aactagagca agatttagat catttgaaag atgaaaaaga aaaattgctc   1620

aaagaaaaag gagaaaatga caaaagcctt cacctactga aaaaacaact cagcacctta   1680

tatctcgaag ttttcagcat gctacgtgat gaagatggaa aaccttattc tcctagtgaa   1740

tactccctgc agcaaacaag agatggcaat gttttccttg ttcccaaaag taagaagcca   1800

gatgttaaga aaaactag                                                 1818
```

<210> SEQ ID NO 49
<211> LENGTH: 605
<212> TYPE: PRT
<213> ORGANISM: Homo sapiens
<220> FEATURE:
<221> NAME/KEY: MISC_FEATURE
<223> OTHER INFORMATION: hNRF2

<400> SEQUENCE: 49

```
Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160
```

```
Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
```

-continued 580 585 590

Leu Val Pro Lys Ser Lys Lys Pro Asp Val Lys Lys Asn
595 600 605

<210> SEQ ID NO 50
<211> LENGTH: 2754
<212> TYPE: DNA
<213> ORGANISM: Homo sapiens
<220> FEATURE:
<221> NAME/KEY: misc_feature
<223> OTHER INFORMATION: hHK1

<400> SEQUENCE: 50
atgatcgccg cgcagctcct ggcctattac ttcacggagc tgaaggatga ccaggtcaaa 60
aagattgaca agtatctcta tgccatgcgg ctctccgatg aaactctcat agatatcatg 120
actcgcttca ggaaggagat gaagaatggc ctctcccggg attttaatcc aacagccaca 180
gtcaagatgt tgccaacatt cgtaaggtcc attcctgatg gctctgaaaa gggagatttc 240
attgccctgg atcttggtgg gtcttccttt cgaattctgc gggtgcaagt gaatcatgag 300
aaaaaccaga atgttcacat ggagtccgag gtttatgaca ccccagagaa catcgtgcac 360
ggcagtggaa gccagctttt tgatcatgtt gctgagtgcc tgggagattt catggagaaa 420
aggaagatca aggacaagaa gttacctgtg ggattcacgt tttcttttcc ttgccaacaa 480
tccaaaatag atgaggccat cctgatcacc tggacaaagc gatttaaagc gagcggagtg 540
gaaggagcag atgtggtcaa actgcttaac aaagccatca aaaagcgagg ggactatgat 600
gccaacatcg tagctgtggt gaatgacaca gtgggcacca tgatgacctg tggctatgac 660
gaccagcact gtgaagtcgg cctgatcatc ggcactggca ccaatgcttg ctacatggag 720
gaactgaggc acattgatct ggtggaagga gacgagggga ggatgtgtat caatacagaa 780
tggggagcct ttggagacga tggatcatta gaagacatcc ggacagagtt tgacagggag 840
atagaccggg gatccctcaa ccctggaaaa cagctgtttg agaagatggt cagtggcatg 900
tacttgggag agctggttcg actgatccta gtcaagatgg ccaaggaggg cctcttattt 960
gaagggcgga tcaccccgga gctgctcacc cgagggaagt ttaacaccag tgatgtgtca 1020
gccatcgaaa agaataagga aggcctccac aatgccaaag aaatcctgac ccgcctggga 1080
gtggagccgt ccgatgatga ctgtgtctca gtccagcacg tttgcaccat tgtctcattt 1140
cgctcagcca acttggtggc tgccacactg ggcgccatct tgaaccgcct gcgtgataac 1200
aagggcacac ccaggctgcg gaccacggtt ggtgtcgacg gatctcttta caagacgcac 1260
ccacagtatt cccggcgttt ccacaagact ctaaggcgct tggtgccaga ctccgatgtg 1320
cgcttcctcc tctcggagag tggcagcggc aagggggctg ccatggtgac ggcggtggcc 1380
taccgcttgg ccgagcagca ccggcagata gaggagaccc tggctcattt ccacctcacc 1440
aaggacatgc tgctggaggt gaagaagagg atgcgggccg agatggagct ggggctgagg 1500
aagcagacgc acaacaatgc cgtggttaag atgctgccct ccttcgtccg gagaactccc 1560
gacgggaccg agaatggtga cttcttggcc ctggatcttg gaggaaccaa tttccgtgtg 1620
ctgctggtga aaatccgtag tgggaaaaag agaacggtgg aaatgcacaa caagatctac 1680
gccattccta ttgaaatcat gcagggcact ggggaagagc tgtttgatca cattgtctcc 1740
tgcatctctg acttcttgga ctacatgggg atcaaaggcc ccaggatgcc tctgggcttc 1800
acgttctcat ttccctgcca gcagacgagt ctggacgcgg gaatcttgat cacgtggaca 1860
aagggtttta aggcaacaga ctgcgtgggc cacgatgtag tcaccttact aagggatgcg 1920

-continued

```
ataaaaagga gagaggaatt tgacctggac gtggtggctg tggtcaacga cacagtgggc   1980

accatgatga cctgtgctta tgaggagccc acctgtgagg ttggactcat tgttgggacc   2040

ggcagcaatg cctgctacat ggaggagatg aagaacgtgg agatggtgga gggggaccag   2100

gggcagatgt gcatcaacat ggagtggggg gcctttgggg acaacgggtg tctggatgat   2160

atcaggacac actacgacag actggtggac gaatattccc taaatgctgg gaaacaaagg   2220

tatgagaaga tgatcagtgg tatgtacctg ggtgaaatcg tccgcaacat cttaatcgac   2280

ttcaccaaga agggattcct cttccgaggg cagatctctg agacgctgaa gacccggggc   2340

atctttgaga ccaagtttct ctctcagatc gagagtgacc gattagcact gctccaggtc   2400

cgggctatcc tccagcagct aggtctgaat agcacctgcg atgacagtat cctcgtcaag   2460

acagtgtgcg gggtggtgtc caggagggcc gcacagctgt gtggcgcagg catggctgcg   2520

gttgtggata agatccgcga gaacagagga ctggaccgtc tgaatgtgac tgtgggagtg   2580

gacgggacac tctacaagct tcatccacac ttctccagaa tcatgcacca gacggtgaag   2640

gaactgtcac caaaatgtaa cgtgtccttc ctcctgtctg aggatggcag cggcaagggg   2700

gccgccctca tcacggccgt gggcgtgcgg ttacgcacag aggcaagcag ctaa         2754
```

<210> SEQ ID NO 51
<211> LENGTH: 917
<212> TYPE: PRT
<213> ORGANISM: Homo sapiens
<220> FEATURE:
<221> NAME/KEY: MISC_FEATURE
<223> OTHER INFORMATION: hHK1

<400> SEQUENCE: 51

```
Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Thr Leu Ile Asp Ile Met Thr Arg Phe Arg Lys Glu Met Lys
        35                  40                  45

Asn Gly Leu Ser Arg Asp Phe Asn Pro Thr Ala Thr Val Lys Met Leu
    50                  55                  60

Pro Thr Phe Val Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val His Met Glu Ser Glu Val Tyr
            100                 105                 110

Asp Thr Pro Glu Asn Ile Val His Gly Ser Gly Ser Gln Leu Phe Asp
        115                 120                 125

His Val Ala Glu Cys Leu Gly Asp Phe Met Glu Lys Arg Lys Ile Lys
    130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
                165                 170                 175

Ala Ser Gly Val Glu Gly Ala Asp Val Val Lys Leu Leu Asn Lys Ala
            180                 185                 190

Ile Lys Lys Arg Gly Asp Tyr Asp Ala Asn Ile Val Ala Val Val Asn
        195                 200                 205
```

-continued

```
Asp Thr Val Gly Thr Met Met Thr Cys Gly Tyr Asp Asp Gln His Cys
    210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Glu Gly Arg Met Cys
                245                 250                 255

Ile Asn Thr Glu Trp Gly Ala Phe Gly Asp Asp Gly Ser Leu Glu Asp
            260                 265                 270

Ile Arg Thr Glu Phe Asp Arg Glu Ile Asp Arg Gly Ser Leu Asn Pro
        275                 280                 285

Gly Lys Gln Leu Phe Glu Lys Met Val Ser Gly Met Tyr Leu Gly Glu
    290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
            340                 345                 350

Lys Glu Ile Leu Thr Arg Leu Gly Val Glu Pro Ser Asp Asp Asp Cys
        355                 360                 365

Val Ser Val Gln His Val Cys Thr Ile Val Ser Phe Arg Ser Ala Asn
    370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415

Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
        435                 440                 445

Ser Gly Lys Gly Ala Ala Met Val Thr Ala Val Ala Tyr Arg Leu Ala
    450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495

Leu Gly Leu Arg Lys Gln Thr His Asn Asn Ala Val Val Lys Met Leu
            500                 505                 510

Pro Ser Phe Val Arg Arg Thr Pro Asp Gly Thr Glu Asn Gly Asp Phe
        515                 520                 525

Leu Ala Leu Asp Leu Gly Gly Thr Asn Phe Arg Val Leu Leu Val Lys
    530                 535                 540

Ile Arg Ser Gly Lys Lys Arg Thr Val Glu Met His Asn Lys Ile Tyr
545                 550                 555                 560

Ala Ile Pro Ile Glu Ile Met Gln Gly Thr Gly Glu Glu Leu Phe Asp
                565                 570                 575

His Ile Val Ser Cys Ile Ser Asp Phe Leu Asp Tyr Met Gly Ile Lys
            580                 585                 590

Gly Pro Arg Met Pro Leu Gly Phe Thr Phe Ser Phe Pro Cys Gln Gln
        595                 600                 605

Thr Ser Leu Asp Ala Gly Ile Leu Ile Thr Trp Thr Lys Gly Phe Lys
    610                 615                 620

Ala Thr Asp Cys Val Gly His Asp Val Val Thr Leu Leu Arg Asp Ala
```

```
625                 630                 635                 640

Ile Lys Arg Arg Glu Glu Phe Asp Leu Asp Val Val Ala Val Val Asn
                645                 650                 655

Asp Thr Val Gly Thr Met Met Thr Cys Ala Tyr Glu Glu Pro Thr Cys
            660                 665                 670

Glu Val Gly Leu Ile Val Gly Thr Gly Ser Asn Ala Cys Tyr Met Glu
        675                 680                 685

Glu Met Lys Asn Val Glu Met Val Glu Gly Asp Gln Gly Gln Met Cys
    690                 695                 700

Ile Asn Met Glu Trp Gly Ala Phe Gly Asp Asn Gly Cys Leu Asp Asp
705                 710                 715                 720

Ile Arg Thr His Tyr Asp Arg Leu Val Asp Glu Tyr Ser Leu Asn Ala
                725                 730                 735

Gly Lys Gln Arg Tyr Glu Lys Met Ile Ser Gly Met Tyr Leu Gly Glu
            740                 745                 750

Ile Val Arg Asn Ile Leu Ile Asp Phe Thr Lys Lys Gly Phe Leu Phe
        755                 760                 765

Arg Gly Gln Ile Ser Glu Thr Leu Lys Thr Arg Gly Ile Phe Glu Thr
    770                 775                 780

Lys Phe Leu Ser Gln Ile Glu Ser Asp Arg Leu Ala Leu Leu Gln Val
785                 790                 795                 800

Arg Ala Ile Leu Gln Gln Leu Gly Leu Asn Ser Thr Cys Asp Asp Ser
                805                 810                 815

Ile Leu Val Lys Thr Val Cys Gly Val Val Ser Arg Arg Ala Ala Gln
            820                 825                 830

Leu Cys Gly Ala Gly Met Ala Ala Val Val Asp Lys Ile Arg Glu Asn
        835                 840                 845

Arg Gly Leu Asp Arg Leu Asn Val Thr Val Gly Val Asp Gly Thr Leu
    850                 855                 860

Tyr Lys Leu His Pro His Phe Ser Arg Ile Met His Gln Thr Val Lys
865                 870                 875                 880

Glu Leu Ser Pro Lys Cys Asn Val Ser Phe Leu Leu Ser Glu Asp Gly
                885                 890                 895

Ser Gly Lys Gly Ala Ala Leu Ile Thr Ala Val Gly Val Arg Leu Arg
            900                 905                 910

Thr Glu Ala Ser Ser
        915


<210> SEQ ID NO 52
<211> LENGTH: 1578
<212> TYPE: DNA
<213> ORGANISM: Homo sapiens
<220> FEATURE:
<221> NAME/KEY: misc_feature
<223> OTHER INFORMATION: hPDI

<400> SEQUENCE: 52

atgagccgcc agcttctgcc tgtactgctg ctgctgctgc tcagggcttc gtgcccatgg     60

ggtcaggaac agggagcgag gagcccctcg gaggagcctc cagaggagga aatccccaag    120

gaggatggga tcttggtgct gagccgccac accctgggcc tggccctgcg ggagcaccct    180

gccctgctgg tggaattcta tgccccgtgg tgtgggcact gccaggccct ggcccccgag    240

tacagcaagg cagctgccgt gctcgcggcc gagtcaatgg tggtcacgct ggccaaggtg    300

gatgggcccg cgcagcgcga gctggctgag gagtttggtg tgacggagta ccctacgctc    360
```

```
aagttcttcc gcaatgggaa ccgcacgcac ccggaggagt acacaggacc acgggacgct    420

gagggcattg ccgagtggct gcgacggcgg gtggggccca gtgccatgcg gctggaggac    480

gaggcggccg cccaggcgct gatcggtggc cgggacctag tggtcattgg cttcttccag    540

gacctgcagg acgaggacgt ggccaccttc ttggccttgg cccaggacgc cctggacatg    600

acctttggcc tcacagaccg gccgcggctc tttcagcagt ttggcctcac caaggacact    660

gtggttctct tcaagaagtt tgatgagggg cgggcagact tccccgtgga cgaggagctt    720

ggcctggacc tgggggatct gtcgcgcttc ctggtcacac acagcatgcg cctggtcacg    780

gagttcaaca gccagacgtc tgccaagatc ttcgcggcca ggatcctcaa ccacctgctg    840

ctgtttgtca accagacgct ggctgcgcac cgggagctcc tagcgggctt tggggaggca    900

gctccccgct tccgggggca ggtgctgttc gtggtggtgg acgtggcggc cgacaatgag    960

cacgtgctgc agtactttgg actcaaggct gaggcagccc ccactctgcg cttggtcaac   1020

cttgaaacca ctaagaagta tgcgcctgtg gatgggggcc ctgtcaccgc agcgtccatc   1080

actgctttct gccatgcagt cctcaacggc caagtcaagc cctatctcct gagccaggag   1140

atacccccctg attgggatca gcggccagtt aagaccctcg tgggcaagaa ttttgagcag   1200

gtggcttttg acgaaaccaa gaatgtgttt gtcaagttct atgccccgtg gtgcacccac   1260

tgcaaggaga tggcccctgc ctgggaggca ttggctgaga agtaccaaga ccacgaggac   1320

atcatcattg ctgagctgga tgccacggcc aacgagctgg atgccttcgc tgtgcacggc   1380

ttccctactc tcaagtactt cccagcaggg ccaggtcgga aggtgattga atacaaaagc   1440

accagggacc tggagacttt ctccaagttc ctggacaacg gggcgtgct gcccacggag    1500

gagcccccgg aggagccagc agccccgttc ccggagccac cggccaactc cactatgggg   1560

tccaaggagg aactgtag                                                 1578
```

<210> SEQ ID NO 53
<211> LENGTH: 525
<212> TYPE: PRT
<213> ORGANISM: Homo sapiens
<220> FEATURE:
<221> NAME/KEY: MISC_FEATURE
<223> OTHER INFORMATION: hPDI

<400> SEQUENCE: 53

```
Met Ser Arg Gln Leu Leu Pro Val Leu Leu Leu Leu Leu Leu Arg Ala
1               5                   10                  15

Ser Cys Pro Trp Gly Gln Glu Gln Gly Ala Arg Ser Pro Ser Glu Glu
            20                  25                  30

Pro Pro Glu Glu Glu Ile Pro Lys Glu Asp Gly Ile Leu Val Leu Ser
        35                  40                  45

Arg His Thr Leu Gly Leu Ala Leu Arg Glu His Pro Ala Leu Leu Val
    50                  55                  60

Glu Phe Tyr Ala Pro Trp Cys Gly His Cys Gln Ala Leu Ala Pro Glu
65                  70                  75                  80

Tyr Ser Lys Ala Ala Ala Val Leu Ala Ala Glu Ser Met Val Val Thr
                85                  90                  95

Leu Ala Lys Val Asp Gly Pro Ala Gln Arg Glu Leu Ala Glu Glu Phe
            100                 105                 110

Gly Val Thr Glu Tyr Pro Thr Leu Lys Phe Phe Arg Asn Gly Asn Arg
        115                 120                 125

Thr His Pro Glu Glu Tyr Thr Gly Pro Arg Asp Ala Glu Gly Ile Ala
    130                 135                 140
```

```
Glu Trp Leu Arg Arg Arg Val Gly Pro Ser Ala Met Arg Leu Glu Asp
145                 150                 155                 160

Glu Ala Ala Ala Gln Ala Leu Ile Gly Gly Arg Asp Leu Val Val Ile
                165                 170                 175

Gly Phe Phe Gln Asp Leu Gln Asp Glu Asp Val Ala Thr Phe Leu Ala
            180                 185                 190

Leu Ala Gln Asp Ala Leu Asp Met Thr Phe Gly Leu Thr Asp Arg Pro
        195                 200                 205

Arg Leu Phe Gln Gln Phe Gly Leu Thr Lys Asp Thr Val Val Leu Phe
    210                 215                 220

Lys Lys Phe Asp Glu Gly Arg Ala Asp Phe Pro Val Asp Glu Glu Leu
225                 230                 235                 240

Gly Leu Asp Leu Gly Asp Leu Ser Arg Phe Leu Val Thr His Ser Met
                245                 250                 255

Arg Leu Val Thr Glu Phe Asn Ser Gln Thr Ser Ala Lys Ile Phe Ala
            260                 265                 270

Ala Arg Ile Leu Asn His Leu Leu Leu Phe Val Asn Gln Thr Leu Ala
        275                 280                 285

Ala His Arg Glu Leu Leu Ala Gly Phe Gly Glu Ala Ala Pro Arg Phe
    290                 295                 300

Arg Gly Gln Val Leu Phe Val Val Val Asp Val Ala Ala Asp Asn Glu
305                 310                 315                 320

His Val Leu Gln Tyr Phe Gly Leu Lys Ala Glu Ala Ala Pro Thr Leu
                325                 330                 335

Arg Leu Val Asn Leu Glu Thr Thr Lys Lys Tyr Ala Pro Val Asp Gly
            340                 345                 350

Gly Pro Val Thr Ala Ala Ser Ile Thr Ala Phe Cys His Ala Val Leu
        355                 360                 365

Asn Gly Gln Val Lys Pro Tyr Leu Leu Ser Gln Glu Ile Pro Pro Asp
    370                 375                 380

Trp Asp Gln Arg Pro Val Lys Thr Leu Val Gly Lys Asn Phe Glu Gln
385                 390                 395                 400

Val Ala Phe Asp Glu Thr Lys Asn Val Phe Val Lys Phe Tyr Ala Pro
                405                 410                 415

Trp Cys Thr His Cys Lys Glu Met Ala Pro Ala Trp Glu Ala Leu Ala
            420                 425                 430

Glu Lys Tyr Gln Asp His Glu Asp Ile Ile Ile Ala Glu Leu Asp Ala
        435                 440                 445

Thr Ala Asn Glu Leu Asp Ala Phe Ala Val His Gly Phe Pro Thr Leu
    450                 455                 460

Lys Tyr Phe Pro Ala Gly Pro Gly Arg Lys Val Ile Glu Tyr Lys Ser
465                 470                 475                 480

Thr Arg Asp Leu Glu Thr Phe Ser Lys Phe Leu Asp Asn Gly Gly Val
                485                 490                 495

Leu Pro Thr Glu Glu Pro Pro Glu Glu Pro Ala Ala Pro Phe Pro Glu
            500                 505                 510

Pro Pro Ala Asn Ser Thr Met Gly Ser Lys Glu Glu Leu
        515                 520                 525
```

<210> SEQ ID NO 54
<211> LENGTH: 492
<212> TYPE: DNA
<213> ORGANISM: Homo sapiens
<220> FEATURE:

<221> NAME/KEY: misc_feature
<223> OTHER INFORMATION: hPIN1

<400> SEQUENCE: 54
atggcggacg aggagaagct gccgcccggc tgggagaagc gcatgagccg cagctcaggc 60
cgagtgtact acttcaacca catcactaac gccagccagt gggagcggcc cagcggcaac 120
agcagcagtg gtggcaaaaa cgggcagggg gagcctgcca gggtccgctg ctcgcacctg 180
ctggtgaagc acagccagtc acggcggccc tcgtcctggc ggcaggagaa gatcacccgg 240
accaaggagg aggccctgga gctgatcaac ggctacatcc agaagatcaa gtcgggagag 300
gaggactttg agtctctggc ctcacagttc agcgactgca gctcagccaa ggccagggga 360
gacctgggtg ccttcagcag aggtcagatg cagaagccat ttgaagacgc ctcgtttgcg 420
ctgcggacgg gggagatgag cgggcccgtg ttcacggatt ccggcatcca catcatcctc 480
cgcactgagt ga 492

<210> SEQ ID NO 55
<211> LENGTH: 163
<212> TYPE: PRT
<213> ORGANISM: Homo sapiens
<220> FEATURE:
<221> NAME/KEY: MISC_FEATURE
<223> OTHER INFORMATION: hPIN1

<400> SEQUENCE: 55

Met Ala Asp Glu Glu Lys Leu Pro Pro Gly Trp Glu Lys Arg Met Ser
1 5 10 15

Arg Ser Ser Gly Arg Val Tyr Tyr Phe Asn His Ile Thr Asn Ala Ser
20 25 30

Gln Trp Glu Arg Pro Ser Gly Asn Ser Ser Ser Gly Gly Lys Asn Gly
35 40 45

Gln Gly Glu Pro Ala Arg Val Arg Cys Ser His Leu Leu Val Lys His
50 55 60

Ser Gln Ser Arg Arg Pro Ser Ser Trp Arg Gln Glu Lys Ile Thr Arg
65 70 75 80

Thr Lys Glu Glu Ala Leu Glu Leu Ile Asn Gly Tyr Ile Gln Lys Ile
85 90 95

Lys Ser Gly Glu Glu Asp Phe Glu Ser Leu Ala Ser Gln Phe Ser Asp
100 105 110

Cys Ser Ser Ala Lys Ala Arg Gly Asp Leu Gly Ala Phe Ser Arg Gly
115 120 125

Gln Met Gln Lys Pro Phe Glu Asp Ala Ser Phe Ala Leu Arg Thr Gly
130 135 140

Glu Met Ser Gly Pro Val Phe Thr Asp Ser Gly Ile His Ile Ile Leu
145 150 155 160

Arg Thr Glu

<210> SEQ ID NO 56
<211> LENGTH: 264
<212> TYPE: DNA
<213> ORGANISM: Homo sapiens
<220> FEATURE:
<221> NAME/KEY: misc_feature
<223> OTHER INFORMATION: hSEPW1

<400> SEQUENCE: 56
atggctctcg ccgtccgagt cgtttattgt ggcgcttgag gctacaagtc caagtatctt 60

-continued

```
cagctcaaga agaagttaga agatgagttc cccggccgcc tggacatctg cggcgaggga    120

actccccagg ccaccgggtt ctttgaagtg atggtagccg ggaagttgat tcactctaag    180

aagaaaggcg atggctacgt ggacacagaa agcaagtttc tgaagttggt ggccgccatc    240

aaagccgcct tggctcaggg ctaa                                           264
```

<210> SEQ ID NO 57
<211> LENGTH: 87
<212> TYPE: PRT
<213> ORGANISM: Homo sapiens
<220> FEATURE:
<221> NAME/KEY: MISC_FEATURE
<223> OTHER INFORMATION: hSEPW1
<220> FEATURE:
<221> NAME/KEY: MISC_FEATURE
<222> LOCATION: (13)..(13)
<223> OTHER INFORMATION: Special amino acid selenocysteine (U)

<400> SEQUENCE: 57

```
Met Ala Leu Ala Val Arg Val Val Tyr Cys Gly Ala Xaa Gly Tyr Lys
1               5                   10                  15

Ser Lys Tyr Leu Gln Leu Lys Lys Lys Leu Glu Asp Glu Phe Pro Gly
            20                  25                  30

Arg Leu Asp Ile Cys Gly Glu Gly Thr Pro Gln Ala Thr Gly Phe Phe
        35                  40                  45

Glu Val Met Val Ala Gly Lys Leu Ile His Ser Lys Lys Lys Gly Asp
    50                  55                  60

Gly Tyr Val Asp Thr Glu Ser Lys Phe Leu Lys Leu Val Ala Ala Ile
65                  70                  75                  80

Lys Ala Ala Leu Ala Gln Gly
                85
```

<210> SEQ ID NO 58
<211> LENGTH: 1254
<212> TYPE: DNA
<213> ORGANISM: Homo sapiens
<220> FEATURE:
<221> NAME/KEY: misc_feature
<223> OTHER INFORMATION: hCALR

<400> SEQUENCE: 58

```
atgctgctat ccgtgccgct gctgctcggc ctcctcggcc tggccgtcgc cgagcctgcc     60

gtctacttca aggagcagtt tctggacgga gacgggtgga cttcccgctg gatcgaatcc    120

aaacacaagt cagattttgg caaattcgtt ctcagttccg gcaagttcta cggtgacgag    180

gagaaagata aaggtttgca gacaagccag gatgcacgct tttatgctct gtcggccagt    240

ttcgagcctt tcagcaacaa aggccagacg ctggtggtgc agttcacggt gaaacatgag    300

cagaacatcg actgtggggg cggctatgtg aagctgtttc ctaatagttt ggaccagaca    360

gacatgcacg gagactcaga atacaacatc atgtttggtc ccgacatctg tggccctggc    420

accaagaagg ttcatgtcat cttcaactac aagggcaaga acgtgctgat caacaaggac    480

atccgttgca aggatgatga gtttacacac ctgtacacac tgattgtgcg gccagacaac    540

acctatgagg tgaagattga caacagccag gtggagtccg gctccttgga agacgattgg    600

gacttcctgc cacccaagaa gataaaggat cctgatgctt caaaaccgga agactgggat    660

gagcgggcca agatcgatga tcccacagac tccaagcctg aggactggga caagcccgag    720

catatccctg accctgatgc taagaagccc gaggactggg atgaagagat ggacggagag    780

tgggaacccc cagtgattca gaaccctgag tacaagggtg agtggaagcc ccggcagatc    840
```

-continued

```
gacaacccag attacaaggg cacttggatc cacccagaaa ttgacaaccc cgagtattct    900

cccgatccca gtatctatgc ctatgataac tttggcgtgc tgggcctgga cctctggcag    960

gtcaagtctg gcaccatctt tgacaacttc ctcatcacca acgatgaggc atacgctgag   1020

gagtttggca acgagacgtg gggcgtaaca aaggcagcag agaaacaaat gaaggacaaa   1080

caggacgagg agcagaggct taaggaggag gaagaagaca agaaacgcaa agaggaggag   1140

gaggcagagg acaaggagga tgatgaggac aaagatgagg atgaggagga tgaggaggac   1200

aaggaggaag atgaggagga agatgtcccc ggccaggcca aggacgagct gtag         1254


<210> SEQ ID NO 59
<211> LENGTH: 417
<212> TYPE: PRT
<213> ORGANISM: Homo sapiens
<220> FEATURE:
<221> NAME/KEY: MISC_FEATURE
<223> OTHER INFORMATION: hCALR

<400> SEQUENCE: 59

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285
```

```
Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu


<210> SEQ ID NO 60
<211> LENGTH: 656
<212> TYPE: PRT
<213> ORGANISM: Homo sapiens
<220> FEATURE:
<221> NAME/KEY: MISC_FEATURE
<223> OTHER INFORMATION: DroBiP

<400> SEQUENCE: 60

Met Lys Phe Pro Met Val Ala Ala Ala Leu Leu Leu Leu Cys Ala Val
1               5                   10                  15

Arg Ala Glu Glu Lys Lys Glu Lys Asp Lys Glu Leu Gly Thr Val Ile
            20                  25                  30

Gly Ile Asp Leu Gly Thr Thr Tyr Ser Cys Val Gly Val Tyr Lys Asn
        35                  40                  45

Gly Arg Val Glu Ile Ile Ala Asn Asp Gln Gly Asn Arg Ile Thr Pro
    50                  55                  60

Ser Tyr Val Ala Phe Thr Ala Asp Gly Glu Arg Leu Ile Gly Asp Ala
65                  70                  75                  80

Ala Lys Asn Gln Leu Thr Thr Asn Pro Glu Asn Thr Val Phe Asp Ala
                85                  90                  95

Lys Arg Leu Ile Gly Arg Glu Trp Ser Asp Thr Asn Val Gln His Asp
            100                 105                 110

Ile Lys Phe Phe Pro Phe Lys Val Val Glu Lys Asn Ser Lys Pro His
        115                 120                 125

Ile Ser Val Asp Thr Ser Gln Gly Ala Lys Val Phe Ala Pro Glu Glu
    130                 135                 140

Ile Ser Ala Met Val Leu Gly Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Val Ile Ala Gly
            180                 185                 190

Leu Gln Val Met Arg Ile Ile Asn Glu Pro Thr Ala Ala Ala Ile Ala
        195                 200                 205

Tyr Gly Leu Asp Lys Lys Glu Gly Glu Lys Asn Val Leu Val Phe Asp
    210                 215                 220
```

-continued

```
Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Asp His Phe Ile Lys Leu Tyr Lys Lys
            260                 265                 270

Lys Lys Gly Lys Asp Ile Arg Lys Asp Asn Arg Ala Val Gln Lys Leu
        275                 280                 285

Arg Arg Glu Val Glu Lys Ala Lys Arg Ala Leu Ser Gly Ser His Gln
    290                 295                 300

Val Arg Ile Glu Ile Glu Ser Phe Phe Glu Gly Asp Asp Phe Ser Glu
305                 310                 315                 320

Thr Leu Thr Arg Ala Lys Phe Glu Glu Leu Asn Leu Asp Leu Phe Arg
                325                 330                 335

Ser Thr Leu Lys Pro Val Gln Lys Val Leu Glu Asp Ala Asp Met Asn
            340                 345                 350

Lys Lys Asp Val His Glu Ile Val Leu Val Gly Gly Ser Thr Arg Ile
        355                 360                 365

Pro Lys Val Gln Gln Leu Val Lys Asp Phe Phe Gly Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Glu Gln Asp Thr Asp Ala Ile Val Leu
                405                 410                 415

Leu Asp Val Asn Pro Leu Thr Met Gly Ile Glu Thr Val Gly Gly Val
            420                 425                 430

Met Thr Lys Leu Ile Pro Arg Asn Thr Val Ile Pro Thr Lys Lys Ser
        435                 440                 445

Gln Val Phe Ser Thr Ala Ser Asp Asn Gln His Thr Val Thr Ile Gln
    450                 455                 460

Val Tyr Glu Gly Glu Arg Pro Met Thr Lys Asp Asn His Leu Leu Gly
465                 470                 475                 480

Lys Phe Asp Leu Thr Gly Ile Pro Pro Ala Pro Arg Gly Ile Pro Gln
                485                 490                 495

Ile Glu Val Ser Phe Glu Ile Asp Ala Asn Gly Ile Leu Gln Val Ser
            500                 505                 510

Ala Glu Asp Lys Gly Thr Gly Asn Lys Glu Lys Ile Val Ile Thr Asn
        515                 520                 525

Asp Gln Asn Arg Leu Thr Pro Glu Asp Ile Asp Arg Met Ile Arg Asp
    530                 535                 540

Ala Glu Lys Phe Ala Asp Glu Asp Lys Lys Leu Lys Glu Arg Val Glu
545                 550                 555                 560

Ser Arg Asn Glu Leu Glu Ser Tyr Ala Tyr Ser Leu Lys Asn Gln Ile
                565                 570                 575

Gly Asp Lys Asp Lys Leu Gly Ala Lys Leu Ser Asp Asp Glu Lys Asn
            580                 585                 590

Lys Leu Glu Ser Ala Ile Asp Glu Ser Ile Lys Trp Leu Glu Gln Asn
        595                 600                 605

Pro Asp Ala Asp Pro Glu Glu Tyr Lys Lys Gln Lys Lys Asp Leu Glu
    610                 615                 620

Ala Ile Val Gln Pro Val Ile Ala Lys Leu Tyr Gln Gly Ala Gly Gly
625                 630                 635                 640
```

```
Ala Pro Pro Pro Glu Gly Gly Asp Asp Ala Asp Leu Lys Asp Glu Leu
                645                 650                 655


<210> SEQ ID NO 61
<211> LENGTH: 1371
<212> TYPE: DNA
<213> ORGANISM: Homo sapiens
<220> FEATURE:
<221> NAME/KEY: misc_feature
<223> OTHER INFORMATION: hDDOST

<400> SEQUENCE: 61

atggggtact tccggtgtgc aggtgctggg tccttcggca ggaggaggaa gatggagccc      60

agcaccgcgg cccgggcttg ggccctcttt tggttgctgc tgcccttgct tggcgcggtt     120

tgcgccagcg gaccccgcac cttagtgctg ctggacaacc tcaacgtgcg ggagactcat     180

tcgcttttct tccggagcct gaaggaccgg ggctttgagc tcacattcaa gaccgctgat     240

gaccccagcc tgtctctcat aaagtatggg gaattcctct atgacaatct catcattttc     300

tccccttcgg tagaagattt tggaggcaac atcaacgtgg agaccatcag tgcctttatt     360

gacggcggag gcagtgtgct ggtagctgcc agctccgaca ttggtgaccc tcttcgagag     420

ctgggcagtg agtgcgggat tgagtttgac gaggagaaaa cggctgtcat tgaccatcac     480

aactatgaca tctcagacct tggccagcat acgctcatcg tggctgacac tgagaacctg     540

ctgaaggccc caaccatcgt tgggaaatca tctctaaatc ccatcctctt tcgaggtgtt     600

gggatggtgg ccgatcctga taaccctttg gtgctggaca tcctgacggg ctcttccacc     660

tcttactcct tcttcccgga caagcctatc acccagtatc cacatgcggt ggggaagaac     720

accctcctca ttgctgggct ccaggccagg aacaatgccc gcgtcatctt cagcggctcc     780

ctcgacttct tcagcgactc cttcttcaac tcagcagtgc agaaggcggc gcccggctcc     840

cagaggtatt cccagacagg caactatgaa ctagctgtgg ccctctcccg ctgggtgttc     900

aaggaggagg gtgtcctccg tgtggggcct gtgtcccatc atcgggtggg cgagacagcc     960

ccacccaatg cctacactgt cactgaccta gtggagtata gcatcgtgat ccagcagctc    1020

tcaaatggca aatgggtccc ctttgatggc gatgacattc agctggagtt tgtccgcatt    1080

gatccttttg tgaggacctt cctgaagaag aaaggtggca aatacagtgt tcagttcaag    1140

ttgcccgacg tgtatggtgt attccagttt aaagtggatt acaaccggct aggctacaca    1200

cacctgtact cttccactca ggtatccgtg cggccactcc agcacacgca gtatgagcgc    1260

ttcatcccct cggcctaccc ctactacgcc agcgccttct ccatgatgct ggggctcttc    1320

atcttcagca tcgtcttctt gcacatgaag gagaaggaga agtccgactg a             1371


<210> SEQ ID NO 62
<211> LENGTH: 456
<212> TYPE: PRT
<213> ORGANISM: Homo sapiens
<220> FEATURE:
<221> NAME/KEY: MISC_FEATURE
<223> OTHER INFORMATION: hDDOST

<400> SEQUENCE: 62

Met Gly Tyr Phe Arg Cys Ala Gly Ala Gly Ser Phe Gly Arg Arg Arg
1               5                   10                  15

Lys Met Glu Pro Ser Thr Ala Ala Arg Ala Trp Ala Leu Phe Trp Leu
            20                  25                  30

Leu Leu Pro Leu Leu Gly Ala Val Cys Ala Ser Gly Pro Arg Thr Leu
        35                  40                  45
```

```
Val Leu Leu Asp Asn Leu Asn Val Arg Glu Thr His Ser Leu Phe Phe
    50                  55                  60

Arg Ser Leu Lys Asp Arg Gly Phe Glu Leu Thr Phe Lys Thr Ala Asp
65                  70                  75                  80

Asp Pro Ser Leu Ser Leu Ile Lys Tyr Gly Glu Phe Leu Tyr Asp Asn
                85                  90                  95

Leu Ile Ile Phe Ser Pro Ser Val Glu Asp Phe Gly Gly Asn Ile Asn
            100                 105                 110

Val Glu Thr Ile Ser Ala Phe Ile Asp Gly Gly Gly Ser Val Leu Val
        115                 120                 125

Ala Ala Ser Ser Asp Ile Gly Asp Pro Leu Arg Glu Leu Gly Ser Glu
    130                 135                 140

Cys Gly Ile Glu Phe Asp Glu Glu Lys Thr Ala Val Ile Asp His His
145                 150                 155                 160

Asn Tyr Asp Ile Ser Asp Leu Gly Gln His Thr Leu Ile Val Ala Asp
                165                 170                 175

Thr Glu Asn Leu Leu Lys Ala Pro Thr Ile Val Gly Lys Ser Ser Leu
            180                 185                 190

Asn Pro Ile Leu Phe Arg Gly Val Gly Met Val Ala Asp Pro Asp Asn
        195                 200                 205

Pro Leu Val Leu Asp Ile Leu Thr Gly Ser Ser Thr Ser Tyr Ser Phe
    210                 215                 220

Phe Pro Asp Lys Pro Ile Thr Gln Tyr Pro His Ala Val Gly Lys Asn
225                 230                 235                 240

Thr Leu Leu Ile Ala Gly Leu Gln Ala Arg Asn Asn Ala Arg Val Ile
                245                 250                 255

Phe Ser Gly Ser Leu Asp Phe Phe Ser Asp Ser Phe Phe Asn Ser Ala
            260                 265                 270

Val Gln Lys Ala Ala Pro Gly Ser Gln Arg Tyr Ser Gln Thr Gly Asn
        275                 280                 285

Tyr Glu Leu Ala Val Ala Leu Ser Arg Trp Val Phe Lys Glu Glu Gly
    290                 295                 300

Val Leu Arg Val Gly Pro Val Ser His His Arg Val Gly Glu Thr Ala
305                 310                 315                 320

Pro Pro Asn Ala Tyr Thr Val Thr Asp Leu Val Glu Tyr Ser Ile Val
                325                 330                 335

Ile Gln Gln Leu Ser Asn Gly Lys Trp Val Pro Phe Asp Gly Asp Asp
            340                 345                 350

Ile Gln Leu Glu Phe Val Arg Ile Asp Pro Phe Val Arg Thr Phe Leu
        355                 360                 365

Lys Lys Lys Gly Gly Lys Tyr Ser Val Gln Phe Lys Leu Pro Asp Val
    370                 375                 380

Tyr Gly Val Phe Gln Phe Lys Val Asp Tyr Asn Arg Leu Gly Tyr Thr
385                 390                 395                 400

His Leu Tyr Ser Ser Thr Gln Val Ser Val Arg Pro Leu Gln His Thr
                405                 410                 415

Gln Tyr Glu Arg Phe Ile Pro Ser Ala Tyr Pro Tyr Tyr Ala Ser Ala
            420                 425                 430

Phe Ser Met Met Leu Gly Leu Phe Ile Phe Ser Ile Val Phe Leu His
        435                 440                 445

Met Lys Glu Lys Glu Lys Ser Asp
    450                 455
```

<210> SEQ ID NO 63
<211> LENGTH: 1023
<212> TYPE: DNA
<213> ORGANISM: Homo sapiens
<220> FEATURE:
<221> NAME/KEY: misc_feature
<223> OTHER INFORMATION: hHSP40

<400> SEQUENCE: 63
atgggtaaag actactacca gacgttgggc ctggcccgcg gcgcgtcgga cgaggagatc 60
aagcgggcct accgccgcca ggcgctgcgc taccacccgg acaagaacaa ggagcccggc 120
gccgaggaga agttcaagga gatcgctgag gcctacgacg tgctcagcga cccgcgcaag 180
cgcgagatct tcgaccgcta cggggaggaa ggcctaaagg ggagtggccc cagtggcggt 240
agcggcggtg gtgccaatgg tacctctttc agctacacat tccatggaga ccctcatgcc 300
atgtttgctg agttcttcgg tggcagaaat ccctttgaca ccttttttgg gcagcggaac 360
ggggaggaag gcatggacat tgatgaccca ttctctggct tccctatggg catgggtggc 420
ttcaccaacg tgaactttgg ccgctcccgc tctgcccaag agcccgcccg aaagaagcaa 480
gatcccccag tcacccacga ccttcgagtc tcccttgaag agatctacag cggctgtacc 540
aagaagatga aaatctccca caagcggcta aaccccgacg gaaagagcat tcgaaacgaa 600
gacaaaatat tgaccatcga agtgaagaag gggtggaaag aaggaaccaa aatcactttc 660
cccaaggaag gagaccagac ctccaacaac attccagctg atatcgtctt tgttttaaag 720
gacaagcccc acaatatctt taagagagat ggctctgatg tcatttatcc tgccaggatc 780
agcctccggg aggctctgtg tggctgcaca gtgaacgtcc ccactctgga cggcaggacg 840
atacccgtcg tattcaaaga tgttatcagg cctggcatgc ggcgaaaagt tcctggagaa 900
ggcctccccc tccccaaaac acccgagaaa cgtggggacc tcattattga gtttgaagtg 960
atcttccccg aaaggattcc ccagacatca agaaccgtac ttgagcaggt tcttccaata 1020
tag 1023

<210> SEQ ID NO 64
<211> LENGTH: 340
<212> TYPE: PRT
<213> ORGANISM: Homo sapiens
<220> FEATURE:
<221> NAME/KEY: MISC_FEATURE
<223> OTHER INFORMATION: hHSP40

<400> SEQUENCE: 64

Met Gly Lys Asp Tyr Tyr Gln Thr Leu Gly Leu Ala Arg Gly Ala Ser
1 5 10 15

Asp Glu Glu Ile Lys Arg Ala Tyr Arg Arg Gln Ala Leu Arg Tyr His
20 25 30

Pro Asp Lys Asn Lys Glu Pro Gly Ala Glu Glu Lys Phe Lys Glu Ile
35 40 45

Ala Glu Ala Tyr Asp Val Leu Ser Asp Pro Arg Lys Arg Glu Ile Phe
50 55 60

Asp Arg Tyr Gly Glu Glu Gly Leu Lys Gly Ser Gly Pro Ser Gly Gly
65 70 75 80

Ser Gly Gly Gly Ala Asn Gly Thr Ser Phe Ser Tyr Thr Phe His Gly
85 90 95

Asp Pro His Ala Met Phe Ala Glu Phe Phe Gly Gly Arg Asn Pro Phe
100 105 110

```
Asp Thr Phe Phe Gly Gln Arg Asn Gly Glu Glu Gly Met Asp Ile Asp
        115                 120                 125

Asp Pro Phe Ser Gly Phe Pro Met Gly Met Gly Gly Phe Thr Asn Val
    130                 135                 140

Asn Phe Gly Arg Ser Arg Ser Ala Gln Glu Pro Ala Arg Lys Lys Gln
145                 150                 155                 160

Asp Pro Pro Val Thr His Asp Leu Arg Val Ser Leu Glu Glu Ile Tyr
                165                 170                 175

Ser Gly Cys Thr Lys Lys Met Lys Ile Ser His Lys Arg Leu Asn Pro
            180                 185                 190

Asp Gly Lys Ser Ile Arg Asn Glu Asp Lys Ile Leu Thr Ile Glu Val
        195                 200                 205

Lys Lys Gly Trp Lys Glu Gly Thr Lys Ile Thr Phe Pro Lys Glu Gly
    210                 215                 220

Asp Gln Thr Ser Asn Asn Ile Pro Ala Asp Ile Val Phe Val Leu Lys
225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
            260                 265                 270

Val Pro Thr Leu Asp Gly Arg Thr Ile Pro Val Val Phe Lys Asp Val
        275                 280                 285

Ile Arg Pro Gly Met Arg Arg Lys Val Pro Gly Glu Gly Leu Pro Leu
    290                 295                 300

Pro Lys Thr Pro Glu Lys Arg Gly Asp Leu Ile Ile Glu Phe Glu Val
305                 310                 315                 320

Ile Phe Pro Glu Arg Ile Pro Gln Thr Ser Arg Thr Val Leu Glu Gln
                325                 330                 335

Val Leu Pro Ile
            340
```

<210> SEQ ID NO 65
<211> LENGTH: 1662
<212> TYPE: DNA
<213> ORGANISM: Homo sapiens
<220> FEATURE:
<221> NAME/KEY: misc_feature
<223> OTHER INFORMATION: hATP5A1

<400> SEQUENCE: 65

```
atgctgtccg tgcgcgttgc tgcggccgtg gtccgcgccc ttcctcggcg ggccggactg      60

gtctccagaa atgctttggg ttcatctttc attgctgcaa ggaacttcca tgcctctaac     120

actcatcttc aaaagactgg gactgctgag atgtcctcta ttcttgaaga gcgtattctt     180

ggagctgata cctctgttga tcttgaagaa actgggcgtg tcttaagtat tggtgatggt     240

attgcccgcg tacatgggct gaggaatgtt caagcagaag aaatggtaga gttttcttca     300

ggcttaaagg gtatgtcctt gaacttggaa cctgacaatg ttggtgttgt cgtgtttgga     360

aatgataaac taattaagga aggagatata gtgaagagga caggagccat tgtggacgtt     420

ccagttggtg aggagctgtt gggtcgtgta gttgatgccc ttggtaatgc tattgatgga     480

aagggtccaa ttggttccaa gacgcgtagg cgagttggtc tgaaagcccc cggtatcatt     540

cctcgaattt cagtgcggga accaatgcag actggcatta aggctgtgga tagcttggtg     600

ccaattggtc gtggtcagcg tgaactgatt attggtgacc gacagactgg gaaaacctca     660

attgctattg acacaatcat taaccagaaa cgtttcaatg atggatctga tgaaaagaag     720
```

-continued

```
aagctgtact gtatttatgt tgctattggt caaaagagat ccactgttgc ccagttggtg    780

aagagactta cagatgcaga tgccatgaag tacaccattg tggtgtcggc tacggcctcg    840

gatgctgccc cacttcagta cctggctcct tactctggct gttccatggg agagtatttt    900

agagacaatg gcaaacatgc tttgatcatc tatgacgact tatccaaaca ggctgttgct    960

taccgtcaga tgtctctgtt gctccgccga ccccctggtc gtgaggccta tcctggtgat   1020

gtgttctacc tacactcccg gttgctggag agagcagcca aaatgaacga tgcttttggt   1080

ggtggctcct tgactgcttt gccagtcata gaaacacagg ctggtgatgt gtctgcttac   1140

attccaacaa atgtcatttc catcactgac ggacagatct tcttggaaac agaattgttc   1200

tacaaaggta tccgccctgc aattaacgtt ggtctgtctg tatctcgtgt cggatccgct   1260

gcccaaacca gggctatgaa gcaggtagca ggtaccatga agctggaatt ggctcagtat   1320

cgtgaggttg ctgcttttgc ccagttcggt tctgacctcg atgctgccac tcaacaactt   1380

ttgagtcgtg gcgtgcgtct aactgagttg ctgaagcaag gacagtattc tcccatggct   1440

attgaagaac aagtggctgt tatctatgcg ggtgtaaggg gatatcttga taaactggag   1500

cccagcaaga ttacaaagtt tgagaatgct ttcttgtctc atgtcgtcag ccagcaccaa   1560

gccttgttgg gcactatcag ggctgatgga aagatctcag aacaatcaga tgcaaagctg   1620

aaagagattg taacaaattt cttggctgga tttgaagctt aa                      1662
```

```
<210> SEQ ID NO 66
<211> LENGTH: 553
<212> TYPE: PRT
<213> ORGANISM: Homo sapiens
<220> FEATURE:
<221> NAME/KEY: MISC_FEATURE
<223> OTHER INFORMATION: hATP5A1

<400> SEQUENCE: 66

Met Leu Ser Val Arg Val Ala Ala Ala Val Val Arg Ala Leu Pro Arg
1               5                   10                  15

Arg Ala Gly Leu Val Ser Arg Asn Ala Leu Gly Ser Ser Phe Ile Ala
            20                  25                  30

Ala Arg Asn Phe His Ala Ser Asn Thr His Leu Gln Lys Thr Gly Thr
        35                  40                  45

Ala Glu Met Ser Ser Ile Leu Glu Glu Arg Ile Leu Gly Ala Asp Thr
    50                  55                  60

Ser Val Asp Leu Glu Glu Thr Gly Arg Val Leu Ser Ile Gly Asp Gly
65                  70                  75                  80

Ile Ala Arg Val His Gly Leu Arg Asn Val Gln Ala Glu Glu Met Val
                85                  90                  95

Glu Phe Ser Ser Gly Leu Lys Gly Met Ser Leu Asn Leu Glu Pro Asp
            100                 105                 110

Asn Val Gly Val Val Val Phe Gly Asn Asp Lys Leu Ile Lys Glu Gly
        115                 120                 125

Asp Ile Val Lys Arg Thr Gly Ala Ile Val Asp Val Pro Val Gly Glu
    130                 135                 140

Glu Leu Leu Gly Arg Val Val Asp Ala Leu Gly Asn Ala Ile Asp Gly
145                 150                 155                 160

Lys Gly Pro Ile Gly Ser Lys Thr Arg Arg Arg Val Gly Leu Lys Ala
                165                 170                 175

Pro Gly Ile Ile Pro Arg Ile Ser Val Arg Glu Pro Met Gln Thr Gly
            180                 185                 190
```

```
Ile Lys Ala Val Asp Ser Leu Val Pro Ile Gly Arg Gly Gln Arg Glu
        195                 200                 205

Leu Ile Ile Gly Asp Arg Gln Thr Gly Lys Thr Ser Ile Ala Ile Asp
    210                 215                 220

Thr Ile Ile Asn Gln Lys Arg Phe Asn Asp Gly Ser Asp Glu Lys Lys
225                 230                 235                 240

Lys Leu Tyr Cys Ile Tyr Val Ala Ile Gly Gln Lys Arg Ser Thr Val
                245                 250                 255

Ala Gln Leu Val Lys Arg Leu Thr Asp Ala Asp Ala Met Lys Tyr Thr
            260                 265                 270

Ile Val Val Ser Ala Thr Ala Ser Asp Ala Ala Pro Leu Gln Tyr Leu
        275                 280                 285

Ala Pro Tyr Ser Gly Cys Ser Met Gly Glu Tyr Phe Arg Asp Asn Gly
    290                 295                 300

Lys His Ala Leu Ile Ile Tyr Asp Asp Leu Ser Lys Gln Ala Val Ala
305                 310                 315                 320

Tyr Arg Gln Met Ser Leu Leu Leu Arg Arg Pro Pro Gly Arg Glu Ala
                325                 330                 335

Tyr Pro Gly Asp Val Phe Tyr Leu His Ser Arg Leu Leu Glu Arg Ala
            340                 345                 350

Ala Lys Met Asn Asp Ala Phe Gly Gly Gly Ser Leu Thr Ala Leu Pro
        355                 360                 365

Val Ile Glu Thr Gln Ala Gly Asp Val Ser Ala Tyr Ile Pro Thr Asn
    370                 375                 380

Val Ile Ser Ile Thr Asp Gly Gln Ile Phe Leu Glu Thr Glu Leu Phe
385                 390                 395                 400

Tyr Lys Gly Ile Arg Pro Ala Ile Asn Val Gly Leu Ser Val Ser Arg
                405                 410                 415

Val Gly Ser Ala Ala Gln Thr Arg Ala Met Lys Gln Val Ala Gly Thr
            420                 425                 430

Met Lys Leu Glu Leu Ala Gln Tyr Arg Glu Val Ala Ala Phe Ala Gln
        435                 440                 445

Phe Gly Ser Asp Leu Asp Ala Ala Thr Gln Gln Leu Leu Ser Arg Gly
    450                 455                 460

Val Arg Leu Thr Glu Leu Leu Lys Gln Gly Gln Tyr Ser Pro Met Ala
465                 470                 475                 480

Ile Glu Glu Gln Val Ala Val Ile Tyr Ala Gly Val Arg Gly Tyr Leu
                485                 490                 495

Asp Lys Leu Glu Pro Ser Lys Ile Thr Lys Phe Glu Asn Ala Phe Leu
            500                 505                 510

Ser His Val Val Ser Gln His Gln Ala Leu Leu Gly Thr Ile Arg Ala
        515                 520                 525

Asp Gly Lys Ile Ser Glu Gln Ser Asp Ala Lys Leu Lys Glu Ile Val
    530                 535                 540

Thr Asn Phe Leu Ala Gly Phe Glu Ala
545                 550
```

<210> SEQ ID NO 67
<211> LENGTH: 3129
<212> TYPE: DNA
<213> ORGANISM: Homo sapiens
<220> FEATURE:
<221> NAME/KEY: misc_feature
<223> OTHER INFORMATION: hSERCA2

-continued

<400> SEQUENCE: 67

```
atggagaacg cgcacaccaa gacggtggag gaggtgctgg gccacttcgg cgtcaacgag      60
agtacggggc tgagcctgga acaggtcaag aagcttaagg agagatgggg ctccaacgag     120
ttaccggctg aagaaggaaa aaccttgctg gaacttgtga ttgagcagtt tgaagacttg     180
ctagttagga ttttattact ggcagcatgt atatcttttg ttttggcttg gtttgaagaa     240
ggtgaagaaa caattacagc ctttgtagaa ccttttgtaa ttttactcat attagtagcc     300
aatgcaattg tgggtgtatg gcaggaaaga aatgctgaaa atgccatcga agcccttaag     360
gaatatgagc ctgaaatggg caaagtgtat cgacaggaca gaaagagtgt gcagcggatt     420
aaagctaaag acatagttcc tggtgatatt gtagaaattg ctgttggtga caaagttcct     480
gctgatataa ggttaacttc catcaaatct accacactaa gagttgacca gtcaattctc     540
acaggtgaat ctgtctctgt catcaagcac actgatcccg tccctgaccc acgagctgtc     600
aaccaagata aaaagaacat gctgttttct ggtacaaaca ttgctgctgg gaaagctatg     660
ggagtggtgg tagcaactgg agttaacacc gaaattggca agatccggga tgaaatggtg     720
gcaacagaac aggagagaac accccttcag caaaaactag atgaatttgg ggaacagctt     780
tccaaagtca tctcccttat ttgcattgca gtctggatca taaatattgg gcacttcaat     840
gacccggttc atggagggtc ctggatcaga ggtgctattt actactttaa aattgcagtg     900
gccctggctg tagcagccat tcctgaaggt ctgcctgcag tcatcaccac ctgcctggct     960
cttggaactc gcagaatggc aaagaaaaat gccattgttc gaagcctccc gtctgtggaa    1020
acccttggtt gtacttctgt tatctgctca gacaagactg gtacacttac aacaaaccag    1080
atgtcagtct gcaggatgtt cattctggac agagtggaag gtgatacttg ttcccttaat    1140
gagtttacca taactggatc aacttatgca cctattggag aagtgcataa agatgataaa    1200
ccagtgaatt gtcaccagta tgatggtctg gtagaattag caacaatttg tgctctttgt    1260
aatgactctg ctttggatta caatgaggca aagggtgtgt atgaaaaagt tggagaagct    1320
acagagactg ctctcacttg cctagtagag aagatgaatg tatttgatac cgaattgaag    1380
ggtctttcta aaatagaacg tgcaaatgcc tgcaactcag tcattaaaca gctgatgaaa    1440
aaggaattca ctctagagtt ttcacgtgac agaaagtcaa tgtcggttta ctgtacacca    1500
aataaaccaa gcaggacatc aatgagcaag atgtttgtga agggtgctcc tgaaggtgtc    1560
attgacaggt gcacccacat tcgagttgga agtactaagg ttcctatgac ctctggagtc    1620
aaacagaaga tcatgtctgt cattcgagag tggggtagtg gcagcgacac actgcgatgc    1680
ctggccctgg ccactcatga caacccactg agaagagaag aaatgcacct tgaggactct    1740
gccaacttta ttaaatatga gaccaatctg accttcgttg gctgcgtggg catgctggat    1800
cctccgagaa tcgaggtggc ctcctccgtg aagctgtgcc ggcaagcagg catccgggtc    1860
atcatgatca ctggggacaa caagggcact gctgtggcca tctgtcgccg catcggcatc    1920
ttcgggcagg atgaggacgt gacgtcaaaa gctttcacag gccgggagtt tgatgaactc    1980
aacccctccg cccagcgaga cgcctgcctg aacgcccgct gttttgctcg agttgaaccc    2040
tcccacaagt ctaaaatcgt agaatttctt cagtcttttg atgagattac agctatgact    2100
ggcgatggcg tgaacgatgc tcctgctctg aagaaagccg agattggcat tgctatgggc    2160
tctggcactg cggtggctaa aaccgcctct gagatggtcc tggcggatga caacttctcc    2220
accattgtgg ctgccgttga ggaggggcgg gcaatctaca acaacatgaa acagttcatc    2280
cgctacctca tctcgtccaa cgtcggggaa gttgtctgta ttttcctgac agcagccctt    2340
```

-continued

```
ggatttcccg aggctttgat tcctgttcag ctgctctggg tcaatctggt gacagatggc   2400

ctgcctgcca ctgcactggg gttcaaccct cctgatctgg acatcatgaa taaacctccc   2460

cggaacccaa aggaaccatt gatcagcggg tggctctttt tccgttactt ggctattggc   2520

tgttacgtcg gcgctgctac cgtgggtgct gctgcatggt ggttcattgc tgctgacggt   2580

ggtccaagag tgtccttcta ccagctgagt catttcctac agtgtaaaga ggacaacccg   2640

gactttgaag gcgtggattg tgcaatcttt gaatccccat acccgatgac aatggcgctc   2700

tctgttctag taactataga aatgtgtaac gccctcaaca gcttgtccga aaaccagtcc   2760

ttgctgagga tgcccccctg ggagaacatc tggctcgtgg gctccatctg cctgtccatg   2820

tcactccact tcctgatcct ctatgtcgaa cccttgccac tcatcttcca gatcacaccg   2880

ctgaacgtga cccagtggct gatggtgctg aaaatctcct tgcccgtgat tctcatggat   2940

gagacgctca agtttgtggc ccgcaactac ctggaacctg gtaaagagtg tgtgcagcct   3000

gccaccaaat cctgctcgtt ctcggcatgc accgatggga tttcctggcc gtttgtgctg   3060

ctcataatgc cctggtgat ctgggtctat agcacagaca ctaactttag cgatatgttc   3120

tggtcttga                                                            3129
```

```
<210> SEQ ID NO 68
<211> LENGTH: 1042
<212> TYPE: PRT
<213> ORGANISM: Homo sapiens
<220> FEATURE:
<221> NAME/KEY: MISC_FEATURE
<223> OTHER INFORMATION: hSERCA2

<400> SEQUENCE: 68

Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
            180                 185                 190

Pro Val Pro Asp Pro Arg Ala Val Asn Gln Asp Lys Lys Asn Met Leu
        195                 200                 205
```

```
Phe Ser Gly Thr Asn Ile Ala Ala Gly Lys Ala Met Gly Val Val Val
    210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
                245                 250                 255

Gly Glu Gln Leu Ser Lys Val Ile Ser Leu Ile Cys Ile Ala Val Trp
            260                 265                 270

Ile Ile Asn Ile Gly His Phe Asn Asp Pro Val His Gly Gly Ser Trp
        275                 280                 285

Ile Arg Gly Ala Ile Tyr Tyr Phe Lys Ile Ala Val Ala Leu Ala Val
    290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
            340                 345                 350

Thr Gly Thr Leu Thr Thr Asn Gln Met Ser Val Cys Arg Met Phe Ile
        355                 360                 365

Leu Asp Arg Val Glu Gly Asp Thr Cys Ser Leu Asn Glu Phe Thr Ile
    370                 375                 380

Thr Gly Ser Thr Tyr Ala Pro Ile Gly Glu Val His Lys Asp Asp Lys
385                 390                 395                 400

Pro Val Asn Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
            420                 425                 430

Val Tyr Glu Lys Val Gly Glu Ala Thr Glu Thr Ala Leu Thr Cys Leu
        435                 440                 445

Val Glu Lys Met Asn Val Phe Asp Thr Glu Leu Lys Gly Leu Ser Lys
    450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
            500                 505                 510

Val Lys Gly Ala Pro Glu Gly Val Ile Asp Arg Cys Thr His Ile Arg
        515                 520                 525

Val Gly Ser Thr Lys Val Pro Met Thr Ser Gly Val Lys Gln Lys Ile
    530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Arg Arg Glu Glu Met His
                565                 570                 575

Leu Glu Asp Ser Ala Asn Phe Ile Lys Tyr Glu Thr Asn Leu Thr Phe
            580                 585                 590

Val Gly Cys Val Gly Met Leu Asp Pro Pro Arg Ile Glu Val Ala Ser
        595                 600                 605

Ser Val Lys Leu Cys Arg Gln Ala Gly Ile Arg Val Ile Met Ile Thr
    610                 615                 620

Gly Asp Asn Lys Gly Thr Ala Val Ala Ile Cys Arg Arg Ile Gly Ile
```

-continued

```
625                 630                 635                 640

Phe Gly Gln Asp Glu Asp Val Thr Ser Lys Ala Phe Thr Gly Arg Glu
                645                 650                 655

Phe Asp Glu Leu Asn Pro Ser Ala Gln Arg Asp Ala Cys Leu Asn Ala
            660                 665                 670

Arg Cys Phe Ala Arg Val Glu Pro Ser His Lys Ser Lys Ile Val Glu
        675                 680                 685

Phe Leu Gln Ser Phe Asp Glu Ile Thr Ala Met Thr Gly Asp Gly Val
    690                 695                 700

Asn Asp Ala Pro Ala Leu Lys Lys Ala Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
        755                 760                 765

Gly Glu Val Val Cys Ile Phe Leu Thr Ala Ala Leu Gly Phe Pro Glu
    770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
        835                 840                 845

Gly Ala Ala Ala Trp Trp Phe Ile Ala Ala Asp Gly Gly Pro Arg Val
    850                 855                 860

Ser Phe Tyr Gln Leu Ser His Phe Leu Gln Cys Lys Glu Asp Asn Pro
865                 870                 875                 880

Asp Phe Glu Gly Val Asp Cys Ala Ile Phe Glu Ser Pro Tyr Pro Met
                885                 890                 895

Thr Met Ala Leu Ser Val Leu Val Thr Ile Glu Met Cys Asn Ala Leu
            900                 905                 910

Asn Ser Leu Ser Glu Asn Gln Ser Leu Leu Arg Met Pro Pro Trp Glu
        915                 920                 925

Asn Ile Trp Leu Val Gly Ser Ile Cys Leu Ser Met Ser Leu His Phe
    930                 935                 940

Leu Ile Leu Tyr Val Glu Pro Leu Pro Leu Ile Phe Gln Ile Thr Pro
945                 950                 955                 960

Leu Asn Val Thr Gln Trp Leu Met Val Leu Lys Ile Ser Leu Pro Val
                965                 970                 975

Ile Leu Met Asp Glu Thr Leu Lys Phe Val Ala Arg Asn Tyr Leu Glu
            980                 985                 990

Pro Gly Lys Glu Cys Val Gln Pro  Ala Thr Lys Ser Cys  Ser Phe Ser
        995                 1000                1005

Ala Cys  Thr Asp Gly Ile Ser  Trp Pro Phe Val Leu  Leu Ile Met
    1010                1015                1020

Pro Leu  Val Ile Trp Val Tyr  Ser Thr Asp Thr Asn  Phe Ser Asp
    1025                1030                1035

Met Phe  Trp Ser
    1040
```

<210> SEQ ID NO 69
<211> LENGTH: 1938
<212> TYPE: DNA
<213> ORGANISM: Homo sapiens
<220> FEATURE:
<221> NAME/KEY: misc_feature
<223> OTHER INFORMATION: hPDIA4

<400> SEQUENCE: 69

```
atgaggcccc ggaaagcctt cctgctcctg ctgctcttgg ggctggtgca gctgctggcc     60
gtggcgggtg ccgagggccc ggacgaggat tcttctaaca gagaaaatgc cattgaggat    120
gaagaggagg aggaggagga agatgatgat gaggaagaag acgacttgga agttaaggaa    180
gaaaatggag tcttggtcct aaatgatgca aactttgata attttgtggc tgacaaagac    240
acagtgctgc tggagtttta tgctccatgg tgtggacatt gcaagcagtt tgctccggaa    300
tatgaaaaaa ttgccaacat attaaaggat aaagatcctc ccattcctgt tgccaagatc    360
gatgcaacct cagcgtctgt gctggccagc aggtttgatg tgagtggcta ccccaccatc    420
aagatcctta agaaggggca ggctgtagac tacgagggct ccagaaccca ggaagaaatt    480
gttgccaagg tcagagaagt ctcccagccc gactggacgc ctccaccaga agtcacgctt    540
gtgttgacca aagagaactt tgatgaagtt gtgaatgatg cagatatcat tctggtggag    600
ttttatgccc catggtgtgg acactgcaag aaacttgccc ccgagtatga gaaggccgcc    660
aaggagctca gcaagcgttc tcctccaatt cccctggcaa aggtcgacgc caccgcagaa    720
acagacctgg ccaagaggtt tgatgtctct ggctatccca ccctgaaaat tttccgcaaa    780
ggaaggcctt atgactacaa cggcccacga gaaaaatatg gaatcgttga ttacatgatc    840
gagcagtccg ggcctccctc caaggagatt ctgaccctga agcaggtcca ggagttcctg    900
aaggatggag acgatgtcat catcatcggg gtctttaagg gggagagtga cccagcctac    960
cagcaatacc aggatgccgc taacaacctg agagaagatt acaaatttca ccacactttc   1020
agcacagaaa tagcaaagtt cttgaaagtc tcccaggggc agttggttgt aatgcagcct   1080
gagaaattcc agtccaagta tgagccccgg agccacatga tggacgtcca gggctccacc   1140
caggactcgg ccatcaagga cttcgtgctg aagtacgccc tgcccctggt tggccaccgc   1200
aaggtgtcaa acgatgctaa gcgctacacc aggcgccccc tggtggtcgt ctactacagt   1260
gtggacttca gctttgatta cagagctgca actcagtttt ggcggagcaa agtcctagag   1320
gtggccaagg acttccctga gtacaccttt gccattgcgg acgaagagga ctatgctggg   1380
gaggtgaagg acctggggct cagcgagagt ggggaggatg tcaatgccgc catcctggac   1440
gagagtggga agaagttcgc catggagcca gaggagtttg actctgacac cctccgcgag   1500
tttgtcactg ctttcaaaaa aggaaaactg aagccagtca tcaaatccca gccagtgccc   1560
aagaacaaca agggacccgt caaggtcgtg gtgggaaaga cctttgactc cattgtgatg   1620
gaccccaaga aggacgtcct catcgagttc tacgcgccat ggtgcgggca ctgcaagcag   1680
ctagagcccg tgtacaacag cctggccaag aagtacaagg gccaaaaggg cctggtcatc   1740
gccaagatgg acgccactgc caacgacgtc cccagcgacc gctataaggt ggagggcttc   1800
cccaccatct acttcgcccc cagtggggac aaaaagaacc cagttaaatt tgagggtgga   1860
gacagagatc tggagcattt gagcaagttt atagaagaac atgccacaaa actgagcagg   1920
accaaggaag agctttga                                                 1938
```

<210> SEQ ID NO 70
<211> LENGTH: 645
<212> TYPE: PRT
<213> ORGANISM: Homo sapiens
<220> FEATURE:
<221> NAME/KEY: MISC_FEATURE
<223> OTHER INFORMATION: hPDIA4

<400> SEQUENCE: 70

Met Arg Pro Arg Lys Ala Phe Leu Leu Leu Leu Leu Leu Gly Leu Val
1 5 10 15

Gln Leu Leu Ala Val Ala Gly Ala Glu Gly Pro Asp Glu Asp Ser Ser
20 25 30

Asn Arg Glu Asn Ala Ile Glu Asp Glu Glu Glu Glu Glu Glu Glu Asp
35 40 45

Asp Asp Glu Glu Glu Asp Asp Leu Glu Val Lys Glu Glu Asn Gly Val
50 55 60

Leu Val Leu Asn Asp Ala Asn Phe Asp Asn Phe Val Ala Asp Lys Asp
65 70 75 80

Thr Val Leu Leu Glu Phe Tyr Ala Pro Trp Cys Gly His Cys Lys Gln
85 90 95

Phe Ala Pro Glu Tyr Glu Lys Ile Ala Asn Ile Leu Lys Asp Lys Asp
100 105 110

Pro Pro Ile Pro Val Ala Lys Ile Asp Ala Thr Ser Ala Ser Val Leu
115 120 125

Ala Ser Arg Phe Asp Val Ser Gly Tyr Pro Thr Ile Lys Ile Leu Lys
130 135 140

Lys Gly Gln Ala Val Asp Tyr Glu Gly Ser Arg Thr Gln Glu Glu Ile
145 150 155 160

Val Ala Lys Val Arg Glu Val Ser Gln Pro Asp Trp Thr Pro Pro Pro
165 170 175

Glu Val Thr Leu Val Leu Thr Lys Glu Asn Phe Asp Glu Val Val Asn
180 185 190

Asp Ala Asp Ile Ile Leu Val Glu Phe Tyr Ala Pro Trp Cys Gly His
195 200 205

Cys Lys Lys Leu Ala Pro Glu Tyr Glu Lys Ala Ala Lys Glu Leu Ser
210 215 220

Lys Arg Ser Pro Pro Ile Pro Leu Ala Lys Val Asp Ala Thr Ala Glu
225 230 235 240

Thr Asp Leu Ala Lys Arg Phe Asp Val Ser Gly Tyr Pro Thr Leu Lys
245 250 255

Ile Phe Arg Lys Gly Arg Pro Tyr Asp Tyr Asn Gly Pro Arg Glu Lys
260 265 270

Tyr Gly Ile Val Asp Tyr Met Ile Glu Gln Ser Gly Pro Pro Ser Lys
275 280 285

Glu Ile Leu Thr Leu Lys Gln Val Gln Glu Phe Leu Lys Asp Gly Asp
290 295 300

Asp Val Ile Ile Ile Gly Val Phe Lys Gly Glu Ser Asp Pro Ala Tyr
305 310 315 320

Gln Gln Tyr Gln Asp Ala Ala Asn Asn Leu Arg Glu Asp Tyr Lys Phe
325 330 335

His His Thr Phe Ser Thr Glu Ile Ala Lys Phe Leu Lys Val Ser Gln
340 345 350

Gly Gln Leu Val Val Met Gln Pro Glu Lys Phe Gln Ser Lys Tyr Glu
355 360 365

-continued

Pro Arg Ser His Met Met Asp Val Gln Gly Ser Thr Gln Asp Ser Ala
    370                 375                 380

Ile Lys Asp Phe Val Leu Lys Tyr Ala Leu Pro Leu Val Gly His Arg
385                 390                 395                 400

Lys Val Ser Asn Asp Ala Lys Arg Tyr Thr Arg Arg Pro Leu Val Val
                405                 410                 415

Val Tyr Tyr Ser Val Asp Phe Ser Phe Asp Tyr Arg Ala Ala Thr Gln
            420                 425                 430

Phe Trp Arg Ser Lys Val Leu Glu Val Ala Lys Asp Phe Pro Glu Tyr
        435                 440                 445

Thr Phe Ala Ile Ala Asp Glu Glu Asp Tyr Ala Gly Glu Val Lys Asp
    450                 455                 460

Leu Gly Leu Ser Glu Ser Gly Glu Asp Val Asn Ala Ala Ile Leu Asp
465                 470                 475                 480

Glu Ser Gly Lys Lys Phe Ala Met Glu Pro Glu Glu Phe Asp Ser Asp
                485                 490                 495

Thr Leu Arg Glu Phe Val Thr Ala Phe Lys Lys Gly Lys Leu Lys Pro
            500                 505                 510

Val Ile Lys Ser Gln Pro Val Pro Lys Asn Asn Lys Gly Pro Val Lys
        515                 520                 525

Val Val Val Gly Lys Thr Phe Asp Ser Ile Val Met Asp Pro Lys Lys
    530                 535                 540

Asp Val Leu Ile Glu Phe Tyr Ala Pro Trp Cys Gly His Cys Lys Gln
545                 550                 555                 560

Leu Glu Pro Val Tyr Asn Ser Leu Ala Lys Lys Tyr Lys Gly Gln Lys
                565                 570                 575

Gly Leu Val Ile Ala Lys Met Asp Ala Thr Ala Asn Asp Val Pro Ser
            580                 585                 590

Asp Arg Tyr Lys Val Glu Gly Phe Pro Thr Ile Tyr Phe Ala Pro Ser
        595                 600                 605

Gly Asp Lys Lys Asn Pro Val Lys Phe Glu Gly Gly Asp Arg Asp Leu
    610                 615                 620

Glu His Leu Ser Lys Phe Ile Glu Glu His Ala Thr Lys Leu Ser Arg
625                 630                 635                 640

Thr Lys Glu Glu Leu
                645

<210> SEQ ID NO 71
<211> LENGTH: 1941
<212> TYPE: DNA
<213> ORGANISM: Homo sapiens
<220> FEATURE:
<221> NAME/KEY: misc_feature
<223> OTHER INFORMATION: hHSC70 /HSPA8

<400> SEQUENCE: 71
atgtccaagg gacctgcagt tggtattgat cttggcacca cctactcttg tgtgggtgtt 60
ttccagcacg gaaaagtcga gataattgcc aatgatcagg gaaaccgaac cactccaagc 120
tatgtcgcct ttacggacac tgaacggttg atcggtgatg ccgcaaagaa tcaagttgca 180
atgaacccca ccaacacagt ttttgatgcc aaacgtctga ttggacgcag atttgatgat 240
gctgttgtcc agtctgatat gaaacattgg ccctttatgg tggtgaatga tgctggcagg 300
cccaaggtcc aagtagaata caagggagag accaaaagct tctatccaga ggaggtgtct 360
tctatggttc tgacaaagat gaaggaaatt gcagaagcct accttgggaa gactgttacc 420

```
aatgctgtgg tcacagtgcc agcttacttt aatgactctc agcgtcaggc taccaaagat    480

gctggaacta ttgctggtct caatgtactt agaattatta atgagccaac tgctgctgct    540

attgcttacg gcttagacaa aaaggttgga gcagaaagaa acgtgctcat ctttgacctg    600

ggaggtggca cttttgatgt gtcaatcctc actattgagg atggaatctt tgaggtcaag    660

tctacagctg gagacaccca cttgggtgga gaagattttg acaaccgaat ggtcaaccat    720

tttattgctg agtttaagcg caagcataag aaggacatca gtgagaacaa gagagctgta    780

agacgcctcc gtactgcttg tgaacgtgct aagcgtaccc tctcttccag cacccaggcc    840

agtattgaga tcgattctct ctatgaagga atcgacttct atacctccat tacccgtgcc    900

cgatttgaag aactgaatgc tgacctgttc cgtggcaccc tggacccagt agagaaagcc    960

cttcgagatg ccaaactaga caagtcacag attcatgata ttgtcctggt tggtggttct   1020

actcgtatcc ccaagattca gaagcttctc caagacttct tcaatggaaa agaactgaat   1080

aagagcatca accctgatga agctgttgct tatggtgcag ctgtccaggc agccatcttg   1140

tctggagaca agtctgagaa tgttcaagat ttgctgctct tggatgtcac tcctctttcc   1200

cttggtattg aaactgctgg tggagtcatg actgtcctca tcaagcgtaa taccaccatt   1260

cctaccaagc agacacagac cttcactacc tattctgaca accagcctgg tgtgcttatt   1320

caggtttatg aaggcgagcg tgccatgaca aaggataaca acctgcttgg caagtttgaa   1380

ctcacaggca tacctcctgc accccgaggt gttcctcaga ttgaagtcac ttttgacatt   1440

gatgccaatg gtatactcaa tgtctctgct gtggacaaga gtacgggaaa agagaacaag   1500

attactatca ctaatgacaa gggccgtttg agcaaggaag acattgaacg tatggtccag   1560

gaagctgaga agtacaaagc tgaagatgag aagcagaggg acaaggtgtc atccaagaat   1620

tcacttgagt cctatgcctt caacatgaaa gcaactgttg aagatgagaa acttcaaggc   1680

aagattaacg atgaggacaa acagaagatt ctggacaagt gtaatgaaat tatcaactgg   1740

cttgataaga atcagactgc tgagaaggaa gaatttgaac atcaacagaa agagctggag   1800

aaagtttgca accccatcat caccaagctg taccagagtg caggaggcat gccaggagga   1860

atgcctgggg gatttcctgg tggtggagct cctccctctg gtggtgcttc ctcagggccc   1920

accattgaag aggttgatta a                                              1941
```

<210> SEQ ID NO 72
<211> LENGTH: 646
<212> TYPE: PRT
<213> ORGANISM: Homo sapiens
<220> FEATURE:
<221> NAME/KEY: MISC_FEATURE
<223> OTHER INFORMATION: hHSC70 /HSPA8

<400> SEQUENCE: 72

```
Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
```

```
                85                  90                  95
Asp Ala Gly Arg Pro Lys Val Gln Val Glu Tyr Lys Gly Glu Thr Lys
            100                 105                 110
Ser Phe Tyr Pro Glu Glu Val Ser Ser Met Val Leu Thr Lys Met Lys
        115                 120                 125
Glu Ile Ala Glu Ala Tyr Leu Gly Lys Thr Val Thr Asn Ala Val Val
    130                 135                 140
Thr Val Pro Ala Tyr Phe Asn Asp Ser Gln Arg Gln Ala Thr Lys Asp
145                 150                 155                 160
Ala Gly Thr Ile Ala Gly Leu Asn Val Leu Arg Ile Ile Asn Glu Pro
                165                 170                 175
Thr Ala Ala Ala Ile Ala Tyr Gly Leu Asp Lys Lys Val Gly Ala Glu
            180                 185                 190
Arg Asn Val Leu Ile Phe Asp Leu Gly Gly Gly Thr Phe Asp Val Ser
        195                 200                 205
Ile Leu Thr Ile Glu Asp Gly Ile Phe Glu Val Lys Ser Thr Ala Gly
    210                 215                 220
Asp Thr His Leu Gly Gly Glu Asp Phe Asp Asn Arg Met Val Asn His
225                 230                 235                 240
Phe Ile Ala Glu Phe Lys Arg Lys His Lys Lys Asp Ile Ser Glu Asn
                245                 250                 255
Lys Arg Ala Val Arg Arg Leu Arg Thr Ala Cys Glu Arg Ala Lys Arg
            260                 265                 270
Thr Leu Ser Ser Ser Thr Gln Ala Ser Ile Glu Ile Asp Ser Leu Tyr
        275                 280                 285
Glu Gly Ile Asp Phe Tyr Thr Ser Ile Thr Arg Ala Arg Phe Glu Glu
    290                 295                 300
Leu Asn Ala Asp Leu Phe Arg Gly Thr Leu Asp Pro Val Glu Lys Ala
305                 310                 315                 320
Leu Arg Asp Ala Lys Leu Asp Lys Ser Gln Ile His Asp Ile Val Leu
                325                 330                 335
Val Gly Gly Ser Thr Arg Ile Pro Lys Ile Gln Lys Leu Leu Gln Asp
            340                 345                 350
Phe Phe Asn Gly Lys Glu Leu Asn Lys Ser Ile Asn Pro Asp Glu Ala
        355                 360                 365
Val Ala Tyr Gly Ala Ala Val Gln Ala Ala Ile Leu Ser Gly Asp Lys
    370                 375                 380
Ser Glu Asn Val Gln Asp Leu Leu Leu Leu Asp Val Thr Pro Leu Ser
385                 390                 395                 400
Leu Gly Ile Glu Thr Ala Gly Gly Val Met Thr Val Leu Ile Lys Arg
                405                 410                 415
Asn Thr Thr Ile Pro Thr Lys Gln Thr Gln Thr Phe Thr Thr Tyr Ser
            420                 425                 430
Asp Asn Gln Pro Gly Val Leu Ile Gln Val Tyr Glu Gly Glu Arg Ala
        435                 440                 445
Met Thr Lys Asp Asn Asn Leu Leu Gly Lys Phe Glu Leu Thr Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Ser Ala Val Asp Lys Ser Thr Gly
                485                 490                 495
Lys Glu Asn Lys Ile Thr Ile Thr Asn Asp Lys Gly Arg Leu Ser Lys
            500                 505                 510
```

```
Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
    530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
            580                 585                 590

Glu His Gln Gln Lys Glu Leu Glu Lys Val Cys Asn Pro Ile Ile Thr
        595                 600                 605

Lys Leu Tyr Gln Ser Ala Gly Gly Met Pro Gly Gly Met Pro Gly Gly
    610                 615                 620

Phe Pro Gly Gly Gly Ala Pro Pro Ser Gly Gly Ala Ser Ser Gly Pro
625                 630                 635                 640

Thr Ile Glu Glu Val Asp
                645


<210> SEQ ID NO 73
<211> LENGTH: 3000
<212> TYPE: DNA
<213> ORGANISM: Homo sapiens
<220> FEATURE:
<221> NAME/KEY: misc_feature
<223> OTHER INFORMATION: hHYOU1

<400> SEQUENCE: 73

atggcagaca aagttaggag gcagaggccg aggaggcgag tctgttgggc cttggtggct     60

gtgctcttgg cagacctgtt ggcactgagt gatacactgg cagtgatgtc tgtggacctg    120

ggcagtgagt ccatgaaggt ggccattgtc aaacctggag tgcccatgga aattgtcttg    180

aataaggaat ctcggaggaa aacaccggtg atcgtgaccc tgaaagaaaa tgaaagattc    240

tttggagaca gtgcagcaag catggcgatt aagaatccaa aggctacgct acgttacttc    300

cagcacctcc tggggaagca ggcagataac ccccatgtag ctctttacca ggcccgcttc    360

ccggagcacg agctgacttt cgacccacag aggcagactg tgcactttca gatcagctcg    420

cagctgcagt tctcacctga ggaagtgttg ggcatggttc tcaattattc tcgttctcta    480

gctgaagatt ttgcagagca gcccatcaag gatgcagtga tcaccgtgcc agtcttcttc    540

aaccaggccg agcgccgagc tgtgctgcag gctgctcgta tggctggcct caaagtgctg    600

cagctcatca atgacaacac cgccactgcc ctcagctatg gtgtcttccg ccggaaagat    660

attaacacca ctgcccagaa tatcatgttc tatgacatgg gctcaggcag caccgtatgc    720

accattgtga cctaccagat ggtgaagact aaggaagctg ggatgcagcc acagctgcag    780

atccggggag taggatttga ccgtaccctg gggggcctgg agatggagct ccggcttcga    840

gaacgcctgg ctgggctttt caatgagcag cgcaagggtc agagagcaaa ggatgtgcgg    900

gagaacccgc gtgccatggc caagctgctg cgtgaggcta atcggctcaa aaccgtcctc    960

agtgccaacg ctgaccacat ggcacagatt gaaggcctga tggatgatgt ggacttcaag   1020

gcaaaagtga ctcgtgtgga atttgaggag ttgtgtgcag acttgtttga gcgggtgcct   1080

gggcctgtac agcaggccct ccagagtgcc gaaatgagtc tggatgagat tgagcaggtg   1140

atcctggtgg gtggggccac tcgggtcccc agagttcagg aggtgctgct gaaggccgtg   1200
```

ggcaaggagg agctggggaa gaacatcaat gcagatgaag cagccgccat gggggcagtg 1260
taccaggcag ctgcgctcag caaagccttt aaagtgaagc catttgtcgt ccgagatgca 1320
gtggtctacc ccatcctggt ggagttcacg agggaggtgg aggaggagcc tgggattcac 1380
agcctgaagc acaataaacg ggtactcttc tctcggatgg ggccctaccc tcaacgcaaa 1440
gtcatcacct ttaaccgcta cagccatgat ttcaacttcc acatcaacta cggcgacctg 1500
ggcttcctgg ggcctgaaga tcttcgggta tttggctccc agaatctgac cacagtgaag 1560
ctaaaagggg tgggtgacag cttcaagaag tatcctgact acgagtccaa gggcatcaag 1620
gctcacttca acctggatga gagtggcgtg ctcagtctag acagggtgga gtctgtattt 1680
gagacactgg tagaggacag cgcagaagag gaatctactc tcaccaaact tggcaacacc 1740
atttccagcc tgtttggagg cggtaccaca ccagatgcca aggagaatgg tactgatact 1800
gtccaggagg aagaggagag ccctgcagag gggagcaagg acgagcctgg ggagcaggtg 1860
gagctcaagg aggaagctga ggccccagtg gaggatggct ctcagccccc acccccctgaa 1920 cctaagggag atgcaacccc tgagggagaa aaggccacag aaaaagaaaa tggggacaag 1980
tctgaggccc agaaaccaag tgagaaggca gaggcagggc ctgagggcgt cgctccagcc 2040
ccagagggag agaagaagca gaagcccgcc aggaagcggc gaatggtaga ggagatcggg 2100
gtggagctgg ttgttctgga cctgcctgac ttgccagagg ataagctggc tcagtcggtg 2160
cagaaacttc aggacttgac actccgagac ctggagaagc aggaacggga aaaagctgcc 2220
aacagcttgg aagcattcat atttgagacc caggacaagc tgtaccagcc cgagtaccag 2280
gaagtgtcca cagaggagca gcgtgaggag atctctggga agctcagcgc cgcatccacc 2340
tggctggagg atgagggtgt tggagccacc acagtgatgt tgaaggagaa gctggctgag 2400
ctgaggaagc tgtgccaagg gctgtttttt cgggtagagg agcgcaagaa gtggcccgaa 2460
cggctgtctg ccctcgataa tctcctcaac cattccagca tgttcctcaa gggggcccgg 2520
ctcatcccag agatggacca gatcttcact gaggtggaga tgacaacgtt agagaaagtc 2580
atcaatgaga cctgggcctg gaagaatgca actctggccg agcaggctaa gctgcccgcc 2640
acagagaagc ctgtgttgct ctcaaaagac attgaagcta agatgatggc cctggaccga 2700
gaggtgcagt atctgctcaa taaggccaag tttaccaagc cccggccccg gcctaaggac 2760
aagaatggga cccgggcaga gccacccctc aatgccagtg ccagtgacca gggggagaag 2820
gtcatccctc cagcaggcca gactgaagat gcagagccca tttcagaacc tgagaaagta 2880
gagactggat ccgagccagg agacactgag cctttggagt taggaggtcc tggagcagaa 2940
cctgaacaga aagaacaatc gacaggacag aagcggcctt tgaagaacga cgaactataa 3000

<210> SEQ ID NO 74
<211> LENGTH: 999
<212> TYPE: PRT
<213> ORGANISM: Homo sapiens
<220> FEATURE:
<221> NAME/KEY: MISC_FEATURE
<223> OTHER INFORMATION: hHYOU1

<400> SEQUENCE: 74

Met Ala Asp Lys Val Arg Arg Gln Arg Pro Arg Arg Arg Val Cys Trp
1 5 10 15

Ala Leu Val Ala Val Leu Leu Ala Asp Leu Leu Ala Leu Ser Asp Thr
20 25 30

Leu Ala Val Met Ser Val Asp Leu Gly Ser Glu Ser Met Lys Val Ala
35 40 45

-continued

```
Ile Val Lys Pro Gly Val Pro Met Glu Ile Val Leu Asn Lys Glu Ser
    50                  55                  60

Arg Arg Lys Thr Pro Val Ile Val Thr Leu Lys Glu Asn Glu Arg Phe
65                  70                  75                  80

Phe Gly Asp Ser Ala Ala Ser Met Ala Ile Lys Asn Pro Lys Ala Thr
                85                  90                  95

Leu Arg Tyr Phe Gln His Leu Leu Gly Lys Gln Ala Asp Asn Pro His
            100                 105                 110

Val Ala Leu Tyr Gln Ala Arg Phe Pro Glu His Glu Leu Thr Phe Asp
        115                 120                 125

Pro Gln Arg Gln Thr Val His Phe Gln Ile Ser Ser Gln Leu Gln Phe
    130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Val Phe Phe Asn Gln Ala Glu Arg Arg Ala Val Leu Gln Ala Ala
            180                 185                 190

Arg Met Ala Gly Leu Lys Val Leu Gln Leu Ile Asn Asp Asn Thr Ala
        195                 200                 205

Thr Ala Leu Ser Tyr Gly Val Phe Arg Arg Lys Asp Ile Asn Thr Thr
    210                 215                 220

Ala Gln Asn Ile Met Phe Tyr Asp Met Gly Ser Gly Ser Thr Val Cys
225                 230                 235                 240

Thr Ile Val Thr Tyr Gln Met Val Lys Thr Lys Glu Ala Gly Met Gln
                245                 250                 255

Pro Gln Leu Gln Ile Arg Gly Val Gly Phe Asp Arg Thr Leu Gly Gly
            260                 265                 270

Leu Glu Met Glu Leu Arg Leu Arg Glu Arg Leu Ala Gly Leu Phe Asn
        275                 280                 285

Glu Gln Arg Lys Gly Gln Arg Ala Lys Asp Val Arg Glu Asn Pro Arg
    290                 295                 300

Ala Met Ala Lys Leu Leu Arg Glu Ala Asn Arg Leu Lys Thr Val Leu
305                 310                 315                 320

Ser Ala Asn Ala Asp His Met Ala Gln Ile Glu Gly Leu Met Asp Asp
                325                 330                 335

Val Asp Phe Lys Ala Lys Val Thr Arg Val Glu Phe Glu Glu Leu Cys
            340                 345                 350

Ala Asp Leu Phe Glu Arg Val Pro Gly Pro Val Gln Gln Ala Leu Gln
        355                 360                 365

Ser Ala Glu Met Ser Leu Asp Glu Ile Glu Gln Val Ile Leu Val Gly
    370                 375                 380

Gly Ala Thr Arg Val Pro Arg Val Gln Glu Val Leu Leu Lys Ala Val
385                 390                 395                 400

Gly Lys Glu Glu Leu Gly Lys Asn Ile Asn Ala Asp Glu Ala Ala Ala
                405                 410                 415

Met Gly Ala Val Tyr Gln Ala Ala Ala Leu Ser Lys Ala Phe Lys Val
            420                 425                 430

Lys Pro Phe Val Val Arg Asp Ala Val Val Tyr Pro Ile Leu Val Glu
        435                 440                 445

Phe Thr Arg Glu Val Glu Glu Glu Pro Gly Ile His Ser Leu Lys His
    450                 455                 460
```

-continued

```
Asn Lys Arg Val Leu Phe Ser Arg Met Gly Pro Tyr Pro Gln Arg Lys
465                 470                 475                 480

Val Ile Thr Phe Asn Arg Tyr Ser His Asp Phe Asn Phe His Ile Asn
                485                 490                 495

Tyr Gly Asp Leu Gly Phe Leu Gly Pro Glu Asp Leu Arg Val Phe Gly
            500                 505                 510

Ser Gln Asn Leu Thr Thr Val Lys Leu Lys Gly Val Gly Asp Ser Phe
        515                 520                 525

Lys Lys Tyr Pro Asp Tyr Glu Ser Lys Gly Ile Lys Ala His Phe Asn
    530                 535                 540

Leu Asp Glu Ser Gly Val Leu Ser Leu Asp Arg Val Glu Ser Val Phe
545                 550                 555                 560

Glu Thr Leu Val Glu Asp Ser Ala Glu Glu Glu Ser Thr Leu Thr Lys
                565                 570                 575

Leu Gly Asn Thr Ile Ser Ser Leu Phe Gly Gly Gly Thr Thr Pro Asp
            580                 585                 590

Ala Lys Glu Asn Gly Thr Asp Thr Val Gln Glu Glu Glu Glu Ser Pro
        595                 600                 605

Ala Glu Gly Ser Lys Asp Glu Pro Gly Glu Gln Val Glu Leu Lys Glu
    610                 615                 620

Glu Ala Glu Ala Pro Val Glu Asp Gly Ser Gln Pro Pro Pro Pro Glu
625                 630                 635                 640

Pro Lys Gly Asp Ala Thr Pro Glu Gly Glu Lys Ala Thr Glu Lys Glu
                645                 650                 655

Asn Gly Asp Lys Ser Glu Ala Gln Lys Pro Ser Glu Lys Ala Glu Ala
            660                 665                 670

Gly Pro Glu Gly Val Ala Pro Ala Pro Glu Gly Glu Lys Lys Gln Lys
        675                 680                 685

Pro Ala Arg Lys Arg Arg Met Val Glu Glu Ile Gly Val Glu Leu Val
    690                 695                 700

Val Leu Asp Leu Pro Asp Leu Pro Glu Asp Lys Leu Ala Gln Ser Val
705                 710                 715                 720

Gln Lys Leu Gln Asp Leu Thr Leu Arg Asp Leu Glu Lys Gln Glu Arg
                725                 730                 735

Glu Lys Ala Ala Asn Ser Leu Glu Ala Phe Ile Phe Glu Thr Gln Asp
            740                 745                 750

Lys Leu Tyr Gln Pro Glu Tyr Gln Glu Val Ser Thr Glu Glu Gln Arg
        755                 760                 765

Glu Glu Ile Ser Gly Lys Leu Ser Ala Ala Ser Thr Trp Leu Glu Asp
    770                 775                 780

Glu Gly Val Gly Ala Thr Thr Val Met Leu Lys Glu Lys Leu Ala Glu
785                 790                 795                 800

Leu Arg Lys Leu Cys Gln Gly Leu Phe Phe Arg Val Glu Glu Arg Lys
                805                 810                 815

Lys Trp Pro Glu Arg Leu Ser Ala Leu Asp Asn Leu Leu Asn His Ser
            820                 825                 830

Ser Met Phe Leu Lys Gly Ala Arg Leu Ile Pro Glu Met Asp Gln Ile
        835                 840                 845

Phe Thr Glu Val Glu Met Thr Thr Leu Glu Lys Val Ile Asn Glu Thr
    850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
```

```
                885                 890                 895

Ala Leu Asp Arg Glu Val Gln Tyr Leu Leu Asn Lys Ala Lys Phe Thr
            900                 905                 910

Lys Pro Arg Pro Arg Pro Lys Asp Lys Asn Gly Thr Arg Ala Glu Pro
        915                 920                 925

Pro Leu Asn Ala Ser Ala Ser Asp Gln Gly Glu Lys Val Ile Pro Pro
    930                 935                 940

Ala Gly Gln Thr Glu Asp Ala Glu Pro Ile Ser Glu Pro Glu Lys Val
945                 950                 955                 960

Glu Thr Gly Ser Glu Pro Gly Asp Thr Glu Pro Leu Glu Leu Gly Gly
            965                 970                 975

Pro Gly Ala Glu Pro Glu Gln Lys Glu Gln Ser Thr Gly Gln Lys Arg
            980                 985                 990

Pro Leu Lys Asn Asp Glu Leu
        995


<210> SEQ ID NO 75
<211> LENGTH: 1305
<212> TYPE: DNA
<213> ORGANISM: Homo sapiens
<220> FEATURE:
<221> NAME/KEY: misc_feature
<223> OTHER INFORMATION: hCMP-SAS

<400> SEQUENCE: 75

atggactcgg tggagaaggg ggccgccacc tccgtctcca acccgcgggg gcgaccgtcc      60

cggggccggc cgccgaagct gcagcgcaac tctcgcggcg gccagggccg aggtgtggag     120

aagcccccgc acctggcagc cctaattctg gcccggggag gcagcaaagg catccccctg     180

aagaacatta agcacctggc gggggtcccg ctcattggct gggtcctgcg tgcggccctg     240

gattcagggg ccttccagag tgtatgggtt tcgacagacc atgatgaaat tgagaatgtg     300

gccaaacaat ttggtgcaca agttcatcga agaagttctg aagtttcaaa agacagctct     360

acctcactag atgccatcat agaatttctt aattatcata atgaggttga cattgtagga     420

aatattcaag ctacttctcc atgtttacat cctactgatc ttcaaaaagt tgcagaaatg     480

attcgagaag aaggatatga ttctgttttc tctgttgtga gacgccatca gtttcgatgg     540

agtgaaattc agaaaggagt tcgtgaagtg accgaacctc tgaatttaaa tccagctaaa     600

cggcctcgtc gacaagactg ggatggagaa ttatatgaaa atggctcatt ttattttgct     660

aaaagacatt tgatagagat gggttacttg cagggtggaa aaatggcata ctacgaaatg     720

cgagctgaac atagtgtgga tatagatgtg gatattgatt ggcctattgc agagcaaaga     780

gtattaagat atggctattt tggcaaagag aagcttaagg aaataaaact tttggtttgc     840

aatattgatg gatgtctcac caatggccac atttatgtat caggagacca aaaagaaata     900

atatcttatg atgtaaaaga tgctattggg ataagtttat taaagaaaag tggtattgag     960

gtgaggctaa tctcagaaag ggcctgttca aagcagacgc tgtcttcttt aaaactggat    1020

tgcaaaatgg aagtcagtgt atcagacaag ctagcagttg tagatgaatg gagaaaagaa    1080

atgggcctgt gctggaaaga agtggcatat cttggaaatg aagtgtctga tgaagagtgc    1140

ttgaagagag tgggcctaag tggcgctcct gctgatgcct gttctactgc ccagaaggct    1200

gttggataca tttgcaaatg taatggtggc cgtggtgcca tccgagaatt tgcagagcac    1260

atttgcctac taatggaaaa ggttaataat tcatgccaaa aatag                    1305
```

<210> SEQ ID NO 76
<211> LENGTH: 434
<212> TYPE: PRT
<213> ORGANISM: Homo sapiens
<220> FEATURE:
<221> NAME/KEY: MISC_FEATURE
<223> OTHER INFORMATION: hCMP-SAS

<400> SEQUENCE: 76

```
Met Asp Ser Val Glu Lys Gly Ala Ala Thr Ser Val Ser Asn Pro Arg
1               5                   10                  15

Gly Arg Pro Ser Arg Gly Arg Pro Pro Lys Leu Gln Arg Asn Ser Arg
            20                  25                  30

Gly Gly Gln Gly Arg Gly Val Glu Lys Pro Pro His Leu Ala Ala Leu
        35                  40                  45

Ile Leu Ala Arg Gly Gly Ser Lys Gly Ile Pro Leu Lys Asn Ile Lys
    50                  55                  60

His Leu Ala Gly Val Pro Leu Ile Gly Trp Val Leu Arg Ala Ala Leu
65                  70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
            100                 105                 110

Ser Glu Val Ser Lys Asp Ser Ser Thr Ser Leu Asp Ala Ile Ile Glu
        115                 120                 125

Phe Leu Asn Tyr His Asn Glu Val Asp Ile Val Gly Asn Ile Gln Ala
    130                 135                 140

Thr Ser Pro Cys Leu His Pro Thr Asp Leu Gln Lys Val Ala Glu Met
145                 150                 155                 160

Ile Arg Glu Glu Gly Tyr Asp Ser Val Phe Ser Val Val Arg Arg His
                165                 170                 175

Gln Phe Arg Trp Ser Glu Ile Gln Lys Gly Val Arg Glu Val Thr Glu
            180                 185                 190

Pro Leu Asn Leu Asn Pro Ala Lys Arg Pro Arg Arg Gln Asp Trp Asp
        195                 200                 205

Gly Glu Leu Tyr Glu Asn Gly Ser Phe Tyr Phe Ala Lys Arg His Leu
    210                 215                 220

Ile Glu Met Gly Tyr Leu Gln Gly Gly Lys Met Ala Tyr Tyr Glu Met
225                 230                 235                 240

Arg Ala Glu His Ser Val Asp Ile Asp Val Asp Ile Asp Trp Pro Ile
                245                 250                 255

Ala Glu Gln Arg Val Leu Arg Tyr Gly Tyr Phe Gly Lys Glu Lys Leu
            260                 265                 270

Lys Glu Ile Lys Leu Leu Val Cys Asn Ile Asp Gly Cys Leu Thr Asn
        275                 280                 285

Gly His Ile Tyr Val Ser Gly Asp Gln Lys Glu Ile Ile Ser Tyr Asp
    290                 295                 300

Val Lys Asp Ala Ile Gly Ile Ser Leu Leu Lys Lys Ser Gly Ile Glu
305                 310                 315                 320

Val Arg Leu Ile Ser Glu Arg Ala Cys Ser Lys Gln Thr Leu Ser Ser
                325                 330                 335

Leu Lys Leu Asp Cys Lys Met Glu Val Ser Val Ser Asp Lys Leu Ala
            340                 345                 350

Val Val Asp Glu Trp Arg Lys Glu Met Gly Leu Cys Trp Lys Glu Val
        355                 360                 365
```

```
Ala Tyr Leu Gly Asn Glu Val Ser Asp Glu Glu Cys Leu Lys Arg Val
    370                 375                 380

Gly Leu Ser Gly Ala Pro Ala Asp Ala Cys Ser Thr Ala Gln Lys Ala
385                 390                 395                 400

Val Gly Tyr Ile Cys Lys Cys Asn Gly Gly Arg Gly Ala Ile Arg Glu
                405                 410                 415

Phe Ala Glu His Ile Cys Leu Leu Met Glu Lys Val Asn Asn Ser Cys
            420                 425                 430

Gln Lys


<210> SEQ ID NO 77
<211> LENGTH: 1353
<212> TYPE: DNA
<213> ORGANISM: Homo sapiens
<220> FEATURE:
<221> NAME/KEY: misc_feature
<223> OTHER INFORMATION: hBeclin-1

<400> SEQUENCE: 77

atggaagggt ctaagacgtc caacaacagc accatgcagg tgagcttcgt gtgccagcgc     60

tgcagccagc ccctgaaact ggacacgagt ttcaagatcc tggaccgtgt caccatccag    120

gaactcacag ctccattact taccacagcc caggcgaaac caggagagac ccaggaggaa    180

gagactaact caggagagga gccatttatt gaaactcctc gccaggatgg tgtctctcgc    240

agattcatcc ccccagccag gatgatgtcc acagaaagtg ccaacagctt cactctgatt    300

ggggaggcat ctgatggcgg caccatggag aacctcagcc gaagactgaa ggtcactggg    360

gaccttttg acatcatgtc gggccagaca gatgtggatc acccactctg tgaggaatgc     420

acagatactc ttttagacca gctggacact cagctcaacg tcactgaaaa tgagtgtcag    480

aactacaaac gctgtttgga gatcttagag caaatgaatg aggatgacag tgaacagtta    540

cagatggagc taaaggagct ggcactagag gaggagaggc tgatccagga gctggaagac    600

gtggaaaaga accgcaagat agtggcagaa aatctcgaga aggtccaggc tgaggctgag    660

agactggatc aggaggaagc tcagtatcag agagaataca gtgaatttaa acgacagcag    720

ctggagctgg atgatgagct gaagagtgtt gaaaaccaga tgcgttatgc ccagacgcag    780

ctggataagc tgaagaaaac caacgtcttt aatgcaacct tccacatctg gcacagtgga    840

cagtttggca caatcaataa cttcaggctg ggtcgcctgc ccagtgttcc cgtggaatgg    900

aatgagatta atgctgcttg gggccagact gtgttgctgc tccatgctct ggccaataag    960

atgggtctga aatttcagag ataccgactt gttccttacg gaaaccattc atatctggag   1020

tctctgacag acaaatctaa ggagctgccg ttatactgtt ctgggggtt gcggtttttc    1080

tgggacaaca agtttgacca tgcaatggtg gctttcctgg actgtgtgca gcagttcaaa   1140

gaagaggttg agaaaggcga gacacgtttt tgtcttccct acaggatgga tgtggagaaa   1200

ggcaagattg aagacacagg aggcagtggc ggctcctatt ccatcaaaac ccagtttaac   1260

tctgaggagc agtggacaaa agctctcaag ttcatgctga cgaatcttaa gtggggtctt   1320

gcttgggtgt cctcacaatt ttataacaaa tga                                1353


<210> SEQ ID NO 78
<211> LENGTH: 450
<212> TYPE: PRT
<213> ORGANISM: Homo sapiens
<220> FEATURE:
<221> NAME/KEY: MISC_FEATURE
<223> OTHER INFORMATION: hBeclin-1
```

<400> SEQUENCE: 78

Met Glu Gly Ser Lys Thr Ser Asn Asn Ser Thr Met Gln Val Ser Phe
1 5 10 15

Val Cys Gln Arg Cys Ser Gln Pro Leu Lys Leu Asp Thr Ser Phe Lys
20 25 30

Ile Leu Asp Arg Val Thr Ile Gln Glu Leu Thr Ala Pro Leu Leu Thr
35 40 45

Thr Ala Gln Ala Lys Pro Gly Glu Thr Gln Glu Glu Glu Thr Asn Ser
50 55 60

Gly Glu Glu Pro Phe Ile Glu Thr Pro Arg Gln Asp Gly Val Ser Arg
65 70 75 80

Arg Phe Ile Pro Pro Ala Arg Met Met Ser Thr Glu Ser Ala Asn Ser
85 90 95

Phe Thr Leu Ile Gly Glu Ala Ser Asp Gly Gly Thr Met Glu Asn Leu
100 105 110

Ser Arg Arg Leu Lys Val Thr Gly Asp Leu Phe Asp Ile Met Ser Gly
115 120 125

Gln Thr Asp Val Asp His Pro Leu Cys Glu Glu Cys Thr Asp Thr Leu
130 135 140

Leu Asp Gln Leu Asp Thr Gln Leu Asn Val Thr Glu Asn Glu Cys Gln
145 150 155 160

Asn Tyr Lys Arg Cys Leu Glu Ile Leu Glu Gln Met Asn Glu Asp Asp
165 170 175

Ser Glu Gln Leu Gln Met Glu Leu Lys Glu Leu Ala Leu Glu Glu Glu
180 185 190

Arg Leu Ile Gln Glu Leu Glu Asp Val Glu Lys Asn Arg Lys Ile Val
195 200 205

Ala Glu Asn Leu Glu Lys Val Gln Ala Glu Ala Glu Arg Leu Asp Gln
210 215 220

Glu Glu Ala Gln Tyr Gln Arg Glu Tyr Ser Glu Phe Lys Arg Gln Gln
225 230 235 240

Leu Glu Leu Asp Asp Glu Leu Lys Ser Val Glu Asn Gln Met Arg Tyr
245 250 255

Ala Gln Thr Gln Leu Asp Lys Leu Lys Lys Thr Asn Val Phe Asn Ala
260 265 270

Thr Phe His Ile Trp His Ser Gly Gln Phe Gly Thr Ile Asn Asn Phe
275 280 285

Arg Leu Gly Arg Leu Pro Ser Val Pro Val Glu Trp Asn Glu Ile Asn
290 295 300

Ala Ala Trp Gly Gln Thr Val Leu Leu Leu His Ala Leu Ala Asn Lys
305 310 315 320

Met Gly Leu Lys Phe Gln Arg Tyr Arg Leu Val Pro Tyr Gly Asn His
325 330 335

Ser Tyr Leu Glu Ser Leu Thr Asp Lys Ser Lys Glu Leu Pro Leu Tyr
340 345 350

Cys Ser Gly Gly Leu Arg Phe Phe Trp Asp Asn Lys Phe Asp His Ala
355 360 365

Met Val Ala Phe Leu Asp Cys Val Gln Gln Phe Lys Glu Glu Val Glu
370 375 380

Lys Gly Glu Thr Arg Phe Cys Leu Pro Tyr Arg Met Asp Val Glu Lys
385 390 395 400

Gly Lys Ile Glu Asp Thr Gly Gly Ser Gly Gly Ser Tyr Ser Ile Lys

-continued

```
            405                 410                 415

Thr Gln Phe Asn Ser Glu Glu Gln Trp Thr Lys Ala Leu Lys Phe Met
        420                 425                 430

Leu Thr Asn Leu Lys Trp Gly Leu Ala Trp Val Ser Ser Gln Phe Tyr
    435                 440                 445

Asn Lys
    450
```

<210> SEQ ID NO 79
<211> LENGTH: 1077
<212> TYPE: DNA
<213> ORGANISM: Homo sapiens
<220> FEATURE:
<221> NAME/KEY: misc_feature
<223> OTHER INFORMATION: hERdj3

<400> SEQUENCE: 79

```
atggctccgc agaacctgag caccttttgc ctgttgctgc tatacctcat cggggcggtg     60

attgccggac gagatttcta taagatcttg ggggtgcctc gaagtgcctc tataaaggat    120

attaaaaagg cctataggaa actagccctg cagcttcatc ccgaccggaa ccctgatgat    180

ccacaagccc aggagaaatt ccaggatctg ggtgctgctt atgaggttct gtcagatagt    240

gagaaacgga aacagtacga tacttatggt gaagaaggat taaaagatgg tcatcagagc    300

tcccatggag acattttttc acacttcttt ggggattttg gtttcatgtt tggaggaacc    360

cctcgtcagc aagacagaaa tattccaaga ggaagtgata ttattgtaga tctagaagtc    420

actttggaag aagtatatgc aggaaatttt gtggaagtag ttagaaacaa acctgtggca    480

aggcaggctc ctggcaaacg gaagtgcaat tgtcggcaag agatgcggac cacccagctg    540

ggccctgggc gcttccaaat gacccaggag gtggtctgcg acgaatgccc taatgtcaaa    600

ctagtgaatg aagaacgaac gctggaagta gaaatagagc ctggggtgag agacggcatg    660

gagtacccct ttattggaga aggtgagcct cacgtggatg gggagcctgg agatttacgg    720

ttccgaatca aagttgtcaa gcacccaata tttgaaagga gaggagatga tttgtacaca    780

aatgtgacaa tctcattagt tgagtcactg gttggctttg agatggatat tactcacttg    840

gatggtcaca aggtacatat ttcccgggat aagatcacca ggccaggagc gaagctatgg    900

aagaaagggg aagggctccc caactttgac aacaacaata tcaagggctc tttgataatc    960

acttttgatg tggattttcc aaaagaacag ttaacagagg aagcgagaga aggtatcaaa   1020

cagctactga aacaagggtc agtgcagaag gtatacaatg gactgcaagg atattga      1077
```

<210> SEQ ID NO 80
<211> LENGTH: 358
<212> TYPE: PRT
<213> ORGANISM: Homo sapiens
<220> FEATURE:
<221> NAME/KEY: MISC_FEATURE
<223> OTHER INFORMATION: hERdj3

<400> SEQUENCE: 80

```
Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
```

-continued

```
    50                  55                  60

Glu Lys Phe Gln Asp Leu Gly Ala Ala Tyr Glu Val Leu Ser Asp Ser
65                  70                  75                  80

Glu Lys Arg Lys Gln Tyr Asp Thr Tyr Gly Glu Glu Gly Leu Lys Asp
                85                  90                  95

Gly His Gln Ser Ser His Gly Asp Ile Phe Ser His Phe Phe Gly Asp
            100                 105                 110

Phe Gly Phe Met Phe Gly Gly Thr Pro Arg Gln Gln Asp Arg Asn Ile
        115                 120                 125

Pro Arg Gly Ser Asp Ile Ile Val Asp Leu Glu Val Thr Leu Glu Glu
    130                 135                 140

Val Tyr Ala Gly Asn Phe Val Glu Val Val Arg Asn Lys Pro Val Ala
145                 150                 155                 160

Arg Gln Ala Pro Gly Lys Arg Lys Cys Asn Cys Arg Gln Glu Met Arg
                165                 170                 175

Thr Thr Gln Leu Gly Pro Gly Arg Phe Gln Met Thr Gln Glu Val Val
            180                 185                 190

Cys Asp Glu Cys Pro Asn Val Lys Leu Val Asn Glu Glu Arg Thr Leu
        195                 200                 205

Glu Val Glu Ile Glu Pro Gly Val Arg Asp Gly Met Glu Tyr Pro Phe
    210                 215                 220

Ile Gly Glu Gly Glu Pro His Val Asp Gly Glu Pro Gly Asp Leu Arg
225                 230                 235                 240

Phe Arg Ile Lys Val Val Lys His Pro Ile Phe Glu Arg Arg Gly Asp
                245                 250                 255

Asp Leu Tyr Thr Asn Val Thr Ile Ser Leu Val Glu Ser Leu Val Gly
            260                 265                 270

Phe Glu Met Asp Ile Thr His Leu Asp Gly His Lys Val His Ile Ser
        275                 280                 285

Arg Asp Lys Ile Thr Arg Pro Gly Ala Lys Leu Trp Lys Lys Gly Glu
    290                 295                 300

Gly Leu Pro Asn Phe Asp Asn Asn Asn Ile Lys Gly Ser Leu Ile Ile
305                 310                 315                 320

Thr Phe Asp Val Asp Phe Pro Lys Glu Gln Leu Thr Glu Glu Ala Arg
                325                 330                 335

Glu Gly Ile Lys Gln Leu Leu Lys Gln Gly Ser Val Gln Lys Val Tyr
            340                 345                 350

Asn Gly Leu Gln Gly Tyr
        355
```

<210> SEQ ID NO 81
<211> LENGTH: 1764
<212> TYPE: DNA
<213> ORGANISM: Cricetulus griseus
<220> FEATURE:
<221> NAME/KEY: misc_feature
<223> OTHER INFORMATION: CHO_AGE

<400> SEQUENCE: 81

```
atgaaaggaa ttctgtgggg agcgttttgt gggaaagcta atgagctgag gcagcgcctg      60

gagctgaaag aaaagggcag gcacgtggtg ctggaggcca cagagaatga ggtggagggc     120

aaaggcggca tgcttctgag ctcaggacag gcctgttgtg aggagaaggg cctggatgct     180

gaggacggtg gtggggacag caatgacctc agcagcgtca gcgagaccac agacagcaca     240

gatgtcaaag acagctcaga gacctctctg actctgcctc ctagagcctc accctgccct     300
```

gcaggctttt ggattcttga aactggagct agccaaagac agtttcaggc ctggtttact 360
gcggaggagg gtccgctgcc accttcgcct ccttttggcc ctgaactgac ttgcagatgg 420
agcagtctag aacagctaaa ggacatcttg gcgctcggag cacagcctca ctgggtccac 480
aagctccaag gcttctggtt tgttgaggtt atcttgtcag caaaaagatt acaggacatg 540
gagaaggagc gggcttcact gcaggcctgg aaggatcgtg tggcaaagga acttgacagc 600
gtggtcgctt tctggctgca gcactcccat gatcaggaac acgggggttt cttcacatgc 660
cttgcccgca atgggcaggt ctatgatgac cttaaatata tctggctgca ggggagacag 720
gtatggatgt attgtcgctt gtaccgcaat tttgagcgct tccgccgcgc tgagcttcta 780
gatgctgcaa aagcaggtgg tgagtttttg ctgcgttttg cacgggtggc accgcctgcc 840
aagaagtgtg cctttgtgtt gactcgggac ggccgtccag tgaaggtgca gcggaccatt 900
ttcagcgagt gtttctacac cattgctatg aatgagcttt ggagagtaac aaaggaatca 960
cgttaccaga atgaagctgt ggagatgatg gaccagattg tccactgggt acgggaagac 1020
ccagctgggc taggccggcc tcagctctca gggaccccgg atgcagagtc catggcagtg 1080
cccatgatgc tgatgaatct ggtggaccag ctttccgagg aagatgaggc actgacaaag 1140
aaatatgcag agctatggga ctggtgtgcc cagaggattc ttcagcatgt gcagagggat 1200
ggaaaagcta tactagagaa tgtatctcat gatggcaagg aactcactgg ttgccttgga 1260
agacatcaga acccaggcca cgcaatagag gctggctggt tcctgctcca gtatgcccgc 1320
aagaaaggtg acgccaaact tcgtgcacac atcatcgaca agtttctctt gttgcctttc 1380
cgctctggat gggacgctga gcatgggggc ctcttctact tccaggatgt tgatggtttc 1440
tgccccaccc agctggagtg ggacatgaag ctgtggtggc cacacaatga agccatgatt 1500
tccttcctaa tgggttacag ggacagtggt gacccagcct tgctacaaat cttcaatcag 1560
gtggctgagt acaccttcaa gcattttcat gatcccgaga acggcgaatg gttcggctat 1620
ctgaaccgag agggcaaggt ggccctcaac tttaagggag gcccatttaa aggctgcttc 1680
cacgtgccgc ggtgcctggc catgtgcgag aagatgttgg gagacctgct ccaccgtggg 1740
agcgcccctg ctggctcgaa ataa 1764

<210> SEQ ID NO 82
<211> LENGTH: 587
<212> TYPE: PRT
<213> ORGANISM: Cricetulus griseus
<220> FEATURE:
<221> NAME/KEY: MISC_FEATURE
<223> OTHER INFORMATION: CHO_AGE

<400> SEQUENCE: 82

Met Lys Gly Ile Leu Trp Gly Ala Phe Cys Gly Lys Ala Asn Glu Leu
1 5 10 15

Arg Gln Arg Leu Glu Leu Lys Glu Lys Gly Arg His Val Val Leu Glu
20 25 30

Ala Thr Glu Asn Glu Val Glu Gly Lys Gly Gly Met Leu Leu Ser Ser
35 40 45

Gly Gln Ala Cys Cys Glu Glu Lys Gly Leu Asp Ala Glu Asp Gly Gly
50 55 60

Gly Asp Ser Asn Asp Leu Ser Ser Val Ser Glu Thr Thr Asp Ser Thr
65 70 75 80

Asp Val Lys Asp Ser Ser Glu Thr Ser Leu Thr Leu Pro Pro Arg Ala
85 90 95

```
Ser Pro Cys Pro Ala Gly Phe Trp Ile Leu Glu Thr Gly Ala Ser Gln
            100                 105                 110

Arg Gln Phe Gln Ala Trp Phe Thr Ala Glu Glu Gly Pro Leu Pro Pro
        115                 120                 125

Ser Pro Pro Phe Gly Pro Glu Leu Thr Cys Arg Trp Ser Ser Leu Glu
    130                 135                 140

Gln Leu Lys Asp Ile Leu Ala Leu Gly Ala Gln Pro His Trp Val His
145                 150                 155                 160

Lys Leu Gln Gly Phe Trp Phe Val Glu Val Ile Leu Ser Ala Lys Arg
                165                 170                 175

Leu Gln Asp Met Glu Lys Glu Arg Ala Ser Leu Gln Ala Trp Lys Asp
            180                 185                 190

Arg Val Ala Lys Glu Leu Asp Ser Val Val Ala Phe Trp Leu Gln His
        195                 200                 205

Ser His Asp Gln Glu His Gly Gly Phe Phe Thr Cys Leu Ala Arg Asn
    210                 215                 220

Gly Gln Val Tyr Asp Asp Leu Lys Tyr Ile Trp Leu Gln Gly Arg Gln
225                 230                 235                 240

Val Trp Met Tyr Cys Arg Leu Tyr Arg Asn Phe Glu Arg Phe Arg Arg
                245                 250                 255

Ala Glu Leu Leu Asp Ala Ala Lys Ala Gly Gly Glu Phe Leu Leu Arg
            260                 265                 270

Phe Ala Arg Val Ala Pro Pro Ala Lys Lys Cys Ala Phe Val Leu Thr
        275                 280                 285

Arg Asp Gly Arg Pro Val Lys Val Gln Arg Thr Ile Phe Ser Glu Cys
    290                 295                 300

Phe Tyr Thr Ile Ala Met Asn Glu Leu Trp Arg Val Thr Lys Glu Ser
305                 310                 315                 320

Arg Tyr Gln Asn Glu Ala Val Glu Met Met Asp Gln Ile Val His Trp
                325                 330                 335

Val Arg Glu Asp Pro Ala Gly Leu Gly Arg Pro Gln Leu Ser Gly Thr
            340                 345                 350

Pro Asp Ala Glu Ser Met Ala Val Pro Met Met Leu Met Asn Leu Val
        355                 360                 365

Asp Gln Leu Ser Glu Glu Asp Glu Ala Leu Thr Lys Lys Tyr Ala Glu
    370                 375                 380

Leu Trp Asp Trp Cys Ala Gln Arg Ile Leu Gln His Val Gln Arg Asp
385                 390                 395                 400

Gly Lys Ala Ile Leu Glu Asn Val Ser His Asp Gly Lys Glu Leu Thr
                405                 410                 415

Gly Cys Leu Gly Arg His Gln Asn Pro Gly His Ala Ile Glu Ala Gly
            420                 425                 430

Trp Phe Leu Leu Gln Tyr Ala Arg Lys Lys Gly Asp Ala Lys Leu Arg
        435                 440                 445

Ala His Ile Ile Asp Lys Phe Leu Leu Leu Pro Phe Arg Ser Gly Trp
    450                 455                 460

Asp Ala Glu His Gly Gly Leu Phe Tyr Phe Gln Asp Val Asp Gly Phe
465                 470                 475                 480

Cys Pro Thr Gln Leu Glu Trp Asp Met Lys Leu Trp Trp Pro His Asn
                485                 490                 495

Glu Ala Met Ile Ser Phe Leu Met Gly Tyr Arg Asp Ser Gly Asp Pro
            500                 505                 510
```

```
Ala Leu Leu Gln Ile Phe Asn Gln Val Ala Glu Tyr Thr Phe Lys His
        515                 520                 525

Phe His Asp Pro Glu Asn Gly Glu Trp Phe Gly Tyr Leu Asn Arg Glu
    530                 535                 540

Gly Lys Val Ala Leu Asn Phe Lys Gly Gly Pro Phe Lys Gly Cys Phe
545                 550                 555                 560

His Val Pro Arg Cys Leu Ala Met Cys Glu Lys Met Leu Gly Asp Leu
                565                 570                 575

Leu His Arg Gly Ser Ala Pro Ala Gly Ser Lys
            580                 585


<210> SEQ ID NO 83
<211> LENGTH: 1818
<212> TYPE: DNA
<213> ORGANISM: Homo sapiens
<220> FEATURE:
<221> NAME/KEY: misc_feature
<223> OTHER INFORMATION: hWip1

<400> SEQUENCE: 83

atggcggggc tgtactcgct gggagtgagc gtcttctccg accagggcgg gaggaagtac     60

atggaggacg ttactcaaat cgttgtggag cccgaaccga cggctgaaga aaagccctcg    120

ccgcggcggt cgctgtctca gccgttgcct ccgcggccgt cgccggccgc ccttcccggc    180

ggcgaagtct cggggaaagg cccagcggtg gcagcccgag aggctcgcga ccctctcccg    240

gacgccgggg cctcgccggc acctagccgc tgctgccgcc gccgttcctc cgtggccttt    300

ttcgccgtgt gcgacgggca cggcgggcgg gaggcggcac agtttgcccg ggagcacttg    360

tggggtttca tcaagaagca gaagggtttc acctcgtccg agccggctaa ggtttgcgct    420

gccatccgca aaggctttct cgcttgtcac cttgccatgt ggaagaaact ggcggaatgg    480

ccaaagacta tgacgggtct tcctagcaca tcagggacaa ctgccagtgt ggtcatcatt    540

cggggcatga agatgtatgt agctcacgta ggtgactcag gggtggttct tggaattcag    600

gatgacccga aggatgactt tgtcagagct gtggaggtga cacaggacca taagccagaa    660

cttcccaagg aaagagaacg aatcgaagga cttggtggga gtgtaatgaa caagtctggg    720

gtgaatcgtg tagtttggaa acgacctcga ctcactcaca atggacctgt tagaaggagc    780

acagttattg accagattcc ttttctggca gtagcaagag cacttggtga tttgtggagc    840

tatgatttct tcagtggtga atttgtggtg tcacctgaac cagacacaag tgtccacact    900

cttgaccctc agaagcacaa gtatattata ttggggagtg atggactttg gaatatgatt    960

ccaccacaag atgccatctc aatgtgccag gaccaagagg agaaaaaata cctgatgggt   1020

gagcatggac aatcttgtgc caaaatgctt gtgaatcgag cattgggccg ctggaggcag   1080

cgtatgctcc gagcagataa cactagtgcc atagtaatct gcatctctcc agaagtggac   1140

aatcagggaa actttaccaa tgaagatgag ttatacctga acctgactga cagcccttcc   1200

tataatagtc aagaaacctg tgtgatgact ccttccccat gttctacacc accagtcaag   1260

tcactggagg aggatccatg gccaagggtg aattctaagg accatatacc tgccctggtt   1320

cgtagcaatg ccttctcaga gaatttttta gaggtttcag ctgagatagc tcgagagaat   1380

gtccaaggtg tagtcatacc ctcaaaagat ccagaaccac ttgaagaaaa ttgcgctaaa   1440

gccctgactt taaggataca tgattctttg aataatagcc ttccaattgg ccttgtgcct   1500

actaattcaa caaacactgt catggaccaa aaaaatttga agatgtcaac tcctggccaa   1560

atgaaagccc aagaaattga aagaacccct ccaacaaact ttaaaaggac attagaagag   1620
```

```
tccaattctg gccccctgat gaagaagcat agacgaaatg gcttaagtcg aagtagtggt   1680

gctcagcctg caagtctccc cacaacctca cagcgaaaga actctgttaa actcaccatg   1740

cgacgcagac ttaggggcca gaagaaaatt ggaaatcctt tacttcatca acacaggaaa   1800

actgtttgtg tttgctga                                                 1818


<210> SEQ ID NO 84
<211> LENGTH: 605
<212> TYPE: PRT
<213> ORGANISM: Homo sapiens
<220> FEATURE:
<221> NAME/KEY: MISC_FEATURE
<223> OTHER INFORMATION: hWip1

<400> SEQUENCE: 84

Met Ala Gly Leu Tyr Ser Leu Gly Val Ser Val Phe Ser Asp Gln Gly
1               5                   10                  15

Gly Arg Lys Tyr Met Glu Asp Val Thr Gln Ile Val Val Glu Pro Glu
            20                  25                  30

Pro Thr Ala Glu Glu Lys Pro Ser Pro Arg Arg Ser Leu Ser Gln Pro
        35                  40                  45

Leu Pro Pro Arg Pro Ser Pro Ala Ala Leu Pro Gly Gly Glu Val Ser
    50                  55                  60

Gly Lys Gly Pro Ala Val Ala Ala Arg Glu Ala Arg Asp Pro Leu Pro
65                  70                  75                  80

Asp Ala Gly Ala Ser Pro Ala Pro Ser Arg Cys Cys Arg Arg Arg Ser
                85                  90                  95

Ser Val Ala Phe Phe Ala Val Cys Asp Gly His Gly Gly Arg Glu Ala
            100                 105                 110

Ala Gln Phe Ala Arg Glu His Leu Trp Gly Phe Ile Lys Lys Gln Lys
        115                 120                 125

Gly Phe Thr Ser Ser Glu Pro Ala Lys Val Cys Ala Ala Ile Arg Lys
    130                 135                 140

Gly Phe Leu Ala Cys His Leu Ala Met Trp Lys Lys Leu Ala Glu Trp
145                 150                 155                 160

Pro Lys Thr Met Thr Gly Leu Pro Ser Thr Ser Gly Thr Thr Ala Ser
                165                 170                 175

Val Val Ile Ile Arg Gly Met Lys Met Tyr Val Ala His Val Gly Asp
            180                 185                 190

Ser Gly Val Val Leu Gly Ile Gln Asp Asp Pro Lys Asp Asp Phe Val
        195                 200                 205

Arg Ala Val Glu Val Thr Gln Asp His Lys Pro Glu Leu Pro Lys Glu
    210                 215                 220

Arg Glu Arg Ile Glu Gly Leu Gly Gly Ser Val Met Asn Lys Ser Gly
225                 230                 235                 240

Val Asn Arg Val Val Trp Lys Arg Pro Arg Leu Thr His Asn Gly Pro
                245                 250                 255

Val Arg Arg Ser Thr Val Ile Asp Gln Ile Pro Phe Leu Ala Val Ala
            260                 265                 270

Arg Ala Leu Gly Asp Leu Trp Ser Tyr Asp Phe Phe Ser Gly Glu Phe
        275                 280                 285

Val Val Ser Pro Glu Pro Asp Thr Ser Val His Thr Leu Asp Pro Gln
    290                 295                 300

Lys His Lys Tyr Ile Ile Leu Gly Ser Asp Gly Leu Trp Asn Met Ile
305                 310                 315                 320
```

-continued

```
Pro Pro Gln Asp Ala Ile Ser Met Cys Gln Asp Gln Glu Glu Lys Lys
                325                 330                 335

Tyr Leu Met Gly Glu His Gly Gln Ser Cys Ala Lys Met Leu Val Asn
            340                 345                 350

Arg Ala Leu Gly Arg Trp Arg Gln Arg Met Leu Arg Ala Asp Asn Thr
        355                 360                 365

Ser Ala Ile Val Ile Cys Ile Ser Pro Glu Val Asp Asn Gln Gly Asn
    370                 375                 380

Phe Thr Asn Glu Asp Glu Leu Tyr Leu Asn Leu Thr Asp Ser Pro Ser
385                 390                 395                 400

Tyr Asn Ser Gln Glu Thr Cys Val Met Thr Pro Ser Pro Cys Ser Thr
                405                 410                 415

Pro Pro Val Lys Ser Leu Glu Glu Asp Pro Trp Pro Arg Val Asn Ser
            420                 425                 430

Lys Asp His Ile Pro Ala Leu Val Arg Ser Asn Ala Phe Ser Glu Asn
        435                 440                 445

Phe Leu Glu Val Ser Ala Glu Ile Ala Arg Glu Asn Val Gln Gly Val
    450                 455                 460

Val Ile Pro Ser Lys Asp Pro Glu Pro Leu Glu Glu Asn Cys Ala Lys
465                 470                 475                 480

Ala Leu Thr Leu Arg Ile His Asp Ser Leu Asn Asn Ser Leu Pro Ile
                485                 490                 495

Gly Leu Val Pro Thr Asn Ser Thr Asn Thr Val Met Asp Gln Lys Asn
            500                 505                 510

Leu Lys Met Ser Thr Pro Gly Gln Met Lys Ala Gln Glu Ile Glu Arg
        515                 520                 525

Thr Pro Pro Thr Asn Phe Lys Arg Thr Leu Glu Glu Ser Asn Ser Gly
    530                 535                 540

Pro Leu Met Lys Lys His Arg Arg Asn Gly Leu Ser Arg Ser Ser Gly
545                 550                 555                 560

Ala Gln Pro Ala Ser Leu Pro Thr Thr Ser Gln Arg Lys Asn Ser Val
                565                 570                 575

Lys Leu Thr Met Arg Arg Arg Leu Arg Gly Gln Lys Lys Ile Gly Asn
            580                 585                 590

Pro Leu Leu His Gln His Arg Lys Thr Val Cys Val Cys
        595                 600                 605
```

<210> SEQ ID NO 85
<211> LENGTH: 741
<212> TYPE: DNA
<213> ORGANISM: Homo sapiens
<220> FEATURE:
<221> NAME/KEY: misc_feature
<223> OTHER INFORMATION: hRTP4

<400> SEQUENCE: 85

```
atggttgtag atttctggac ttgggagcag acatttcaag aactaatcca agaggcaaaa     60

ccccgggcca catggacgct gaagttggat ggcaaccttc agctagactg cctggctcaa    120

gggtggaagc aataccaaca gagagcattt ggctggttcc ggtgttcctc ctgccagcga    180

agttgggctt ccgcccaagt gcagattctg tgccacacgt actgggagca ctggacatcc    240

cagggtcagg tgcgtatgag gctctttggc caaaggtgcc agaagtgctc ctggtcccaa    300

tatgagatgc ctgagttctc ctcggatagc accatgagga ttctgagcaa cctggtgcag    360

catatactga agaaatacta tggaaatggc acgaggaagt ctccagaaat gccagtaatc    420
```

```
ctggaagtgt ccctggaagg atcccatgac acagccaatt gtgaggcatg cactttgggc    480

atctgtggac agggcttaaa aagctgcatg acaaagccgt ccaaatccct actcccccac    540

ctaaagactg ggaattcctc acctggaatt ggtgctgtgt acctcgcaaa ccaagccaag    600

aaccagtcag ctgaggcaaa agaggctaag ggagtgggt atgagaaatt agggcccagt    660

cgagacccag atccactgaa catctgtgtc tttattttgc tgcttgtatt tattgtagtc    720

aaatgcttta catcagaatg a                                              741
```

<210> SEQ ID NO 86
<211> LENGTH: 246
<212> TYPE: PRT
<213> ORGANISM: Homo sapiens
<220> FEATURE:
<221> NAME/KEY: MISC_FEATURE
<223> OTHER INFORMATION: hRTP4

<400> SEQUENCE: 86

```
Met Val Val Asp Phe Trp Thr Trp Glu Gln Thr Phe Gln Glu Leu Ile
1               5                   10                  15

Gln Glu Ala Lys Pro Arg Ala Thr Trp Thr Leu Lys Leu Asp Gly Asn
            20                  25                  30

Leu Gln Leu Asp Cys Leu Ala Gln Gly Trp Lys Gln Tyr Gln Gln Arg
        35                  40                  45

Ala Phe Gly Trp Phe Arg Cys Ser Ser Cys Gln Arg Ser Trp Ala Ser
    50                  55                  60

Ala Gln Val Gln Ile Leu Cys His Thr Tyr Trp Glu His Trp Thr Ser
65                  70                  75                  80

Gln Gly Gln Val Arg Met Arg Leu Phe Gly Gln Arg Cys Gln Lys Cys
                85                  90                  95

Ser Trp Ser Gln Tyr Glu Met Pro Glu Phe Ser Ser Asp Ser Thr Met
            100                 105                 110

Arg Ile Leu Ser Asn Leu Val Gln His Ile Leu Lys Lys Tyr Tyr Gly
        115                 120                 125

Asn Gly Thr Arg Lys Ser Pro Glu Met Pro Val Ile Leu Glu Val Ser
    130                 135                 140

Leu Glu Gly Ser His Asp Thr Ala Asn Cys Glu Ala Cys Thr Leu Gly
145                 150                 155                 160

Ile Cys Gly Gln Gly Leu Lys Ser Cys Met Thr Lys Pro Ser Lys Ser
                165                 170                 175

Leu Leu Pro His Leu Lys Thr Gly Asn Ser Ser Pro Gly Ile Gly Ala
            180                 185                 190

Val Tyr Leu Ala Asn Gln Ala Lys Asn Gln Ser Ala Glu Ala Lys Glu
        195                 200                 205

Ala Lys Gly Ser Gly Tyr Glu Lys Leu Gly Pro Ser Arg Asp Pro Asp
    210                 215                 220

Pro Leu Asn Ile Cys Val Phe Ile Leu Leu Leu Val Phe Ile Val Val
225                 230                 235                 240

Lys Cys Phe Thr Ser Glu
                245
```

<210> SEQ ID NO 87
<211> LENGTH: 765
<212> TYPE: DNA
<213> ORGANISM: Homo sapiens
<220> FEATURE:
<221> NAME/KEY: misc_feature
<223> OTHER INFORMATION: hREEP2

<400> SEQUENCE: 87

```
atggtgtcct ggatcatctc tcgcctggtg gtgctcatct ttggcaccct gtacccagcc     60
tattcttcct acaaggccgt gaagacaaaa aacgtgaagg aatatgtgaa atggatgatg    120
tactggatcg tctttgcctt cttcaccacg gccgagacgc tcacggatat agtgctctcc    180
tggttcccct tctactttga actgaagatc gccttcgtga tatggctgct gtccccttac    240
accaagggct ccagcgtgct ctaccgcaag ttcgtgcacc caacgctgtc caacaaggag    300
aaggagatcg acgagtacat cacgcaggcc cgagacaaga gctatgagac catgatgagg    360
gtgggcaaga ggggcctgaa ccttgccgcc aatgctgcag tcacagctgc cgccaagggc    420
cagggggtgc tgtcagagaa gctccgcagc ttcagcatgc aggacctgac cctgatccgg    480
gacgaggacg cactgcccct gcagaggcct gacggccgcc tccgacccag ccctggcagc    540
ctcctggaca ccatcgagga cttaggagat gaccctgccc tgagtctaag gtccagcaca    600
aacccggcag attcccggac agaggcttct gaggatgaca tgggagacaa agctcccaag    660
agggccaaac ccatcaaaaa agcgcccaaa gctgagccac tggcttccaa gacactgaag    720
acccggccca agaagaagac ctctggcggg ggcgactcag cttga                    765
```

<210> SEQ ID NO 88
<211> LENGTH: 254
<212> TYPE: PRT
<213> ORGANISM: Homo sapiens
<220> FEATURE:
<221> NAME/KEY: MISC_FEATURE
<223> OTHER INFORMATION: hREEP2

<400> SEQUENCE: 88

```
Met Val Ser Trp Ile Ile Ser Arg Leu Val Val Leu Ile Phe Gly Thr
1               5                   10                  15

Leu Tyr Pro Ala Tyr Ser Ser Tyr Lys Ala Val Lys Thr Lys Asn Val
            20                  25                  30

Lys Glu Tyr Val Lys Trp Met Met Tyr Trp Ile Val Phe Ala Phe Phe
        35                  40                  45

Thr Thr Ala Glu Thr Leu Thr Asp Ile Val Leu Ser Trp Phe Pro Phe
    50                  55                  60

Tyr Phe Glu Leu Lys Ile Ala Phe Val Ile Trp Leu Leu Ser Pro Tyr
65                  70                  75                  80

Thr Lys Gly Ser Ser Val Leu Tyr Arg Lys Phe Val His Pro Thr Leu
                85                  90                  95

Ser Asn Lys Glu Lys Glu Ile Asp Glu Tyr Ile Thr Gln Ala Arg Asp
            100                 105                 110

Lys Ser Tyr Glu Thr Met Met Arg Val Gly Lys Arg Gly Leu Asn Leu
        115                 120                 125

Ala Ala Asn Ala Ala Val Thr Ala Ala Ala Lys Gly Gln Gly Val Leu
    130                 135                 140

Ser Glu Lys Leu Arg Ser Phe Ser Met Gln Asp Leu Thr Leu Ile Arg
145                 150                 155                 160

Asp Glu Asp Ala Leu Pro Leu Gln Arg Pro Asp Gly Arg Leu Arg Pro
                165                 170                 175

Ser Pro Gly Ser Leu Leu Asp Thr Ile Glu Asp Leu Gly Asp Asp Pro
            180                 185                 190

Ala Leu Ser Leu Arg Ser Ser Thr Asn Pro Ala Asp Ser Arg Thr Glu
        195                 200                 205
```

```
Ala Ser Glu Asp Asp Met Gly Asp Lys Ala Pro Lys Arg Ala Lys Pro
    210                 215                 220

Ile Lys Lys Ala Pro Lys Ala Glu Pro Leu Ala Ser Lys Thr Leu Lys
225                 230                 235                 240

Thr Arg Pro Lys Lys Lys Thr Ser Gly Gly Gly Asp Ser Ala
                245                 250


<210> SEQ ID NO 89
<211> LENGTH: 783
<212> TYPE: DNA
<213> ORGANISM: Homo sapiens
<220> FEATURE:
<221> NAME/KEY: misc_feature
<223> OTHER INFORMATION: hDPM1

<400> SEQUENCE: 89

atggcctcct tggaagtcag tcgtagtcct cgcaggtctc ggcgggagct ggaagtgcgc      60

agtccacgac agaacaaata ttcggtgctt ttacctacct acaacgagcg cgagaacctg     120

ccgctcatcg tgtggctgct ggtgaaaagc ttctccgaga gtggaatcaa ctatgaaatt     180

ataatcatag atgatggaag cccagatgga acaagggatg ttgctgaaca gttggagaag     240

atctatgggt cagacagaat tcttctaaga ccacgagaga aaaagttggg actaggaact     300

gcatatattc atggaatgaa acatgccaca ggaaactaca tcattattat ggatgctgat     360

ctctcacacc atccaaaatt tattcctgaa tttattagga agcaaaagga gggtaatttt     420

gatattgtct ctggaactcg ctacaaagga aatggaggtg tatatggctg ggatttgaaa     480

agaaaaataa tcagccgtgg ggccaatttt ttaactcaga tcttgctgag accaggagca     540

tctgatttaa caggaagttt cagattatac cgaaaagaag ttctagagaa attaatagaa     600

aaatgtgttt ctaaaggcta cgtcttccag atggagatga ttgttcgggc aagacagttg     660

aattatacta ttggcgaggt tccaatatca tttgtggatc gtgtttatgg tgaatccaag     720

ttgggaggaa atgaaatagt atctttcttg aaaggattat tgactctttt tgctactaca     780

taa                                                                   783


<210> SEQ ID NO 90
<211> LENGTH: 260
<212> TYPE: PRT
<213> ORGANISM: Homo sapiens
<220> FEATURE:
<221> NAME/KEY: MISC_FEATURE
<223> OTHER INFORMATION: hDPM1

<400> SEQUENCE: 90

Met Ala Ser Leu Glu Val Ser Arg Ser Pro Arg Arg Ser Arg Arg Glu
1               5                   10                  15

Leu Glu Val Arg Ser Pro Arg Gln Asn Lys Tyr Ser Val Leu Leu Pro
            20                  25                  30

Thr Tyr Asn Glu Arg Glu Asn Leu Pro Leu Ile Val Trp Leu Leu Val
        35                  40                  45

Lys Ser Phe Ser Glu Ser Gly Ile Asn Tyr Glu Ile Ile Ile Ile Asp
    50                  55                  60

Asp Gly Ser Pro Asp Gly Thr Arg Asp Val Ala Glu Gln Leu Glu Lys
65                  70                  75                  80

Ile Tyr Gly Ser Asp Arg Ile Leu Leu Arg Pro Arg Glu Lys Lys Leu
                85                  90                  95

Gly Leu Gly Thr Ala Tyr Ile His Gly Met Lys His Ala Thr Gly Asn
```

```
            100                 105                 110

Tyr Ile Ile Ile Met Asp Ala Asp Leu Ser His His Pro Lys Phe Ile
        115                 120                 125

Pro Glu Phe Ile Arg Lys Gln Lys Glu Gly Asn Phe Asp Ile Val Ser
    130                 135                 140

Gly Thr Arg Tyr Lys Gly Asn Gly Gly Val Tyr Gly Trp Asp Leu Lys
145                 150                 155                 160

Arg Lys Ile Ile Ser Arg Gly Ala Asn Phe Leu Thr Gln Ile Leu Leu
                165                 170                 175

Arg Pro Gly Ala Ser Asp Leu Thr Gly Ser Phe Arg Leu Tyr Arg Lys
            180                 185                 190

Glu Val Leu Glu Lys Leu Ile Glu Lys Cys Val Ser Lys Gly Tyr Val
        195                 200                 205

Phe Gln Met Glu Met Ile Val Arg Ala Arg Gln Leu Asn Tyr Thr Ile
    210                 215                 220

Gly Glu Val Pro Ile Ser Phe Val Asp Arg Val Tyr Gly Glu Ser Lys
225                 230                 235                 240

Leu Gly Gly Asn Glu Ile Val Ser Phe Leu Lys Gly Leu Leu Thr Leu
                245                 250                 255

Phe Ala Thr Thr
            260


<210> SEQ ID NO 91
<211> LENGTH: 2109
<212> TYPE: DNA
<213> ORGANISM: Homo sapiens
<220> FEATURE:
<221> NAME/KEY: misc_feature
<223> OTHER INFORMATION: hDRiP78

<400> SEQUENCE: 91

atggcccaga agcaccccgg agaaagaggg ttgtatggag cccaccacag tggtggtgcc      60

tccctcagga ctttaggacc ctccgtggac cctgaaatac cttcattctc aggactcagg     120

gactcagcag ggactgctcc taatggtacc cgctgcctca cagagcactc tggtcctaag     180

cacacacagc acccaaaccc agcccattgg ttggacccaa gccatggccc cccagggggt     240

ccaggaccac ctagagatgc agaggaccct gatcagagtg agacgtcttc agaagaagaa     300

tcaggagtgg accaggaact ctcaaaagaa aacgagactg ggaaccagaa ggatgggaac     360

tcttttcttt ccattccatc tgcttgcaac tgccagggaa cacctggaat tccagaaggg     420

ccttactctg agggaggaaa tggttcttct agcaactttt gccaccactg tacctctcca     480

gctttggggg aagatgagtt ggaagaggaa tatgatgatg aagaatctct caagttcccc     540

agtgattttt cacgtgtgtc cagcggaaag aaacccccat cccggagaca gcggcaccgc     600

tttccaacga aggaggatac tcgggagggt ggacgtaggg atcccaggtc ccctggtcga     660

catcggctgg gtcggaaacg aagtcaggca gataagcgca aaggcctggg attgtgggga     720

gccgaggaac tatgtcaact tggacaggca ggcttttggt ggctgattga actgctggta     780

ttggtgggag agtacgtaga aacttgtggc catctcatct atgcctgcag gcaactgaaa     840

agcagtgatt tggacctttt tcgagtttgg atgggagtgt ggacagggcg gttagggggc     900

tgggcccagg tcatgtttca gtttctaagc caggggtttt actgtggagt aggactgttt     960

actcgttttc ttaagctgct gggtgctttg ctgctcctgg ctctggccct ctttttgggc    1020

tttctacagt tgggatggcg gtttctggtg ggactaggtg accggttagg ctggagggat    1080
```

```
aaggctacct ggctcttctc ttggctggat tctccagcct tgcagcgttg cttgactctg   1140

ctgagagata gcaggccatg gcagcggctg gtaagaatag ttcagtgggg ctggctggag   1200

ttgccttggg tcaagcagaa tattaatagg caggggaatg cacctgtagc tagtgggcgc   1260

tactgccagc ctgaagagga agtggctcga ctcttgacca tggctggggt tcctgaggat   1320

gagctaaacc ctttccatgt actgggggtt gaggccacag catcagatgt tgaactgaag   1380

aaggcctata gacagctggc agtgatggtt catcctgaca aaaatcatca tccccgggct   1440

gaggaggcct tcaaggtttt gcgagcagct tgggacattg tcagcaatgc tgaaaagcga   1500

aaggagtatg agatgaaacg aatggcagag aatgagctga gccggtcagt aaatgagttt   1560

ctgtccaagc tgcaagatga cctcaaggag gcaatgaata ctatgatgtg tagccgatgc   1620

caaggaaagc ataggaggtt tgaaatggac cgggaaccta agagtgccag atactgtgct   1680

gagtgtaata ggctgcatcc tgctgaggaa ggagactttt gggcagagtc aagcatgttg   1740

ggcctcaaga tcacctactt tgcactgatg gatggaaagg tgtatgacat cacagagtgg   1800

gctggatgcc agcgtgtagg tatctcccca gatacccaca gagtccccta tcacatctca   1860

tttggttctc ggattccagg caccagaggg cggcagagag ccaccccaga tgcccctcct   1920

gctgatcttc aggatttctt gagtcggatc tttcaagtac ccccagggca gatgcccaat   1980

gggaacttct ttgcagctcc tcagcctgcc cctggagccg ctgcagcctc taagcccaac   2040

agcacagtac ccaagggaga agccaaacct aagcggcgga agaaagtgag gaggcccttc   2100

caacgttga                                                           2109
```

<210> SEQ ID NO 92
<211> LENGTH: 702
<212> TYPE: PRT
<213> ORGANISM: Homo sapiens
<220> FEATURE:
<221> NAME/KEY: MISC_FEATURE
<223> OTHER INFORMATION: hDRiP78

<400> SEQUENCE: 92

```
Met Ala Gln Lys His Pro Gly Glu Arg Gly Leu Tyr Gly Ala His His
1               5                   10                  15

Ser Gly Gly Ala Ser Leu Arg Thr Leu Gly Pro Ser Val Asp Pro Glu
            20                  25                  30

Ile Pro Ser Phe Ser Gly Leu Arg Asp Ser Ala Gly Thr Ala Pro Asn
        35                  40                  45

Gly Thr Arg Cys Leu Thr Glu His Ser Gly Pro Lys His Thr Gln His
    50                  55                  60

Pro Asn Pro Ala His Trp Leu Asp Pro Ser His Gly Pro Pro Gly Gly
65                  70                  75                  80

Pro Gly Pro Pro Arg Asp Ala Glu Asp Pro Asp Gln Ser Glu Thr Ser
                85                  90                  95

Ser Glu Glu Glu Ser Gly Val Asp Gln Glu Leu Ser Lys Glu Asn Glu
            100                 105                 110

Thr Gly Asn Gln Lys Asp Gly Asn Ser Phe Leu Ser Ile Pro Ser Ala
        115                 120                 125

Cys Asn Cys Gln Gly Thr Pro Gly Ile Pro Glu Gly Pro Tyr Ser Glu
    130                 135                 140

Gly Gly Asn Gly Ser Ser Ser Asn Phe Cys His His Cys Thr Ser Pro
145                 150                 155                 160

Ala Leu Gly Glu Asp Glu Leu Glu Glu Glu Tyr Asp Asp Glu Glu Ser
                165                 170                 175
```

```
Leu Lys Phe Pro Ser Asp Phe Ser Arg Val Ser Ser Gly Lys Lys Pro
            180                 185                 190

Pro Ser Arg Arg Gln Arg His Arg Phe Pro Thr Lys Glu Asp Thr Arg
        195                 200                 205

Glu Gly Gly Arg Arg Asp Pro Arg Ser Pro Gly Arg His Arg Leu Gly
    210                 215                 220

Arg Lys Arg Ser Gln Ala Asp Lys Arg Lys Gly Leu Gly Leu Trp Gly
225                 230                 235                 240

Ala Glu Glu Leu Cys Gln Leu Gly Gln Ala Gly Phe Trp Trp Leu Ile
                245                 250                 255

Glu Leu Leu Val Leu Val Gly Glu Tyr Val Glu Thr Cys Gly His Leu
            260                 265                 270

Ile Tyr Ala Cys Arg Gln Leu Lys Ser Ser Asp Leu Asp Leu Phe Arg
        275                 280                 285

Val Trp Met Gly Val Trp Thr Gly Arg Leu Gly Gly Trp Ala Gln Val
    290                 295                 300

Met Phe Gln Phe Leu Ser Gln Gly Phe Tyr Cys Gly Val Gly Leu Phe
305                 310                 315                 320

Thr Arg Phe Leu Lys Leu Leu Gly Ala Leu Leu Leu Leu Ala Leu Ala
                325                 330                 335

Leu Phe Leu Gly Phe Leu Gln Leu Gly Trp Arg Phe Leu Val Gly Leu
            340                 345                 350

Gly Asp Arg Leu Gly Trp Arg Asp Lys Ala Thr Trp Leu Phe Ser Trp
        355                 360                 365

Leu Asp Ser Pro Ala Leu Gln Arg Cys Leu Thr Leu Leu Arg Asp Ser
    370                 375                 380

Arg Pro Trp Gln Arg Leu Val Arg Ile Val Gln Trp Gly Trp Leu Glu
385                 390                 395                 400

Leu Pro Trp Val Lys Gln Asn Ile Asn Arg Gln Gly Asn Ala Pro Val
                405                 410                 415

Ala Ser Gly Arg Tyr Cys Gln Pro Glu Glu Glu Val Ala Arg Leu Leu
            420                 425                 430

Thr Met Ala Gly Val Pro Glu Asp Glu Leu Asn Pro Phe His Val Leu
        435                 440                 445

Gly Val Glu Ala Thr Ala Ser Asp Val Glu Leu Lys Lys Ala Tyr Arg
    450                 455                 460

Gln Leu Ala Val Met Val His Pro Asp Lys Asn His His Pro Arg Ala
465                 470                 475                 480

Glu Glu Ala Phe Lys Val Leu Arg Ala Ala Trp Asp Ile Val Ser Asn
                485                 490                 495

Ala Glu Lys Arg Lys Glu Tyr Glu Met Lys Arg Met Ala Glu Asn Glu
            500                 505                 510

Leu Ser Arg Ser Val Asn Glu Phe Leu Ser Lys Leu Gln Asp Asp Leu
        515                 520                 525

Lys Glu Ala Met Asn Thr Met Met Cys Ser Arg Cys Gln Gly Lys His
    530                 535                 540

Arg Arg Phe Glu Met Asp Arg Glu Pro Lys Ser Ala Arg Tyr Cys Ala
545                 550                 555                 560

Glu Cys Asn Arg Leu His Pro Ala Glu Glu Gly Asp Phe Trp Ala Glu
                565                 570                 575

Ser Ser Met Leu Gly Leu Lys Ile Thr Tyr Phe Ala Leu Met Asp Gly
            580                 585                 590
```

-continued

```
Lys Val Tyr Asp Ile Thr Glu Trp Ala Gly Cys Gln Arg Val Gly Ile
        595                 600                 605

Ser Pro Asp Thr His Arg Val Pro Tyr His Ile Ser Phe Gly Ser Arg
    610                 615                 620

Ile Pro Gly Thr Arg Gly Arg Gln Arg Ala Thr Pro Asp Ala Pro Pro
625                 630                 635                 640

Ala Asp Leu Gln Asp Phe Leu Ser Arg Ile Phe Gln Val Pro Pro Gly
                645                 650                 655

Gln Met Pro Asn Gly Asn Phe Phe Ala Ala Pro Gln Pro Ala Pro Gly
            660                 665                 670

Ala Ala Ala Ala Ser Lys Pro Asn Ser Thr Val Pro Lys Gly Glu Ala
        675                 680                 685

Lys Pro Lys Arg Arg Lys Lys Val Arg Arg Pro Phe Gln Arg
    690                 695                 700


<210> SEQ ID NO 93
<211> LENGTH: 1020
<212> TYPE: DNA
<213> ORGANISM: Cricetulus griseus
<220> FEATURE:
<221> NAME/KEY: misc_feature
<223> OTHER INFORMATION: Rad51

<400> SEQUENCE: 93

atggctatgc agatgcagct tgaagcaaat gcagatactt cagtggaaga agaaagcttt      60

ggtccacaac ctatttcacg gttagagcaa tgtggcataa gtgccaatga tgtgaagaaa     120

ttagaagaag ctggtttcca tacggtggag gctgttgctt atgcaccaaa gaaggaactc     180

ataaatatta agggaattag tgaagccaaa gcagacaaaa ttctggctga ggccgctaaa     240

ttagttccaa tgggtttcac cactgcaact gaatttcacc aaaggcgttc agaaatcata     300

cagattacta ctggctccaa agagcttgac aaactgcttc aaggtggaat tgagactgga     360

tctatcacag agatgtttgg agaattccga actgggaaga cacagatctg tcatacattg     420

gctgtaacat gccagcttcc cattgatcgt ggtggaggtg aaggaaaggc catgtacatt     480

gacaccgagg gtacgtttag gccagaacgg ctgctagcag tggctgagag gtatggtctg     540

tctggcagcg atgtcctaga taatgtagca tatgctcgag ggttcaacac agaccaccaa     600

acccagctcc tttatcaagc atcagccatg atggtagaat ccagatatgc actgcttatt     660

gtagacagtg ctactgccct ctacagaaca gactactcag gtcgaggaga gctttcagcc     720

aggcaaatgc atttggccag atttctgagg atgctgctgc gacttgctga tgagtttggt     780

gtagcagtgg taatcaccaa ccaggtagta gcccaagtgg atggagcagc catgttcact     840

gcagatccca aaaaacccat tggaggaaac atcattgccc atgcatcaac aaccaggctg     900

tacctgagga aaggaagagg ggagaccaga atctgcaaag tctatgactc tccctgtctc     960

cctgaagctg aagccatgtt tgccattaat gcagatggag taggagatgc caaggactga    1020


<210> SEQ ID NO 94
<211> LENGTH: 1053
<212> TYPE: DNA
<213> ORGANISM: Cricetulus griseus
<220> FEATURE:
<221> NAME/KEY: misc_feature
<223> OTHER INFORMATION: Rad51b

<400> SEQUENCE: 94

atgagcaaca agaaactaag acgagtaggt ttatcacaag agctgtgtga ccgtttgagc      60
```

agacatcaga ttgttaattg tcaggacttt ttaggtcttt ccccactgga acttatgaaa 120
gtgactggcc tgagttatgg aggtgtccag gagcttctgt atatggtcag cagggcctgt 180
gccccacaga tgcaaacagc ctatgatata aagatgcgga ggtctgctga actctcccca 240
gcgttcctgt ctactaccct ttctgctttg gacaaagccc tgcatggtgg tgtggcttgt 300
ggatcgctca cagagattac aggtccgcca ggttgtggga aaactcagtt ttgtataatg 360
atgagtgttt tagctacatt gcccaccaac atgggaggat tagaagggac tgtcgtgtat 420
attgacaccg agtctgcgtt tactgctgaa agactggtcg agattgcaga atcccgtttt 480
ccactctatt ttaacacaga agaaaaactg cttttgatga gcagtaaagt tcatcttcac 540
cgggaactca gctgtgaggc agttctgcaa aggcttgaat ctttggagga agagattatt 600
tccaaaggag ttaagcttgt gattgttgac tctattgctt ctgtggtcag aaaggagttc 660
gatcctcagc ttcagggcaa catcaaagaa aggaacaagt tcttggccaa acaagcatcc 720
ttgctgaagt acctggctga ggaattttca ctcccagtta tcttgacgaa tcaaattacg 780
acccatctga gtggagccct cccttctcaa gcagacctgg tgtctccggc tgatgatttg 840
tccctgtctg aaggcacttc tggatccagc tgtgtggtag ccgcactggg aaactcatgg 900
agtcactgtg tgaacacccg gctgattctc cagtaccttg actcagagag aaggcagatt 960
ctcattgcca agtcacctct ggctgccttc acctccttca tctataccat caagggggaa 1020
ggcctagttc ttcaaggcca agaaaggcca tag 1053

<210> SEQ ID NO 95
<211> LENGTH: 1101
<212> TYPE: DNA
<213> ORGANISM: Cricetulus griseus
<220> FEATURE:
<221> NAME/KEY: misc_feature
<223> OTHER INFORMATION: Rad51c

<400> SEQUENCE: 95
atgcagcggg agctagtgag tttcccgctg tctcccacgg tgcgagtgaa gctggtggct 60
gcgggtttcc agacggccga ggacgtcctg ggggtgaagc cctctgagct cagcaaagaa 120
gttgggatat ctaaagagga agctttagaa actctacaaa ttgtaagaag agagagtctc 180
acagacaaac ccagatgtgc tggtgcatct gtggcaggca agaagtacac cgcactggaa 240
cttcttgagc aggagcacac ccagggcttc ataatcacct tctgctcagc gctagataac 300
attcttgggg gtggaatacc cctaatgaaa acaacggaag tttgtggtgt accaggtgtt 360
ggaaaaacac agttatgtat gcagttggca gtggatgtgc agattccaga gtgttttgga 420
ggagtggcag gtgaagcagt gtttattgat acggagggaa gttttatggt tgatagagtg 480
gtcacccttg caaatgcctg cattcagcac cttcacctta tagcaggaac acacaaggat 540
gaagaacacc agaaagcctt ggagggcttt actcttgaaa atattctttc tcatatttat 600
tatttccgtt gtcatgatta tactgagttg ctggcacaag tctatctcct tccagatttc 660
ctttcaaatc attcaaaggt gcagttagtg ataatagatg gcattgctct tccttttcga 720
catgaccttg atgatctatc ccttcgtact cgattactaa atggccttgc ccaacaaatg 780
atcagcctgg caaataatca cagattagct gttattttaa ctaatcagat gacaacaaag 840
attgataaaa atcaagcatt gcttgttcct gcattagggg aaagctgggg acatgctgct 900
acaataagac ttatttttca ctgggagcaa aagcaaaggt ttgcaacatt gtacaagtca 960
ccaagccaga aggagtccac aataccattt cagatcacac cacagggatt tagagatgct 1020

```
gctgtcactg cttcttcatc acagacagaa ggttcttcaa atctccggaa acggtcacga   1080

gaaccagagg aaggatgctg a                                              1101


<210> SEQ ID NO 96
<211> LENGTH: 1002
<212> TYPE: DNA
<213> ORGANISM: Cricetulus griseus
<220> FEATURE:
<221> NAME/KEY: misc_feature
<223> OTHER INFORMATION: Rad51d

<400> SEQUENCE: 96

aaacatgggc gtgctcaggg tggggctgtg cccgggcctc accgaagaga tcgtccagct     60

tctgaagggc caaaggatca agacagtggc ggacctggca gctgctaacc tggaggaggt    120

agcccagaag tgtggcttgt cctacaaggc cctggttgcc ctgaggaggg tattgctggc    180

gcagttctcg gctttcccat taaacggagc agacctatat gaggaactga agacttccac    240

tgccatcctg tccacaggca ttggaagcct ggacaaacta cttgatgctg gcctctatac    300

aggggaggtg actgaaattg taggaggtcc aggtagcgga aaaacccagg tgtgcctgtg    360

tgtggctgca aatgtggccc atagcctgca gcagaatgta ctgtatgttg attccagtgg    420

aggaatgaca gcatcccgcc tcctgcagct actacaggct agaacccaag atgaggagaa    480

acaggcaggt gctctccaga ggatacaggt ggtgcatgta tttgacatct tccagatgct    540

ggatatgcta caggaccttc ggggctccat ggcccagcag tcgacatctt cttcaggcac    600

tgtgaaggtt gtgattgtgg attctgtcac tgccgtgatt gccccacttc tgggaggtca    660

gcagagggaa ggcctggcct tgatgatgca gctggcccga gagctcaaga tcctggcccg    720

ggacctagct gtggcagtgg tggtgaccaa ccacttgacc cgagacaggg atggtaggag    780

gttcaaacct gctctgggac gctcctggag ctttgtgccc agtacccgga ttctcctgga    840

tgtcaccaaa ggggctggaa cattaggcag aggccaacgc acagtgtgtc tgaccaagtc    900

tccccgccag ccaacaggtc tacaggaggt gatagacatt gggacattgg ggactgagga    960

gcagagccca gaattgcctg ccaaacagac atgatgctgt tt                      1002


<210> SEQ ID NO 97
<211> LENGTH: 1257
<212> TYPE: DNA
<213> ORGANISM: Cricetulus griseus
<220> FEATURE:
<221> NAME/KEY: misc_feature
<223> OTHER INFORMATION: Rad52

<400> SEQUENCE: 97

atggctggag ctgaggaaac agtccgtgga ggctgtgaca cccatcctcc ctttgctggt     60

gggaaatctg tgctgtgctt tgggcagagc cagtacacag cagaggaata ccaggctatc    120

cagagggctc tgaggcagcg gctgggcccg gagtacatca gcagccgcat ggctggagga    180

ggccagaagg tgtgttatat tgaaggtcat cgagtaatta acctggccaa tgagatgttt    240

ggttacaatg gctgggcaca ctccatcacc cagcagaatg tggattttgt tgacttcaac    300

aatggcaaat tctacgtggg agtctgtgca tttgtaaggg tgcagttaaa ggatggttcc    360

tatcatgagg acgtgggtta tggagttagt gagggcctaa ggtcaaaggc cttgtcactg    420

gagaaggcca ggaaggaggc tgtgactgac gggctgaagc gggcactcag gagttttgga    480

aatgcacttg gaaactgcat tctggacaaa gactatctga ggtcactaaa taagcttcca    540

cgacagctcc ctcttgaagt ggatttaact aaagcaaaga gagaagattt tgaaccatct    600
```

```
gtggaacagg caagatataa tagctgccta cagaatgaag caccgggacc cccaaaacca    660

caagaagcgg cttccccttg cagaccaagc cacccacatg attcgaacat taggctgcag    720

ggggctaagg actgcagcag ctcctgcagt ctggccgccc ccatggagag tgatgccatt    780

caccagcgca agctccggaa gctccggcag aaacagctgc agcagcagtt ccggcagcag    840

atggaggccc acctacaggg ccacacacct gccgtaaaag tgaaagccga gcgtgaggca    900

gtgcttccag accttcctcc aaaacacagt acccctgtaa ctgctgcctc agaactcctc    960

agggagaaag ccatttttcc agataaccct gaagacaacc ttgaaatgtg ggacctgact   1020

ccggatttag aggacatcat taagcccttg tctagaccag aaccacctca aacctctgcc   1080

accagagtcc aggtgatcca ggatggtgtc ctacacggcc tttgccacca gatgccacca   1140

gaaaaacatg aagctggtca cctgcaggcc cacagcactc accagcatgt attaggaaac   1200

tctgactctc ataggaagag ccaggacctg aagaaaagga aactggatcc atcctga      1257
```

<210> SEQ ID NO 98
<211> LENGTH: 2235
<212> TYPE: DNA
<213> ORGANISM: Cricetulus griseus
<220> FEATURE:
<221> NAME/KEY: misc_feature
<223> OTHER INFORMATION: Rad54

<400> SEQUENCE: 98

```
atgaggagga gcttagctcc cagccagttg gccaggagga aaccagaagg cagatcatct     60

gatgatgaag actggcagcc tgggacagta actcctaaga aacaaaaatc cagtaatgag    120

acccagtgct tcctgtctcc ttttcggaaa cctttgactc agttaatcaa ccgaccgcct    180

tgtctggata gcagtcaaca tgaagcgttt attcgaagca ttttgtcaaa gcctttcaag    240

gtccccattc caaattatca aggtcctctg ggctgtcgag cattgggctt gaaaaaggct    300

ggtattcgtc gtgccctcca tgaccctctg gaagaaggtg ccttggttct gtatgagcct    360

cccccactaa gcgtccatga ccaactgaag ctggacaagg agaaactccc tgtccacgtg    420

gttgttgatc ctattctcag taaggtgttg cggcctcatc agagagaggg agtgaagttc    480

ctatgggagt gtgtcaccag tcgtcgaatc cctggaagcc atggctgtat catggctgat    540

gagatgggcc tgggaaagac actacagtgc atcacattga tgtggacact tttacgccag    600

agcccagagt gcaagccaga aattgagaaa gcagtggtag tgtcaccttc cagcttggtg    660

aagaactggt acaatgaggt tggaaagtgg cttggaggca ggatccaacc tctggccatc    720

gacggaggct ctaaggacga gatagaccga aaactggaag gattcatgaa ccagcgtgga    780

gcgagagtgc cttctcctat tctcatcatt tcctatgaga cttttcgcct tcatgtcgga    840

gtccttaaaa aaggaaatgt tggactggtc atatgtgatg agggacacag gcttaaaaac    900

tctgagaatc agacttacca ggccctggac agcttgaata ccagtcgtcg ggtgctcatc    960

tctgggaccc ccatccaaaa tgacttgctt gaatatttca gcttggtgca cttcgttaat   1020

tcaggcattt tgggaactgc ccaggagttc aagaagcatt ttgagctgcc aattttgagg   1080

agtcgagatg cagctgccag cgaggcagac aggcagctag gggaggaacg tcttcgagag   1140

ctcatcagta tagtgaatag gtgcctgata cggagaacat cagatatcct ctctaaatat   1200

ctgccagtga agattgagca ggtggtttgt tgtaggctga caccccttca aactgagtta   1260

tataagagat ttctgagaca ggctaagcct gaagaagaat tgcgtgaagg caagatgagc   1320

gtgtcttccc tgtcttctat cacctctcta aagaagctat gtaaccatcc agccctaatc   1380
```

```
tatgacaagt gtgtgtcagg ggaagatggc tttgaggata ctttggatat cttcccacct   1440

ggttatactt ctaaagctgt agaaccacag ctttcaggta aaatgctggt ccttgattac   1500

attctggcca tgactcgaag ccgcagcagt gataaagttg tgctggtgtc taattatact   1560

caaacgttgg atctctttga aaagctgtgc cgagctcgaa ggtacttgta tgttcgcctg   1620

gatggtacaa tgtccattaa gaagcgagcc aaggttgtgg agcgcttcaa tagtccatcg   1680

agtcccgatt ttgtcttcat gctgagcagc aaagctgggg gctgtggact taatctcatt   1740

ggtgctaacc ggctggtcat gtttgatcct gactggaacc cagccaatga tgaacaagct   1800

atggcccgag tctggcgtga tggtcaaaag aagacctgct atatttaccg actgctatct   1860

gctggaacca tagaagagaa gatctttcag cggcagagcc ataagaaggc actgagcagc   1920

tgtgtggttg atgaggagca agatgtagag agacatttct ctcttggcga gctcaaagag   1980

ctgtttaccc tggatgaagc tagcctcagc gacacacatg acaggctgca ttgccgccgt   2040

tgtgtaaaca gacgccaggt ctggccaccc cctgacggtt ctgactgtac ttcagatctg   2100

gctcagtgga accatagcac agataaacgg ggactccagg atgaggtact ccaggctgcc   2160

tgggatgctt cacctacagc catcaccttc gtcttccatc atcgttctca tgaggagcag   2220

cggggtctcc actga                                                    2235
```

<210> SEQ ID NO 99
<211> LENGTH: 837
<212> TYPE: DNA
<213> ORGANISM: Cricetulus griseus
<220> FEATURE:
<221> NAME/KEY: misc_feature
<223> OTHER INFORMATION: Xrcc2

<400> SEQUENCE: 99

```
atgtgcagcg actttcgtaa ggccgagtcc gggacggagc tccttgcccg gcttgaaggc     60

agaagctccc tgaaagaact agaacccaac ctgtttgctg atgaagattc accagtacat    120

ggtgatgttc ttgaatttca tggtccagaa ggaacaggaa aaacagaaat gctttatcat    180

ttaacagccc gatgtatact tccaaaatca gagggtggac tgcaaataga agtcttattt    240

attgacacag attaccactt tgacatgctc cggcttgtga cagtgctcga gcacagactg    300

tctcgaagct ccgaggagac catcaagctc tgcctgggaa gattgttcct ggcctactgc    360

agcagcagct tgcagctact gctcacgctg cactcactgg aagccctgtt ctgtagtcac    420

ccctctctct gccttctcat tgtggatagc ctgtcggctt tttactggac agaccgcgcc    480

agtggaggag agagtgtggc cctgcaggaa tccactctga agaagtgttc tcagctccta    540

gagaggcttg tcactgagta ccgcttggtg cttttcacaa caacacaaag tctaatgcag    600

aaagcctctg actcagcgga gcagcctgct tcctccaagc tcccaggtga cggagacaca    660

gactacagag cctatctctg caaggcctgg cagaaggtgg tgaagcacag agtcatcttc    720

tccagagagg acgaggctaa gagcagccgc ttctcattag tttcacgtca tttaaaaagt    780

aacagtttaa aaaaacatgc ttttatgatc agagaaagtg gggtggaatt ctgttga       837
```

<210> SEQ ID NO 100
<211> LENGTH: 1050
<212> TYPE: DNA
<213> ORGANISM: Cricetulus griseus
<220> FEATURE:
<221> NAME/KEY: misc_feature
<223> OTHER INFORMATION: Xrcc3

<400> SEQUENCE: 100
atggacttgg atcaactgga cctaaatccc agaattactg ctgcaattaa gaaggggaga 60
ctgaggtcag tgaaggaggt tctgtgctac tcgggaccag acctgcagag gctcaccagc 120
ctgtccaccc acgatgtgca gcacctactg agagtggccg ctctgcacct ccagggcagc 180
cgggtcctca cagcactgca gctgttccag cagagggaga gcttccccga gcagcatcaa 240
cgcctgagcc tgggctgccc ggtcttggat cagttcctgg gtggcggcct gcccctggag 300
ggcatcactg acctggctgg tcgaagctct gcagggaaga cccagctggg gctacagctc 360
tgcttgactg tgcagttccc acgacaatat ggaggcctgg aggctggggc tgtctacatc 420
tgcacagagg atgccttccc cagcaagcgg ctgtggcagc tcattgaaca gcaacagcag 480
ctgcggacgg atgttcctgg ggaggtgatc cagaagatca gattcagcaa ccacatcttc 540
atcgagcatg cggccgacgt ggacgccttg ctggagtgtg tgagcaagag ggttcccatt 600
ctgctgtcaa gggggatggc ccgcctggta gtggttgact ctgttgctgc cccattccgt 660
tgtgagtatg atgctcaggc cttggccacc agggccaagc acctgcagtc tctgggagcc 720
gcgctccgca gactgagcag taccttccgg agccctgtgc tgtgcatcaa ccaggtgatg 780
gaaacggtgg aggagcaaga gtctatgccc aggccactgg gggcctggga tgagcacctc 840
tctccagccc ttggcatcac ctgggccaac cagatcctga tgagactgat ggttgaccgg 900
gcacatgagg acgatgcctc catgggctta cccagaagcc cggcacggac catacgggtg 960
ctctctgccc cgcacctgcc cctctcctcc tgctgctaca cggtcagtgc ggaaggcatc 1020
agagggatac cgggaaccga gtcctgctaa 1050

<210> SEQ ID NO 101
<211> LENGTH: 5373
<212> TYPE: DNA
<213> ORGANISM: Cricetulus griseus
<220> FEATURE:
<221> NAME/KEY: misc_feature
<223> OTHER INFORMATION: Brca1

<400> SEQUENCE: 101
atggatttat ctgctgttca aatcgaagaa gtacaaaatg tccttcatgc tatgcagaaa 60
atcctggagt gtccaatctg tttggaattg atcaaagaac ccatttccac aaagtgtgac 120
cacatatttt gcaaattttg tatgctgaaa cttcttaacc agaagaaagg gccttcacaa 180
tgtcctttgt gtaagaatga gataaccaaa aggagcctgc aaggaagcac gaggtttagt 240
cagcttgttg aagagctgtt gaaaatcact gatgcttttg agcttgacac aggaatacag 300
tatgcaaacg gttacagtat ttcaaaattg aaaaattctt ctgaaccttt gaatgaggaa 360
gcttccatca tccagagtgt gggctaccga aaccgcggca aaagacttag acagattgaa 420
tctggaaatg ccaccttgaa ggacagtctc agtgtccagc tgtctaacct tggaattgtg 480
agatcaacaa agaaaaatca tcagacacag cctcgaaata aatctgtgta cattgaatta 540
gagtctgatt cttctgaaga gacagttagt aaaccagatg actgcagtgt gagagaccag 600
gaactgttac aaaccacctc tctgggagct ggagatgaag tcagtttgga ttcttcaacc 660
agagctgctt gtgagttttc tgaggacgta acaaatattg atctgcacca gtgcagtaat 720
aaagatttgg accccattga gaatcatgca actggaagat atccagaaaa atgtcaggat 780
atttctgttt caaacttaca tgtggagcca tgtggcacag atattcatgc cagctcgtta 840
cagcatgaga acagcagctt attactcact gaagacagaa tgaatgtaga aaaggctgag 900

-continued

```
ttctataata aaagcaaaca gtctggctta gccaggagcc aacagaacag atgggctgaa    960
agtaaagaaa catgtaatga taggcagatt cccagcactg agaaaaaggt agatccaaat   1020
actgattcct tctgtgggag aaaaaaatgg aaaaatcaga aaagtctgtg tcctgagaat   1080
tctagagcta cccaggatgt tccttggatg acactgaata gcagcattca gaaagtcaac   1140
gagtggtttt ccaaaactgg tgaaatgcta acttgtgatg gcacatctga caggaggcat   1200
gagtcaaatg ctggagcagc tgttgtgtta gaagtttcag atgaagtaga tggatgttcc   1260
agttcttcaa aagaaatgga cttagtggcc tctgatcccc ataatgcttt aaagtgtaaa   1320
agtgaaagcg acctctccaa accagtagag aacaatatcc gagataaaat atttgggaaa   1380
acgtatcaga gaaagggaag tctccctcac ttgaaccacg taactgaaat tataggcaca   1440
tttattgcag aaccacagat aacacaagaa caccccttca caaataaatt aaaacgtaaa   1500
aggagaacta catgccttca tcctgaggat tttatcaaga aagcagattt aacagttact   1560
caaaagactt ctaaaaatgt aaatcaagga actgaccaaa tggagccaga tggcctagtg   1620
atgggtatta ccagtaatgg tcaagagaat gaaacacaag gtaataatct tcagaaagag   1680
aaaaatgcta atccagtgaa gtccttggaa aaggggtctg tttccacaac taaagccaaa   1740
actataagca acagtataag tgatttggag ctagaattaa atgtccacaa ttcacaggca   1800
cctaagaaaa gtcggctgag gaggaagtct tcaaccagat gtgttcttgc actggaacca   1860
gtcagtagga atccaagccc acctgcttgt actgaatttc aaattgatag ttgtagcagc   1920
agtgaagaaa cagagaaaaa caattccaac ccaacaccag tcaagaacat tagaaagcct   1980
caactcacgg aggacacaga acctgcagca gattccaaga agaataaaga gccaaatgaa   2040
caaagaagga agagaagggc cagtgatcct ttcccagaag agaaatttat gcctggctta   2100
ttaactaact gtccaagttc tagtaaacct caaggacctg ccaatcctag ccctcagaga   2160
aaggaagtag agaaacttga aacaagccaa atgtctgaca gtaccaaaga cctgagggat   2220
ctgttgctgg atggagaaca gggtttgccc actgagaggt cggaggagag taccagtgtt   2280
tcattggtgc ctgacactga ttatgacact cagaacagtg tgtcattgct ggaagctaat   2340
gctgtcagat atgcaaaaac agtatcaagc cagtgtatga cccagtttgt agcaagtgat   2400
aaccctaacg aactggtcca tggttctaaa gatgctggaa gtggcacaga gtgcttcaag   2460
catccattga gacacgaact tagccacatt caggagacca tagaaatgga agagagtgaa   2520
cttgatactc agtatttaca gaatacattt caagcttcaa agcgtcagtc atttacttta   2580
ttttcaaaac caagagatcc ccaagaggag tgtgtaacag cttgtgcttc ctctgtgtcc   2640
ttaagggaca tgagtccaaa agtgacttct gaaggtgaac aacaagaaga aagtcgggga   2700
cacgaagagg ctgaaatcag tcacatacag gcagggcctg cgacagtggg cgtgcctctg   2760
cctcgtcagg aaggtgatcc aggcgctgat acaatgcatg ctgcagtgtg cagcctttgt   2820
ccatcatctc agtacagaag caatgaaaac tcacatccta aacaatcagc ttctcccatc   2880
atgtcttcta taaaaactgg ccatgggaaa accctgtcag aggaacaatc tgagaaacat   2940
acattgtcaa atgaaaaggc aatgggaaat gagacctttg ttcaaagcac aatgcacaca   3000
attagccaaa accacagaaa aaatggttgt caagaagcca actcaggcag tattaatgaa   3060
gtgccttcca gtggtgaaaa cttccaagga cagctaggcc gaaacagaag gactaagtta   3120
aacactgtgc ttccactagg tcttatgcaa cctggagtct gtaagcatag ttttcctgtc   3180
agtgattata aatatcttga aataaaaaag caggaaggtg agaatgttgg tgcacacttc   3240
tcttcgtgtc tgttttcaga taagctcgaa caacctgtag ggagtggtaa tgtttttcag   3300
```

```
atttgttctg agacacctga tgacctgttg gatgatgttg aaatacagga aaatactagc   3360

tttggtgaag ttgacataat ggagaagtct gctgttttta acgggagtgt ccagagacga   3420

gagctcagta ggagccctag ccctttaacc catgcatcgc tggctcggaa tctccagaga   3480

cggtctagga agttagagtc ctcagaagac agcggatctt gtgaggatga agaccttccc   3540

tgcttccaac acttacttgg ccaagtaagc aaaacacctg aacctagcag tgttgtgaca   3600

cagcctctgt cagagaaagc agaggggacc caagtgccat ggaagagtag tgttggtgac   3660

tctgataacg aggtgatctt gatagaggca tctcaggaac atcaccctag tgaggatgca   3720

aaatactctg gcagcatgtt ctcttctcag cccagtgctg tacaaggttc aactgcaaat   3780

acaagctccc aggacccctt gtttaacctt tccaaacaaa agagtcacca gtctgaggat   3840

gaggaagatt ttctaagtga caaggaattg atttcagatg atgaggaaat gggaacttgc   3900

ctagaagaag ataatgatca agaagaggat attataatcc cagattcagc tgaagcggca   3960

tctggatatg agagtgaaac aaacctttct gaagattgct cacagagtga tattttaacc   4020

actcagcaga gggccaccat gaaggataac ctgataaagc tccagcagga gatggcccac   4080

ctggaggctg tgctagaaca gcaaggggac cagccttctg tccactcctc gtctctcaca   4140

gctgaacctt gtgcccctga agacctacca aacgcagaac aaaacttatc aggaacagca   4200

attttaactt caaagaatat taatgaaaat cctgtaagcc ggaatccagc atgcgtttct   4260

gctgacaagt tccaaccaca acctccagac agttccagca gtgaaaataa agagtcaagg   4320

gaaggaaggc cttccctttt taaatctccg ttggcaggca gtaggtgctc tgcacacagc   4380

cgctctggga gtcttcaaaa cagaaactgc ccatctcaag aggagctcct ttggactgtt   4440

gaagcaggga agtcagaagg aacgccatac ctggaatctg gaatcagcct tttctctaat   4500

agagaccctg aatctgagtc ccctaaagag ccagcttatg tttgcaccac accagcttca   4560

acctctgcac ggacaatatc ccagtatcag gtttctgact ctttcgagag tccggctgct   4620

actcatgctc atactgcagt gatagaaact gtgagcaaga aaaagccaga attgacatct   4680

tcaaaaggaa gagccaataa aggaatatcc atggtggtgt caggcttgac ccccaaagaa   4740

gtaatgattg tgcaaaagtt tgctgaaaaa taccgcctca ctttaactga tgcaattact   4800

gaggagacta cccatgtcat tatgaaaaca gatgctgagc ttgtgtgtga acggacactg   4860

aaatattttc tgggaattgc aggaggaaaa tggatagtta gctattcatg ggtgattcag   4920

tctattcaag aaagaaaact tctgagtgtg catgaatttg aagtcagagg agatgttgtg   4980

actggaagaa accaccaagg tccaaagcga tccagagaat cccaggaaaa gctcttcaaa   5040

ggcctaacaa tctgttgttg tgagcccttc accaacatgc ccaaagatga gctggagaag   5100

atgctgcagc tgtgtggggc ttccgtggtg aaggagcttt cgtcactcac ccctgacacc   5160

ggtgttcatc caattgtgat tgtacagcca agtgcctgga cagaagagaa tggctgccct   5220

gagattgacc agctgtgtgg ggcgcacctg gtgatgtggg actgggtgtt ggacagtata   5280

tccgtctacc ggtgtcggga tctggacgcc tacctggtac agaatatcac ccatggccac   5340

gacagcagcg agccacagga ccccaatgat tag                                 5373
```

<210> SEQ ID NO 102
<211> LENGTH: 10098
<212> TYPE: DNA
<213> ORGANISM: Cricetulus griseus
<220> FEATURE:
<221> NAME/KEY: misc_feature
<223> OTHER INFORMATION: Brca2

<400> SEQUENCE: 102

```
atgtccaatg aatacaaaag gagaccaact ttttttgaaa tttttaaggc acgatgcagc     60
acagcagact taggacctat aagcctgaat tggtttgaag aactttcttc agaagcccca    120
ccatataatt ttgagcctcc agaagaatat gaatataaga ccaacaatta tgagccacag    180
ctgtttaaaa cgccacagag gaagctctct taccatctgt tggcttcaac tccaataata    240
ttcaatgaac aaggtcaaac tctaccagta gaccagtcgc ctttcaaaga actagggaag    300
actcttggaa atagtagaca taaaaatcac cacagaacca aggccaaaat ggactccatg    360
gttgatgttg ccagtccacc tctgaagtct tgtctcagtg aaagccctct tactctgcga    420
tgcacacagg ttgtaccaca aagagaaaag ccagtgatgt gtggaagttt attttctaca    480
ccaaaaatcg aggagggtca gacacctaaa cctatttctg aaagtctggg agttgaggtg    540
gatcctgata tgtcttggtc cagttcatta gctacaccac caacccttag ttccactgtg    600
ctcatagccc gagatgggga agcacgagga attgtgtttc ctgaagactc ccccgctgtt    660
ttgaaaagct acttttccag ccacaatgaa agtctgaaaa agagtggtat atcagttccc    720
tctgtgactg acagcgagaa caaaaaccag agggaagctt ttagtcatgg attggggaaa    780
acgttagagg attcatctgg caaaacaaac agcttcaaag attgccttag gcagtcaata    840
ccaaatgttc tagaagatgg ggagacagct gcagatactt ctgaagaaga tagtttctca    900
ttatgttttc ctaagcataa aaccagaaaa atgcaaaaaa tgagaatggg caagaccagg    960
aagaaaattt tcagtgaaat aagaactgat gaattaagtg aagaaactag aagtggagct   1020
gatggaaaac attcatttgc acttgaaatt gacccaagag atagtgatcc cttagatcca   1080
gatgtgacaa accagaaatg ctttgacaat gggaatgagg aaatctgcga ggaagttgta   1140
cagtcttcag acactcgatg gtctcagcta accctttctc gtctaactgg tacccagaag   1200
ggaaaaatac ctctacctcc tatttcttct tgtaaccaaa ataattcaga aaaagacttc   1260
atagatacga aggaagaagg tattgactct gttactttag aaaattcttt gcctcatatt   1320
tctagttttc cagaaccaga aaagatgttc tgtgagaaaa ctctggtaga taaggaacat   1380
gagggacagc atcttgaatc acatgagaac tccattgcag ggaagcaagt ggtatctgga   1440
acttgtcaag cagcttgcct attgagagag ccacttgaag agtctctggg taatctcttc   1500
tcagagagtg tgactagctc agcctttaca gaagaaccca gtgcctctgc aagtggattg   1560
ggaatatgtg ctgtgtcctc acagagagag gattctttgt gtcctagttc aggtgacact   1620
ggaaactggc catcaactct cactcacact tctgcaactg tgaacaatac aggtttaata   1680
tccagtctaa aaactaaaag aagaaagttt atttactctg tcggtgacag tgcatctcat   1740
caaggaaaaa tactacaggc agacagaaag tcagagctca ctaacacttc tgctcagttc   1800
gaaacaagtg cttttgaagc gccattcacg tttacaaatg ggaattcagg tttatcagat   1860
tcttctctcc aaagaagctg tttacagaat gatgctgaag agccatcttt gtccttatcc   1920
acctcatttg tgactgcttc caagaaagaa agtagttata gtaatgcatt gatatctcag   1980
gatctccatg acaaagaagc aatagtcagt gaagaaaaac tgcagccaca tacagccctg   2040
gaaactgatt gtctgtcgtg cttgccagaa agacaatgtg aatatgatcc aaagggtccc   2100
aaagtttcag atggaaaaga agaagtctta gtctcagcat gtcatcctgc aggacagcac   2160
acagcagcag cacagcccag cagcattagc tttgaattac aggaagaccc tgtcaatggc   2220
cacaatagta caagtcctaa agaaactcct agcttgaagg tgcttctgtc aaagccagtt   2280
```

-continued gtgctttcta gaggaaaagt gtcatgtaaa atgccagaga aactgcagtg tgagagttat 2340
aaagataata ctgaattaag caaaagcatt cccttgggag gaaataaaat acacatccta 2400
agtgaaaatt ctaaacctcc tgagcttctg ccacctggaa aatatgtaac agaagcatcc 2460
cccacagtga agtctcagtt caatcagaat acaaatctag cagtcaaaaa aaatgaccaa 2520
gaagaaacgc cttttatttc agaagtaaca gtcaatgtga gttctggaga acttttccca 2580
gacaatgaga ataatttcgc ctttcaagta actcatgaaa ataataagac tgccttagga 2640
agtactgtgg aactgcagga agaagacctc cgccatgcta aagggcctaa tctcaacaac 2700
tctcccacag cagtagatgg agacataggt gatgagcaag cagctcatgc actgattatg 2760
gaagactccg attcctcagc tttagtccat gagtgtgcaa agaagagcag aaatactata 2820
gagcagcatc tgaaaggaac cacagacaaa gatttcaatt cctccttgga tgtgaaatca 2880
gatgggaaca atgactatac agacaaatgg ccaggatttt tggatccagt ttttaagcat 2940
aaatttggag gtagcttcag aacagcttcc aataaagaaa taaaactttc agaacataat 3000
gttaagaaaa gcaaaatgtt cttcaaagat attgaagagg agtatcctac tagtttaacc 3060
tgtattgaca tagttaatgc ctcaccatta gcaaaccagg agatactaag tggaccttat 3120
acatttgatt tgcagtcagt cactaccatg tctgcccatc cacagagtca ggcatctgtt 3180
tcttgtgaag atactcacac atcacttcag gtgttacctt caaagcaaga ttttcattcg 3240
aatcacaatt taacacccag ccaaaaggca gaaattacag aactttctac tatcttggaa 3300
gaatcaggaa gtcagtttga attcacacag ttcaaaaagc caagccatgt agcacagaat 3360
aatatacctg aagtgcctgg aaaacagacg gttgccataa atactacttc tgaggggtgg 3420
aaaaggattg gtcttcatct cacagtggat cctgcctctg tagctcagac agatgacagc 3480
aagaaatttg aaggttctgc tggatttaga caaagctttc cttgcctgtt gaaaagcagt 3540
tgtaacaaaa atacatctag tttttagca aatgtaaatg aaatggagtt tcgaggattt 3600
cgttctgctc ttggcacaaa gcttagtgtg tctagtgagg ctctgcaaaa agctgtgaaa 3660
ctcttcagtg acattgaaag tggtagtgag gagacttcca caaaagtcga cccaagagct 3720
ttgtcttcag gtgctcgtca tgattctggt gcttctgtgt ttaagataag gaaacaaaac 3780
agtggtaaaa gttttgatga gaaaactagt aagtgccaag taacattaca gaataatacc 3840
gaagtgacta ctggtatttt tgttgacaga aatcctgaaa attatgcaag aaatacaaaa 3900
tgtgaagata acaactctac tggttttcaa agaagtcctt ataaattaaa aaactcggag 3960
gatagtgaat caagtacaag cggcacagtt tctgttcatc aagatgatgg tgacttacca 4020
tgtgctgctg atcactgcag caagtaccct gagtcgtgtt cccaatatgt aagggaggaa 4080
aacacacaaa ttaaggaatg tgtatcagat ttaacatgtt tggaagtcat gaaagctgag 4140
gaaacatgct atattcaacc ttcagataaa gaacaattac cttcaggtaa gatggaacaa 4200
aatagaaaag attttaatat atcctttcag actgcaagtg ggaaaaatgt cagagtctct 4260
gaggagtcat taagtaaaag tatgaatatt ttaaatcaag taacagatga atcgatcatc 4320
tcttcagatt ctttgaattc taaatttcat tgtggcacaa ataacaacaa gatgggtatt 4380
tcacatcaca aggaaactac cagtactaaa aaggtatttg aagaacgttt cccagttggg 4440
actgtcagtc aattaccaac tctccagcag catcctagat gtgaaataga aagtatcaaa 4500
gaacctgctc tgttgggttt tcataccgct agtggaaaaa aagtcaaaat tatgcagaaa 4560
tctttagaca aagtgaaaaa ccttttgat gagacacagt atgttagtca tcaagggtca 4620
aaacccttga aggacagaga gaactgcaaa gaaggacttg cattaggatg tgagacaatt 4680

```
gaaatacctg cctccaagtg tgaagaaatg cagaagagct ttctctctaa ggagtctgaa   4740
gtgctatcta agcaaagtga tcgtttgtat aggtcgactg aaaatctcag aacatcaaat   4800
ggtacctctt ctaaagctaa tgtacatgga aacatagaaa gtgaaataga aaaaagtcct   4860
acaacttgct gcattagtca tttatcttat tcagtcactg aagattctgc tttgacatgt   4920
gacacaggac acggtagaaa aacttgtgtc agtgagtctt ctctatccaa agacagaaaa   4980
tggcttagag accgactggg tgataagctt caaaaaagag atgctgccga aattgaatgt   5040
gtaaaagaac atactgaggg ttatgctgga gatgcctcat gtgagcatag tttagacagt   5100
atcagaaatg aagttgatat aaattgtgtc tctgaaaatc aaacttcagc cctctttagt   5160
gaccctagca tgtgtcatag ctgtccatcc cattttggtt gtcattgtga taacaagcat   5220
aatgactcag gatatttctc aaaaaataaa atttattctg atactcagcc agacacgaag   5280
aatgaagaca ctgccaattt ttccagtgta tatgctacaa aagaagtaaa tatatacccg   5340
ccaactgtaa atgaagatat ttgtgttcag aaacttgaga ctaactcttc accacataca   5400
aataaaaatg tagccattga cttggctata gcagattcaa ggaattgtaa ggtatgccca   5460
tccaagttca ttacagatca ctcacaagaa actgtgaaaa cagtaaaagc aatatttaca   5520
cataacagtg ataaaacaat taagcaaaac acaaagagta aaccagatac ttgccggaca   5580
agctgtcaga aagcattgga taattcagag gattttatat gtcctagctc tttagaagat   5640
gactatatga actcacataa gacttctgtt tatacccacg atgaacaaat attacagcat   5700
aacctaagtg tgtctggact ggagaaagct caaataccac ctgttcactt ggaaacttgg   5760
gataagtgta aatctacaag ggaacttgca caggcagcct gttcttcaca catgccgggg   5820
atttttagca cagcaagtgg aaaagctgta caggtatcag acgcttcatt agaaaaggca   5880
aggcaagtgt tttctgagat ggatggtggt gctaaacagt tactttccac attgtctctg   5940
gaaagtcatg aacaatcaga ccactctggg agaagagaaa actctgtgac acataaccct   6000
gaggatgtat tgtcactccc aaaaaccttt gcaagcaatg ccaattcatc tgtattctct   6060
ggatttagta cagcaggtgg taaacgggtc acagtttcag aaagtgcctt acacaaagtt   6120
aagggaatgt tagaggaatt tgatttgatc ggaactgaac atactctcca gtgtccacct   6180
acatctgaag gtgtatcaaa aatacttcct caatattgtg ttgaaaagag aaccccagaa   6240
taccctataa actctaaatt gcagaaaacc tatgatgata aattcagttt accaaacaac   6300
tataaagaaa gtgcttcttt ggggaatact cattctcttg aagcttctcc ccaactctct   6360
cagtttaagc aagacacacg gttggtatta ggaaccaaag tatcccttct ggaaaaagaa   6420
caaaccttcc ctcaaaatat aaaaacagaa agtggtgtaa tggaaacttg tcctgatgtc   6480
cctgtgagaa caaatgtagg agactgttct gctttcgaca aaaagccaga gaactgtttt   6540
gaaacagaag cggtggagat tgccaaagct tttatggaag atgatgagct gacggattct   6600
gaaccaagtc acgacaaata ctcattgttt acctgccccc aaaatgaggc tttgttaaat   6660
ttgagaacta gaaagagaag aggaatggct gttgatgcag ttggacaacc cccaatcaaa   6720
agaagcttat taaatgagtt tgacaggata atagaaaata aaggaaaatc cttaaagcct   6780
tcaaaaagtg ctccagatgg tacaataaaa gacagaagat tgttcacgca ccacatttct   6840
ctagagccag ttacctgtgg acccttctgc tctaccagag aaaggcaaga aatgcagagt   6900
ccacatttca ctgcacctgc tcaaggactt ctgtctaaag ggcatccttc tgtgcgttcg   6960
gctttggaaa aatcttcaag caattctaca gtttcagtcc agccgactca taaagtttct   7020
```

-continued

```
gctacaagga atgaaaggac aggatgctca gtcacaggca aatcccacaa agtcttcgtc   7080
ccacctttca aaatgaaatc acagtttcac agagataaac atttgaataa caagaatatt   7140
aattcagagg aaaagaacca aaagagcaga gatggagaca gtgaagatgt gaacgacggt   7200
gacattcgtc aatttaaaaa aggcagcttc catcaagagg ccgctagaat tgtcacagag   7260
tgtgaagaag agcctttaga tttaatgaca agccttcaga atgccagaga cctacagaat   7320
atacgaatta aaaagaaaga aaggcatcag ctctgtccac agccaggcag tctgtatctt   7380
accaagtcat ccactctgcc tcggatctct ctgcaggccg cagtaggagg ccggcttccc   7440
tctgcgtgtt ctcataagca gctctatatg tatggcgttt ctaaagagtg cataagcatt   7500
aacagcaaaa atgcggaata ttttcagttt gacattcagg attattttgg taaagaggac   7560
ctgtgtgctg gaaagggcat tcagctggct gatggtggat ggctgatccc ctccaatgaa   7620
gggaaggctg gaaaagaaga attctatagg gctctgtgtg acactccagg tgtggatcca   7680
aagcttattt ctagcctctg ggtctctaat cactaccggt ggattgtgtg gaaactggca   7740
gctatggaat ttgcttttcc taaggaattt gctaacagat gcctaacccc agaaagagtg   7800
ctgcttcaac taaaatacag atacgatgtg gaaattgaca acagcagcag atcagcccta   7860
aagaagatcc tggaaaggga tgatactgct gcaaaaacac tcgttctctg tgtttctgac   7920
gtcatgtcac taagcacaac tggatcagaa acttcaggcg gcaaaactag tggtgcagat   7980
cccaagagca tagacacgat cgaactcaca gacggatggt atgctgtcaa ggcccagcta   8040
gaccctccac ttgtggctct tgtaaagagc aggagactga ctgtgggtca gaaaatcatt   8100
acccaagggg cagaactggt gggatctcct gatgcctgcg cacctctgga agcaccagac   8160
tctcttagac tgaagatttc tgccaacagc acacggcctg ctcgctggca cagcaaactg   8220
gggttctttc atgaccccag gcctttccct ctgcccttgt cctcactgtt cggtgatgga   8280
ggaagcgttg gctgtgtgga catcattgtt cagagagtgt accctttaca gtgggtggag   8340
aagacggcat caggattgta catattccgt aatgagagag aagaggagaa ggaagcagtg   8400
agatttgcag cggcccaaca gaagaaactg gaggccttgt tcaccaaaat ccaggcagag   8460
tttaaagacc atgaagaaga ctcagcgcag cggcgcgtgc tgtcccatgc actcacaagg   8520
cagcaggtct atgctctgca agatggtgca gagctctatg cagcggtgca gagtgcattg   8580
gatccagatc accttgaggg ttgtttcagt gaagagcagc tgagagcctt gaacaaacac   8640
agacaaatgt tgaatgataa gaagcaagca cagatccaat cagaattccg gaaggccgtg   8700
gagtccgctg agcaagagga gggcttatca agggatgttt caactgtgtg gaagcttcga   8760
gttacaagct acgagagaaa agaaaagtca gctctgctga gtatctggcg tccatcatca   8820
gacttacact ccctgttaac agaaggaaag agatacagaa tctatcatct ggcagtatca   8880
aaatctagga gtacatttga acgacctagc atccagttaa cagctacgaa aagaactcag   8940
tatcagcagc taccggctgc cagtgaaacc gtattccagg tttaccagcc gagggagccg   9000
cttgacttca gcagactgtt agagacagcc tttcagcctc cttgttctga agtggacctc   9060
gtaggagctg tagtttctgt tgtaagaaca acaggtcttg ctcctttggt ctacctatca   9120
gacgaatgcc ttaatttatt agtggtaaag tttgggatag accttaatga agacataaag   9180
ccacatgtgc taattgctgc aagcaacctc cagtggcacc cagaatccag atcaggagtg   9240
ccaacgttat ttgccgggaa tctttccata gtttctgcca gtccaaagga ggtctacttc   9300
cagaagcgag tcaacagaat gaggcaaact gttgagaata tcgatacatt ttacaaggag   9360
gcagaaaaga agcttttaca tctgcttaat ggaaacagtc ccaagtggtc caccccaaat   9420
```

```
aaagactcta ctcagccggc ctacacttgc cctgcttcag agctccttgc tacaggaggt   9480

cagctaatga ggttctcacc taatagtgag caaagttatc caagtccttt atcacattgc   9540

acaccaaaag aaaagtctac acccctggct cggtcagccc agatggcatc aaagtcttgt   9600

aacagggaga gagagactga tgaccgaaaa acctgcagaa aaagaagagc cttggatttt   9660

ctgagtcggc tgcccttacc tcccccggtc agtcccattt gtacctttgt ctctccggct   9720

gcacagaagg cttttcagcc gccacggagt tgtggcacca aatatgcaac acctatgaag   9780

aaaaaagaac ccagttcccc tcagaggagg acgccatttc agaaggacag tggcatttct   9840

cttctggaac aagattcggt agctgatgaa gaacttgcct tcctcaatac ccaagctctt   9900

gtacctggct caccagaaga aaatcaacaa gtacttcctg gtgactccac aagaacctct   9960

gtgccccaca acaaaagaac ccccagccag cacagaggcc agaccagcat gtaggacccc  10020

gatccaggaa ggggagtcta tctcagggat tacagaggtg gcaagggcag tgatggaaaa  10080

ttagctgtcg agtcttag                                                10098
```

<210> SEQ ID NO 103
<211> LENGTH: 888
<212> TYPE: DNA
<213> ORGANISM: Cricetulus griseus
<220> FEATURE:
<221> NAME/KEY: misc_feature
<223> OTHER INFORMATION: Cyclin D1

<400> SEQUENCE: 103

```
atggaacacc agctcctgtg ctgcgaagtg gagaccatcc gccgcgcgta ccctgacacc     60

aacctcctga acgaccgagt gctgcgagcc atgctcaaga ccgaggagac ctgcgcgccc    120

tccgtgtctt acttcaagtg cgtgcagagg gagattgtgc cgtccatgcg gaaaatcgtg    180

gccacctgga tgctggaggt ctgcgaggag cagaagtgcg aagaggaggt cttccctctg    240

gccatgaact acctggaccg tttcctgtct ctggagcccc taaaaaagag ccgcctgcag    300

ctgctagggg ccacctgcat gttcgtggcc tccaagatga aggagaccat tcctttgacc    360

gccgagaagt tgtgcatcta cactgacaac tctatccggc ccgaggagct gctgcaaatg    420

gaactccttc tggtgaacaa acttaagtgg aacctggccg ccatgactcc ccacgatttc    480

atcgaacact tcctctccaa aatgccagag gcggatgaga acaagcagat catccgcaag    540

catgcgcaga cctttgtggc cctctgtgcc acagacgtga agttcatttc caacccgccc    600

tccatggtgg ctgccgggag cgtggtggct gcaatgcaag gcctgaacct gggcagcccc    660

aacaactacc tgtcctgcta ccgcacaacg cactttcttt ccagagtaat caagtgtgac    720

ccggactgcc tccgcgcctg ccaggaacag attgaggccc ttctggagtc cagcctgcgc    780

caggcccagc agaacatcaa ccccaaggcc accgaggaag agggagaagc agagggagag    840

actgacctgg cctgcacacc caccgatgta cgagatgtgg acatctga                 888
```

<210> SEQ ID NO 104
<211> LENGTH: 882
<212> TYPE: DNA
<213> ORGANISM: Cricetulus griseus
<220> FEATURE:
<221> NAME/KEY: misc_feature
<223> OTHER INFORMATION: Ercc1

<400> SEQUENCE: 104

```
atggaccttg ggaaagacga gggaagcctg ccgcagccca ccaggaagaa gtttgtgatc     60
```

```
ccactggaag acgaggcccc tcctgcaggg gccaagccct tattcagatc ctcacggaac    120

cccagcacca cggccccctc ggtcccagcg gcccctcaga cgtacgccga gtatgccatt    180

gcccagcctc caggaggggc tgggcccaca gggcccacag gctctgaacc tgtgaaggga    240

gagaaccccg gccagacggt gaaaacggga gcgaaatcca atagcatcct tgtgagcccc    300

cggcagaggg gcaaccctgt gttgaagttc gtgcgcaacg tgccctggga attcggcgag    360

gtgacccctg actatgtgct gggacagagc acttgcgccc ttttcctcag cctccgctac    420

cacaatctcc atccagacta catccacgaa cggctgcaga gcctggggaa gagctttgcc    480

ctgcgtgtgc tgttggtcca agtggatgtg aaagatcctc agaaggccct gaaggacctg    540

gctaaaatgt gtatcttagc ggactgcacc ctggtcctgg cctggagtgc cgaggaagca    600

ggacggtacc tggagaccta caaggcatat gagcagaagc ccgctgacct cctcatggag    660

aagctggagc agaacttcct gtcccgggcc accgagtgtc tgaccaccgt gaagtcagtc    720

aacaaaaccg acagccagac cctcctggct acatttggat cccttgaaca gctcttgacg    780

gcatcacggg aggacctagc cttgtgcccc ggcctgggcc cccagaaggc ccgcaggctc    840

tttgacgtcc tccatgaacc cttcctcaaa gtgccccgat ga                       882
```

<210> SEQ ID NO 105
<211> LENGTH: 4473
<212> TYPE: DNA
<213> ORGANISM: Cricetulus griseus
<220> FEATURE:
<221> NAME/KEY: misc_feature
<223> OTHER INFORMATION: MDC1

<400> SEQUENCE: 105

```
atggaaaaca cccaggttat tgactgggat gctgaagagg aggaggagac agaaataccc     60

agtgggtcct tggggtatag cttggagcct atagggcagc tgcgtctctt cagtagtact    120

catggaccag aaagagattt cccactctac cttggcaaga atgtaattgg ccgaagcccc    180

gactgctctg tggccctgcc ttttccatcc atctctaaac agcatgcagt aattgaaatc    240

tcagcttgca acaaagcccc tatcctccag gattgtggga gcctcaatgg cactcaactg    300

gtaaagcccc caaaggtcct aacccctgga gtgagccatc gtctgaagga ccaggaatta    360

attctgtttg cagactttcc ctgccagtac cgtcgcttgg atgtccctcc acctttggtc    420

tctcggggac ttctaactat agagaagacc cccagaatac agggagggtc ccaaacctcc    480

agagttttgt tggctgagga ttcggaggag gaagtagatt ttccttctgg aaggtatgtg    540

gcaaatggat caaggaatcc aacgtctcca tcagcaacag tagtaccaga aagtgatgaa    600

gaggggtctt ctccagccca aagtgtccgt gggccgtctt tgccctttga cttgggcagt    660

gacacagatg aagagctatg tccacagcca gcagttgggg agtcctcttc agttgccagg    720

gatggtgctg ctgcagaggc caagcagctg gaagctaatg gagtgacatc tggtatccag    780

ctggtactgg ctcagcctgc tgagcaaaag ctcagagatg caaaagtcaa gagtgaggct    840

ggcaatggag cggctgtggt tgggaggggc tccactgtgg gtaaggacag caacacggaa    900

atgggtgaag aacaccagcc ttccggcttt gtggacagcg atacagacgt ggaagaagac    960

aggatccctg tgaccccccc tgtagttccg gggaagaagc aagtcctgct tggagttggt   1020

aaaaaggacc ctggagcacc tgtcgtgacc catctgcagg acagcccagc tggtcgtggc   1080

acaggtgtgg aagaaggcaa gactccagtg gctggccctc cagagagaaa ccacacggcc   1140

atggtgatca gcagcgacac agatgaggaa gatggagtct cagcagcagt caccttggcc   1200
```

-continued

```
catctgaaag acagggggat ggctctgtgg agcagggagc caggcatgga agaggtcaag   1260
tcccaaccac aggtcctcgt agaacgaagc cagagtgcct ctgggaaaga cagtgacaca   1320
gacgtggagg aggaaaagag agaagtggtc cctgacagcc ccatggacac agatgaggct   1380
cttactgtcc cacattcaga gagccaagct ccccatagag ccagtgatga tgtagaccag   1440
ggtgtggata tgggctcccc tggtggtcag ctagagggaa accaggcctc ctctgccaca   1500
gtagaagaca gtagtgcaca agcagggaag gaagtcctgc ctcctgagga ggcctgggaa   1560
acagctgtgg aggaaggctc atcttcagca gcggcagatg taagacaaag caagcagcca   1620
ggagtagaag atgctgggac agagtgggct gcaactgttt gtgagcaggc gagcatgctt   1680
gaggtggggg tccaaggcag gtcacctgct acactggtag agccagtggt ggtgcctaca   1740
gctactctgg gggatcccac tcagccacag agagagggag cccagacccc cacaggaaag   1800
gagagaggag tacaaatggg caggaccaag aatgccaaag actgccgtga tgcagagtct   1860
gaagatgtgt gccttccggc tacccagtgc tttgtagaca gggagggcca gagctcagaa   1920
gctgtccaga gtttggaaga tgagcctacg caagtctttc catgcactct tccccaagag   1980
cctgggcctt cccacctcag cctgcagacg ccaggtccag gtgcccagga tgtgccttgg   2040
gaagtcttag ctacacagcc gttttgtctg agagaagctg aggcctctga actgcagctc   2100
atggacaccc accctgcagc tcatgaatcc cacccatctg tgtctagtgc atcagcagga   2160
cagcagcatc tggttcacac agagccgctg ggaattgaag gcggagagat gcaaactgtg   2220
gagaaagcca tgggccaatt gagttgcaag atggcatctg ctggagagga ctcaaggggt   2280
gatccagaac cctcggccca tcgcctgctt tctccagttc ctgaagcttc ttctccacct   2340
cagagtctgc tcacctctca gagccaaaag ccgtctacac cccagtctct gttacttacc   2400
tctcccccttt ctgagctaca ccttcctgaa actcctcaca ccaagcctaa tgtcaggcct   2460
cggcggtcct ccaggatgac ctcctcccca cactcctctg ctgcccttaa gccctatact   2520
acctgcccca caaacctgcc tgctgcccct agaccaacat ctcgggctac tcggggcagg   2580
ggcagggcaa ataggtcctc taccaggacc ccggaaccag ttgtccctac agactctgag   2640
cttcaacctc ccacctccac agaacagtct gtcatcccca aacccacatc tccagtcact   2700
cagggcagca taaatggttc ctttgttaaa acgcctgaac cagttgttct cacaggtccc   2760
aaaatccagc ctcccacctc cacagaacag cctgttaccc caaaccccac acctcaggcc   2820
actcggggca ggccacatag gtcttccatc cagaccccag aaccacttac tcccactggt   2880
cctgacctcc agcctcccac ctccacagaa cagcctgtca tacctaaacc cacatctcgg   2940
gctgctcggg gcaggtcacg taagtcttct accaggaccc cagaaccagc tgtccccact   3000
ggtcctgacc tccagcctcc cacctccaca gaacagcctg tcacacctaa acccacatct   3060
cgggccactc ggggcaggtc acgtaagtct gtcagaaccc cagaaccagc tgtccccact   3120
ggtcctgacc tccagcttcc cacctccaca gctctgggca ctttgggaag ggcatgtaag   3180
tcctccattg aggattctga atcagttgga ccagtagcct ctgattttga acctcccatc   3240
tccacagacc ttgttgcccc tgaggtgaca ggtcagagca taacactaaa gtcttcacca   3300
ctaagtgctt ctccagtttc tgccacctct gaactccagc cacctgtccc cacagcccag   3360
cctgttctcc tggagcccat tcctcaagcc aaccaccgaa ggcggcggaa ggctgctggg   3420
aaacggggct cccacacagt tcccattggc caaaagcctt actctgcacc ctctgaacct   3480
ggttcccaat cttcaatcaa tcaaggcttg gcattggaag ccgctgagtc tattactgtt   3540
gctcctgagc ctgctgtttc ccaggctcca gagacctcca ctcagaatcc cgtggtgcaa   3600
```

```
aatgaagcag ctgggagatc agggctcatt cccaagcccc agcctgaggt ttctcgatcc   3660
cgcaagaagc cttctactac cacaacctca ccaattcaaa aacgtccccg aagacaaata   3720
ccccagaaga caatagtccc caaggaagaa gatcctgagg aaatgccagt gaaggaagag   3780
cctcaggaga tagcaattcc aacacccggc aaaagaaaga gggaccgtgt agaggatgag   3840
acccagggaa acccaagtcg gagccggcgg gctaaaccta accaagaagc agcagccccc   3900
aaggtactgt tcacaggagt tgtggattct cggggagagc gtgcagtcct ggctctgggt   3960
ggcagtctag ccagctcagt aaatgaggcc tcccacttgg tcactgatcg catccgaaga   4020
acggtcaagt tcttgtgtgc cctggggaag ggcatcccta tcctctccct gaactggctg   4080
tatcagtcca gaaaggctgg tcacttcctg ccacctgatg actacttggt gactgaccct   4140
gaacaagaga agaactttag cttcagcctt cgggactccc tgagccgggc tcggcaacaa   4200
aaactgctgg agggctatga gatttacgtg acccctggag tgcagccacc cccacctcag   4260
atgggcgaga tcatcagctg ctgtgggggc accaacctgc ccagcatgcc ccagtcctat   4320
aagccttacc gagttgtcat aacttgcact gaagacctac ctcgctgcgc tatcccatct   4380
cgactggggc tgcccctcct ctctcctgag ttcctcctga ctggagtgct aaagcaggaa   4440
gtcacaccag aggcctttgt cctttcaaat tag                                4473
```

<210> SEQ ID NO 106
<211> LENGTH: 2412
<212> TYPE: DNA
<213> ORGANISM: Cricetulus griseus
<220> FEATURE:
<221> NAME/KEY: misc_feature
<223> OTHER INFORMATION: Bard1

<400> SEQUENCE: 106

```
atgcaacttt ctgagtctgt ggttggacta ctaggtaggt acacaagccc tgctcgggaa     60
cgaaacccac gaggagcccc gccccttggc gttgagggcg tggccttggg ccgcgctcct    120
ctcagaaatt cgagcgcgct ctcattgcct ctcccctccc tcttacttgc tataaaggag    180
caacccagga tggtctgctg tctgcttcgg ctcatcatca tccagagtgt cgagttcttt    240
gaaatcatca ctaatattct gaaggagcca gtatgcttag gagggtgtga gcacatcttc    300
tgtagtgtgt gtataagtga ttgcgttgga tcaggatgtc ccgtgtgtta cacaccagcc    360
tggatcctag acctcaagat aaacagacaa ttggacaaca tgattcagct ttataggaag    420
cttcaaaatt tgctacatga caataaactt tcagatccaa aagacaacac atctaggaca    480
ggttcatttg atgatgcaga aagcaagaag aattcaataa aaatgtggtt tagtcctcga    540
agtaagaagg ttagatgtgt tgtgaataaa gtatcagtgc caacccagcc tcaaaagaca    600
aaagatgaca aagcccagga agcctccata tacgaatttg tttccacaag tccccctgaa    660
gttgtttcta agagggctaa aacagcttct agaacatctg caaaaaagca gcagaagaaa    720
tctttagctg agatcaacaa gaaggggaat tcaaggccag aaacagaaga tagcaggttt    780
gattctaaag aggaactgaa agaggagagg gttgtctcct gtagccaaat accagttatg    840
gaaagtccac aggtaaatgg tgaaatagac ttgttagcta gtggttctgt tgcagaatct    900
gaatgttctg gaagattgac cgaagtttct ttaccattgg ctgagcatat agtatctcca    960
ggcactgtga gcaagagtga agagactcct gagaagaaag tctgtgtaaa agatcttctt   1020
tcagtagggc gtaatgaaaa tcacaaatac tgtagcaggc ctcctgatcc tacttctaag   1080
aattgtgaga gaagcattcc gagcaccagc agagatgtca ttaaaccaac agtgcttgca   1140
```

gaaaatatac tgttggttga ctgttcttca ctgccttcag accagcttca agttgatgtc 1200
acactcagga gaaagagtaa catatcagat aactccctta gcctttcacc aggcacaccc 1260
ccaccactgc tgaataattc aactcccaga caaatgatgt caaaaccctc catagtgaag 1320
ctgtcaccca gcattaccgc caggaaaaga aaccacagag gagagactct gcttcatatt 1380
gcttctatta agggcgatat accttctgtt gaatacctct tgcaaaacgg aaacgacccc 1440
aatgttaaag accatgctgg atggacacca ttgcatgaag cctgcagtca tgggcacctg 1500
aaggtagtgg aattgctgct ccagcataac gctttggtga ataccacagg ctatcagaat 1560
gacacaccac tgcacgatgc agtcaagaac ggccatgtgg atatagtcag ggtgttactg 1620
tccaatggcg cctccaggaa tgctgttaac atatttggtg tacggcctgt ggattataca 1680
gacaatgaaa atataagatc attattgctg ctaccagaga agagtgaatc atcctcaact 1740
agccagtgtg cagttgtgac tgctggacag cgaagaaatg ggcctctggt gcttataggc 1800
agtgggcttt cttcccaaca gcagaaaatg ctcagcaaac ttgagacagt tctcaaggct 1860
aaaagatgtg ctgagtttga cagtacagta actcatgtca ttgttcctga tgatgaagct 1920
caaagtactc tgaagtgtat gcttgggatt ctcaatgggt gttggatcct gaagtttgac 1980
tgggtgaaag cttgtttgca cagcaaagta cgtgaacagg aagaaaagta cgaagttcct 2040
ggaggtccgc agaagagcag gctcaacaga gagcagctgt tgccaaagct atttgatgga 2100
tgctacttct ttttgggggg aaacttcaaa catcatccaa agaatgatct ccttaagctc 2160
attactgcag caggaggcaa ggtgctcagt agaaagccca agccagacag tgacgtgact 2220
cagaccatca acactgttgc ataccatgcc aaccctgact ctgaccagcg cttctgtaca 2280
cagtacatcg tctatgaaga tctgtttaat tgtcgcccag aaagggttcg gcagggcaaa 2340
gtctggatgg ctccttccac ttggcttatc agctgtgtga tggcctttga attgcttcct 2400
cttgacagct ga 2412

<210> SEQ ID NO 107
<211> LENGTH: 2796
<212> TYPE: DNA
<213> ORGANISM: Cricetulus griseus
<220> FEATURE:
<221> NAME/KEY: misc_feature
<223> OTHER INFORMATION: Lig1 (Ligase 1)

<400> SEQUENCE: 107
atgagaaaaa aagaaccaga gaggaaaggg gagaactctg ctgccaccat gcagaaaagt 60
atcaggtcat ttttccaacc catgaaagag ggtaaagcac agaagccgga gaaggagaca 120
gctaacagca ccaaagagaa ggagccacct ccaaaggtgg cactgaagga gaggaatcga 180
gcagtgcctg agagtgattc tccagtgaag aggcctggaa ggaaggcagc ccaggtccta 240
agcagcgaag gggaggagga agatgaagcc cccagcaccc ctaaagtcca gaagtctgtg 300
tcagactcca aacaaagctc tcctcccagc cctgacgcat gtcctgagaa cagtcctttc 360
cacagtagcc cctccatgga gatctcccca tcaggattcc cgaagcgtcg cactgctcgg 420
aagcagctcc cgaaacggac aattgaggac actgtggagg agcagaatga ggacaaaggc 480
agagcagcca agaaaaggaa gaaggaagaa gaagcacaga ctccaatgga aagcctcaca 540
gagagtgaag atgtaaaacc caaggaagaa aaggaggagg gcaagcatgc tgaggcttcc 600
aagtcccctg agtcgggaac cttgacaaag acagagacca tcccagtgtg taaggccggc 660
gtgaaacaga agcctcagga agaggagcag agcaagcctc ctgccagagg cgccaagaca 720

```
ctcagcagct tcttcactcc ccggaagcca gcagagaaag ccatagtgaa acaagaagag    780
ccaggtactc cagggaagga agagaccaag ggagccctgg atccaacaaa ttacaatcct    840
tccaagagaa actaccaccc cattgaagat gcctgctgga aacatggcca gaaagtccct    900
tttctcgctg tggcccggac ctttgagaag attgaggagg tttctgctcg gctcaagatg    960
gtggagacac tgagcaactt gctgcgctcg gtggtggccc tgtcacctcc agacctgctt   1020
cctgttcttt acctcagcct caaccgcctt gggccacctc agcagggact agagctgggt   1080
gttggtgatg gtgtcctcct taaggcagtt gcccaggcca caggccgtca gctggagtcc   1140
atccgggctg aggtagctga gaagggtgac gtgggactgg tggccgagaa cagccgcagc   1200
actcagagac tcatgctgcc ccctcctccg ctcaccacct ccggggtctt taccaaattc   1260
tgtgacattg cccggctcac tggcagtgct tccatggcca agaagttgga tgtcatcaag   1320
ggcctgtttg ttgcctgccg tcactcggaa gcccggttca ttgccaggtc cctaagtgga   1380
cgcctgcgcc tcgggctggc tgagcagtcc gtcttggctg cccttgccct ggctgtgagc   1440
ctcacacccc ctggccaaga atttccccca gctgttgtgg atgctgggaa gggcaagacc   1500
acagaggcca gaaagacatg gttggaagaa caaggcatga tcttgaagca gaccttctgt   1560
gaggtacctg acctggaccg aatcatcccg gtgctgctgg aacatggcct ggaacgcctc   1620
ccagagcact gcaggctgag cccaggggtc cctcttaaac caatgctggc tcatcccact   1680
cggggtgtca gcgaggtact gaaacgcttt gaggaggtgg actttacctg cgagtacaaa   1740
tatgacgggc agcgggccca gattcatgtt ctggaaggtg gagaggtgaa gatcttcagt   1800
aggaaccagg aagacaacac aggaaagtac ccggacatca tcagccgcat ccccaagatt   1860
aaactcccct cggtcacctc ctttatcctg gacactgagg ctgtggcctg ggaccgggaa   1920
aagaagcaga tccagccatt ccaagtgctc accacacgca agcgcaagga ggttgacgcc   1980
tcggagatac aggtgcaggt gtgtctgtat gcctttgatc tcatctacct caacggagag   2040
tccctgattc gccagcccct gtctcgacgt cggcagctgc tccgggagaa ctttgtggag   2100
acagagggtg agtttgtctt cgccacctcc ctggacacca aggacatcga gcagatcgct   2160
gagttcttgg agcagtccgt gaaggactcc tgtgagggac tgatggtgaa gaccctggat   2220
gttgatgcca cctatgagat tgccaagagg tctcacaact ggctcaagct aaagaaggac   2280
taccttgacg gtgtgggcga cactctggac cttgtggtga ttggcgccta cctgggccgg   2340
gggaagcgtg ccggccggta tgggggcttc ctcttggctg cctatgatga ggagagtgaa   2400
gagctgcagg ccatatgcaa gctgggaact ggattcagtg atgaagagct ggaggagcat   2460
caccagagcc taaaggccct agtgttgccg accccacgcc cctatgtgag gatcgatggg   2520
gcagttgccc cagaccactg gctggaccca aaggtcgtat gggaggtgaa gtgtgcggat   2580
ctctccctgt cccctatcta ccctgctgcg cggggcctgg tggacaaaga gaaagggatc   2640
tcccttcgtt tccctcggtt cattcgtgtc cgtgaagaca agcagccaga gcaggccacc   2700
accagtgacc aggtggcctg tttgtaccgg aagcagagtc agatacagaa ccagcacaac   2760
tcagacttgg actccgactt tgaggactgc tattaa                             2796
```

<210> SEQ ID NO 108
<211> LENGTH: 2121
<212> TYPE: DNA
<213> ORGANISM: Cricetulus griseus
<220> FEATURE:
<221> NAME/KEY: misc_feature
<223> OTHER INFORMATION: Mre11

<400> SEQUENCE: 108
atgagccctg cagatccact tgatgatgaa gacactttta aaatcctggt tgccactgat 60
attcaccttg gatttatgga gaaagatgca gttcgaggaa atgatacatt tgtgacactt 120
aatgaaattt taaaacttgc cctggaaaat gaagtggatt ttattttgtt aggtggtgat 180
cttttccatg aaaacaagcc ctcaaggaaa actcttcata gttgcttgga gttgcttagg 240
aagtactgta tgggtgatcg ccctgtgcag tttgagatca tcagtgacca gtcagtcaac 300
tttggtttta gtaggtttcc atgggtgaac tatcaggatg gcaatctcaa catttccatt 360
ccagtgttta gtatccatgg caaccatgac gatcccacag gggcagatgc cctctgtgcc 420
ctggatattt taagctgtgc tgggtttgtg aatcactttg gacggtcaat gtctgtggag 480
aagattgaca ttagtccagt tctgctgcag aaaggaagca caaaacttgc tctgtacggc 540
ctagggtcca ttcctgatga aaggctctat cggatgtttg tcaataaaaa agtaacaatg 600
ctgagaccaa aggaagatga gaactcatgg tttaacttat ttgtgattca tcagaacagg 660
agtaaacatg gaagtaccaa cttcatccca gaacagtttt tggatgactt cattgacctc 720
gttatctggg gccatgaaca cgagtgtaaa attggcccaa ccaaaaatga gcagcagctc 780
ttctatgtgt ctcagcctgg aagctcagtg gtgacttctc tttcccctgg agaagctgtt 840
aagaaacacg tgggcttgct gcgcgttaaa gggaggaaga tgaacctgca gaagctgcct 900
ctccgcacag tgcggcagtt cttcatggag gatgtggttc tcgctaacca cccaaacctg 960
ttcaaccctg acaatcctaa ggtgacccag gccatccaga gcttctgctt ggagaagatt 1020
gaagaaatgc ttgaaaatgc cgagcgcgaa cggctaggga attctcttca accagagaag 1080
cctcttatcc gactacgggt ggactacagt ggaggctttg aaccttttag tgttcttcgc 1140
tttagccaga aatttgtgga tcgggtcgct aaccccaaag atatcatcca ctttttcagg 1200
catagggagc aaaagggaaa aacaggtgaa gagatcaact ttgggaagct tgtttcaaaa 1260
tctccttcgg aaggaacgac actcagagta gaagacctgg tgaagcagta tttccagact 1320
gcggagaaga atgttcagct ctcactgctg acagaaagag ggatgggtga agccgttcaa 1380
gaatttgtgg acaaggaaga aaaagatgcc atcgaggaat tagtgaagta ccagctggag 1440
aaaacacagc ggtttcttaa ggagcgccat atcgatgctc tggaagacaa gattgacgaa 1500
gaggtccggc gtttcagaga aagcagacag agaaatacca acgaagaaga cgatgaagtg 1560
cgagaggcca tgagcagggc ccgggcgctc agatcgcagt cagagaactc tgcctcagcc 1620
ttcagtgctg acgacctgag tttcgatata gcagaacaga cagcaaatga ctctgatgac 1680
agcctgtcag cagtgcccag cagaggccgg ggccgaggcc gaggtcgaag aggaggcaga 1740
gggcagagca ccgcatcaag aggaggatct cagagaggcc gagacactgg gcaggagacg 1800
gctactcgag gcagatgctc aaaggccact acatcgacct ctagaaatat gtccattcta 1860
gacgctttca gatctactcg acagcagcct tccagaaaca ctgccactaa aaattactca 1920
gagactattg aagtggatga atctgatgaa gatgacattt ttcctaccag ttccaaggct 1980
gatcaaaggt ggccaggcac aacatctagc aaacggatgt cccagagcca gatagccaag 2040
ggggttgact ttgaatcaga tgaggacgat gacgatgacc ctttcatgag cagtagttct 2100
ctaagaagcc gaagataata a 2121

<210> SEQ ID NO 109
<211> LENGTH: 5973
<212> TYPE: DNA

<213> ORGANISM: Cricetulus griseus
<220> FEATURE:
<221> NAME/KEY: misc_feature
<223> OTHER INFORMATION: 53BP1

<400> SEQUENCE: 109
atgccagggg agcagatgga ccctactgga agtcagttgg attcagattt ctctcagcaa 60
gatactcctt gcctgataat tgaagattct cagcctgaaa gccaggttct ggaagaagat 120
gcgggctctc acttcagtgt gctgtctcga caccttccca atctgcagat acacaaagag 180
aaccctgtgt tggatattgt gtccaatccg gaacaagcag ctgcagaaga gcaaggagac 240
aataatagct ccttcaatga acatctgaaa gagaacaaag ctgctgcaga tcctgtggat 300
tccactcatt tgggcacatg tgattccatc agtcaggtca tagaacagtt gcctcagcca 360
aacaggacaa gcagtgttct gggagtgaca gtggaagctg cttctcttcc agaagaggag 420
aaggaggaag agctggaaga ggagaatgaa gaggtgggag cagatgctgc tgatgccgct 480
ccgtgctccc ttggtgctga agattctgct tcatcacagt tgggctttgg ggttctggaa 540
ctgtcccaga gccaggatgt tgaagaacat acagtgccat atgatgtcaa ccaagaacat 600
atgcagttgg ttaccaccaa ctcgggttct tcccagctgt ctgacatgga tgcaaataat 660
gttaaatgtg aagaacagtc cactgaagat acctccatgg cagaacaacc taacaaagac 720
atccctgtta cagtcgagca cagtaaaggt atccctgtgg tagatgagca aaatctacca 780
ccggcaaggc cagaggatct gccttccagt cctcaagcct ctgctgcagc tgtggaaaca 840
aaggaagagg tacctgccca agagttgcca gaaggggcgc tggaggttca gatgtcctcg 900
gagcctgagg tctcgtccac tcaggaggac ttgtttgagc agagtagtaa aacagcttct 960
gatggttgtt ctactccttc aagggaggaa ggtgggtgtt ctccggtttc cacacccgcc 1020
accaccctgc aactcctgca gctgtctggt cagaggcccc ttgtccagga cagtctttcc 1080
acgaattcct cagatcttgt tgctccttcc cctgatgctt tccgacctac cccttttatc 1140
gttcctagca gtcccacaga gcaaggaggg agaaaagttg agcccttgga tatgtcagtg 1200
atgcctgaag aaggagggga gactttgcag aagcttcagg atgacgaagc agtggagata 1260
gaaaagcccc atctcccatc tcagccggct gtttccccac aagtgtcaac accagtgtct 1320
cagagcacac ctgtcttcac tccaggctct cttcccatcc cgtcccagcc tgaattttct 1380
catgacattt tcattccatc accaagtttg gaagaaccat caagtgatgg gaagaaaggt 1440
ggcgatttgc acagctcatc tttgactgtg gagtgttcta agacttcaga gagtgaacca 1500
aagaatttca ctgctgatct tgggctctcc ttgacagggg agtcttgcaa actgatgctt 1560
tcttcaagtg agtatagtca atcctcaaag atggagagct tggcttctcc caggagtgag 1620
ggagatggag agaataccca gattgaggac actgaaccgt tgtctccagt caccaattct 1680
aaacttcctg ctgaaagtga tgatgtcctg atgaatccag caccagatga ccaagtagaa 1740
atgaatcaga atgatgacaa agtaaaagag ggtgacacag agaacacagg tgaccatggt 1800
gttttagctg ctggtagtaa aggcagagaa gaaaccgttg ctgaagatgt ttgcattgat 1860
ctcacttgtg attctgggag tcaggcagtt ccgtctcccg ctactcggtc cgaggcactt 1920
tctagtgtct tagatcagga ggaagctatg gaaattaaag aacagcatcc agaggagggg 1980
ttttcgggat ctgaggtaga agaagtcccc gagactccct gtgaaagtca cagagaggag 2040
cccaaggaag aaacgatgga gagtatccca ctgcaccttt ctcttactga aacacagtcc 2100
caggcattgt gtcttcagaa ggaaatgccc aaagaagaat gcccagaggc catggaagtg 2160

-continued

```
gaaccctctg tgattagtgt tgactctccc cagaagctgc cggtactcga ccaggagtca   2220
gagcataagg agccagaggc ctgggaagaa gccgcgtcgg aggactcaag tgtggaggac   2280
tcaagtgtgg ttatcgttga tgtgaaggag ccctcgccaa gagttgtccc ctgcgaacct   2340
ttggagggag cagagaaatg ctcagattcc cactcctggg aggatgtggt gcccgaggtg   2400
gaaccgtgtg ctgcaaatag agtagacact ccggaggaaa agattgtaga atgtgacgga   2460
gatgtgaaag cagagaccac aagaaaggac tctgtagagg aagactcccc acagcctcct   2520
ttgccttcag tgaaagacga gcctcccaga gacgagcctc ccagacccga ccaggagatg   2580
cagcagtccc agcttcaaga gaaagagagc ccagtgacca tagatgcaaa agtggctgat   2640
gccaagcagc tggagtcaga gggagcatcc cagcagcttt cgaaagcccc tgcccgcgac   2700
tcacaaagtt tctgtgaaag ttctagtgaa accccatttc atttcacttt gcctaaagaa   2760
ggtgatatta tcccaccatt gactggtgca accccacctc acattgggca cctaaaattg   2820
gatcgcaaca gacatagtac tccaattggg attggcaact atccagaaag caccatagca   2880
accagtgatg tcatgtctga aagcatggtg gagatcaatg atcctctact tgggagtgaa   2940
aaaggagatt ctgagtctgc cccagaaatg gacggaaaac tgtatctgaa aatgaaactg   3000
gttagtcctg agacagaggc cagtgaagaa tctttgcagt ttagcctgga aaagcctgct   3060
actgctgaga gaaaaaatgg atcaactgct gttgctgagc ctgttgcaaa aaatggatca   3120
actgctgttg ctgagcctgt tgccagtccc cagaagaccg tgcctgtgtt tagctgcagg   3180
caagaggagg tttggagtga ggaccctccc tctgtaccca tcagggcaaa cttgctccat   3240
tttccaagtg ttgaagaaga ggacaaagaa aaactggatg gtaccccaaa gcttaggcag   3300
agtgaacagc ctgtgaggcc cgttgggctg gtcaaggatg ctgctacttc tgaggactct   3360
gcttcttctg ttccccagca gagagcaaca caggggtcat tcagccctca aggagaagtg   3420
atggaaacag acctgctaga aggactgagt gctaaccagg aaaaaccgtg taaggtcttg   3480
atggaaaggc ccacccagag taacatagga atccagacca tggaccattc cctgtgtgct   3540
ccagaaactg tttcagcagc aacccagact gtgaagagtg tatgtgaaca agggaccagt   3600
acagtggacc agaactctgg gaaacaagat gccactgtgc agaccgagag ggggggtgtc   3660
gagaaacagg cccctgtgga cgatacagaa tccctccaca gccagggaga agaagaattt   3720
gaaatgcccc agcctccaca tggccatgtc ttgcatcgtc acatgagaac catccgtgaa   3780
gtccggacac ttgtcacccg tgtcatcaca gatgtttact atgtggatgg gacagaagtg   3840
gaaaggaaag taactgagga gactgaagaa ccaattgtag aatgtcagga atgtgaaaca   3900
gaggtttccc cttcccagac tggaggctct tctggagacc tgggagacat cagttccttc   3960
tcctccaaag catccagctc acaccataca tcaagtggga caagtctctc agccatgcat   4020
agcagtggca gctcaggacg aggagccggg ccactcaaag ggaaaaccag cgggacagaa   4080
cctgcagatt ttgctttacc cagttcccga ggaggcccag gaaaactgag tcctagaaaa   4140
gggatcaatc agacaggggc accagtgtgt gaggaagatg gtgatgcagg ccttggcatc   4200
agacagggag ggaaggctcc tgtcacacct cgtggtcgtg gtcgaagggg ccgcccacct   4260
tctcggacca ctggaacaag agatgcagtt gtgtctggtc cgttgggcat agaagacatt   4320
tcacctagca tgtcaccaga tgacaagtcc ttcacccgaa ttgtgccccg tgtaccagac   4380
tctaccaaac gaattgatac cagttctact gttttgaggc ggagtgattc cccagagatt   4440
ccttttcagg ctgctactgg gtcttctgat ggcttggatg cctcatctcc aggaaatagc   4500
tttgtcgggc tccgtgttgt agccaagtgg tcatccaatg gctattttta ctctgggaaa   4560
```

```
atcacacggg atgttggagc tgggaagtat aagctgctct tcgatgatgg gtatgaatgt   4620

gatgtgctgg gcaaagacat tctcctgtgt gaccctatac ccctggacac tgaagtgaca   4680

gccctctcag aagatgagta tttcagtgca ggagtggtca aaggacacag aaaggagtct   4740

ggggagctgt actacagcat tgaaaaagaa ggccaaagga agtggtataa gcggatggca   4800

gtcatcctgt ccttggaaca aggaaacagg ttaagagagc aatatgggct tggcccatat   4860

gaagctgtta cacccctcac aaaggcagca gacatcagcc tagataattt ggtggaagga   4920

aagcggaaac gtcgcagtaa catcagctcc ccagccaccc ccactgcctc cagcagcagc   4980

agcagcagca gcacaacacc cacccgtaaa accacagaga gtccccgtgc ttccacggga   5040

gttccatcag gcaaaaggaa actcatcact tctgaagagg aacggtcccc agctaagcga   5100

ggccgcaagt ctgtcaccgt gaaacctggt acagtggggg caggagaatt tgtgagcccc   5160

tgcgagagtg gagacaacac aggtgaacct tctgtcctgg aagagccaag agggcctttg   5220

cccctcaaca agaccttgtt tctgggctat gcctttctcc ttaccatggc cacaaccaat   5280

gacaagctgg ccagccgctc taaactgcta gatggtccta caggaagcag tgaagaagag   5340

gaggaatttt tagaaattcc tcctttcaac aagcagtata cagaatgcca gcttcgagca   5400

ggagctgggt atatccttga agacttcaat gaagcccagt gtaacacagc ctaccagtgt   5460

ctcctaattg ctgatcagca ttgtcgaacc cggaagtact tcctgtgcct tgccagtgga   5520

attccttgtg tgtctcatgt ctgggtccat gacagctgcc atgccaacca gctccaaaac   5580

taccgtaatt atctgctgcc tgctgggtat agccttgagg agcagcgaat tctggattgg   5640

caacctcgtg aaaacccttt ccagaatctg aaggtactct tggtgtcaga tcaacaacag   5700

aacttcctgg agctctggtc tgagatcctc atgactggag gggcagcctc tgtgaagcag   5760

caccattcaa gtgcccataa caaagacatt gctttagggg tatttgatgt ggtggtgaca   5820

gacccctcat gcccagcctc ggtgctcaag tgtgctgaag ccttgcagct gcctgtggtg   5880

tcacaagagt gggtgatcca gtgcctcatt gttggggaga gaattggatt caagcagcat   5940

ccaaaatata aacatgatta tgtttctcac taa                               5973
```

<210> SEQ ID NO 110
<211> LENGTH: 384
<212> TYPE: DNA
<213> ORGANISM: Human cytomegalovirus
<220> FEATURE:
<221> NAME/KEY: misc_feature
<223> OTHER INFORMATION: CMV IE enhancer

<400> SEQUENCE: 110

```
gttgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atgg                                           384
```

<210> SEQ ID NO 111
<211> LENGTH: 799
<212> TYPE: DNA
<213> ORGANISM: Homo sapiens
<220> FEATURE:
<221> NAME/KEY: misc_feature
<223> OTHER INFORMATION: Human GAPDH promoter

<400> SEQUENCE: 111

```
gagaagttcc ccaactttcc cgcctctcag cctttgaaag aaagaaaggg gagggggcag     60

gccgcgtgca gccgcgagcg gtgctgggct ccggctccaa ttccccatct cagtcgttcc    120

caaagtcctc ctgtttcatc caagcgtgta agggtccccg tccttgactc cctagtgtcc    180

tgctgcccac agtccagtcc tgggaaccag caccgatcac ctcccatcgg gccaatctca    240

gtcccttccc ccctacgtcg gggcccacac gctcggtgcg tgcccagttg aaccaggcgg    300

ctgcggaaaa aaaaaagcgg ggagaaagta gggcccggct actagcggtt ttacgggcgc    360

acgtagctca ggcctcaaga ccttgggctg ggactggctg agcctggcgg gaggcggggt    420

ccgagtcacc gcctgccgcc gcgcccccgg tttctataaa ttgagcccgc agcctcccgc    480

ttcgctctct gctcctcctg ttcgacagtc agccgcatct tcttttgcgt cgccaggtga    540

agacgggcgg agagaaaccc gggaggctag ggacggcctg aaggcggcag gggcgggcgc    600

aggccggatg tgttcgcgcc gctgcggggt gggcccgggc ggcctccgca ttgcaggggc    660

gggcggagga cgtgatgcgg cgcgggctgg gcatggaggc ctggtggggg aggggagggg    720

aggcgtgtgt gtcggccggg gccactaggc gctcactgtt ctctccctcc gcgcagccga    780

gccacatcgc tcagacacc                                                 799
```

<210> SEQ ID NO 112
<211> LENGTH: 1188
<212> TYPE: DNA
<213> ORGANISM: Homo sapiens
<220> FEATURE:
<221> NAME/KEY: misc_feature
<223> OTHER INFORMATION: Human Ef1 alpha promoter

<400> SEQUENCE: 112

```
catgggtgag gctccggtgc ccgtcagtgg gcagagcgca catcgcccac agtccccgag     60

aagttggggg gaggggtcgg caattgaacc ggtgcctaga gaaggtggcg cggggtaaac    120

tgggaaagtg atgtcgtgta ctggctccgc ctttttcccg agggtggggg agaaccgtat    180

ataagtgcag tagtcgccgt gaacgttctt tttcgcaacg ggtttgccgc cagaacacag    240

gtaagtgccg tgtgtggttc ccgcgggcct ggcctcttta cgggttatgg cccttgcgtg    300

ccttgaatta cttccacctg gctgcagtac gtgattcttg atcccgagct tcgggttgga    360

agtgggtggg agagttcgag gccttgcgct taaggagccc cttcgcctcg tgcttgagtt    420

gaggcctggc ctgggcgctg gggccgccgc gtgcgaatct ggtggcacct tcgcgcctgt    480

ctcgctgctt tcgataagtc tctagccatt taaaattttt gatgacctgc tgcgacgctt    540

tttttctggc aagatagtct tgtaaatgcg ggccaagatc tgcacactgg tatttcggtt    600

tttggggccg cgggcggcga cggggcccgt gcgtcccagc gcacatgttc ggcgaggcgg    660

ggcctgcgag cgcggccacc gagaatcgga cgggggtagt ctcaagctgg ccggcctgct    720

ctggtgcctg gcctcgcgcc gccgtgtatc gccccgccct gggcggcaag gctggcccgg    780

tcggcaccag ttgcgtgagc ggaaagatgg ccgcttcccg gccctgctgc agggagctca    840

aaatggagga cgcggcgctc gggagagcgg gcgggtgagt cacccacaca aaggaaaagg    900

gcctttccgt cctcagccgt cgcttcatgt gactccacgg agtaccgggc gccgtccagg    960

cacctcgatt agttctcgag cttttggagt acgtcgtctt taggttgggg ggaggggttt   1020
```

-continued tatgcgatgg agtttcccca cactgagtgg gtggagactg aagttaggcc agcttggcac 1080
ttgatgtaat tctccttgga atttgccctt tttgagtttg gatcttggtt cattctcaag 1140
cctcagacag tggttcaaag ttttttttctt ccatttcagg tgtcgtga 1188

<210> SEQ ID NO 113
<211> LENGTH: 985
<212> TYPE: DNA
<213> ORGANISM: Simian cytomegalovirus
<220> FEATURE:
<221> NAME/KEY: misc_feature
<223> OTHER INFORMATION: CMV promoter

<400> SEQUENCE: 113
gaccatagcc aattcaatat ggcgtatatg gactcatgcc aattcaatat ggtggatctg 60
gacctgtgcc aattcaatat ggcgtatatg gactcgtgcc aattcaatat ggtggatctg 120
gaccccagcc aattcaatat ggcggacttg gcaccatgcc aattcaatat ggcggacttg 180
gcactgtgcc aactggggag gggtctactt ggcacggtgc caagtttgag gaggggtctt 240
ggccctgtgc caagtccgcc atattgaatt ggcatggtgc caataatggc ggccatattg 300
gctatatgcc aggatcaata tataggcaat atccaatatg gccctatgcc aatatggcta 360
ttggccaggt tcaatactat gtattggccc tatgccatat agtattccat atatgggttt 420
tcctattgac gtagatagcc cctcccaatg ggcggtccca tataccatat atggggcttc 480
ctaataccgc ccatagccac tcccccattg acgtcaatgg tctctatata tggtctttcc 540
tattgacgtc atatgggcgg tcctattgac gtatatggcg cctcccccat tgacgtcaat 600
tacggtaaat ggcccgcctg gctcaatgcc cattgacgtc aataggacca cccaccattg 660
acgtcaatgg gatggctcat tgcccattca tatccgttct cacgcccccct attgacgtca 720 atgacggtaa atggcccact tggcagtaca tcaatatcta ttaatagtaa cttggcaagt 780
acattactat tggaaggacg ccagggtaca ttggcagtac tcccattgac gtcaatggcg 840
gtaaatggcc cgcgatggct gccaagtaca tccccattga cgtcaatggg gaggggcaat 900
gacgcaaatg ggcgttccat tgacgtaaat gggcggtagg cgtgcctaat gggaggtcta 960
tataagcaat gctcgtttag ggaac 985

<210> SEQ ID NO 114
<211> LENGTH: 197
<212> TYPE: DNA
<213> ORGANISM: Simian virus 40
<220> FEATURE:
<221> NAME/KEY: misc_feature
<223> OTHER INFORMATION: SV40 promoter

<400> SEQUENCE: 114
tgcatctcaa ttagtcagca accatagtcc cgcccctaac tccgcccatc ccgcccctaa 60
ctccgcccag ttccgcccat tctccgcccc atcgctgact aattttttttt atttatgcag 120 aggccgaggc cgcctcggcc tctgagctat tccagaagta gtgaggaggc ttttttggag 180
gcctaggctt ttgcaaa 197

<210> SEQ ID NO 115
<211> LENGTH: 999
<212> TYPE: DNA
<213> ORGANISM: Cricetulus griseus
<220> FEATURE:
<221> NAME/KEY: misc_feature
<223> OTHER INFORMATION: CHO Actb promoter

<400> SEQUENCE: 115
gggcggaggc cagtcatgca tgttcgggcc tatggggcca gcacccaacg ccaaaactct 60
ccatcctctt cctcaatctc gctttctctc tctctctctt tttttttttt tttttttttt 120
tttttttttt tttgcaaaag gaggggagag ggggtaaaaa aatgctgcac tgtgcggcta 180
ggccggtgag tgagcggcgc ggagccaatc agcgctcgcc gttccgaaag ttgcctttta 240
tggctcgagt ggccgctgtg gcgtcctata aaacccggcg gcgcaacgcg cagccactgt 300
cgagtccgcg tccacccgcg agcacaggcc tttcgcagct ctttcttcgc cgctccacac 360
ccgccaccag gtaagcaggg acaacaggcc cagccggcca cagccctccc gtgggcagtg 420
accgcgctgc agggtcgcgg gggacactcg gcgcggacac cggggaaggc tggagggtgg 480
tgccgggccg cggagcggac actttcagat ccaactttca gtccagggtg tagacccttt 540
acagccgcat tgccacggtg tagacaccgg tggacccgct ctggctcaga gcacgcggct 600
tgggggaacc cattagggtc gcagtgtggg cgctatgaga gccgatgcag ctttcgggtg 660
ttgaaccgta tctgcccacc ttggggggag gacacaaggt cgggagccaa acgccacgat 720
catgccttgg tggcccatgg gtctttgtct aaaccggttt gcccatttgg cttgccgggc 780
gggcgggcgc ggcgggcccg gctcggccgg gtgggggctg ggttgccact gcgcttgcgc 840
gctctatggc tgggtattgg ggcgcgtgca cgctggggag ggagcccttc ctcttccccc 900
tctcccaagt taaacttgcg cgtgcgtatt gagacttgga gcgcggccac cggggttggg 960
cgagggcggg gccgttgtcc ggaaggggcg gggtcgcag 999

<210> SEQ ID NO 116
<211> LENGTH: 683
<212> TYPE: DNA
<213> ORGANISM: Cricetulus griseus
<220> FEATURE:
<221> NAME/KEY: misc_feature
<223> OTHER INFORMATION: CHO Hspa5 promoter

<400> SEQUENCE: 116
acccgagggg acttaggagg agaaaaggcc gcatactgct tcggggtaag ggacagaccg 60
gggaaggacc caagtcccac cgcccagagg gaactgacac gcagaccccg cagcagtccc 120
cgggggccgg gtgacgggag gacctggacg gttaccggcg gaaacggtct cgggttgaga 180
ggtcacctga gggacaggca gctgctgaac caataggacc ggcgcacagg gcggatgctg 240
cctctcattg gcggccgttg agagtaacca gtagccaatg agtcagcccg gggggcgtag 300
cggtgacgta agttgcggag gaggccgctt cgaatcggca gcggccagct tggtggcatg 360
gaccaatcag cgtcctccaa cgagaagcgc cttcaccaat cggaggcctc cacgacgggg 420
ctggggggag ggtatataag ccaagtcggc ggcggcgcgc tccacactgg ccaagacaac 480
agtgaccgga ggacctgcct ttgcggctcc gagaggtaag cgccgcggcc tgctcttgcc 540
agacctcctt tgagcctgtc tcgtggctcc tcctgacccg gggggcttct gtcgccctca 600
gatcggaacg ccgccgcgct ccgggactac agcctgttgc tggacttcga gactgcagac 660
ggaccgaccg ctgagcactg gcc 683

<210> SEQ ID NO 117
<211> LENGTH: 18
<212> TYPE: PRT
<213> ORGANISM: Artificial Sequence
<220> FEATURE:
<223> OTHER INFORMATION: consensus sequence topoisomerare II
(vertebrates)

<400> SEQUENCE: 117

Arg Asn Tyr Asn Asn Cys Asn Asn Gly Tyr Asn Gly Lys Thr Asn Tyr
1               5                   10                  15

Asn Tyr

<210> SEQ ID NO 118
<211> LENGTH: 15
<212> TYPE: PRT
<213> ORGANISM: Artificial Sequence
<220> FEATURE:
<223> OTHER INFORMATION: consensus sequence topoisomerase II
(Drosophila)

<400> SEQUENCE: 118

Gly Thr Asn Trp Ala Tyr Ala Thr Thr Asn Ala Thr Asn Asn Arg
1               5                   10                  15

<210> SEQ ID NO 119
<211> LENGTH: 20
<212> TYPE: DNA
<213> ORGANISM: Artificial Sequence
<220> FEATURE:
<223> OTHER INFORMATION: GFP forward primer

<400> SEQUENCE: 119
acattatgcc ggacaaagcc 20

<210> SEQ ID NO 120
<211> LENGTH: 25
<212> TYPE: DNA
<213> ORGANISM: Artificial Sequence
<220> FEATURE:
<223> OTHER INFORMATION: GFP-reverse primer

<400> SEQUENCE: 120
ttgtttggta atgatcagca agttg 25

<210> SEQ ID NO 121
<211> LENGTH: 19
<212> TYPE: DNA
<213> ORGANISM: Artificial Sequence
<220> FEATURE:
<223> OTHER INFORMATION: B2M forward primer

<400> SEQUENCE: 121
accactctga aggagccca 19

<210> SEQ ID NO 122
<211> LENGTH: 20
<212> TYPE: DNA
<213> ORGANISM: Artificial Sequence
<220> FEATURE:
<223> OTHER INFORMATION: B2M reverse primer

<400> SEQUENCE: 122
ggaagctcta tctgtgtcaa 20

<210> SEQ ID NO 123
<211> LENGTH: 19
<212> TYPE: RNA
<213> ORGANISM: Artificial Sequence
<220> FEATURE:
<223> OTHER INFORMATION: si RNA 53BP1_1

<400> SEQUENCE: 123
ucagaaugau gacaaagua 19

<210> SEQ ID NO 124
<211> LENGTH: 19
<212> TYPE: RNA
<213> ORGANISM: Artificial Sequence
<220> FEATURE:
<223> OTHER INFORMATION: si RNA 53BP1_2

<400> SEQUENCE: 124
gagcaaggag acaauaaua 19

<210> SEQ ID NO 125
<211> LENGTH: 19
<212> TYPE: RNA
<213> ORGANISM: Artificial Sequence
<220> FEATURE:
<223> OTHER INFORMATION: Si RNA 53BP1_3

<400> SEQUENCE: 125
caaagacauc ccuguuaca 19

<210> SEQ ID NO 126
<211> LENGTH: 19
<212> TYPE: RNA
<213> ORGANISM: Artificial Sequence
<220> FEATURE:
<223> OTHER INFORMATION: si RNA Brca1_1

<400> SEQUENCE: 126
ccacguaacu gaaauuaua 19

<210> SEQ ID NO 127
<211> LENGTH: 19
<212> TYPE: RNA
<213> ORGANISM: Artificial Sequence
<220> FEATURE:
<223> OTHER INFORMATION: si RNA Brca1_2

<400> SEQUENCE: 127
aaggcugagu ucuauaaua 19

<210> SEQ ID NO 128
<211> LENGTH: 19
<212> TYPE: RNA
<213> ORGANISM: Artificial Sequence
<220> FEATURE:
<223> OTHER INFORMATION: si RNA Brca1_3

<400> SEQUENCE: 128
agagccaaau gaacaaaga 19

<210> SEQ ID NO 129
<211> LENGTH: 19
<212> TYPE: RNA
<213> ORGANISM: Artificial Sequence
<220> FEATURE:
<223> OTHER INFORMATION: si RNA Brca2_1

<400> SEQUENCE: 129
gaagcuguuu acagaauga 19

<210> SEQ ID NO 130
<211> LENGTH: 19
<212> TYPE: RNA

<213> ORGANISM: Artificial Sequence
<220> FEATURE:
<223> OTHER INFORMATION: si RNA Brca2_2

<400> SEQUENCE: 130
caaugacuau acagacaaa 19

<210> SEQ ID NO 131
<211> LENGTH: 19
<212> TYPE: RNA
<213> ORGANISM: Artificial Sequence
<220> FEATURE:
<223> OTHER INFORMATION: si RNA Brca2_3

<400> SEQUENCE: 131
aacagacggu ugccauaaa 19

<210> SEQ ID NO 132
<211> LENGTH: 19
<212> TYPE: RNA
<213> ORGANISM: Artificial Sequence
<220> FEATURE:
<223> OTHER INFORMATION: si RNA cycD1_1

<400> SEQUENCE: 132
uggaacuccu ucuggugaa 19

<210> SEQ ID NO 133
<211> LENGTH: 19
<212> TYPE: RNA
<213> ORGANISM: Artificial Sequence
<220> FEATURE:
<223> OTHER INFORMATION: si RNA cycD1_2

<400> SEQUENCE: 133
cgcacuuucu uuccagagu 19

<210> SEQ ID NO 134
<211> LENGTH: 19
<212> TYPE: RNA
<213> ORGANISM: Artificial Sequence
<220> FEATURE:
<223> OTHER INFORMATION: si RNA cycD1_3

<400> SEQUENCE: 134
ugccagaggc ggaugagaa 19

<210> SEQ ID NO 135
<211> LENGTH: 19
<212> TYPE: RNA
<213> ORGANISM: Artificial Sequence
<220> FEATURE:
<223> OTHER INFORMATION: si RNA DNA-PKcs_1

<400> SEQUENCE: 135
ggaucgagcu guucagaaa 19

<210> SEQ ID NO 136
<211> LENGTH: 19
<212> TYPE: RNA
<213> ORGANISM: Artificial Sequence
<220> FEATURE:
<223> OTHER INFORMATION: si RNA DNA-PKcs_2

<400> SEQUENCE: 136
agaugauguu cacucuaaa 19

-continued

<210> SEQ ID NO 137
<211> LENGTH: 19
<212> TYPE: RNA
<213> ORGANISM: Artificial Sequence
<220> FEATURE:
<223> OTHER INFORMATION: DNA-PKcs_3

<400> SEQUENCE: 137
auccaucggu aucuuuaaa 19

<210> SEQ ID NO 138
<211> LENGTH: 19
<212> TYPE: RNA
<213> ORGANISM: Artificial Sequence
<220> FEATURE:
<223> OTHER INFORMATION: si RNA Ku70_1

<400> SEQUENCE: 138
ggugcccuuu acugagaaa 19

<210> SEQ ID NO 139
<211> LENGTH: 19
<212> TYPE: RNA
<213> ORGANISM: Artificial Sequence
<220> FEATURE:
<223> OTHER INFORMATION: si RNA Ku70_2

<400> SEQUENCE: 139
aaagcccaag guagaguua 19

<210> SEQ ID NO 140
<211> LENGTH: 19
<212> TYPE: RNA
<213> ORGANISM: Artificial Sequence
<220> FEATURE:
<223> OTHER INFORMATION: si_RNA Ku70_3

<400> SEQUENCE: 140
acauuuccaa gacacaauu 19

<210> SEQ ID NO 141
<211> LENGTH: 19
<212> TYPE: RNA
<213> ORGANISM: Artificial Sequence
<220> FEATURE:
<223> OTHER INFORMATION: si RNA Ku80_1

<400> SEQUENCE: 141
gaaacugucu auugcuuaa 19

<210> SEQ ID NO 142
<211> LENGTH: 19
<212> TYPE: RNA
<213> ORGANISM: Artificial Sequence
<220> FEATURE:
<223> OTHER INFORMATION: si RNA Ku80_2

<400> SEQUENCE: 142
ccauagggaa gaaguuuga 19

<210> SEQ ID NO 143
<211> LENGTH: 19
<212> TYPE: RNA
<213> ORGANISM: Artificial Sequence
<220> FEATURE:

<223> OTHER INFORMATION: si RNA Ku80_3

<400> SEQUENCE: 143
ggauuccuau gaguguuua 19

<210> SEQ ID NO 144
<211> LENGTH: 19
<212> TYPE: RNA
<213> ORGANISM: Artificial Sequence
<220> FEATURE:
<223> OTHER INFORMATION: si RNA LigIV_1

<400> SEQUENCE: 144
agagccuccu ucaguuaau 19

<210> SEQ ID NO 145
<211> LENGTH: 19
<212> TYPE: RNA
<213> ORGANISM: Artificial Sequence
<220> FEATURE:
<223> OTHER INFORMATION: si RNA LigIV_2

<400> SEQUENCE: 145
cuauacagca gguaaauga 19

<210> SEQ ID NO 146
<211> LENGTH: 19
<212> TYPE: RNA
<213> ORGANISM: Artificial Sequence
<220> FEATURE:
<223> OTHER INFORMATION: si RNA LigIV_3

<400> SEQUENCE: 146
agagguauga uauccuuaa 19

<210> SEQ ID NO 147
<211> LENGTH: 19
<212> TYPE: RNA
<213> ORGANISM: Artificial Sequence
<220> FEATURE:
<223> OTHER INFORMATION: si RNA Rad51_1

<400> SEQUENCE: 147
gugccaauga ugugaagaa 19

<210> SEQ ID NO 148
<211> LENGTH: 77
<212> TYPE: DNA
<213> ORGANISM: Artificial Sequence
<220> FEATURE:
<223> OTHER INFORMATION: Rad51 shRNA coding sequence (Rad51_1)

<400> SEQUENCE: 148
acaagcttgt gccaatgatg tgaagaattc aagagattct tcacatcatt ggcactctag 60
agtcggggcg gccggcc 77

<210> SEQ ID NO 149
<211> LENGTH: 19
<212> TYPE: RNA
<213> ORGANISM: Artificial Sequence
<220> FEATURE:
<223> OTHER INFORMATION: si RNA Rad51_2

<400> SEQUENCE: 149
gggaauuagu gaagccaaa 19

```
<210> SEQ ID NO 150
<211> LENGTH: 77
<212> TYPE: DNA
<213> ORGANISM: Artificial Sequence
<220> FEATURE:
<223> OTHER INFORMATION: Rad51 shRNA coding sequence (Rad51_2)

<400> SEQUENCE: 150

acaagcttgg gaattagtga agccaaattc aagagatttg gcttcactaa ttccctctag      60

agtcggggcg gccggcc                                                    77

<210> SEQ ID NO 151
<211> LENGTH: 19
<212> TYPE: RNA
<213> ORGANISM: Artificial Sequence
<220> FEATURE:
<223> OTHER INFORMATION: si RNA Rad51_3

<400> SEQUENCE: 151

ggcguucaga aaucauaca                                                  19

<210> SEQ ID NO 152
<211> LENGTH: 77
<212> TYPE: DNA
<213> ORGANISM: Artificial Sequence
<220> FEATURE:
<223> OTHER INFORMATION: Rad51 shRNA coding sequence (Rad51_3)

<400> SEQUENCE: 152

acaagcttgg cgttcagaaa tcatacattc aagagatgta tgatttctga acgcctctag      60

agtcggggcg gccggcc                                                    77

<210> SEQ ID NO 153
<211> LENGTH: 19
<212> TYPE: RNA
<213> ORGANISM: Artificial Sequence
<220> FEATURE:
<223> OTHER INFORMATION: si RNA Rad51b_1

<400> SEQUENCE: 153

acagccuaug auauaaaga                                                  19

<210> SEQ ID NO 154
<211> LENGTH: 19
<212> TYPE: RNA
<213> ORGANISM: Artificial Sequence
<220> FEATURE:
<223> OTHER INFORMATION: si RNA Rad51b_2

<400> SEQUENCE: 154

caaguucuug gccaaacaa                                                  19

<210> SEQ ID NO 155
<211> LENGTH: 19
<212> TYPE: RNA
<213> ORGANISM: Artificial Sequence
<220> FEATURE:
<223> OTHER INFORMATION: si RNA Rad51b_3

<400> SEQUENCE: 155

guaccuggcu gaggaauuu                                                  19

<210> SEQ ID NO 156
```

<211> LENGTH: 19
<212> TYPE: RNA
<213> ORGANISM: Artificial Sequence
<220> FEATURE:
<223> OTHER INFORMATION: si RNA Rad51c_1

<400> SEQUENCE: 156
ugaucagccu ggcaaauaa 19

<210> SEQ ID NO 157
<211> LENGTH: 19
<212> TYPE: RNA
<213> ORGANISM: Artificial Sequence
<220> FEATURE:
<223> OTHER INFORMATION: si RNA Rad51c_2

<400> SEQUENCE: 157
agaggaagcu uuagaaacu 19

<210> SEQ ID NO 158
<211> LENGTH: 19
<212> TYPE: RNA
<213> ORGANISM: Artificial Sequence
<220> FEATURE:
<223> OTHER INFORMATION: si RNA Rad51c_3

<400> SEQUENCE: 158
ggaugaagaa caccagaaa 19

<210> SEQ ID NO 159
<211> LENGTH: 19
<212> TYPE: RNA
<213> ORGANISM: Artificial Sequence
<220> FEATURE:
<223> OTHER INFORMATION: si RNA Rad51d_1

<400> SEQUENCE: 159
acggagcaga ccuauauga 19

<210> SEQ ID NO 160
<211> LENGTH: 19
<212> TYPE: RNA
<213> ORGANISM: Artificial Sequence
<220> FEATURE:
<223> OTHER INFORMATION: si RNA Rad51d_2

<400> SEQUENCE: 160
cccaagauga ggagaaaca 19

<210> SEQ ID NO 161
<211> LENGTH: 19
<212> TYPE: RNA
<213> ORGANISM: Artificial Sequence
<220> FEATURE:
<223> OTHER INFORMATION: si RNA Rad51d_3

<400> SEQUENCE: 161
gccuggacaa acuacuuga 19

<210> SEQ ID NO 162
<211> LENGTH: 19
<212> TYPE: RNA
<213> ORGANISM: Artificial Sequence
<220> FEATURE:
<223> OTHER INFORMATION: si RNA Rad52_1

<400> SEQUENCE: 162
ugagauguuu gguuacaau 19

<210> SEQ ID NO 163
<211> LENGTH: 19
<212> TYPE: RNA
<213> ORGANISM: Artificial Sequence
<220> FEATURE:
<223> OTHER INFORMATION: si RNA Rad52_2

<400> SEQUENCE: 163
acugcauucu ggacaaaga 19

<210> SEQ ID NO 164
<211> LENGTH: 19
<212> TYPE: RNA
<213> ORGANISM: Artificial Sequence
<220> FEATURE:
<223> OTHER INFORMATION: si RNA Rad52_3

<400> SEQUENCE: 164
cccugaagac aaccuugaa 19

<210> SEQ ID NO 165
<211> LENGTH: 19
<212> TYPE: RNA
<213> ORGANISM: Artificial Sequence
<220> FEATURE:
<223> OTHER INFORMATION: si RNA Rad54_1

<400> SEQUENCE: 165
agaagaccug cuauauuua 19

<210> SEQ ID NO 166
<211> LENGTH: 19
<212> TYPE: RNA
<213> ORGANISM: Artificial Sequence
<220> FEATURE:
<223> OTHER INFORMATION: si RNA Rad54_2

<400> SEQUENCE: 166
caucagauau ccucucuaa 19

<210> SEQ ID NO 167
<211> LENGTH: 19
<212> TYPE: RNA
<213> ORGANISM: Artificial Sequence
<220> FEATURE:
<223> OTHER INFORMATION: si RNA Rad54_3

<400> SEQUENCE: 167
gaagcuaugu aaccaucca 19

<210> SEQ ID NO 168
<211> LENGTH: 19
<212> TYPE: RNA
<213> ORGANISM: Artificial Sequence
<220> FEATURE:
<223> OTHER INFORMATION: si RNA Xrcc2_1

<400> SEQUENCE: 168
gaaguguucu cagcuccua 19

<210> SEQ ID NO 169
<211> LENGTH: 19
<212> TYPE: RNA

<213> ORGANISM: Artificial Sequence
<220> FEATURE:
<223> OTHER INFORMATION: si RNA Xrcc2_2

<400> SEQUENCE: 169
caacacaaag ucuaaugca 19

<210> SEQ ID NO 170
<211> LENGTH: 19
<212> TYPE: RNA
<213> ORGANISM: Artificial Sequence
<220> FEATURE:
<223> OTHER INFORMATION: si RNA Xrcc2_3

<400> SEQUENCE: 170
aucagagggu ggacugcaa 19

<210> SEQ ID NO 171
<211> LENGTH: 19
<212> TYPE: RNA
<213> ORGANISM: Artificial Sequence
<220> FEATURE:
<223> OTHER INFORMATION: si RNA Xrcc3_1

<400> SEQUENCE: 171
ccacaucuuc aucgagcau 19

<210> SEQ ID NO 172
<211> LENGTH: 19
<212> TYPE: RNA
<213> ORGANISM: Artificial Sequence
<220> FEATURE:
<223> OTHER INFORMATION: si RNA Xrcc3_2

<400> SEQUENCE: 172
acgguggagg agcaagagu 19

<210> SEQ ID NO 173
<211> LENGTH: 19
<212> TYPE: RNA
<213> ORGANISM: Artificial Sequence
<220> FEATURE:
<223> OTHER INFORMATION: si RNA Xrcc3_3

<400> SEQUENCE: 173
gaucagauuc agcaaccac 19

<210> SEQ ID NO 174
<211> LENGTH: 19
<212> TYPE: RNA
<213> ORGANISM: Artificial Sequence
<220> FEATURE:
<223> OTHER INFORMATION: si RNA Xrcc4_1

<400> SEQUENCE: 174
auaugcugau gaauugaga 19

<210> SEQ ID NO 175
<211> LENGTH: 19
<212> TYPE: RNA
<213> ORGANISM: Artificial Sequence
<220> FEATURE:
<223> OTHER INFORMATION: si RNA Xrcc4_2

<400> SEQUENCE: 175
cugaaagaug ucucauuua 19

```
<210> SEQ ID NO 176
<211> LENGTH: 19
<212> TYPE: RNA
<213> ORGANISM: Artificial Sequence
<220> FEATURE:
<223> OTHER INFORMATION: si RNA Xrcc4_3

<400> SEQUENCE: 176

augagcaccu gcagaaaga                                                19


<210> SEQ ID NO 177
<211> LENGTH: 19
<212> TYPE: RNA
<213> ORGANISM: Artificial Sequence
<220> FEATURE:
<223> OTHER INFORMATION: si RNA Negative Control 1

<400> SEQUENCE: 177

agguagugua aucgccuug                                                19


<210> SEQ ID NO 178
<211> LENGTH: 19
<212> TYPE: RNA
<213> ORGANISM: Artificial Sequence
<220> FEATURE:
<223> OTHER INFORMATION: si RNA Negative Control 2

<400> SEQUENCE: 178

gacgacucac auacguaaa                                                19


<210> SEQ ID NO 179
<211> LENGTH: 19
<212> TYPE: RNA
<213> ORGANISM: Artificial Sequence
<220> FEATURE:
<223> OTHER INFORMATION: si RNA Negative Control 3

<400> SEQUENCE: 179

gaauauaucg cgaaaugua                                                19
```